(12) United States Patent
Row et al.

(10) Patent No.: US 10,252,005 B2
(45) Date of Patent: Apr. 9, 2019

(54) ASSISTED MANUAL INJECTOR DEVICES AND METHODS

(71) Applicant: Genentech, Inc., South San Francisco, CA (US)

(72) Inventors: Gordon D. Row, Lexington, MA (US); Andrew I. Poutiatine, Mill Valley, CA (US); Neal Schlatter, South San Francisco, CA (US); Adrian Bischoff, Cambridge, MA (US)

(73) Assignee: GENENTECH, INC., South San Fancisco, CA (US)

( * ) Notice: Subject to any disclaimer, the term of this patent is extended or adjusted under 35 U.S.C. 154(b) by 558 days.

(21) Appl. No.: 14/541,095

(22) Filed: Nov. 13, 2014

(65) Prior Publication Data

US 2015/0165129 A1 Jun. 18, 2015

Related U.S. Application Data

(60) Provisional application No. 61/903,884, filed on Nov. 13, 2013.

(51) Int. Cl.
*A61M 5/315* (2006.01)
*A61M 5/20* (2006.01)
(Continued)

(52) U.S. Cl.
CPC ...... *A61M 5/31501* (2013.01); *A61M 5/2033* (2013.01); *A61M 5/3157* (2013.01);
(Continued)

(58) Field of Classification Search
CPC ................ A61M 5/326; A61M 5/2033; A61M 2005/2073; A61M 5/31501
See application file for complete search history.

(56) References Cited

U.S. PATENT DOCUMENTS

| 3,400,715 A | 9/1968 | Pederson |
|---|---|---|
| 5,295,965 A | 3/1994 | Wilmot |

(Continued)

FOREIGN PATENT DOCUMENTS

| CN | 103079616 | 8/2015 |
|---|---|---|
| FR | 2884722 A1 | 10/2006 |

(Continued)

OTHER PUBLICATIONS

Corne, J. et al. (Mar. 1, 1997). "The Effect of Intravenous Administration of a Chimeric Anti-IgE Antibody on Serum IgE Levels in Atopic Subjects: Efficacy, Safety, and Pharmacokinetics," *J. Clin. Invest.* 99(5):879-887.

(Continued)

*Primary Examiner* — Edelmira Bosques
(74) *Attorney, Agent, or Firm* — Morrison & Foerster LLP

(57) ABSTRACT

Various embodiments disclosed herein relate to needle-based injectors that incorporate a power assembly comprising a stored energy source and a rate control assembly. The power assembly may be further configured to allow the injection to be performed with more force than a user may be capable of delivering, while also allowing the user to maintain control of the injection process after the stored energy source has been released and the injection has begun, such the user may increase or decrease the rate of injection, or stop the injection, during the injection process. In various embodiments, the power assembly may comprise spring- or gas-based stored energy sources, and/or may comprise friction- or tension-based rate control assemblies. Described herein are also methods for injecting an agent using embodiments of the devices described here.

24 Claims, 73 Drawing Sheets

(51) Int. Cl.
*A61M 5/48* (2006.01)
*A61M 5/32* (2006.01)
*A61M 5/31* (2006.01)

(52) U.S. Cl.
CPC ........... *A61M 5/482* (2013.01); *A61M 5/2053* (2013.01); *A61M 5/3204* (2013.01); *A61M 5/326* (2013.01); *A61M 2005/206* (2013.01); *A61M 2005/2086* (2013.01); *A61M 2005/3143* (2013.01); *A61M 2005/3151* (2013.01); *A61M 2205/586* (2013.01)

(56) References Cited

U.S. PATENT DOCUMENTS

| | | | |
|---|---|---|---|
| 5,478,316 A | 12/1995 | Bitdinger et al. | |
| 5,665,071 A * | 9/1997 | Wyrick | A61M 5/002 604/131 |
| 6,030,366 A | 2/2000 | Mitchell | |
| 6,329,509 B1 | 12/2001 | Jardieu et al. | |
| 6,569,143 B2 | 5/2003 | Alchas et al. | |
| 6,613,022 B1 | 9/2003 | Doyle | |
| 6,689,118 B2 | 2/2004 | Alchas et al. | |
| 6,805,686 B1 | 10/2004 | Fathallah et al. | |
| 6,808,507 B2 | 10/2004 | Roser | |
| 6,914,130 B2 | 7/2005 | Gao | |
| 7,229,432 B2 | 6/2007 | Marshall et al. | |
| 7,300,420 B2 | 11/2007 | Doyle | |
| 7,357,791 B2 * | 4/2008 | Kirchhofer | A61M 5/2033 604/135 |
| 7,449,012 B2 | 11/2008 | Young et al. | |
| 7,517,334 B2 * | 4/2009 | Jacobs | A61M 5/31555 604/110 |
| 7,611,495 B1 | 11/2009 | Gianturco | |
| 7,740,612 B2 | 6/2010 | Hochman | |
| 7,789,856 B2 | 9/2010 | Hillios et al. | |
| 7,794,432 B2 | 9/2010 | Young et al. | |
| 7,824,379 B2 | 11/2010 | Doyle | |
| 7,976,499 B2 | 7/2011 | Grunhut et al. | |
| 8,002,753 B2 | 8/2011 | Krumme et al. | |
| 8,133,208 B2 | 3/2012 | Hetherington | |
| 8,235,952 B2 | 8/2012 | Wikner | |
| 8,376,998 B2 | 2/2013 | Daily et al. | |
| 8,425,462 B2 | 4/2013 | Edwards et al. | |
| 8,647,303 B2 * | 2/2014 | Cowe | A61M 5/20 604/134 |
| 8,915,886 B2 * | 12/2014 | Cowe | A61M 5/2033 604/187 |
| 9,248,236 B2 * | 2/2016 | Olson | A61M 5/2033 |
| 2002/0072719 A1 | 6/2002 | Douglas et al. | |
| 2002/0161199 A1 | 10/2002 | Ashkenazi | |
| 2003/0003507 A1 | 1/2003 | Ashkenazi | |
| 2003/0039648 A1 | 2/2003 | Goddard | |
| 2003/0060612 A1 | 3/2003 | Goddard | |
| 2003/0108544 A1 | 6/2003 | Gurney et al. | |
| 2003/0148408 A1 | 8/2003 | Frantz | |
| 2003/0228305 A1 | 12/2003 | Frantz | |
| 2004/0186441 A1 * | 9/2004 | Graf | A61M 5/315 604/207 |
| 2004/0186442 A1 * | 9/2004 | Graf | A61M 5/31553 604/207 |
| 2007/0173770 A1 | 7/2007 | Stamp | |
| 2007/0197976 A1 * | 8/2007 | Jacobs | A61M 5/31555 604/218 |
| 2007/0270762 A1 * | 11/2007 | Kirchhofer | A61M 5/315 604/211 |
| 2009/0005737 A1 | 1/2009 | Chun | |
| 2010/0286655 A1 | 11/2010 | Wallace et al. | |
| 2010/0324485 A1 * | 12/2010 | Cowe | A61M 5/20 604/134 |
| 2011/0092915 A1 | 4/2011 | Olson et al. | |
| 2013/0218128 A1 * | 8/2013 | Cowe | A61M 5/2033 604/506 |
| 2015/0314075 A1 * | 11/2015 | Cowe | A61M 5/31501 604/211 |

FOREIGN PATENT DOCUMENTS

| | | |
|---|---|---|
| RU | 2428213 C2 | 9/2011 |
| WO | WO-92/17207 A1 | 10/1992 |
| WO | WO-99/01556 A2 | 1/1999 |
| WO | WO-00/24441 A1 | 5/2000 |
| WO | WO-2009/098502 A2 | 8/2009 |
| WO | WO2012000836 A1 | 1/2012 |
| WO | WO-2012/038721 A2 | 3/2012 |

OTHER PUBLICATIONS

International Search Report dated Jul. 14, 2015, for PCT Application No. PCT/US2014/065568, filed on Nov. 13, 2014, 6 pages.
Written Opinion dated Jul. 14, 2015, for PCT Application No. PCT/US2014/065568, filed on Nov. 13, 2014, 11 pages.
U.S. Appl. No. 10/177,488, filed Jun. 19, 2002.

* cited by examiner

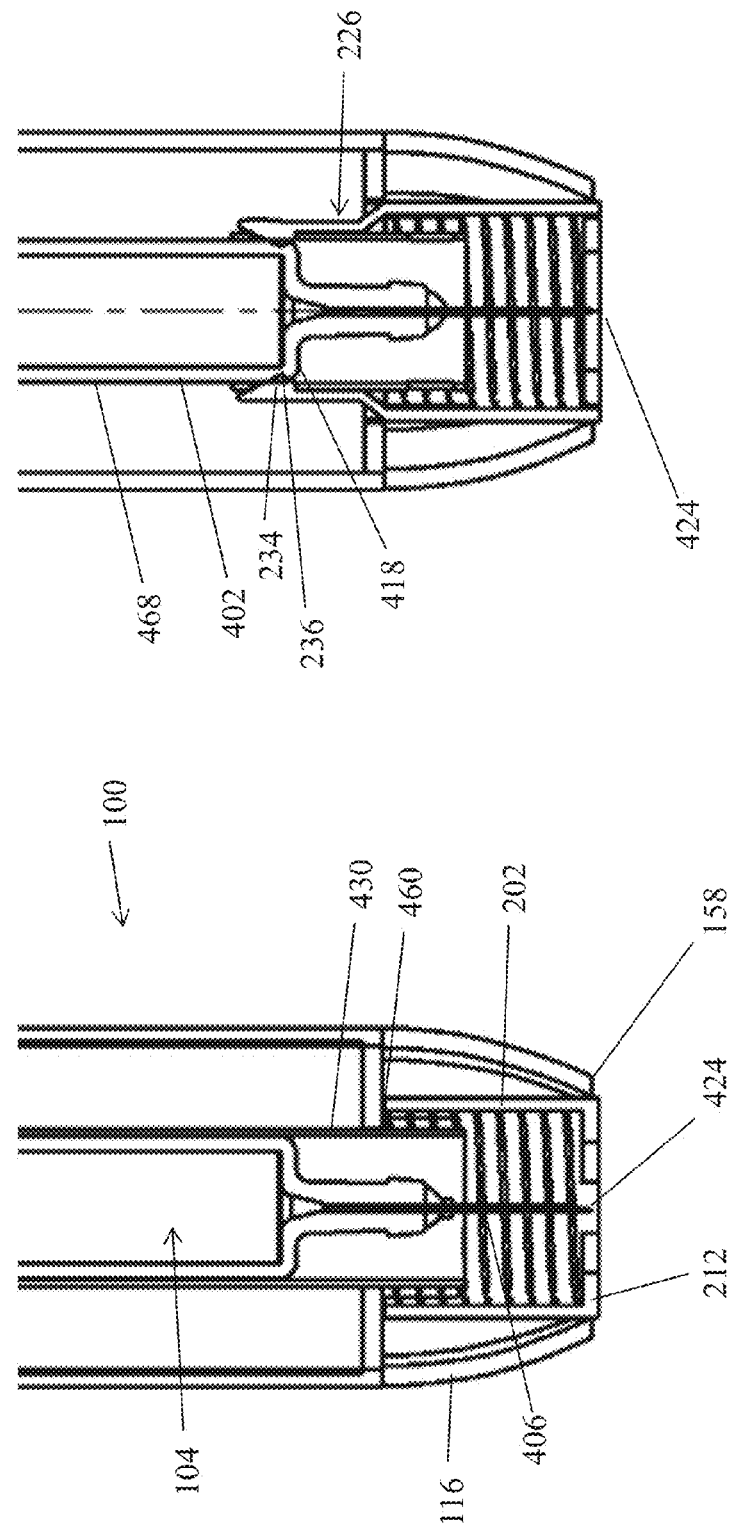

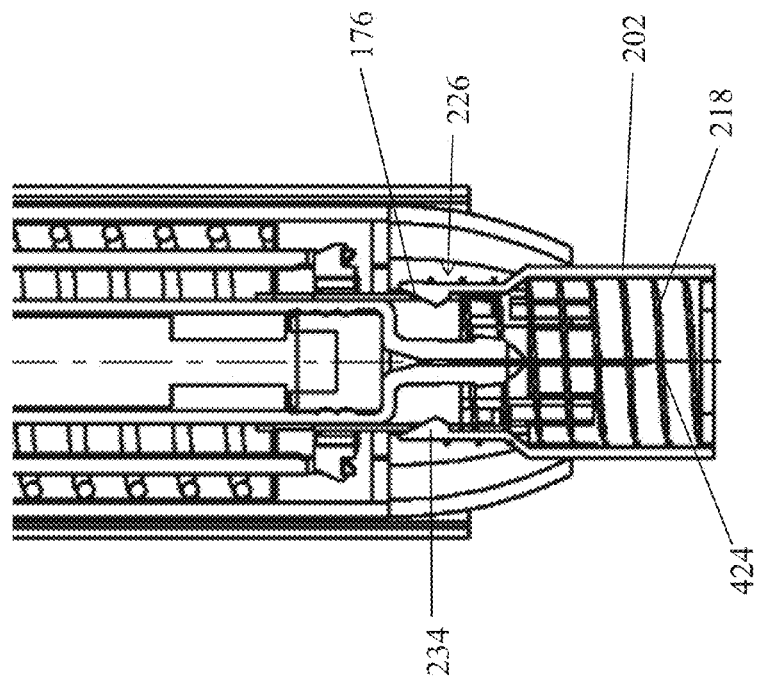
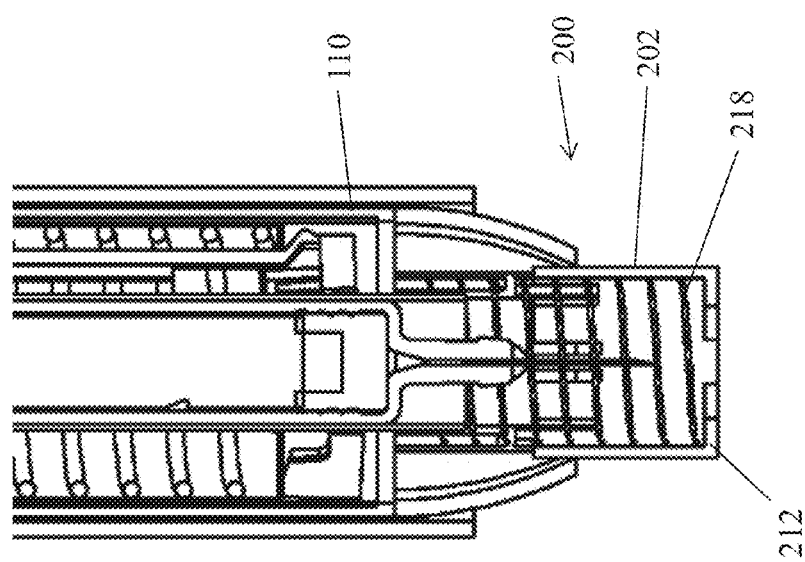

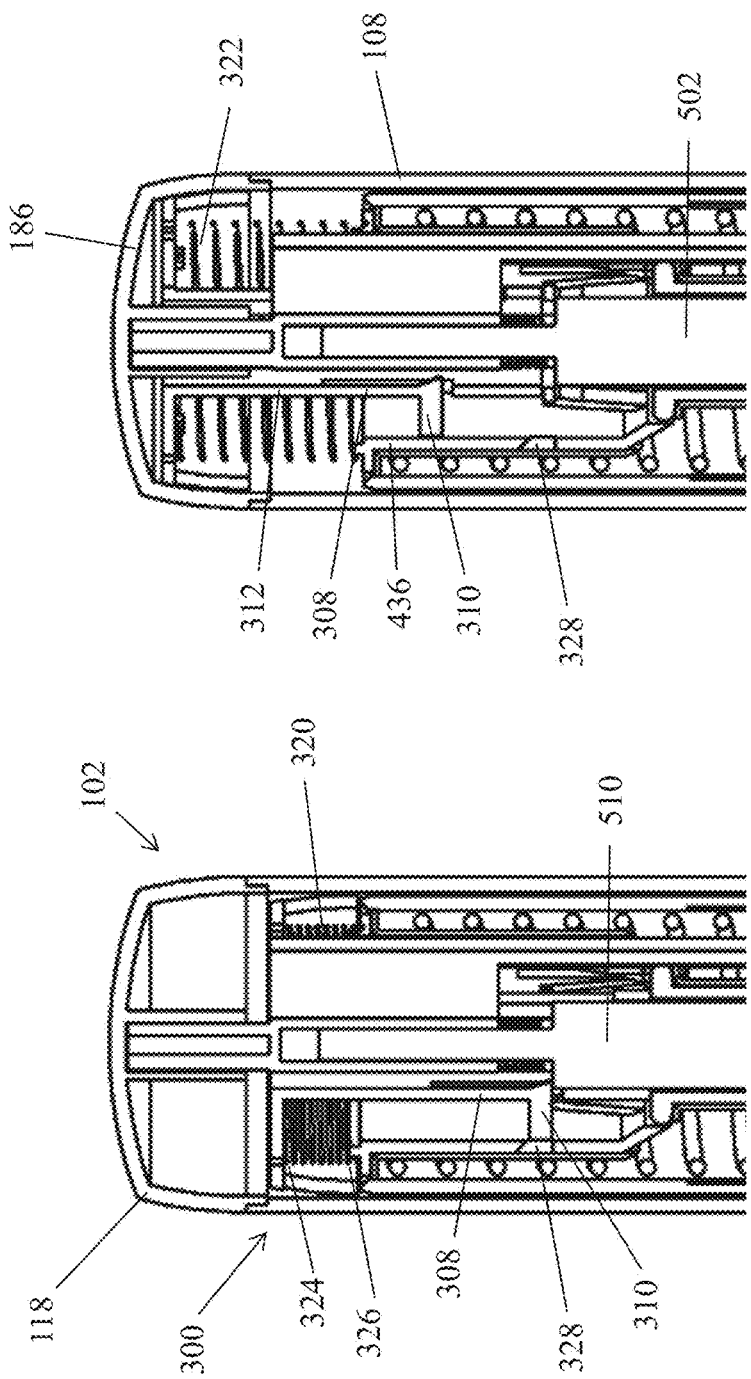

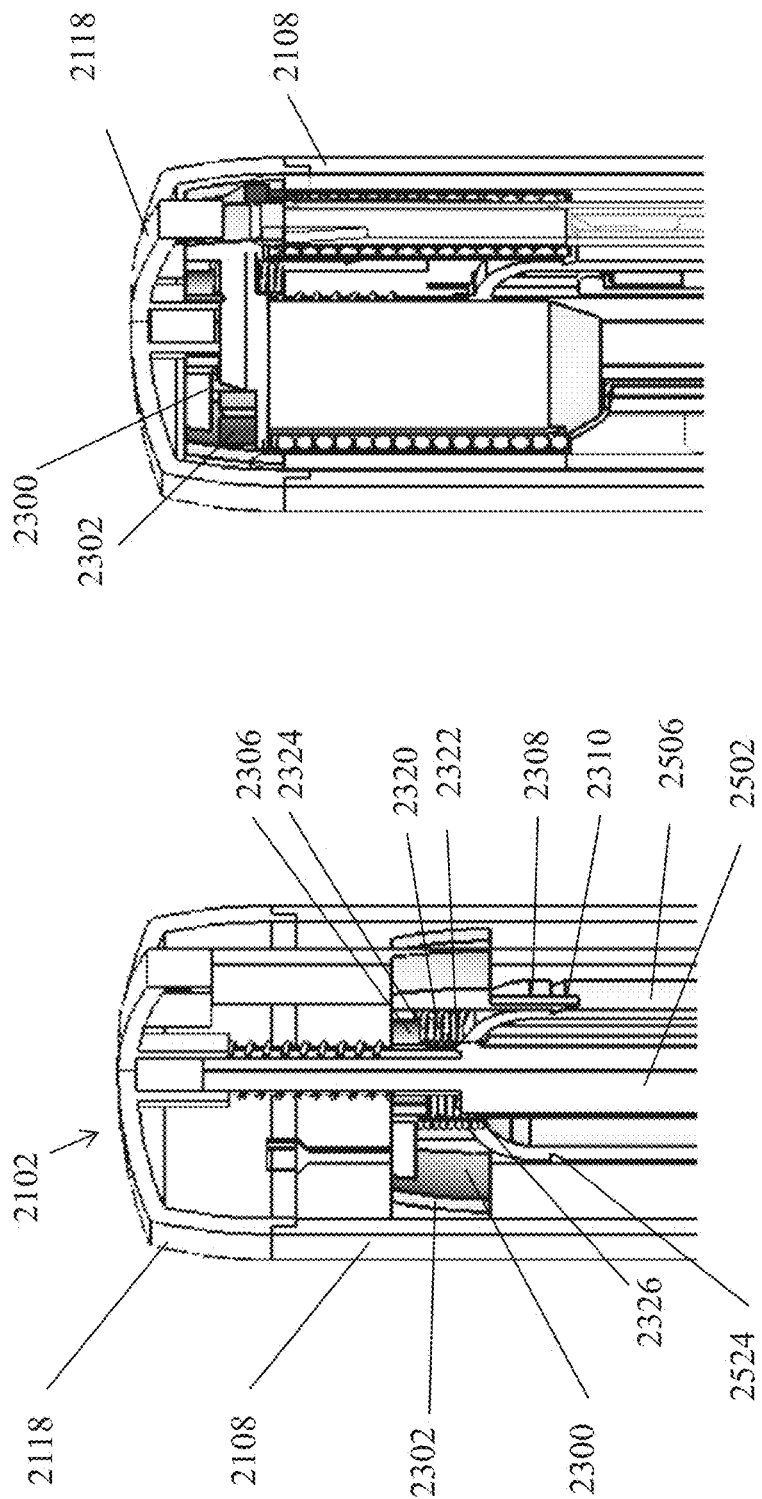

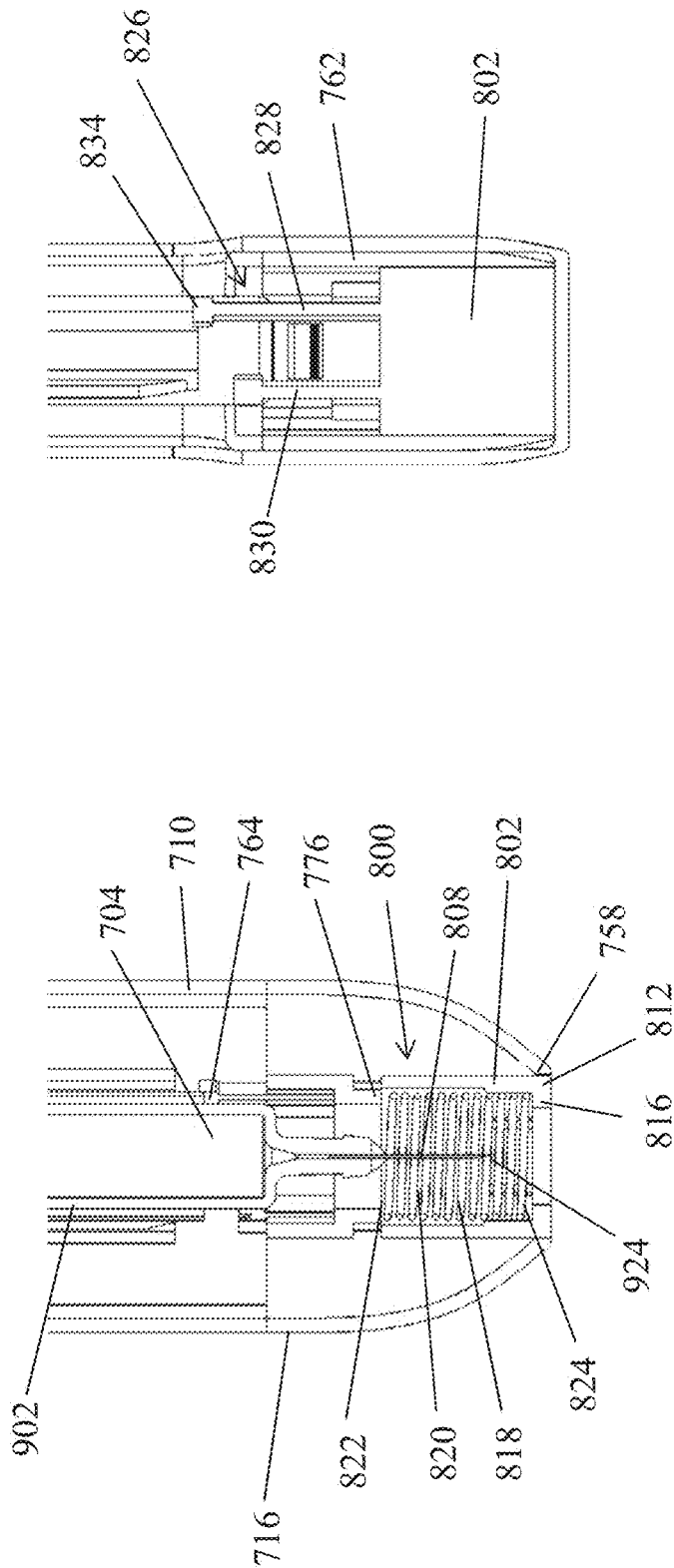

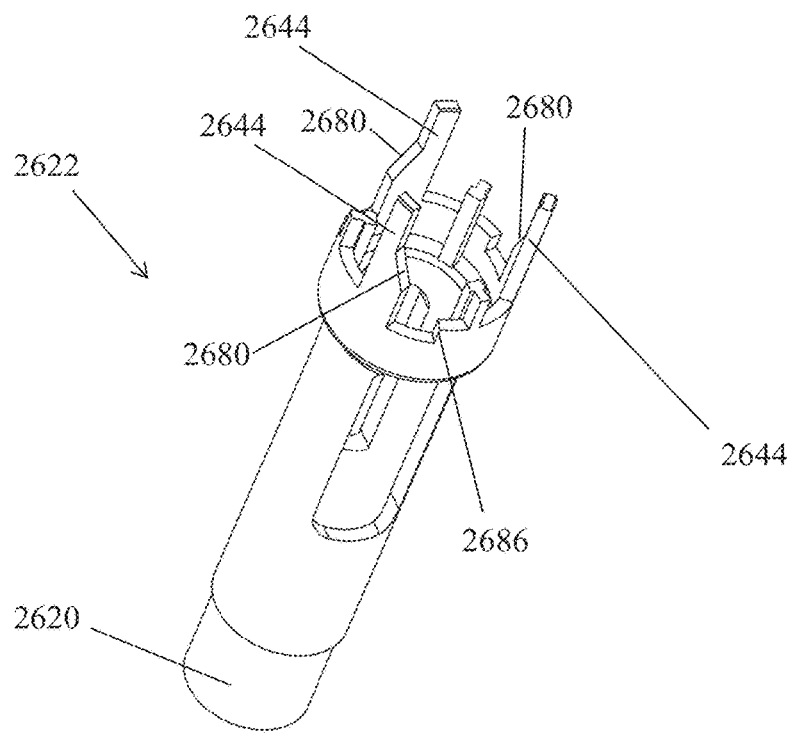
FIG. 29A
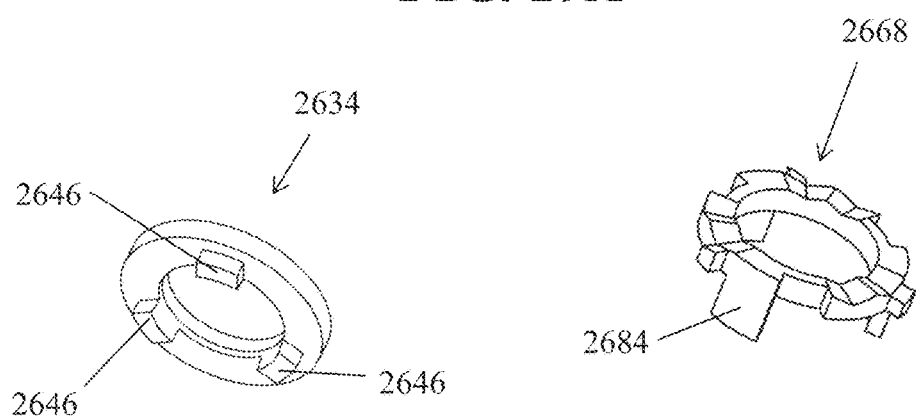
FIG. 29B
FIG. 29C

# ASSISTED MANUAL INJECTOR DEVICES AND METHODS

CROSS-REFERENCE TO RELATED APPLICATIONS

This application claims the priority benefit of U.S. Provisional Application Ser. No. 61/903,884, filed Nov. 13, 2013, which is incorporated herein by reference in its entirety.

FIELD

Described here are power-assisted injection devices that allow a user to selectively increase or decrease the injection rate, and to pause or stop the injection, as desired.

BACKGROUND

The injection of therapeutic agents in hospital, clinic, and home-based settings is a common procedure, but can sometimes be complex and difficult to perform, even for experienced healthcare providers. Drawing a therapeutic agent into a syringe and injecting it into a patient requires a certain level of manual dexterity and strength, in addition to sufficient visual and mental acuity to perform the procedural steps. The risk of needlestick injury also exists throughout all of the steps of a manual injection procedure. In home-based settings, these challenges could lead to reduced patient compliance with treatment regimens.

Nevertheless, as reliance upon home-based injection regimens continues to expand, the challenges with syringe injection have become more diversified. For example, patients with physical or cognitive impairment may need to perform such injections, without assistance from in-home care providers. Also, some injections require more force than users are capable of delivering, for instance if the injected substance has a high viscosity. Furthermore, for some medications, the injection process can cause discomfort related to the rate of injection. In some instances, a user may want to increase the rate of injection, in order to accomplish the injection in a shorter time, or may want to decrease the rate of injection or stop the injection, for example to mitigate injection-related pain. There is therefore a need for a power-assisted injection device, which allows the user to both control a stored energy source and also provide some amount of user supplied power to the injection, and thus increase or decrease the injection rate, or stop the injection, at will.

BRIEF SUMMARY

Various embodiments disclosed herein relate to needle-based injectors that incorporate a power assembly comprising a stored energy source and a rate control assembly. The power assembly may be further configured to allow the injection to be performed with more force than a user may be capable of delivering, while also allowing the user to maintain control of the injection process after the stored energy source has been released and the injection has begun, such the user may increase or decrease the rate of injection, or stop the injection, during the injection process. In various embodiments, the power assembly may comprise spring- or gas-based stored energy sources, and may comprise friction- or tension-based rate control assemblies. Described herein are also methods for injecting an agent using embodiments of the devices described here.

A particular embodiment comprises a device for injecting an agent, comprising a syringe comprising a syringe cavity, a plunger element slidably received in the syringe cavity, and a hollow needle in fluid communication with the syringe cavity, wherein the plunger element is configured to move from a proximal position to a distal position, a power assembly configured to transmit force to the plunger element, and a user-actuated brake assembly that is configured to reversibly resist movement of the plunger element in at least one intermediate position between the proximal position and the distal position. The brake assembly may be biased to resist movement of the plunger element when in an inactivated state, and may permit movement of the plunger element when in an activated state. The brake assembly may be biased by a brake spring to resist movement of the plunger element. The power assembly may comprise a mechanical spring. The plunger element may be further configured to simultaneously receive user-applied force that moves the plunger element toward the distal position. The device may further comprise a housing wherein the syringe is located in the housing. The housing may be coupled to the plunger element. The housing may be configured to transmit user-applied force to the plunger element. The brake assembly may comprise a flexible, elongate brake cord. The brake cord may comprise a releasable friction fit to reversibly resist movement of the plunger element. The releasable friction fit may be provided by releasable tension in the brake cord. The brake assembly may comprise a rigid friction element. The brake assembly may act on an outer surface of the syringe to reversibly resist movement of the plunger element. The brake assembly may act on a surface fixed relative to the syringe to reversibly resist movement of the plunger element. The brake assembly may comprise an opening in which the syringe resides. The power assembly may be configured to pull the plunger element toward the distal position. The power assembly may be configured to push the plunger element toward the distal position. The power assembly may be further configured to push and pull the plunger element toward the distal position. The syringe may be slidably located in the housing and the syringe is configured to move from a retracted position where a distal tip of the needle lies within the housing, toward an extended position where the distal tip of the needle extends distal to the housing. The device may further comprise an extendable needle shroud, wherein the needle shroud may be configured with a releasably locked, retracted state relative to the syringe, and an unlocked state that may permit movement toward an extended position relative to the syringe. The device may further comprise an extendable needle shroud, wherein the needle shroud is configured with a releasably locked, retracted state relative to the syringe, and an unlocked state that permits movement toward an extended position relative to the syringe, and wherein the needle shroud is further configured to change to the unlocked state before the distal tip of the needle extends distal to the housing. The needle shroud may be further configured to relock when the needle shroud reaches the extended state. In other variations the device may comprise an extendable needle shroud, wherein the needle shroud is configured with an unlocked extended state that permits movement toward a retracted position relative to the syringe and a locked extended state. The needle shroud may be configured to enter the locked extended state when the needle shroud extends from a retracted state.

A particular embodiment comprises a device for injecting an agent, comprising a syringe comprising a syringe cavity containing a formulation comprising the agent, and a power assembly configured to act upon the syringe to cause the formulation to be displaced from the syringe cavity, wherein the power assembly comprises a stored energy source and a rate control assembly, wherein the rate control assembly resists the stored energy source acting on the syringe when in a first configuration and allows the stored energy source to act on the syringe when in a second configuration. The rate control assembly may partially resist the stored energy source acting on the syringe in a third configuration. The device may further comprise a housing, wherein the syringe and power assembly are at least partially located within the housing. The rate control assembly may be configured to be changed from the first configuration to the second configuration by application of distal force on the housing. The change from the first configuration to the second configuration may be reversible. The rate control assembly may be configured to be changed from the second configuration to the first configuration by removing or reducing the application of distal force on the housing. The change from the second configuration to the first configuration may be reversible. The housing may comprise a proximal housing and a distal housing, and wherein the application of distal force on the housing may be to the proximal housing. The distal housing may comprise a distal end and a nose located at the distal end, and wherein the nose has a flared shape. The syringe may further comprise a plunger slidable within the syringe cavity and a needle having a lumen in fluid communication with the syringe cavity, wherein the syringe may be configured such that distal movement of the plunger within the syringe cavity may cause the formulation to be displaced from the syringe cavity through the lumen of the needle. In the first configuration, the rate control assembly may resist distal movement of the plunger within the syringe cavity. In the second configuration, the rate control assembly may allow distal movement of the plunger within the syringe cavity. The stored energy source may comprise a spring. The rate control assembly may comprise a longitudinal axis and the housing may comprise a longitudinal axis, and the rate control assembly may be configured to be reversibly moved from the first configuration to the second configuration by moving the longitudinal axis of the rate control assembly toward the longitudinal axis of the housing. The stored energy source may comprise a composite spring, wherein the composite spring may comprise a coaxially arranged compression spring and extension spring. The rate control assembly may comprise a cord comprising at least two portions capable of being under differing amounts of tension. The stored energy source may comprise a compressed gas or liquid propellant in a supercritical state. The device is configured such that the rate at which the formulation is able to be displaced from the syringe cavity may be able to be selectively increased, decreased, or stopped after the plunger has moved distally relative to an initial position within the syringe cavity. The device may be configured such that movement of the plunger distally within the syringe cavity may require application of distal force by a user during the movement.

A particular embodiment comprises a device for injecting an agent, comprising a syringe comprising a syringe cavity containing a formulation comprising the agent to be injected by application of distal force on the device by a user, and a power assembly configured to act upon the syringe, wherein the power assembly is configured to amplify the application of distal force by the user, such that the agent is able to be injected with more distal force than is applied by the user to the device, and wherein the power assembly is configured to reduce the rate of injection of the agent if the distal force is reduced. The power assembly may be configured to stop the injection of the agent if the user stops applying distal force to the device. The formulation may be a liquid formulation. The formulation may be a colloidal formulation.

A particular embodiment comprises a device for injecting an agent, comprising a syringe comprising a syringe cavity, a plunger element slidably received in the syringe cavity, and a hollow needle in fluid communication with the syringe cavity, wherein the plunger is configured to move from a proximal position to a distal position, a pressurized gas assembly with a user-actuated valve opening biased to a closed state, and a flow path between the valve opening and a pressurization region, wherein the flow path is non-linear. The pressurized gas assembly may be configured to apply force to a surface at a fixed position relative to the plunger to move the plunger from the proximal position to the distal position. The plunger may be further configured to simultaneously receive user-applied force that moves the plunger element toward the distal position. The device may further comprise a housing wherein the syringe may be at least partially located in the housing. The housing may be configured to transmit user-applied force to the plunger. The housing may be configured to transmit user-applied force to the valve opening. The valve opening may be configured to be opened by user-applied force to the housing. The syringe may be slidably located in the housing and the syringe may be configured to move from a retracted position where a distal tip of the needle lies within the housing, toward an extended position where the distal tip of the needle extends distal to the housing. The device may further comprise an extendable needle shroud, wherein the needle shroud may be configured with a releasably locked, retracted state relative to the syringe, and an unlocked state that may permit movement toward an extended position relative to the syringe. The device may further comprise an extendable needle shroud, wherein the needle shroud may be configured with a releasably locked, retracted state relative to the syringe, and an unlocked state that may permit movement toward an extended position relative to the syringe, and wherein the needle shroud maybe further configured to change to the unlocked state before the distal tip of the needle extends distal to the housing. The needle shroud may be further configured to relock when the needle shroud reaches the extended state. The pressurization region may be configured to have a variable volume.

A particular embodiment comprises a device for injecting an agent, comprising a housing, and a syringe located within the housing, wherein the housing comprises a needle shroud having activated and inactivated configurations, wherein when the needle shroud is in an activated configuration, it is biased from a retracted position toward an extended position, and wherein the needle shroud is switched from the inactivated configuration to the activated configuration by distal motion of the syringe relative to at least a portion of the housing. The syringe may comprise a needle and the syringe may be slidably located in the housing and may be configured to move from a retracted position where a distal tip of the needle lies within the housing, toward an extended position where the distal tip of the needle extends distal to the housing. The needle shroud may be switched from the inactivated configuration to the activated configuration before the distal tip of the needle extends distal to the housing. The needle shroud may be configured to be maintained in a retracted position by proximal force on the needle shroud after being switched to an activated configuration. The needle shroud may be further configured to be locked in an extended position once moved to an extended position.

A particular embodiment comprises a device for injecting an agent, comprising a housing having a longitudinal axis, a syringe containing the agent located within the housing, a plunger slidable within the syringe, configured to be moveable between a proximal position and a distal position, wherein moving the plunger toward the distal position displaces the agent from the syringe, a biter having a longitudinal axis and comprising a lumen through which the syringe is located, wherein the biter is configured to be moveable between a first configuration wherein the longitudinal axis of the biter is offset from the longitudinal axis of the housing, and a second configuration wherein the longitudinal axis of the biter is less offset from the longitudinal axis of the housing than in the first configuration, and a spring in contact with the biter configured to bias the plunger toward the distal position via the biter when the biter is in the second configuration. The spring may bias the biter toward the first configuration. The syringe may be configured to be moveable between a proximal position and a distal position relative to the housing. The biter may be configured to be moveable between the first configuration and the second configuration by moving an actuation rod between a first position not in contact with the biter and a second position in contact with the biter. The biter may be configured to be moveable between the first configuration and the second configuration by application of distal force on the housing. The spring may apply a distal force on the biter. The distal force on the biter from the spring may be opposed by a proximal frictional force when the biter is in the first configuration. The device may further comprise a retractable needle shroud configured to be moveable between a retracted position and an extended position. The device may further comprise an end-of-dose indicator moveable between an inactivated and an activated configuration.

A particular embodiment may comprise a device for injecting an agent, comprising a housing, a syringe located within the housing, wherein the syringe comprises the agent, a plunger configured to move slidably within the syringe between a proximal and a distal position, a spring configured to bias the plunger toward the distal position, and a cord configured to be reversibly changed between a tensioned configuration and an reduced-tension configuration, wherein the cord is configured to bias the plunger toward the proximal position when in the tensioned configuration. The plunger may be configured to remain fixed relative to the syringe when the cord is in a tensioned configuration. The plunger may be configured to move toward the distal position when the cord is in a reduced-tension configuration. The plunger may comprise a distal end, and the cord may be configured to apply proximal force to the distal end of the plunger when the cord is in the tensioned configuration. The spring may be configured to pull the plunger toward the distal position.

A particular embodiment may comprise a device for injecting an agent, comprising a housing, a syringe located within the housing, and an end-of-dose indicator, wherein the end-of-dose indicator has an inactivated configuration and an activated configuration, and wherein the visual appearance of the end-of-dose indicator through the housing is different in the inactivated and activated configurations. The syringe may further comprise a syringe cavity and a plunger slidably received in the syringe cavity, and a hollow needle in fluid communication with the syringe cavity, wherein the plunger may be configured to move from a proximal position to a distal position, and wherein the end-of-dose indicator is moved from the inactivated configuration to the activated configuration by movement of the plunger toward the distal position.

A particular embodiment may comprise a method for injecting an agent using a device comprising a syringe comprising a syringe cavity, a housing wherein the syringe is located in the housing, a plunger slidably received in the syringe cavity, and a hollow needle in fluid communication with the syringe cavity, wherein the plunger is configured to move from a proximal position to a distal position, a power assembly configured to transmit force to the plunger, and a user-actuated brake assembly that is configured to reversibly resist movement of the plunger in at least one intermediate position between the proximal position and the distal position, comprising applying force to the housing, wherein the force causes the power assembly to transmit force to the plunger to move the plunger toward the distal position, and reducing the applied force to the housing when the plunger is in an intermediate position, wherein reducing the applied force causes the brake assembly to reduce the force transmitted to the plunger by the power assembly. The housing may comprise a proximal housing and a distal housing, and wherein applying force to the housing comprises applying distal force to the proximal housing. The force applied to the housing may further cause the brake assembly to move from an inactivated state to an activated state, wherein the brake assembly may be biased to resist movement of the plunger element when in the inactivated state, and may permit movement of the plunger element when in the activated state. The method may further comprise reapplying force to the housing, wherein the force may cause the power assembly to transmit force to the plunger to move the plunger toward the distal position.

A particular embodiment comprises a device for injecting an agent, comprising a housing having a longitudinal axis, a syringe containing the agent within a syringe cavity, wherein the syringe is located within the housing, a plunger slidable within the syringe, configured to be moveable between a proximal position and a distal position, wherein moving the plunger toward the distal position displaces the agent from the syringe, and a spring in contact with the plunger configured to bias the plunger toward the distal position, wherein the plunger comprises a braking pad configured to be reversibly moveable between a first configuration and a second configuration, wherein the braking pad generates friction to resist movement of the plunger in the second configuration. The braking pad may be configured to be moveable from the first configuration to the second configuration by radially outward movement. The device may further comprise a stopper located within the plunger and movable between a proximal position and a distal position within the plunger, wherein the stopper is configured such that moving the stopper from the distal position to the proximal position moves the braking pad from the first configuration to the second configuration. The stopper may be biased toward the proximal position. The stopper may be configured to be moveable between the proximal position and distal position by application of distal force on the housing. The device may further comprise a retractable needle shroud configured to be moveable between a retracted position and an extended position. The device may further comprise an end-of-dose indicator moveable between an inactivated and an activated configuration.

BRIEF DESCRIPTION OF THE DRAWINGS

FIGS. 2A-2B show two orthogonal cross-sectional views of the device before use. FIGS. 2M-2N show two orthogonal cross-sectional views of the device with the needle shroud extended.

FIGS. 3A-3F are longitudinal cross-sectional views of a distal portion of the injection device of FIG. 1, showing the needle shroud in a retracted position (FIGS. 3A-3B), unlocked from a retracted position (FIGS. 3C-3D), and in an extended position (FIGS. 3E-3F).

FIGS. 4A-4C illustrate longitudinal cross-sectional views of a proximal portion of the injection device of FIG. 1, showing the end-of-dose indicator in inactivated (FIG. 4A), released (FIG. 4B), and activated configurations (FIG. 4C). FIGS. 4D-4E illustrate cut-away elevational side views of a proximal portion of another embodiment of an injection device showing another example of an end-of-dose indicator in inactivated (FIG. 4D) and activated configurations (FIG. 4E).

FIG. 12A depicts the device before use. FIG. 12B depicts the device with the rigid needle shield and cap removed. FIG. 12C depicts the device with the syringe in an extended position. FIG. 12D depicts the device with the plunger moved to the distal position within the syringe cavity. FIG. 12E depicts the device with the end-of-dose indicator in an activated configuration. FIG. 12F depicts the device with the needle shroud extended.

FIGS. 13A-13D depict longitudinal cross-sectional views (FIGS. 13A and 13C) and cut-away elevational side views (FIGS. 13B and 13D) of a distal portion of the injection device of FIG. 10, showing the needle shroud in a retracted position and in an extended position, respectively.

FIG. 19A illustrates the device before use. FIG. 19B illustrates the device with the rigid needle shield and cap removed. FIG. 19C illustrates the device with the syringe in a partially extended position. FIG. 19D illustrates the device with the syringe in a fully extended position. FIG. 19E illustrates the device with the plunger moved partially toward the distal position within the syringe cavity. FIG. 19F illustrates the device with the plunger in the distal position within the syringe cavity. FIG. 19G illustrates the device with the needle shroud extended.

FIG. 27A illustrates the device before use. FIG. 27B illustrates the device with the syringe in a partially extended position. FIG. 27C illustrates the device with the syringe in a fully extended position. FIG. 27D illustrates the device with the ram in contact with the seal. FIG. 27E illustrates the device with the plunger moved partially toward the distal position within the syringe cavity. FIG. 27F illustrates the device with the end-of-dose indicator in an activated configuration. FIG. 27G illustrates the device with the plunger in the distal position within the syringe cavity. FIG. 27H illustrates the device with the needle shroud extended.

FIGS. 29A, 29B, and 29C depict perspective views of the needle safety assembly, interlock ring, and shroud locking ring, respectively, of the injection device of FIG. 26.

DETAILED DESCRIPTION

Figure 1:
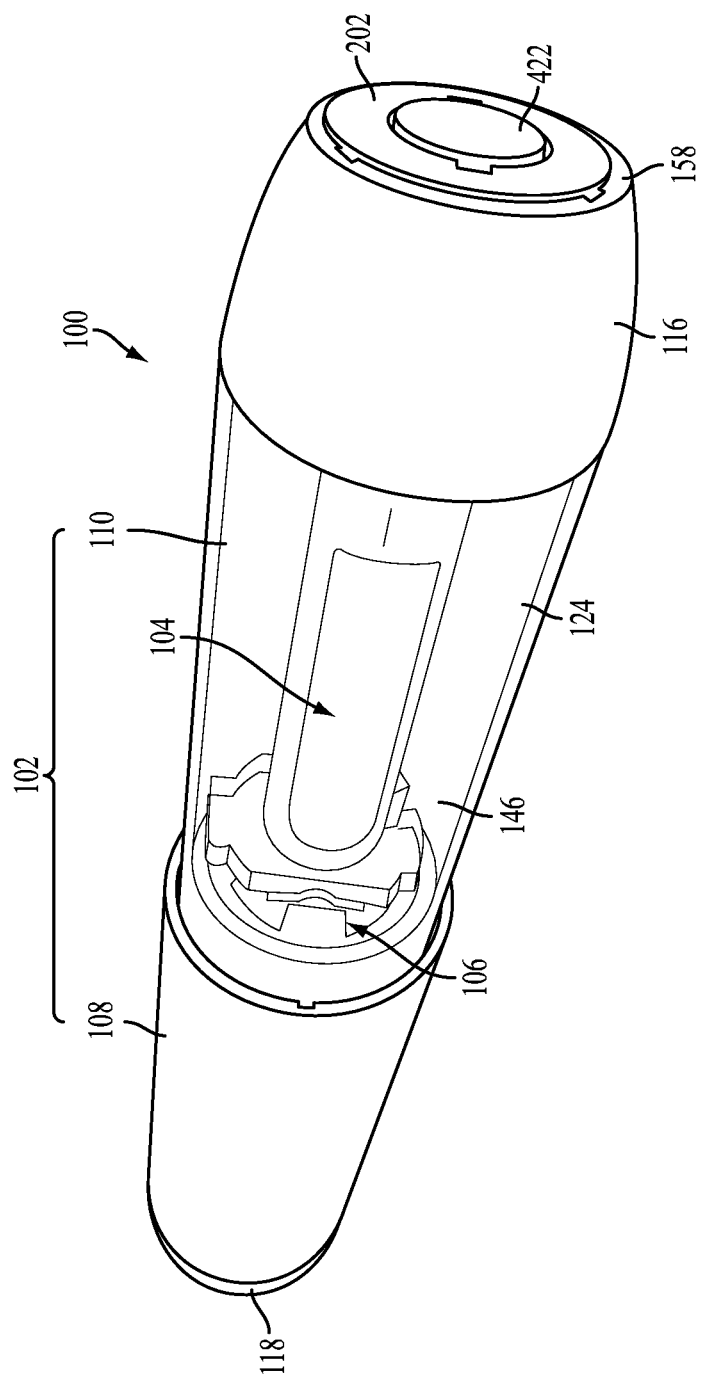
FIG. 1 depicts a perspective view of one embodiment of an injection device.

Generally, the injection devices described herein may comprise a housing, which may contain a syringe and a power assembly. In general, the housing may comprise a proximal housing and a distal housing. The proximal and distal housings may be configured to fit slidably together to form a cavity of variable size. The syringe and power assembly may be located within the cavity formed by the proximal and distal housings, and force applied to the housing may be translated into force on the syringe and/or power assembly to cause an injection to proceed. In some variations, the housing may comprise certain safety features, such as a retractable needle safety assembly, to limit accidental needlesticks, and/or indicators to indicate the progress or completion of the injection.

The syringe may reside within the housing and may comprise a syringe body defining a syringe cavity, and a seal slidably disposed within the syringe cavity defining a reservoir that may hold a formulation comprising a therapeutic or diagnostic agent, a ram comprising a plunger that may fit slidably within the syringe cavity, and a needle at the distal end of the syringe body. The needle may be configured to pierce the tissue of a patient receiving an injection, and may have a lumen therethrough to deliver the contents of the reservoir to the patient's tissue. Movement of the seal within the syringe cavity distally may cause the contents of the reservoir to be displaced through the lumen of the needle.

The power assembly may comprise a stored energy source and a rate control assembly. The stored energy source, when released, may be configured to transmit force to displace the contents of reservoir of the syringe through the lumen of the needle and into the patient. In some variations, the user's input force onto the device may work in conjunction with the stored energy source to also provide force to displace the reservoir contents. In some further variations, the stored energy source may be configured to do so by contributing to the distal motion of the plunger or seal within the syringe cavity. The rate control assembly may limit or restrict the stored energy source from contributing to the displacement of the contents of the reservoir of the syringe. In some variations, the rate control assembly may be configured to do so by limiting or restricting the distal movement of a plunger or seal within the syringe cavity. The rate control assembly may be selectively and reversibly moved between open and closed configurations; in a closed configuration, the rate control assembly may limit or restrict the stored energy source from contributing to the distal movement of the seal within the syringe cavity. Together, the stored energy source and the rate control assembly of the power assembly may allow a user (a patient or another person) to direct the injection process in an intuitive way by directing the injection by pressing the injection device against a patient's skin, but the power assembly may supply a supplemental injection force (or in some variations, the full injection force), such that the user does not need to provide the full force needed to carry out the injection.

As used throughout this specification, the term "proximal" refers to the direction away from the needle of the syringe. The term "distal" refers to the direction of the needle of the syringe.

Figure 2A:
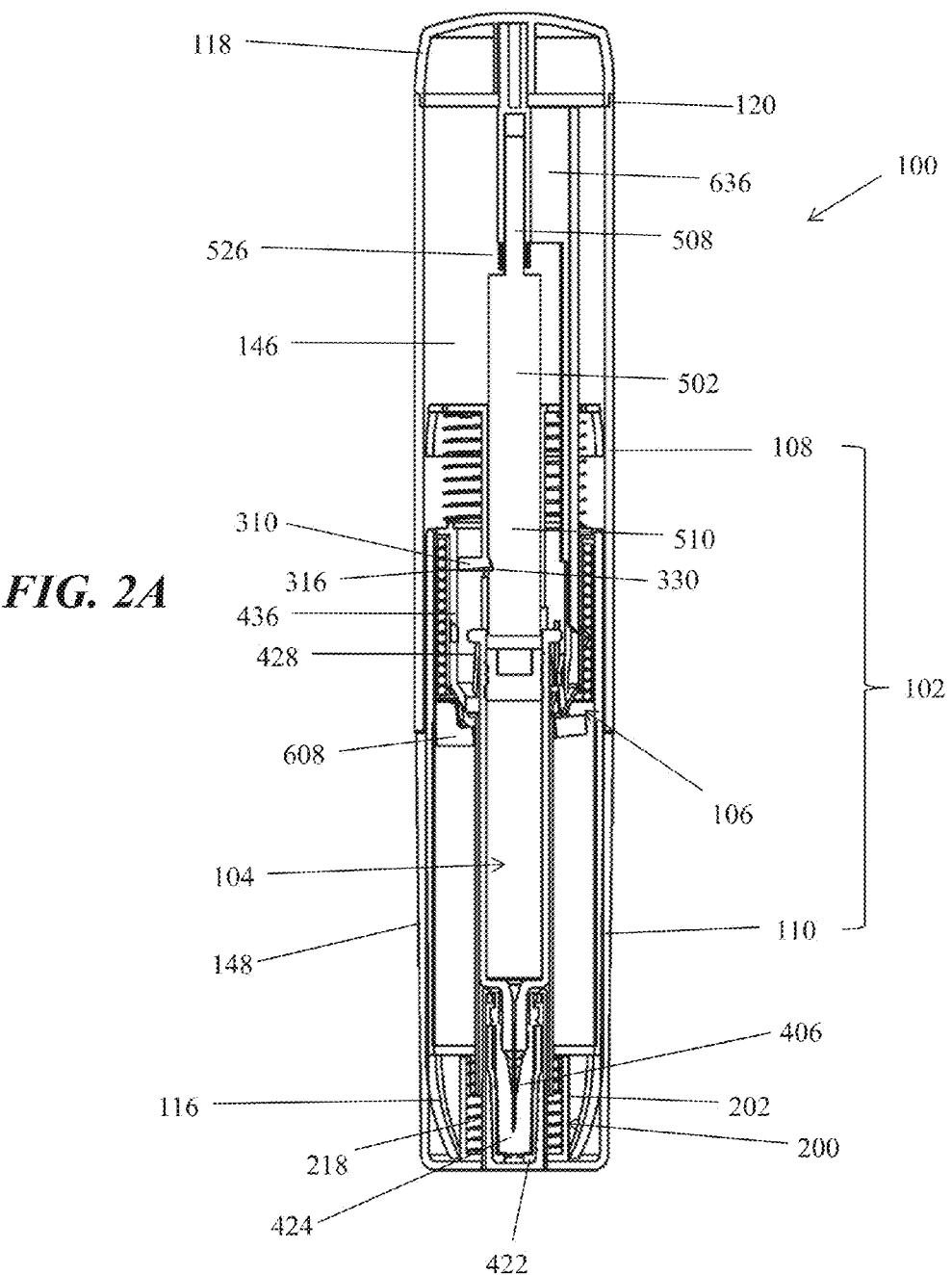
FIGS. 2A-2N are longitudinal cross-sectional views the embodiment of an injection device of FIG. 1 in various stages during use.
Figure 2B:
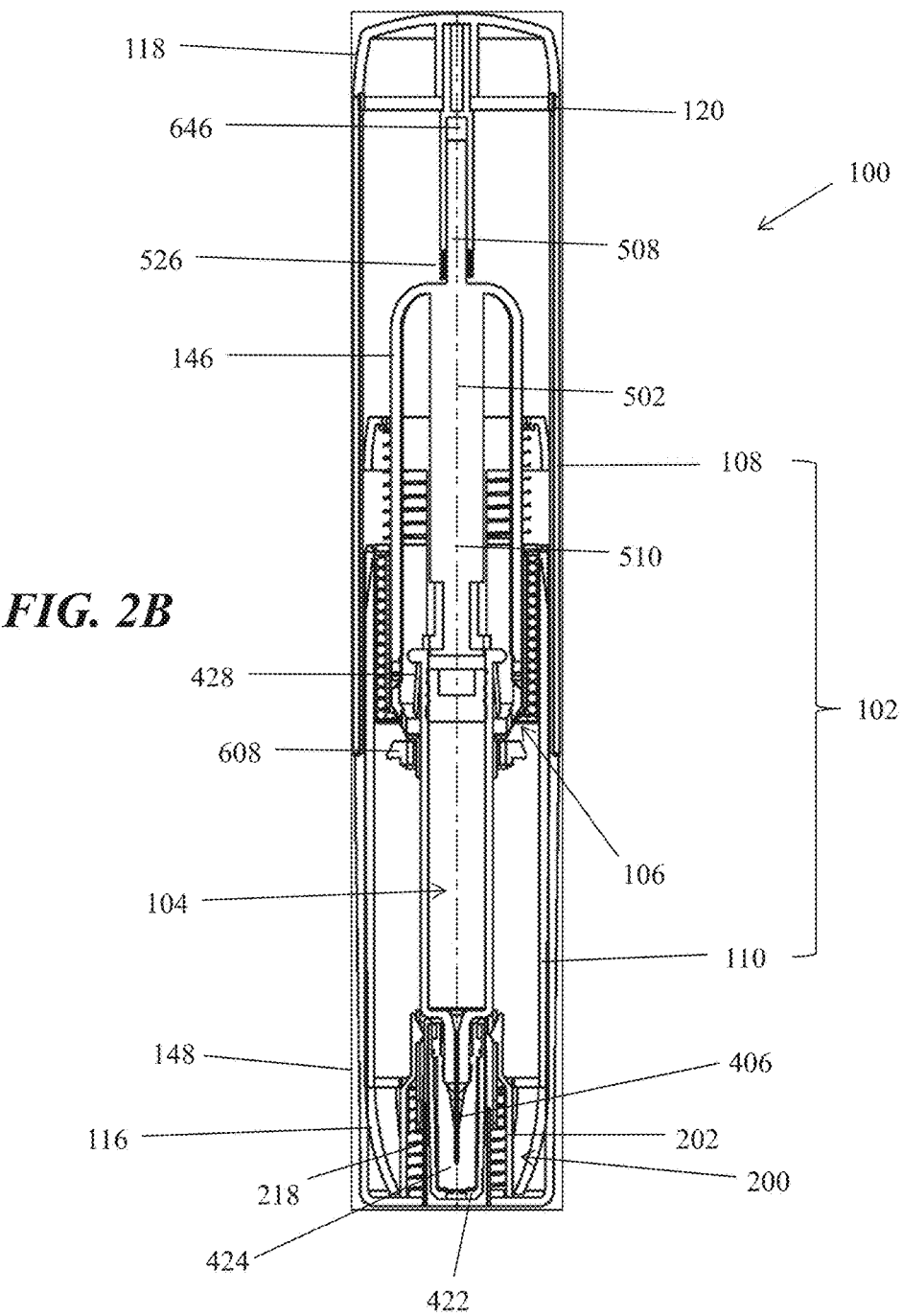
Figure 2C:
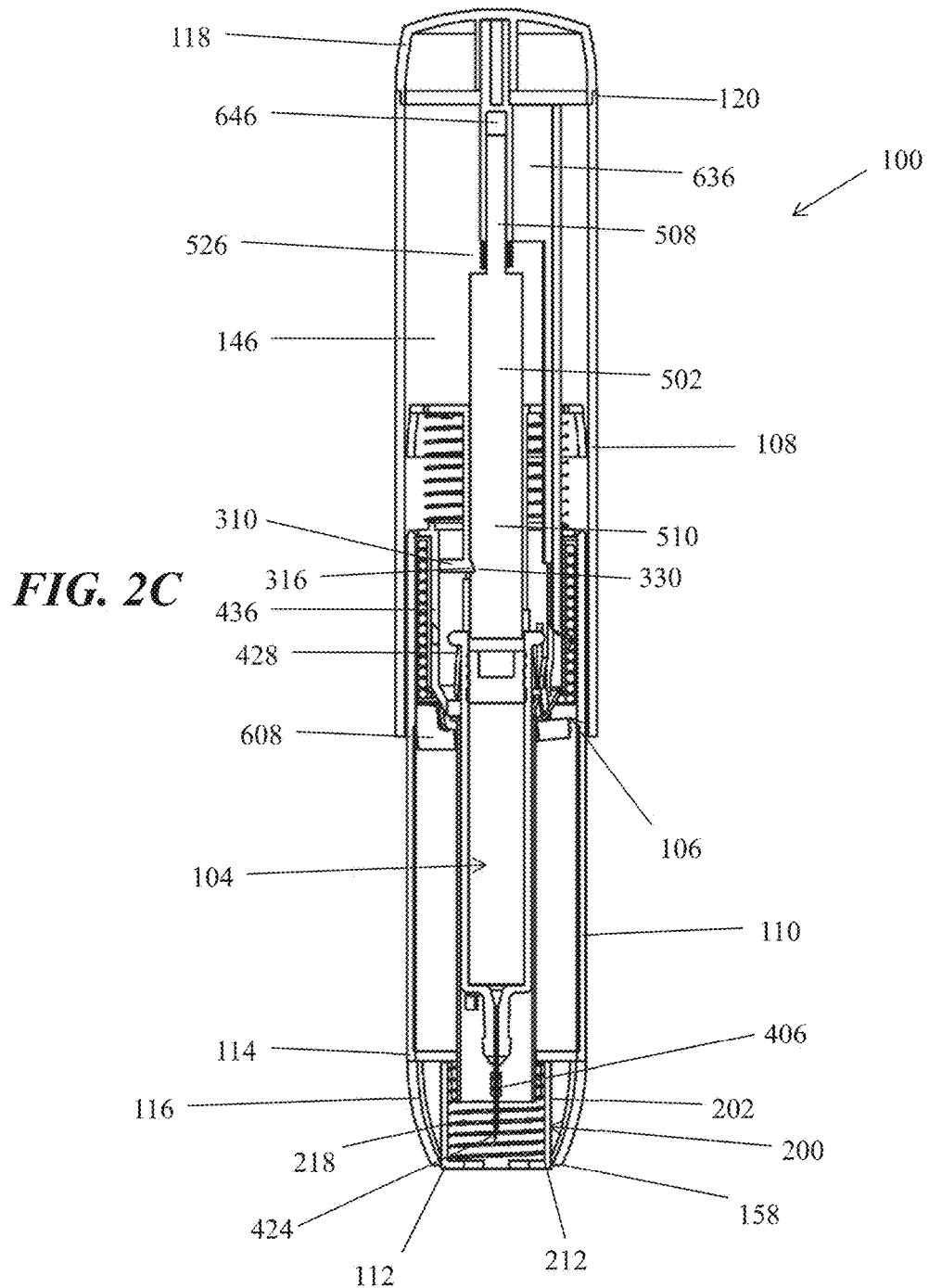
FIGS. 2C-2D show two orthogonal cross-sectional views of the device with the rigid needle shield and cap removed.
Figure 2D:
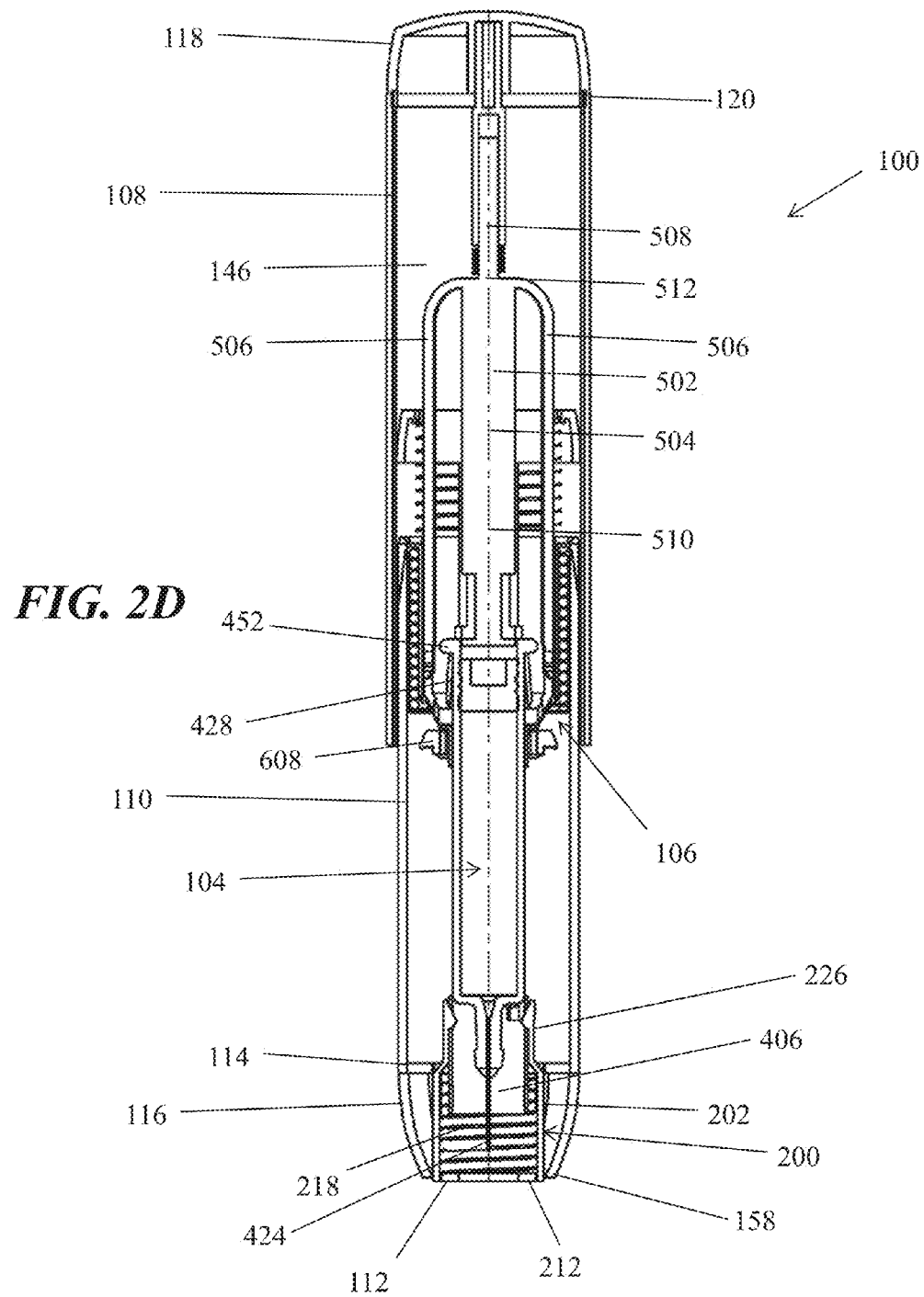
Figure 2E:
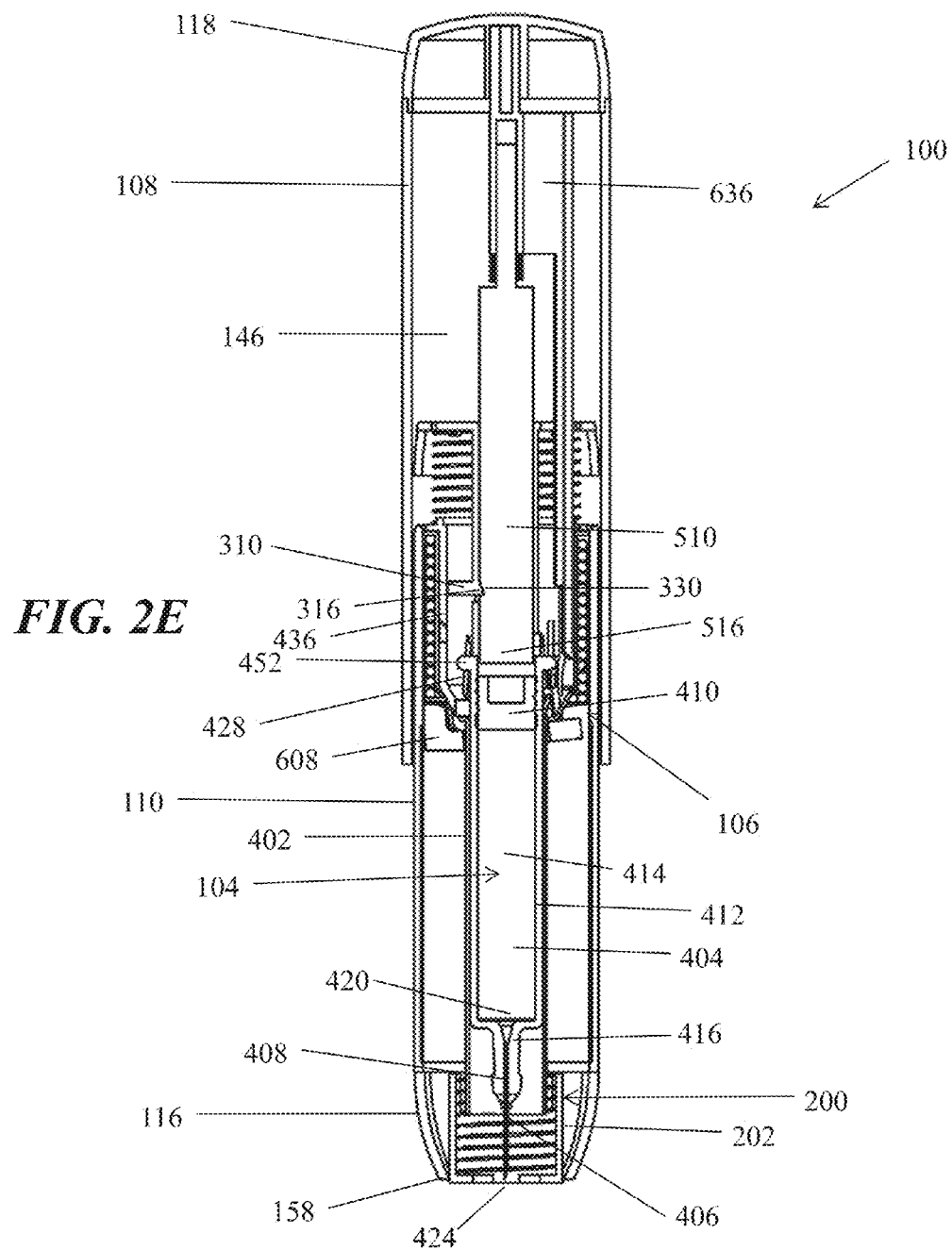
FIGS. 2E-2F show two orthogonal cross-sectional views of the device with the syringe partially moved toward an extended position.
Figure 2F:
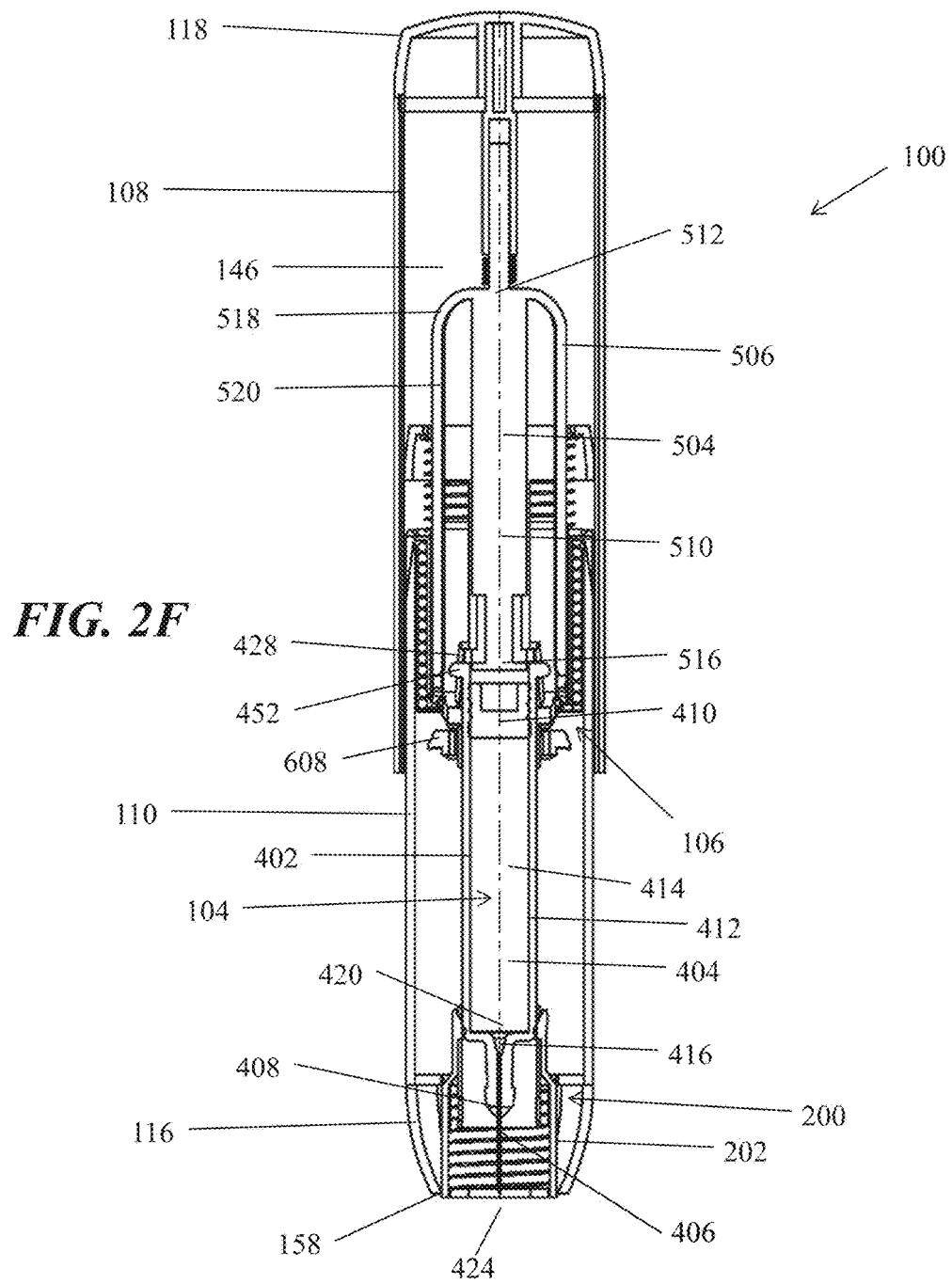
Figure 2G:
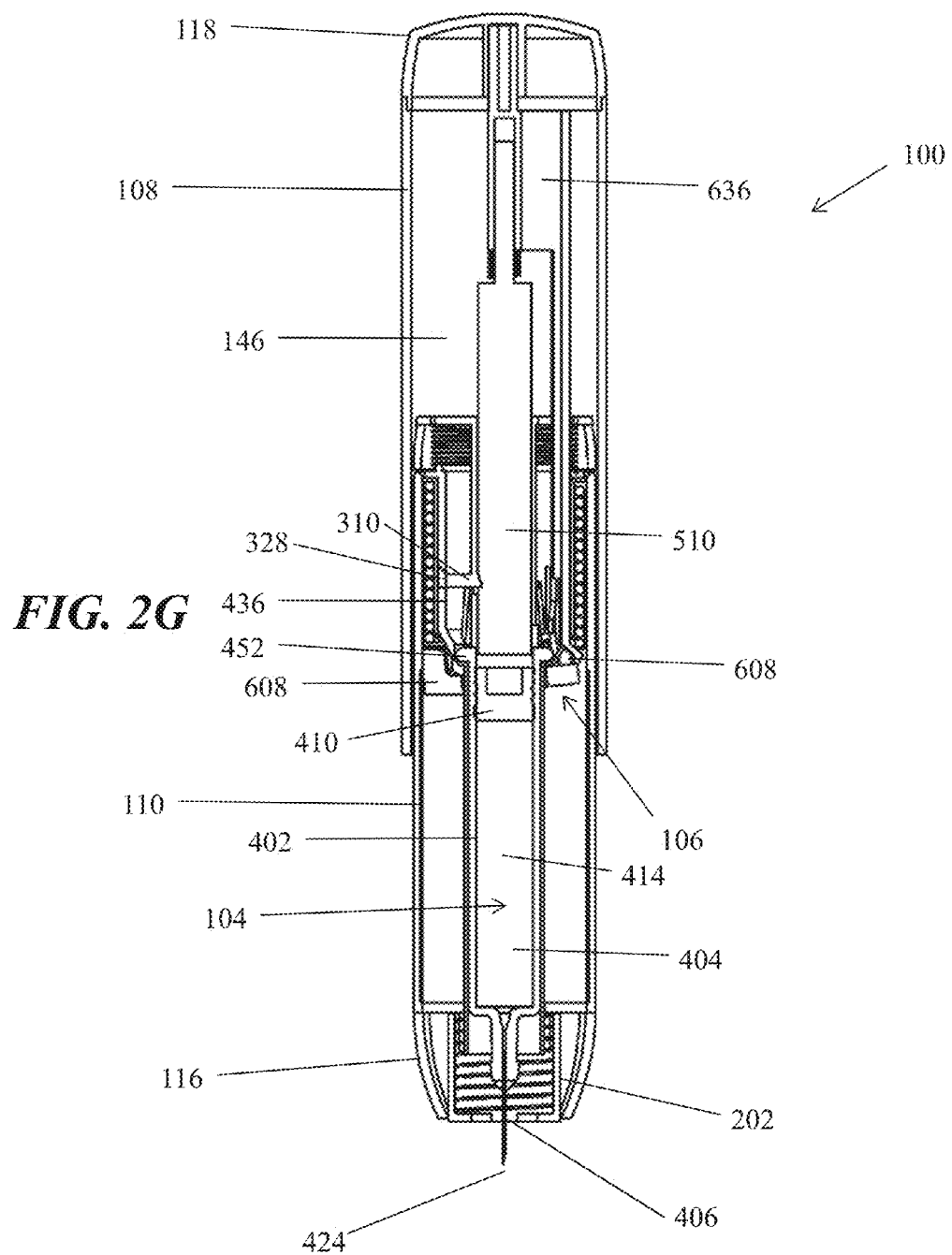
FIGS. 2G-2H show two orthogonal cross-sectional views of the device with the syringe in an extended position.
Figure 2H:
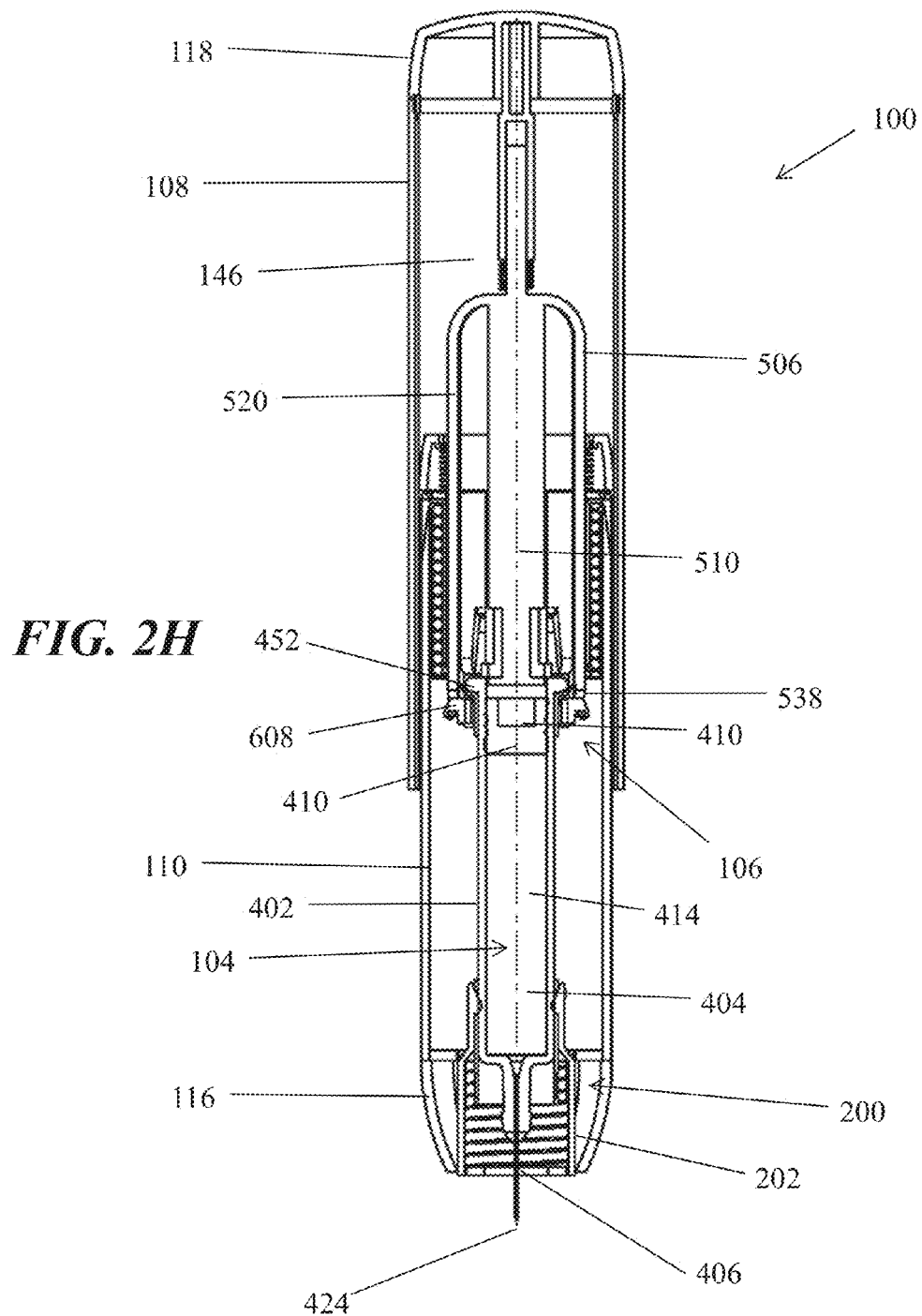
Figure 2I:
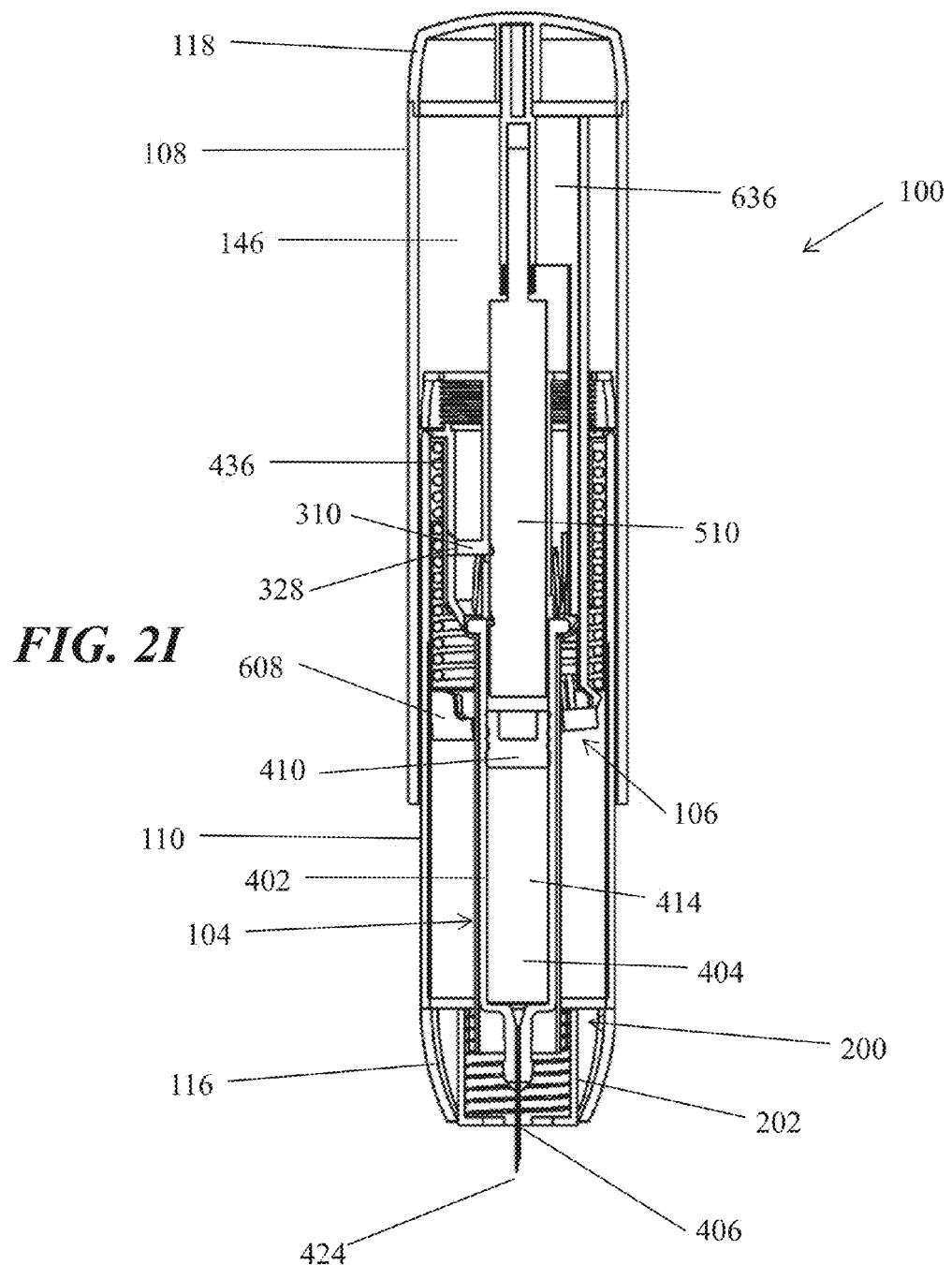
FIGS. 2I-2J show two orthogonal cross-sectional views of the device with the plunger partially moved toward a distal position within the syringe cavity.
Figure 2J:
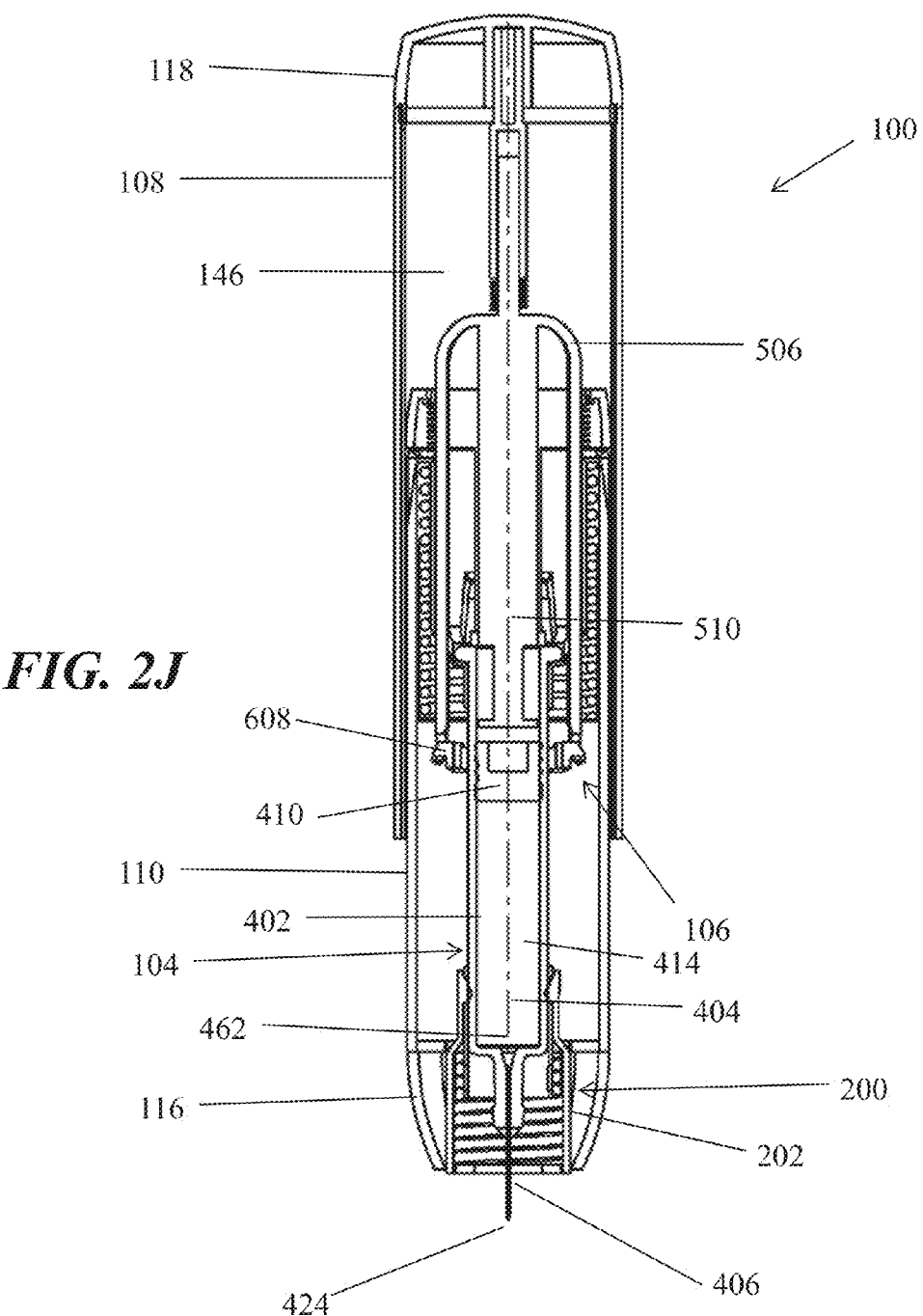
Figure 2K:
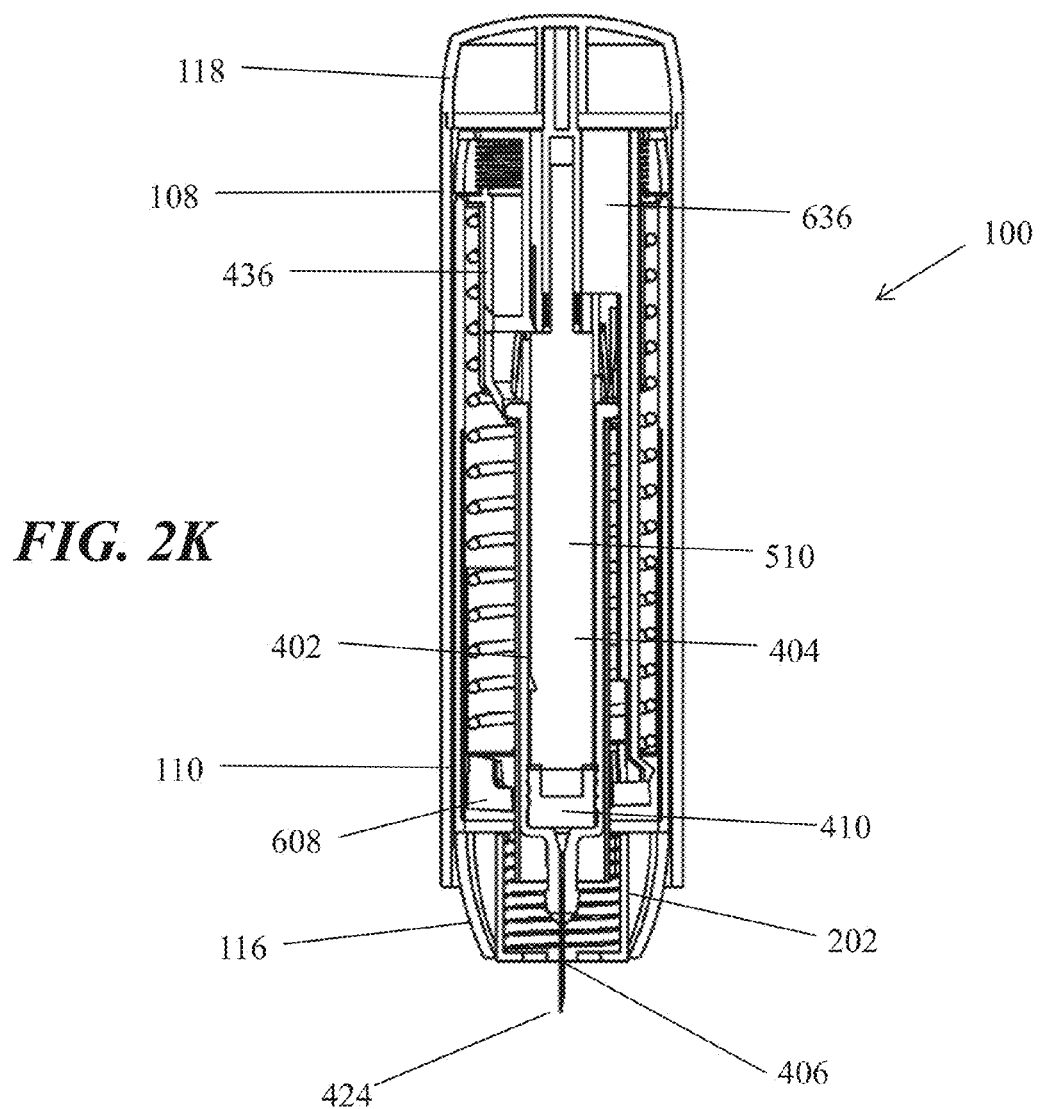
FIGS. 2K-2L two orthogonal cross-sectional views of the device with the plunger moved to the distal position within the syringe cavity.
Figure 2L:
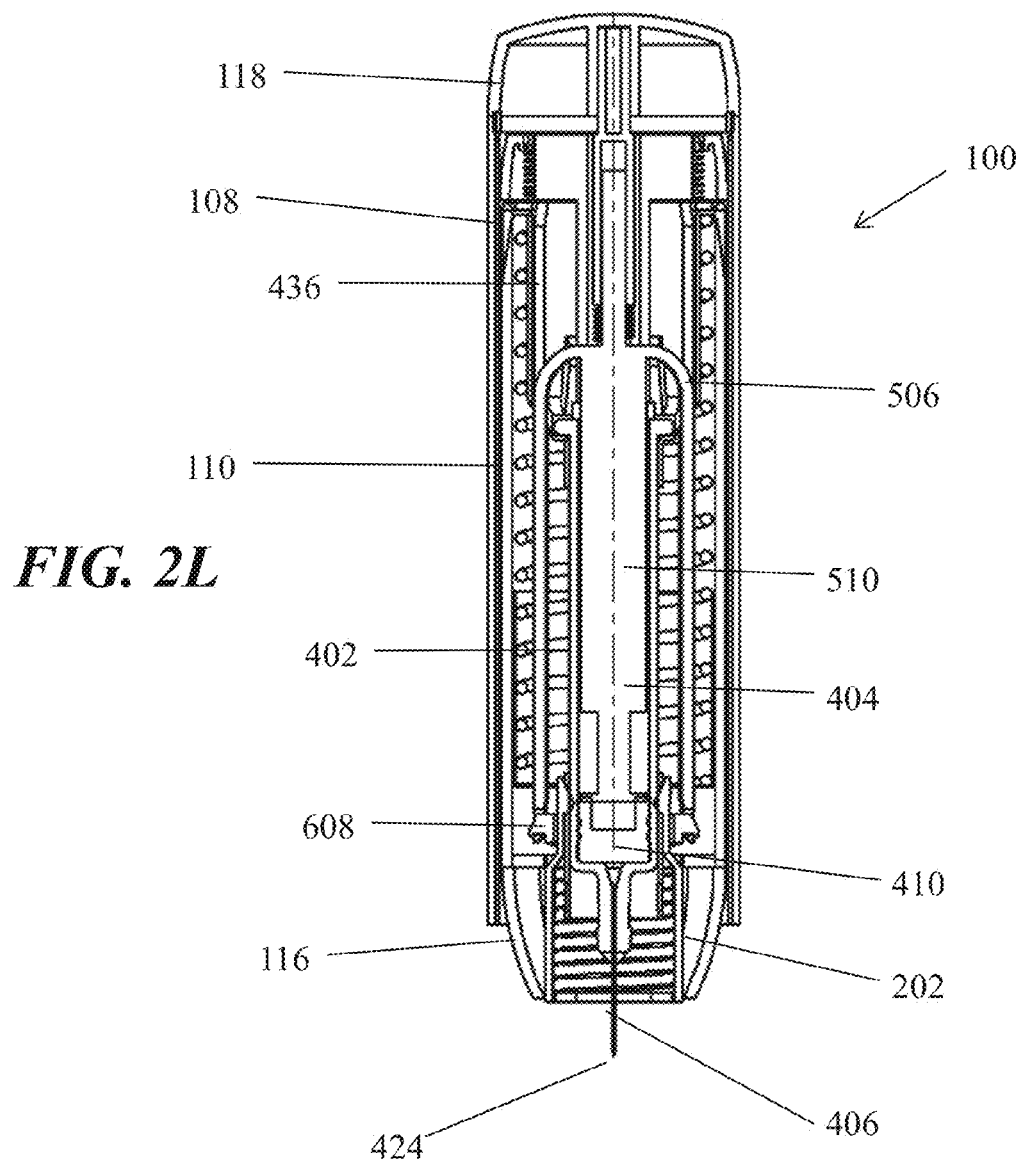
Figure 2M:
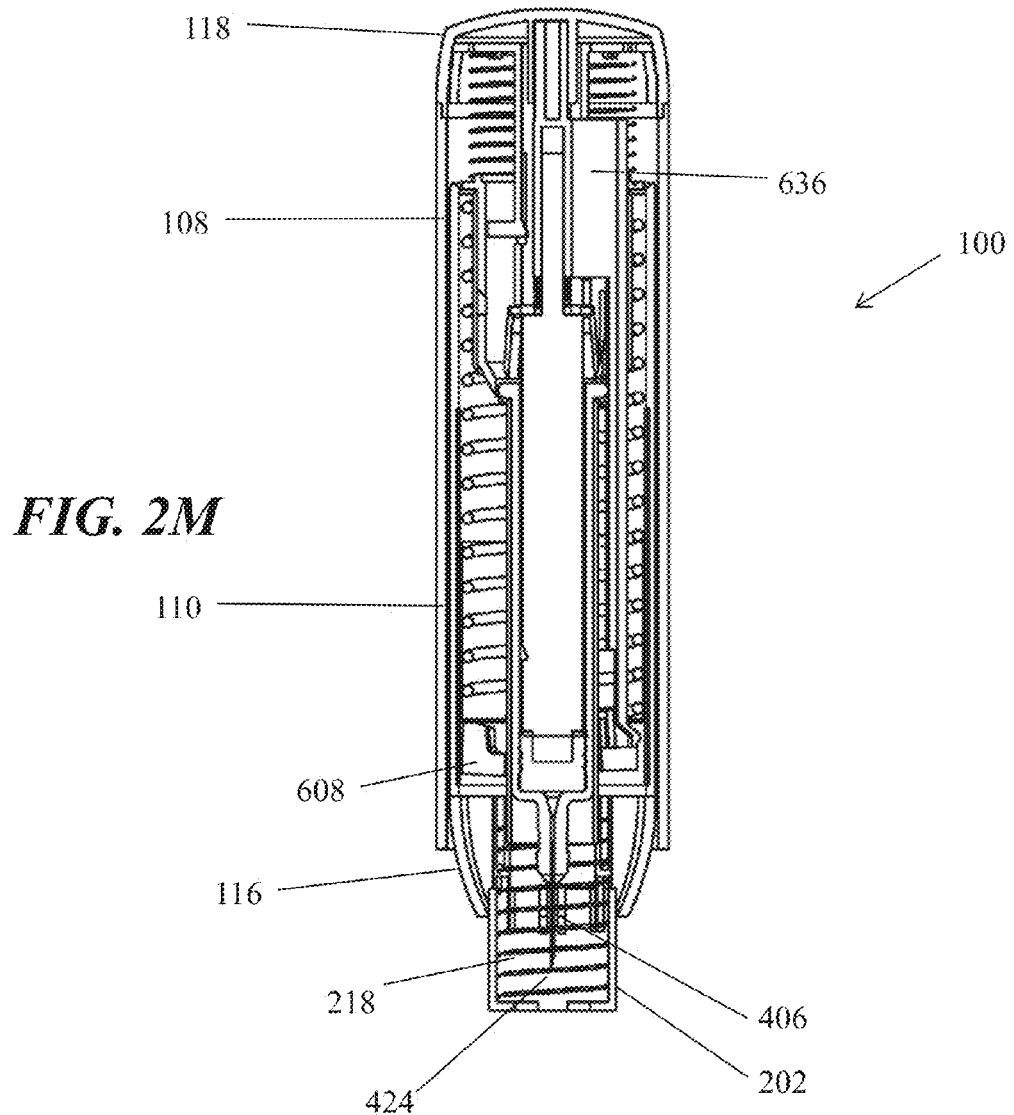
Figure 2N:
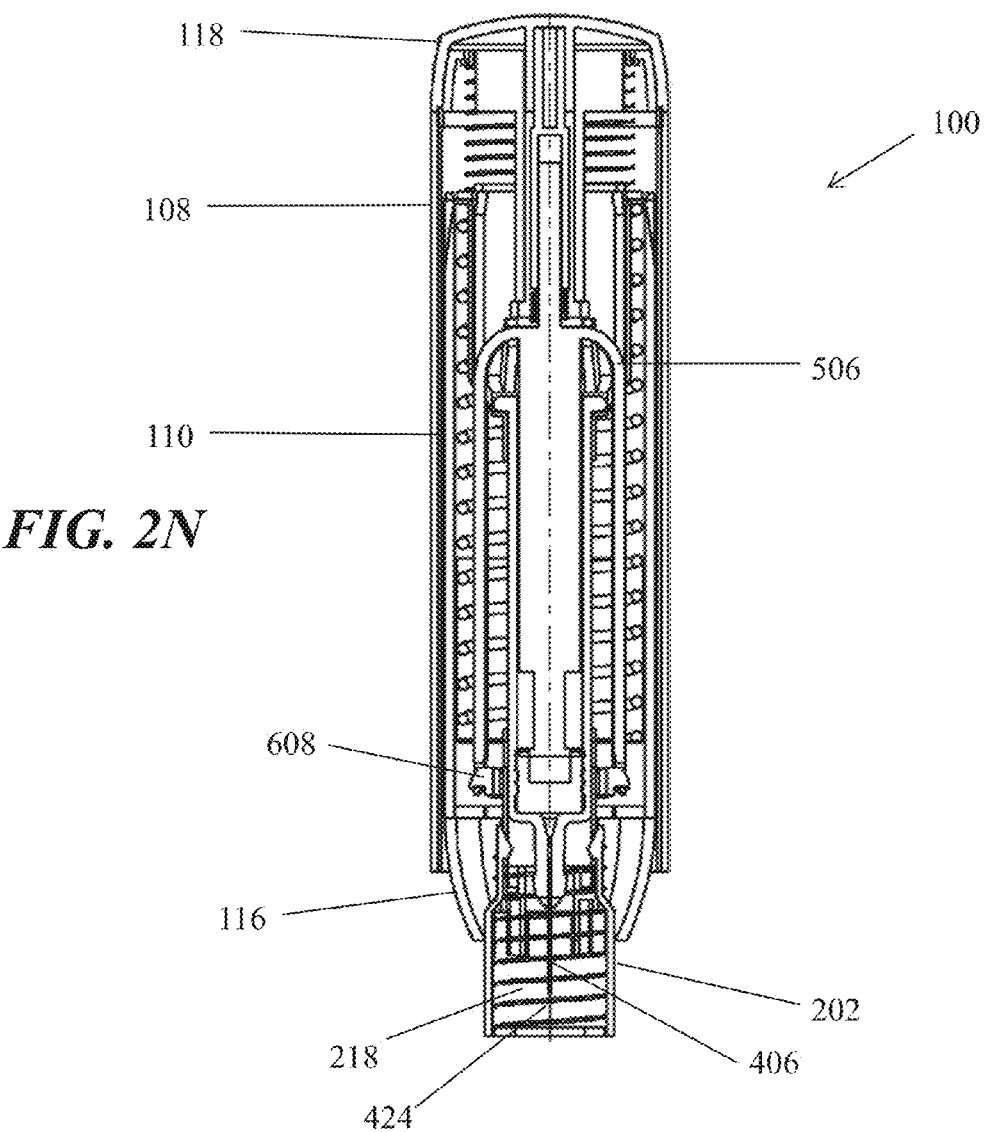

One embodiment of an injection device 100 is depicted in FIGS. 1 and 2A-2N, comprising a housing 102 which contains a syringe 104 and a power assembly 106. In some embodiments, the housing 102 may comprise a proximal housing 108 and a distal housing 110. As described above, the proximal housing 108 and distal housing 110 may be configured to fit slidably together to form a cavity 146. The syringe 104 and power assembly 106 may be located within the cavity 146. It should be appreciated that while the distal housing 110 is shown to fit slidably within the proximal housing 108 in FIGS. 1 and 2A-2N, in other variations the proximal housing may fit slidably within the distal housing. In still other variations, the housing may only comprise a proximal housing, with a syringe projecting distally from the proximal housing, or only distal housing, with a plunger or other actuator projecting distally or otherwise found on the proximal end of the distal housing. The housing 102 may be configured to be moved between an extended configuration (shown in FIGS. 1 and 2A-2D), through a range of intermediate configurations (for example, the configuration shown in FIGS. 2G-2J), and to a compressed configuration, or toward a compressed configuration (shown in FIGS. 2K-2N) by moving the proximal housing 108 distally relative to the distal housing 110. In a retracted configuration, the proximal housing 108 is pushed over the distal housing 110, or otherwise overlaps or telescopes with the distal housing 110, and achieves a shorter overall housing length. In some variations, when in an extended configuration, the length of the housing 102 may be less than about 150 mm, about 160 mm, about 170 mm, about 180 mm, about 190 mm, or about 200 mm. In other variations, the length of the housing 102 may be greater than about 200 mm. In some variations, when in an extended configuration, the length of the housing 102 may be about 150 mm to 155 mm, about 155 mm to 160 mm, about 160 mm to 165 mm, or about 165 mm to about 170 mm.

In some variations, the housing 102 may comprise one or more elements for preventing or resisting the housing 102 from being moved back toward an extended configuration once initial compression has begun. For example, the housing 102 may comprise a one-way ratchet mechanism between proximal housing 108 and distal housing 110. As another example, the distal housing 110 may comprise a groove (not shown) extending around its circumference. The groove which may have a distal face orthogonal to the surface of the distal housing 110, and a proximally angled proximal face. An elastomer loop (e.g., an O-ring) (not shown) may reside in the groove. Due to the shape of the groove, if the proximal housing 108 moves proximally relative to the distal housing 110 (i.e., the housing 102 is moved towards an extended configuration), the elastomer loop may be pulled along the proximal face, preventing further motion. As yet another example, the injection device 100 may comprise a sharp prong (not shown) fixed relative to the distal housing 110 and angled distally, which may travel along the inside of the proximal housing 108. In some variations, the sharp prong may travel along a groove on the inside of the proximal housing 108. The sharp prong may be configured to travel proximally relative to the proximal housing 108 as the proximal housing 108 moves distally, but the sharp prong may not be able to move distally relative to the proximal housing 108, and thus may resist movement of the housing 102 toward an extended configuration. In some variations, the sharp prong may be attached to or integral to the syringe sleeve 430 (described below). In some of these variations, the sharp prong may be attached to or integral to the proximal lip 454 of the syringe sleeve 430 (described below). In some variations, the proximal housing 108 and/or distal housing 110 may comprise one or more elements to resist rotation of the proximal housing 108 and distal housing 110 relative to each other, such as the clocking mechanisms described in more detail below. In other variations, the proximal housing 108 and distal housing 110 may be able to be rotated relative to each other.

Figure 25C:
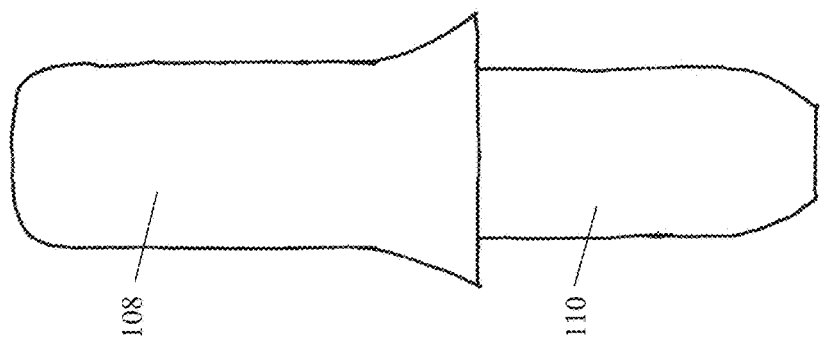
FIGS. 25A-25C show schematic representations of configurations of the proximal and distal housing of injection devices.
Figure 25B:
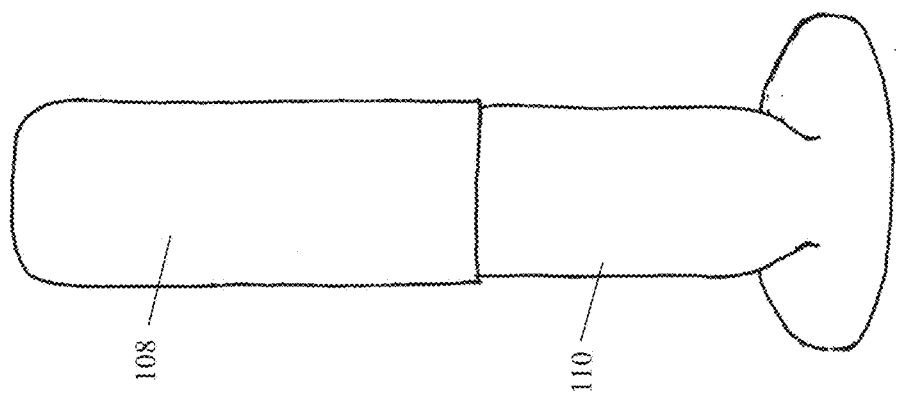
Figure 25A:
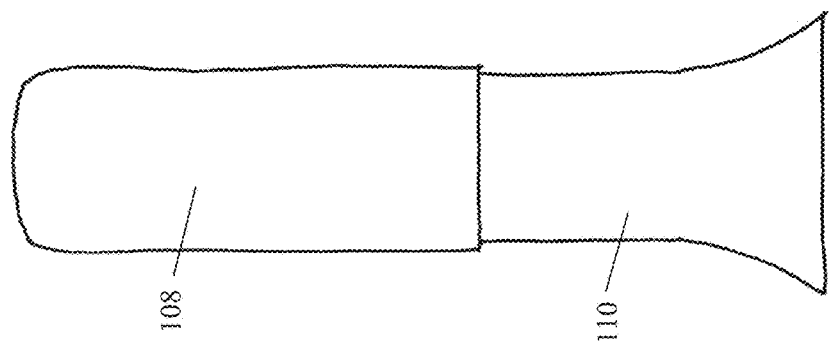

The distal housing 110 may further comprise a nose 116 at the distal end 114, which may have a tapered shape as shown in FIGS. 1 and 2A-2N, but need not. In still other variations, the nose may generally maintain the same size and/or shape as the rest of the distal housing, along its longitudinal length. Or, the nose may have a flared shape wherein the nose has a larger cross-sectional shape than the rest of the distal housing and/or proximal housing. In some variations, the flared shape may help the user maintain the injection device 100 in a perpendicular position with respect to the surface of the injection site, slippage of the injection device 100 as download pressure is being applied by the user, and/or may help allow the tissue to remain relatively flat during the injection process. In some variations, the flared shape may be a gradual outward flaring of the nose, a schematic example of which is shown in FIG. 25A; in other variations, the nose may comprise a flat portion at its distal end having a larger cross-sectional shape than the rest of the distal housing and/or proximal housing (e.g., a flat, disk, oval, ellipse, or the like), a schematic example of which is shown in FIG. 25B. These portions of the nose may be symmetric about the distal housing, or in other variations it may be asymmetric about the distal housing. Additionally or alternatively, the proximal housing may comprise a flared portion at its distal end, having a larger cross-sectional shape than the rest of the proximal housing, a schematic example of which is shown in FIG. 25C. This may assist the user grip and/or apply force to the proximal housing.

The nose 116 may comprise a distal opening 112 at its distal end 158, through which the needle 406 of the syringe 104 may be extended, as described below. In some variations, the nose 116 may be a separate component of distal housing 110, while in other variations it may be integral to distal housing 110. Similarly, the proximal housing 108 may have an end cap 118 at its proximal end 120. In some variations, the end cap 118 may be a separate component of proximal housing 108, while in other variations it may be integral to proximal housing 108. The proximal housing 108 may optionally further comprise a grip (not shown), which may be configured to enhance a user's ability to hold onto or press the proximal housing 108. In some variations, the grip may have an ergonomic shape and/or a material that may enhance a user's ability to hold onto or press the proximal housing 108, such as a rubber grip. While shown in FIGS. 1 and 2A-2N as each having a substantially cylindrical shape, the proximal housing 108 and distal housing 110 may have any suitable shape (e.g., having an elliptical cross-section, oblong cross-section, ovoid cross-section, square cross-section, rectangular cross-section, triangular cross-section, etc.). In some variations, the maximum diameter (or maximum distance transverse to the longitudinal axis) of the housing 102 may be less than about 20 mm, about 22 mm, about 24 mm, about 26 mm, about 28 mm, about 30 mm, about 32 mm, about 34 mm, about 36 mm, about 38 mm, or about 40 mm. In some variations, the maximum diameter (or maximum distance transverse to the longitudinal axis) of the housing may be about 20 mm to 25 mm, about 25 mm to 30 mm, about 30 mm to 35 mm, or about 35 mm to about 40 mm. In some embodiments, the proximal housing 108 and/or distal housing 110 may optionally comprise one or more anti-roll elements (not shown). In some variations, the anti-roll elements may comprise a planar region on the outside of proximal housing 108. In some variations, rolling of the housing 102 may be resisted by the housing 102 having a non-circular cross-sectional shape, such as an elliptical shape or other non-circular shape discussed above, or by the rigid needle shield (discussed below) having an asymmetric shape. The proximal housing 108 and distal housing 110 may comprise any suitable materials, such as but not limited to one or more plastic or metal materials.

In some variations, at least a portion of the distal housing 110 may comprise a viewing region 124 allowing the syringe 104 to be seen from outside the housing 102. In some variations, this may allow the user to visually monitor the progress or completion of the injection (e.g., in variations in which the syringe body also comprises a viewing region or is otherwise transparent or translucent (e.g. as a result of being comprise of a transparent or translucent materials, such as a glass or plastic), by visualizing the position of the plunger or seal within the syringe cavity). In other variations, both the proximal housing 108 and distal housing 110 may comprise a viewing region, only the proximal housing 108 may comprise a viewing region, or neither the proximal housing 108 nor the distal housing 110 may comprise a viewing region. The viewing region(s) (e.g., viewing region 124) may comprise a translucent or transparent material, such as but not limited to a glass or plastic. In other variations, the viewing region(s) (e.g., viewing region 124) may be an opening (e.g., an opening in the distal housing 110). In some other variations, a viewing region may be used as an opening (open or covered) to replace the syringe component of the device for re-use. In some variations, the viewing region(s) may extend around the full circumference of the proximal housing 108 and/or distal housing 110, as shown in FIG. 1. In some variations, the viewing region(s) may comprise substantially all of the distal housing 110, excluding the nose 116, as shown in FIG. 1. In other variations, the viewing region(s) may extend around a portion of the circumference of the proximal housing and/or distal housing.

In some variations, the housing 102 may optionally further comprise a cap. FIGS. 2A-2B show two orthogonal cross-sectional views of the injection device 100 before use with a cap 148 attached. The cap 148 may be configured to fit slidably over the distal housing 110 and may cover the distal opening 112 of nose 116. The cap 148 may be removed by applying force to separate the cap 148 and the remainder of the housing 102. In some variations, this can be done by holding the proximal housing 108 with one hand and the cap 148 with another hand and pulling in opposite directions. In some variations, the cap 148 may further serve to remove the rigid needle shield 422. The cap 148 may be connected to the rigid needle shield 422 in any suitable manner, such that removing the cap may also remove the rigid needle shield 422. For example, the cap 148 may comprise an inside proximal protrusion that may fit around the outside of the rigid needle shield 422. The proximal protrusion may be substantially cylindrical, but may have other shapes. The proximal protrusion may comprise an inwardly facing lip or lips that may fit into a recess or hook (or recesses or hooks) on the outside of the rigid needle shield 422. When the cap 148 is separated from the remainder of the housing 102, the rigid needle shield 422 may also be separated from the syringe 104 due to force on the rigid needle shield 422 from the inwardly facing lip. In some variations, the proximal protrusion may be flexible (e.g., due to a cut-out) to allow the cap to be installed over the distal housing 110 and rigid needle shield 422. In some variations, the cap may comprise a viewing region, which may coincide with the viewing region of the distal housing, when the cap is attached to the remainder of the housing.

FIGS. 2A-2N depict longitudinal cross-sectional views of the injection device 100 of FIG. 1 in various stages during use. FIGS. 2A-2B show two orthogonal cross-sectional views of the device before use. FIGS. 2C-2D show two orthogonal cross-sectional views of the device with the rigid needle shield and cap removed. FIGS. 2E-2F show two orthogonal cross-sectional views of the device with the syringe partially moved toward an extended position. FIGS. 2G-2H show two orthogonal cross-sectional views of the device with the syringe in an extended position. FIGS. 2I-2J show two orthogonal cross-sectional views of the device with the plunger partially moved toward a distal position within the syringe cavity. FIGS. 2K-2L two orthogonal cross-sectional views of the device with the plunger moved to the distal position within the syringe cavity. FIGS. 2M-2N show two orthogonal cross-sectional views of the device with the needle shroud extended. The nose 116 may comprise a needle safety assembly 200. In some variations, the needle safety assembly 200 may comprise an extendable needle shroud 202 that protects the needle 406 after the injection is completed or terminated, a biasing element 218, and a locking assembly 226. The needle safety assembly 200 may be movable between a retracted position (shown in FIGS. 1, 2A-2L, and 3A-3D) and an extended position (shown in FIGS. 2M-2N and 3E-3F). In the retracted position, the needle shroud 202 may allow the needle 406 of the syringe 104 to be exposed when the syringe 104 is in an extended position, as described in detail below. Thus, in the retracted position, the distal end 212 of the needle shroud 202 may be located proximally to the distal tip 424 of the needle 406 when the syringe 104 is in an extended position. In an extended position, the needle shroud 202 may shield the needle 406 from exposure when the syringe 104 is in an extended position; for example, the needle shroud 202 may resist insertion of the needle 406 in a patient's tissue or resist contact between the needle 406 and tissue. Thus, in an extended position, the distal end 212 of the needle shroud 202 may be located distally to the distal tip 424 of the needle 406 when the syringe 104 is in an extended position. In some variations, the displacement of the needle shroud 202 between retracted and extended positions may be about 6 mm to 8 mm, about 8 mm to 10 mm, about 10 mm to 12 mm, about 12 mm to 14 mm, or about 14 mm to 16 mm.

As shown in FIGS. 3A-3D, the needle shroud 202 may fit slidably within the nose 116. In the variations shown in FIGS. 3A-3F, when the needle safety assembly 200 is in a retracted position, the distal end 212 of the needle shroud 202 may be flush with the distal end 158 of the nose 116, while in an extended position, the distal end 212 of the needle shroud 202 may be distal to the distal end 158 of the nose 116. It should be appreciated that in other variations, in a retracted position, the distal end 212 of the needle shroud 202 may be proximal to the distal end 158 of the nose 116, or in other variations, it may be distal to the distal end 158 of the nose 116 in a retracted position.

The needle shroud 202 may have a proximal opening 204 and a distal opening 206, with a lumen 208 extending between the proximal opening 204 and distal opening 206. The needle shroud 202 may have a longitudinal axis 210 aligned with the longitudinal axis 144 of the housing 102. While the needle shroud 202 is shown as having a cylindrical shape in FIGS. 3A-3F, it should be appreciated that the needle shroud may have other shapes (e.g. an elliptical cross-section, oblong cross-section, ovoid cross-section, square cross-section, rectangular cross-section, triangular cross-section, or the like). In some variations, the needle shroud 202 may optionally comprise a stop (not shown) to resist the needle shroud 202 being disconnected from the nose 116 (e.g., to resist the needle shroud 202 sliding distally away from and disengaging with the nose 116). Additionally or alternatively, the needle shroud 202 may comprise a distal lip 216 to hold the biasing element 218, described below. In some variations, the needle shroud 202 may comprise a plastic material, but it should be appreciated that the needle shroud 202 may comprise any suitable material. The needle shroud 202 may be optically opaque, translucent, or transparent. The needle shroud may also optionally comprise apertures or cutouts to permit partial visualization of the needle during or after the injection procedure.

The biasing element 218 may be configured to bias the needle safety assembly 200 toward an extended position. The biasing element 218 may have a compressed configuration and an expanded configuration. The biasing element 218 may be in a compressed configuration when the needle safety assembly 200 is in a retracted configuration, and the biasing element 218 may be in an expanded configuration when the needle safety assembly 200 is in an extended position. In some variations, the biasing element 218 may comprise a compression spring 220. When the compression spring 220 is in a compressed configuration, the compression spring 220 at its proximal end 222 may be connected to or in contact with a portion of the distal housing 110 or nose 116, and at its distal end 224 may be connected to or in contact with a portion of the needle shroud 202. The biasing element 218 (e.g., compression spring 220) may thus bias the needle shroud 202 distally away from the distal housing 110 and nose 116 through the distal opening 112 of the nose 116. In the variation shown in FIGS. 3A-3F, the compression spring 220 may have a cylindrical shape and may fit within the lumen 208 of the needle shroud 202. The proximal end 222 of the compression spring 220 may contact a ledge 156 extending radially inward from the distal end 114 of the distal housing 110, and the distal end 224 of the compression spring 220 may contact the lip 216 extending radially inward from the needle shroud 202. While the lip 216 is shown as located at the distal end 212 of needle shroud 202 in FIGS. 3A-3F, it should be appreciated that in other variations a lip may extend from a location proximal to the distal end 212 of the needle shroud 202. In some variations, the proximal end 222 of the compression spring 220 may be fixedly attached to the distal end 114 of distal housing 110, but it need not be (e.g., it may rest against the distal end 114 of the distal housing 110 but be unattached). Similarly, in some variations, the distal end 224 of the compression spring 220 may be fixedly attached to the needle shroud 202, but it need not be (e.g., it may rest against a portion of the needle shroud 202 but be unattached). It should be appreciated that in other variations the biasing element 218 may not comprise a compression spring 220 and may instead comprise other forms of biasing elements (e.g., an extension spring, torsion spring, or the like) configured so as to bias the needle shroud 202 distally away from the distal housing 110. In some variations, the biasing element 218 may provide about 1 N, about 2 N, about 3 N, about 4 N, about 5 N, about 6 N, about 7 N, or about 8 N of biasing force.

Figures 3A, 3B:
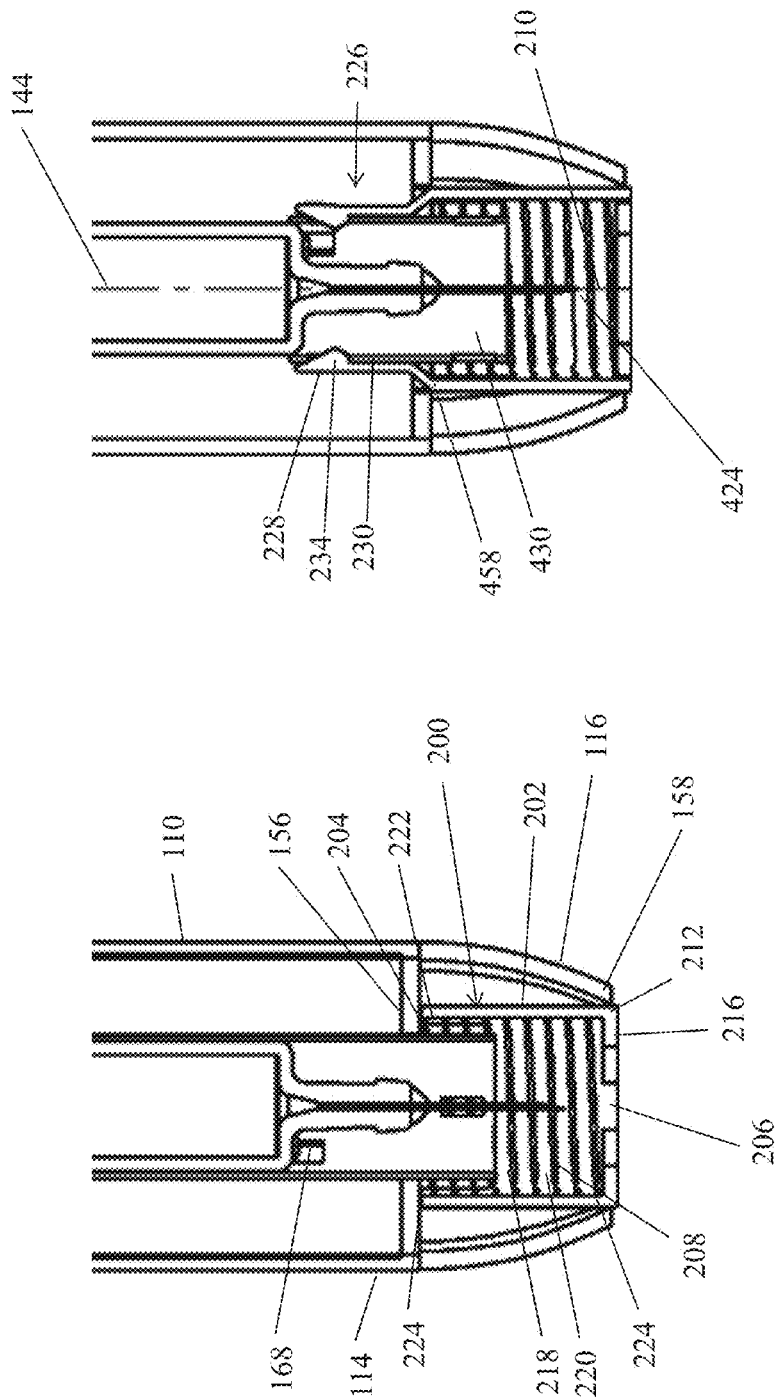

The locking assembly 226 may hold the needle shroud 202 in a retracted position and/or in an extended position. In some variations, the locking assembly 226 may comprise one or more latches 228 that may be configured to connect the needle shroud 202 to the syringe 104. While in the embodiment of FIGS. 3A-3F, the locking assembly 226 may comprise four latches 228 evenly spaced around the needle shroud 202, it should be appreciated that in other variations, the locking assembly 226 may comprise fewer or more latches and may have different positioning (e.g., one, two, three, five, or six latches, etc., which may or may not be evenly spaced from each other). In some variations, the latches 228 may be integral to the needle shroud 202. The latches 228 may each comprise an elongate portion 230 extending proximally from the needle shroud 202, and a tab 234 extending from the elongate portion 230. In some variations, the elongate portions 230 may have different lengths. The elongate portion 230 may extend proximally from the proximal opening 204 of the needle shroud 202, and the tab 234 may extend inwardly from the proximal end of the elongate portion 230. As shown in FIGS. 3A-3B, the latches 228 may be configured to mate with the syringe sleeve 430 (described below), such that when mated, the latches 228 resist motion of the needle shroud 202 relative to the distal housing 110. The syringe sleeve 430 may comprise four proximal slots 168, which may be located on the syringe sleeve 430 such that when the tabs 234 of the latches 228 are mated with the proximal slots 168, the needle shroud 202 may be located in a retracted position. When the tabs 234 are mated with the proximal slots 168, the elongate portion 230 of the latches 228 may be flush against the outer surface 458 of the syringe sleeve 430, while the tabs 234 of the latches 228 may be inserted radially into the proximal slots 168. The locking assembly 226 may resist distal motion due to a biasing force from the biasing element 218 because of the proximally oriented force applied to the distal surface of the tabs 234 by the distal surface of the proximal slots 168.

As shown in FIGS. 3C-3D, the locking assembly 226 may be configured such that the needle shroud 202 may be unlocked from a retracted position (e.g., the locking assembly 226 may no longer hold the needle shroud 202 in a retracted position) by distal motion of the syringe 104. In some variations, the tabs 234 may be configured such that they can be released from the proximal slots 168 by distal movement of the syringe 104 relative to the syringe sleeve 430. For example, in the variation shown in FIGS. 3A-3F, the tabs 234 may have a triangular, proximally tapering shape. Thus, as the syringe 104 is moved distally within the syringe sleeve 430, the distal end 418 of the outer surface 468 of the syringe body 402 may engage the inner surface 236 of the tabs 234 protruding through the proximal slots 168. As the outer surface 468 of the syringe body 402 continues to slide distally along the inner surface 460 of the syringe sleeve 430 (described below), the outer surface 468 of the syringe body 402 gradually pushes the tabs 234 further radially out of the proximal slots 168. Once the outer surface 468 of the syringe body 402 has fully pushed the tabs 234 radially out of the proximal slots 168, the tabs 234 may no longer be mated with the proximal slots 168 and may no longer resist distal motion of the needle shroud 202 relative to the distal housing 110. It should be appreciated that while the latches in the embodiment of FIGS. 3A-3F are connected (or integral) to the needle shroud 202 and fit into slots in the syringe sleeve 430, in other variations, the latches may be connected (or integral) to the syringe sleeve and may fit into slots in the needle shroud. For example, the inner surface of the syringe sleeve may comprise inwardly facing tabs, which may extend inwardly through slots in the needle shroud, such that they may protrude radially within the inner surface of the syringe sleeve. As in the embodiment in FIGS. 3A-3F, distal movement of the syringe may cause the outer surface of the syringe body to push the tabs radially outward through the slots to an extent sufficient to cause the tabs to no longer resist distal motion of the needle shroud relative to the distal housing.

When the needle shroud 202 is unlocked from a retracted position, if a force is then applied that is configured to urge the needle shroud 202 from a retracted position to an extended position (e.g., a biasing force from the biasing element 218), the needle shroud 202 may move from a retracted position to an extended position. However, the force configured to urge the needle shroud 202 from a retracted position to an extended position may be counterbalanced or partially or completely opposed by a proximally directed force on the needle shroud 202. For example, in the variation shown in FIGS. 3A-3F, the distal end 212 of the needle shroud 202 is configured to be pressed against a patient's tissue during an injection. Thus, the tissue may apply a force to the distal end 212 of the needle shroud 202, partially or fully counteracting the biasing force from the biasing element 218 (e.g., compression spring 220) while the injection device 100 is pressed against the tissue. This may resist the needle shroud 202 moving from a retracted position to an extended position, even when the needle shroud 202 is unlocked from a retracted position. However, if the injection device 100 is then moved away from the tissue, there may no longer be a force from the tissue to counteract the biasing force from the biasing element 218, and as a result, the needle shroud 202 may move from a retracted position to an extended position, as shown in FIGS. 3E-3F.

In some variations, such as the variation of FIGS. 3A-3F, the locking assembly 226 may be configured such that the needle shroud 202 may be unlocked from a retracted position just before the distal tip 424 of the needle 406 of the syringe 104 extends from the distal end 158 of the nose 116, as shown in FIGS. 3C-3D. Thus, at any time the needle 406 is exposed such that it is capable of piercing or otherwise contacting a patient's tissue, the needle shroud 202 is unlocked from a retracted position. The exposure of the needle 406 for injection may therefore only be maintained by maintaining a proximal force on the distal end 212 of the needle shroud 202 to hold it in a retracted position (e.g. by pressing the distal end 212 of the needle shroud 202 against a patient's tissue); once the proximal force is removed (e.g., by moving the injection device 100 away from a patient's tissue), the needle shroud 202 may move into an extended position, which may resist piercing of a patient's tissue by the needle 406 or resist contact between the needle 406 and a patient's tissue.

In some variations, the needle shroud 202 of the needle safety assembly 200 may additionally or alternatively be configured to be locked in an extended position once moved to an extended position. That is, the needle shroud 202 may be configured such that once it enters an extended position, it may be unable to return to a retracted position. In some variations wherein the locking assembly comprises one or more latches, the same latches may be used to lock the needle shroud 202 in an extended position. In some of these variations, as shown in FIGS. 3E-3F, the syringe sleeve 430 may comprise four distal slots 176 configured to mate with the tabs 234 of the latches 228 of the locking assembly 226. The distal slots 176 may be located on the syringe sleeve 430 to coincide with the position of the tabs 234 when the needle shroud 202 is in an extended position. When the needle shroud 202 moves into an extended position, the tabs 234 on the latches 228 may mate with the distal slots 176. When the tabs 234 on the latches 228 are mated with the distal slots 176, the locking assembly 226 may resist motion of the needle shroud 202 relative to the syringe sleeve 430, and in turn, may cause the locking assembly 226 to resist motion of the needle shroud 202 relative to the distal housing 110. Once locked in an extended position, the needle shroud 202 may, for example, resist proximal force on the distal end 212 of the needle shroud 202 (e.g., from tissue pressed against the distal end 212 of the needle shroud 202) tending to urge the needle shroud 202 proximally toward a retracted position, and/or the needle shroud 202 may resist distal force applied to it (e.g., from the biasing element 218) tending to urge the needle shroud 202 further away from the distal housing 110. In variations of the injection device configured to lock in an extended position, this feature may limit the ability of a needle to extend from the distal end of the nose to pierce or otherwise contact tissue or other surfaces after the injection device has been removed from a patient's tissue. This may make the injection device safer for the user and/or patient by limiting accidental needlesticks after injection has been fully or partially completed. However, it should be appreciated that in other variations, the needle shroud may not be configured to lock when in an extended position (e.g., in some variations, the needle shroud 202 may retract from an extended position in response to distal force).

In some variations, the needle safety assembly 200 may provide feedback to the user. In some variations, this feedback may include a biohazard indicator, such as a biohazard symbol located on the outside surface of the needle shroud 202, which may be visible when the needle shroud 202 is in an extended position. Additionally or alternatively, all or a portion of the needle shroud 202 may be colored (e.g. red, yellow, orange, green, magenta, blue, or the like) in order to indicate or signal to the user that the injection device 100 has been used.

The housing 102 may comprise an indicator to indicate the progress or completion of the injection. In one variation, the indicator may have a range of configurations corresponding to various levels of progress of the injection. In some such variations, the configurations may have different visual, tactile, or auditory perceptions, such as but not limited to color, numerical, or ordinal cues or indicia, or the position of the proximal housing 108 relative to the distal housing 110. In the same or other variations, the transition between the inactivated configuration and the activated configuration, and/or the transition between the configurations, may produce visual, tactile, or auditory alerts, such as but not limited to color, numerical, or ordinal cues or indicia, or the position of the proximal housing 108 relative to the distal housing 110.

In some variations, the indictor may alert the user that the full dose has been displaced from the reservoir 414 of the syringe 104 and/or that the seal 410 has traveled the full length of the reservoir 414 to the distal end 462 of the syringe cavity 404 (described below). Additionally or alternatively, the end-of-dose indicator may alert the user that nearly (e.g., greater or equal to about 85%, greater or equal to about 90%, greater or equal to about 95%, or more) the full dose has been displaced from the reservoir 414 of the syringe 104 and/or that the seal 410 has traveled nearly (e.g., greater or equal to about 85%, greater or equal to about 90%, greater or equal to about 95%, or more, or within about 1 mm of full displacement, about 2 mm of full displacement, about 3 mm of full displacement, or about 4 mm of full displacement, etc.) the full length of the reservoir 414 to the distal end 462 of the syringe cavity 404.

Figure 4A:
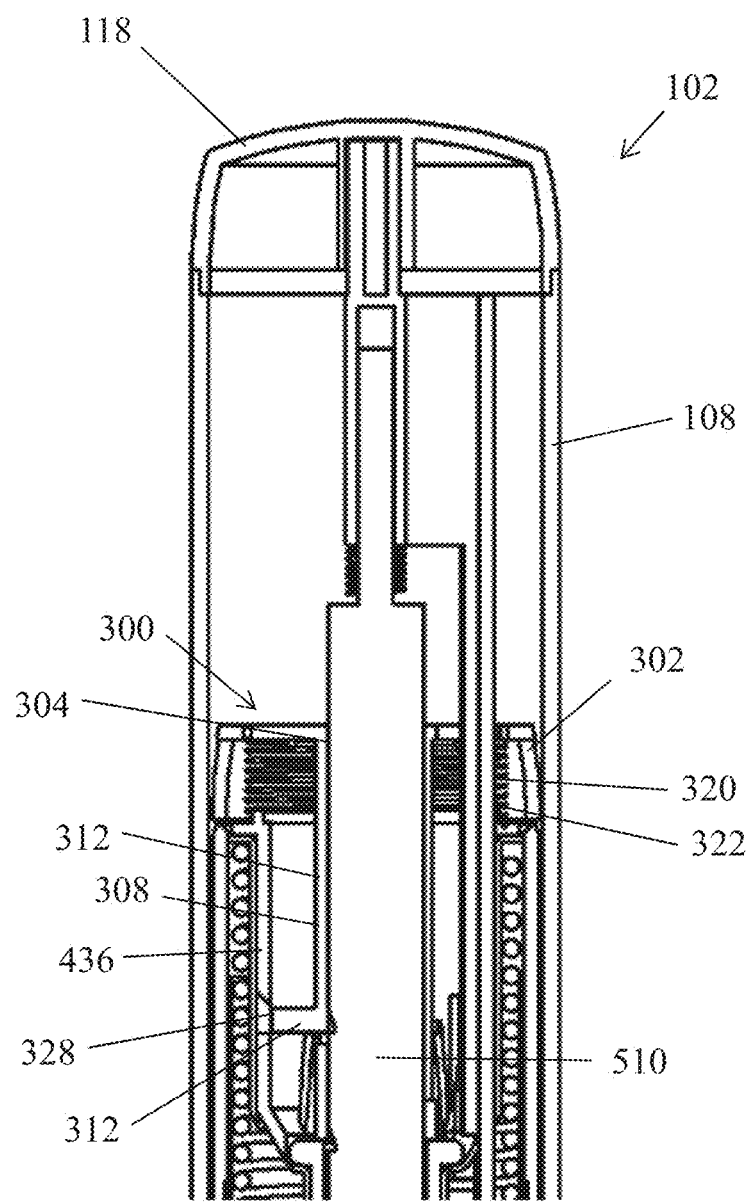

FIGS. 4A-4C illustrate longitudinal cross-sectional views of a proximal portion of the injection device of FIG. 1, showing the end-of-dose indicator 300 having a different visual appearance associated with the inactivated (FIG. 4A) and activated (FIG. 4C) configurations. The indicator 300 may be seen through the housing 102 in the activated configuration, while not seen through the housing 102 in the inactivated configuration. In some variations, at least a portion of the housing 102 may be translucent, transparent, or comprise an opening to allow the visual appearance of the indicator 300 to be different between the activated and inactivated configurations. For example, the indicator 300 may be seen when in an activated configuration through the end cap 118 of the proximal housing 108, which may comprise a transparent or translucent material. While in the variation of FIGS. 4A-4C the transparent or translucent region is in end cap 118, it should be appreciated that in other variations the indicator 300 may be seen through other portions of the housing 102.

In the variation shown in FIGS. 4A-4C, the indicator 300 may comprise a main body 302, a release member 308, and a biasing element 320. The main body 302 and end cap 118 of the proximal housing 108 may be configured such that when the main body 302 is adjacent to the inner surface 186 of the end cap 118, at least a portion of the main body 302 may be seen from outside the end cap 118 through a viewing portion. In some variations, at least a portion of the main body 302 may have a color or pigment that may be capable of being more easily noticed, such as but not limited to red, yellow, orange, green, magenta, blue, and the like. In order for the main body 302 to be seen through at least a portion of end cap 118, in some variations, at least a portion of the end cap 118 may be translucent. In variations in which a portion of the end cap 118 is translucent, the level of translucency may be such that the coloring of the main body 302 may be perceived through the end cap 118 only when the main body 302 is adjacent or nearly adjacent to the viewing portion. In other variations, the end cap 118 may comprise a transparent or open region configured such that the main body 302 is only visible through the viewing portion when the main body 302 is adjacent to the transparent or open region, for example, because of the viewing angle. For instance, in some such variations, the viewing portion may comprise a transparent region around the circumference of the end cap 118, and the main body 302 of the indicator 300 may only be visible through the viewing portion when aligned adjacent to the viewing portion. The main body 302 of the indicator 300 may also comprise a lumen 304 therethrough to allow a portion of the ram 502 (described below) to pass through the main body 302.

The biasing element 320 may be configured to bias the indicator 300 toward an activated configuration. The biasing element 320 may have a compressed configuration and an expanded configuration. The biasing element 320 may be in a compressed configuration when the indicator 300 is in an inactivated configuration, and the biasing element 320 may be in an expanded configuration when the indicator 300 is in an activated configuration. As shown in FIGS. 4A-4C, in some variations the biasing element 320 may comprise a compression spring 322. The proximal end 324 of the compression spring 322 may be connected to or in contact with the main body 302 of the indicator 300, and the distal end 326 of the compression spring 322 may be connected to or in contact with the interlocker 436 (described below). The biasing element 320 may thus bias the main body 302 of the indicator 300 away from the ram 502.

As shown in FIG. 4A, the release member 308 may hold the indicator 300 in an inactivated configuration until released. The release member 308 may comprise an elongate portion 312 and a locking portion 310. The elongate portion 312 may connect the main body 302 and the locking portion 310, and the locking portion 310 may extend radially outward from the distal end of the elongate portion 312. When the indicator 300 is in an inactivated configuration, the radially outer tip of the locking portion 310 may fit within an indicator recess 328 in the interlocker 436. Radially outward pressure from the plunger 510 on the inner end of the locking portion 310 may resist the locking portion 310 from moving radially inward to emerge or disengage from the recess 328. The protrusion of the outer tip of the locking portion 310 into the indicator recess 328 may result in a distally directed force on the locking portion 310 from the proximal surface of the recess 328, which may counteract the biasing force of the compression spring 322, and which may thus hold the indicator 300 in an inactivated configuration.

When the release member 308 is released, the indicator 300 may no longer be held in an inactivated configuration, as shown in FIG. 4B. The release member 308 may be released by the distal motion of the ram 502 as the injection proceeds (as described in more detail below). As the ram 502 moves distally relative to the interlocker 436, the plunger 510 may move distally relative to the locking portion 310 of the release member 308, until the plunger 510 may be fully distal to the locking portion 310, as shown in FIG. 4B. At this point, the plunger 510 may no longer contact the inner end of the locking portion 310 to resist the locking portion 310 from moving radially inward to emerge or disengage from the recess 328. As a result, the locking portion 310 may move radially inward to emerge or disengage from the recess 328, and the proximal surface of the recess 328 may no longer provide a distally directed force on the locking portion 310 to counteract the biasing force from the compression spring 322, thus releasing the release member 308. Once released, the biasing force from the compression spring 322 may cause the indicator 300 to move proximally relative to the interlocker 436 and toward an activated configuration, as shown in FIG. 4C.

FIGS. 4D-4E illustrate cut-away elevational side views of a proximal portion of another embodiment of an injection device showing another example of an end-of-dose indicator in inactivated (FIG. 4D) and activated configurations (FIG. 4E). In the embodiment of FIGS. 4D-4E, the indicator 300 may, like the embodiment of FIGS. 4A-4C, comprise a main body 2302, a release member 2308, and a biasing element 2320, but the proximal end 2324 of the compression spring 2322 may be connected to or in contact with an inner lip 2306 on the main body 2302 of the indicator 2300, and the distal end 2326 of the compression spring 2322 may be connected to or in contact with the arms 506 of the ram 2502. The release member 2308 may comprise one or more latches 2310 that may mate with a slot or other form of recess in the arm 2506 of the ram 2502. When the latches 2310 are mated with the slots or recesses, the release member 2308 may resist distal motion of the main body 2302 of the indicator 2300 relative to the ram 502 (e.g., due to a biasing force from the biasing element 2320). If the latches 2310 are released from the slots or recesses, a force from the biasing element 2320 may cause the indicator 2300 to move into an activated configuration, as shown in FIG. 4E. In the embodiment shown in FIGS. 4D-4E, for example, the release member 2308 may comprise two latches 2310. Each latch 2310 may extend distally from the main body 2302 of the indicator 2300. Each latch 2310 may be configured to mate with an indentation ridge 2524 on the outer surface of an arm 2506 of the ram 2502. When the latches 2310 are mated with the indentation ridge 2524, the proximal side of the indentation ridge may resist proximal motion of the latch 2310 and thus of the main body 2302 of the indicator 2300 due to the biasing force from the compression spring 2322. If the latches 2310 are released from the indentation ridges 2524, however, the biasing force from the compression spring 2322 may urge apart the ram 2502 and the indicator 2300, moving the main body 2302 of the indicator 2300 towards the end cap 2118 of the proximal housing 2108, which may cause the indicator 2300 to be visible through the end cap 2118. The tabs 2103 may be configured to be released from the indentation ridge 2524 by distal movement of the ram 2502 relative to the proximal housing 2108 and end cap 2118. When the ram 2502 has moved distally such that the full dose has been displaced from the reservoir of the syringe and/or nearly the full dose has been displaced from the reservoir of the syringe the latches 2310 may be pushed out of the indentation ridges 2524, moving the indicator 2300 to an activated configuration, as shown in FIG. 4E.

While the indicators in FIGS. 4A-4E are end-of-dose indicators, in other variations, the indicator may be configured to convey the progress of the injection at one or more points throughout the injection. For example, in some variations, the proximal housing 108 and/or distal housing 110 may comprise a viewing region (e.g., a transparent or transparent region, or an opening) such that the location of the interlocker 436 (described below) may be viewed through the viewing region. The location of the interlocker 436 relative to the housing 102 may indicate the progress of the injection. In some of these variations, the interlocker 436 may be colored or comprise a colored region to be more easily visible through the viewing region. In other variations, a separate component, which may also be colored or comprise a colored region, may be attached to the interlocker 436, which may be seen through the viewing region.

As described briefly above, in general, the syringe 104 may comprise a syringe body defining a syringe cavity, a seal slidably disposed within the lumen of the syringe cavity defining a reservoir that may hold a formulation comprising a therapeutic or diagnostic agent, a ram comprising a plunger that may fit slidably within the syringe cavity, and a needle at the distal end of the syringe body. The needle may be configured to pierce the tissue of a patient receiving an injection, and may have a lumen therethrough to deliver the contents of the reservoir to the patient's tissue. Movement of the seal within the syringe cavity distally may cause the contents of the reservoir to be displaced through the lumen of the needle.

Returning to FIGS. 2A-2N, the syringe 104 may comprise, as briefly mentioned above, a syringe body 402, which may define a syringe cavity 404. The syringe cavity 404 may be in fluid communication with the lumen 408 of the needle 406, described in more detail below. A seal 410 may be slidably disposed within the syringe cavity 404 and may form an airtight seal with the inner surface 412 of the syringe body 402. The inner surface 412 of the syringe body 402 and the seal 410 may form a reservoir 414 configured to contain a formulation, such as a solution, comprising a therapeutic or diagnostic agent. The seal 410 may limit the contents of the syringe cavity 404 from flowing or otherwise moving proximally to the seal 410. If the seal 410 is moved distally relative to and within the syringe cavity 404, the volume of the reservoir 414 may be decreased. Thus, distal motion of the seal 410 relative to and within the syringe cavity 404 may cause the contents of the reservoir 414 to be displaced through the lumen 408 of the needle 406. In some variations, the reservoir 414 may be configured to contain a maximum volume of about 1 mL, about 2 mL, about 3 mL, about 4 mL, or about 5 mL. In other variations, the reservoir 414 may be configured to contain a maximum volume of about 0.1 mL to 1 mL, 1 mL to 2 mL, 2 mL to 3 mL, 3 mL to 5 mL, 5 mL to 10 mL, 10 mL to 15 mL, 15 mL to 20 mL, 20 mL to 25 mL, or more. While the syringe 104 is shown as having a circular cross-section, and thus the syringe body 402 forms a barrel, in other variations, the syringe 104 and its component parts may have any suitable shape (e.g., having an elliptical cross-section, oblong cross-section, ovoid cross-section, square cross-section, rectangular cross-section, triangular cross-section, etc.).

The reservoir 414 formed by the inner surface 412 of the syringe body 402 and the seal 410 may contain a formulation comprising one or more therapeutic or diagnostic agents. In some variations, the therapeutic or diagnostic agent may be a substance such as but not limited to a large molecule, small molecule, or a biologic. In some variations, the formulation may further comprise one or more solvents, diluents, and/or adjuvants. The formulation may have any suitable viscosity. Generally, the formulation may have a viscosity of up to 10 cP, up to 20 cP, up to 30 cP, up to 40 cp, up to 50 cP, up to 60 cP, up to 70 cP, up to 80 cP, up to 90 cP, or up to 100 cP. In some instances, the formulation may have a higher viscosity, such as up to 1,000 cP, up to 10,000 cP, or up to 50,000 cP. Examples of higher viscosity injectates include certain dermal fillers used for cosmetic or tissue bulking procedures, such as the treatment of urinary incontinence. In some instances the formulation may have a significantly higher viscosity (e.g., an even higher viscosity, such as up to 500,000 cP or higher.

In some variations, the therapeutic or diagnostic agent may be a substance that may be used with patient populations for whom a power-assisted injection device as described herein may be beneficial, such as but not limited to patient populations having diseases or disorders such as but not limited to multiple sclerosis, rheumatoid arthritis, cancers, Alzheimer's disease, or IgE-mediated disorders (e.g., allergic rhinitis, asthma (e.g., allergic asthma and non-allergic asthma), atopic dermatitis, allergic gastroenteropathy, hypersensitivity (e.g., analphylaxis, urticaria, food allergies, etc.), allergic bronchopulmonary aspergillosis, parasitic diseases, interstitial cystitis, hyper-IgE syndrome, ataxia-telangiectasia, Wiskott-Aldrich syndrome, thymic alymphoplasia, IgE myeloma and graft-versus-host reaction). In some variations, the therapeutic or diagnostic agent may, but need not be, selected from beta interferons (e.g., BETAFERON®, AVONEX®, REBIF®, Extavia®), natalizumab (TYSABRI®), TNFα inhibitors (e.g., etanercept (ENBREL®), infliximab (REMICADE®), adalimumab (HUMIRA®), golimumab (SIMPONI®), and certolizumab pegol (CIMZIA®)), abatacept (Orencia®), anakinra (Kineret®), anti-CD20 antibodies (e.g., rituximab (Rituxan®) or ocrelizumab), anti-IL-6 receptor antibodies (e.g., tocilizumab (Actemra®)), anti-IL-13 antibodies (e.g., lebrikizumab), anti-CD20 antibodies (e.g., obinutuzumab), anti-HER2 antibodies (e.g., trastuzumab), or an anti-Abeta antibodies (e.g., crenezumab).

In some variations, the formulation may comprise a therapeutically effective amount of a protein or proteins, such as but not limited to growth hormone, including human growth hormone and bovine growth hormone; growth hormone releasing factor; parathyroid hormone; thyroid stimulating hormone; lipoproteins; α-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or tissue-type plasminogen activator (t-PA, e.g., Activase®, TNKase®, Retevase®); bombazine; thrombin; tumor necrosis factor-α and -β; enkephalinase; RANTES (regulated on activation normally T-cell expressed and secreted); human macrophage inflammatory protein (MIP-1-α); serum albumin such as human serum albumin; mullerian-inhibiting substance; relaxin A-chain; relaxin B-chain; prorelaxin; mouse gonadotropin-associated peptide; DNase; inhibin; activin; vascular endothelial growth factor (VEGF); receptors for hormones or growth factors; an integrin; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-α and TGF-β, including TGF-(β1, TGF-β2, TGF-β3, TGF-β4, or TGF-β5; insulin-like growth factor-I and -II (IGF-I and IGF-II); des(1-3)-IGF-I (brain IGF-I); insulin-like growth factor binding proteins; CD proteins such as CD3, CD4, CD8, CD19 and CD20; erythropoietin (EPO); thrombopoietin (TPO); osteoinductive factors; immunotoxins; a bone morphogenetic protein (BMP); an interferon such as interferon-α, -β, and -γ; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor (DAF); a viral antigen such as, for example, a portion of the AIDS envelope; transport proteins; homing receptors; addressins; regulatory proteins; immunoadhesins; antibodies; and biologically active fragments or variants of any of the above-listed polypeptides. By "protein" is meant a sequence of amino acids for which the chain length is sufficient to produce the higher levels of tertiary and/or quaternary structure. In some of these variations, the protein which is formulated may be essentially pure and essentially homogeneous (i.e., free from contaminating proteins). "Essentially pure" protein means a composition comprising at least about 90% by weight of the protein, based on total weight of the composition, preferably at least about 95% by weight. "Essentially homogeneous" protein means a composition comprising at least about 99% by weight of protein, based on total weight of the composition.

In some variations, the formulation may comprise high concentrations of large molecular weight proteins, such as antibodies or immunoglobulins. The antibodies may, for example, be antibodies directed against a particular predetermined antigen. In a specific aspect, the antigen is IgE (e.g., rhuMAbE-25, rhuMAbE-26 described in U.S. Pat. No. 6,329,509 and WO 99/01556). Alternatively, the anti-IgE antibody may be CGP-5101 (Hu-901) described in Come et al., J. Clin. Invest. 99(5): 879-887 (1997), WO92/17207, and ATTC Deposit Nos. BRL-10706 and 11130, 11131, 11132, 11133. Alternatively, the antigen may include: the CD proteins CD3, CD4, CD8, CD19, CD20, CD34 and CD40; members of the HER receptor family such as EGF receptor, HER2, HER3 or HER4 receptor; 2C4, 4D5, PSCA, LDP-2, cell adhesion molecules such as LFA-1, Mac1, p150, 95, VLA-4, ICAM-1, VCAM and αv/β3 integrin including the α- and β-subunits thereof (e.g., anti-CD11a, anti-CD18 or anti-CD11b antibodies); growth factors such as VEGF; blood group antigens; flk2/flt3 receptor; obesity (OB) receptor; mp1 receptor, CTLA-4, and protein C. The antibodies may also be those that specifically bind to the antigenic targets disclosed in the following patent applications: U.S. Ser. No. 10/177,488, filed 19 Jun. 2002; U.S. Ser. No. 09/888,257, filed 22 Jun. 2001; U.S. Ser. No. 09/929,769, filed 14 Aug. 2001; U.S. Ser. No. 09/938,418, filed 23 Aug. 2001; U.S. Ser. No. 10/241,220, filed 11 Sep. 2002; U.S. Ser. No. 10/331,496, filed 30 Dec. 2002; U.S. Ser. No. 10/125,166, filed 17 Apr. 2002; U.S. Ser. No. 10/127,966, filed 23 Apr. 2002; U.S. Ser. No. 10/272,051, filed 16 Oct. 2002; U.S. Ser. No. 60/299,500, filed 20 Jun. 2001; U.S. Ser. No. 60/300,880, filed 25 Jun. 2001; U.S. Ser. No. 60/301,880, filed 29 Jun. 2001; U.S. Ser. No. 60/304,813, filed 11 Jul. 2001; U.S. Ser. No. 60/312,312, filed 13 Aug. 2001; U.S. Ser. No. 60/314,280, filed 22 Aug. 2001; U.S. Ser. No. 60/323,268, filed 18 Sep. 2001; U.S. Ser. No. 60/339,227, filed 19 Oct. 2001; U.S. Ser. No. 60/336,827, filed 7 Nov. 2001; U.S. Ser. No. 60/331,906, filed 20 Nov. 2001; U.S. Ser. No. 60/354,444, filed 2 Jan. 2002; U.S. Ser. No. 60/351,885, filed 25 Jan. 2002; U.S. Ser. No. 60/360,066, filed 25 Feb. 2002; U.S. Ser. No. 60/362,004, filed 5 Mar. 2002; U.S. Ser. No. 60/366,869, filed 20 Mar. 2002; U.S. Ser. No. 60/366,284, filed 21 Mar. 2002; U.S. Ser. No. 60/368,679, filed 28 Mar. 2002; U.S. Ser. No. 60/369,724, filed 3 Apr. 2002; U.S. Ser. No. 60/373,160, filed 16 Apr. 2002; U.S. Ser. No. 60/378,885, filed 8 May 2002; U.S. Ser. No. 60/404,809, filed 19 Aug. 2002; U.S. Ser. No. 60/405,645, filed 21 Aug. 2002; U.S. Ser. No. 60/407,087, filed 29 Aug. 2002; U.S. Ser. No. 60/413,192, filed 23 Sep. 2002; U.S. Ser. No. 60/419,008, filed 15 Oct. 2002; U.S. Ser. No. 60/426,847, filed 15 Nov. 2002; U.S. Ser. No. 60/431,250, filed 6 Dec. 2002; U.S. Ser. No. 60/437,344, filed 31 Dec. 2002, U.S. Ser. No. 60/414,971, filed 2 Oct. 2002, U.S. Ser. No. 60/418,988, filed 18 Oct. 2002. The term "antibody" as used herein may include monoclonal antibodies (including full length antibodies which have an immunoglobulin Fc region), antibody compositions with polyepitopic specificity, multispecific antibodies (e.g., bispecific antibodies, diabodies, and single-chain molecules, as well as antibody fragments (e.g., Fab, F(ab')2, and Fv).

In some variations, the therapeutic agent may be a subcutaneous formulation containing high concentrations of large molecular weight proteins, such as immunoglobulins. The immunoglobulins may, for example, be antibodies directed against a particular predetermined antigen, which can include, for example, IgE (e.g., rhuMAbE-25, rhuMAbE-26 and rhuMAbE-27 described in WO 99/01556); the CD proteins, such as, for example, CD3, CD4, CD8, CD19, CD20, CD34 and CD83; members of the HER receptor family such as EGF receptor, HER2, HER3 or HER4 receptor; cell adhesion molecules such as LFA-1, Mol, p150, 95, VLA-4, ICAM-1, VCAM and αv/β3 integrin including the α- and β-subunits thereof (e.g., anti-CD11a, anti-CD18 or anti-CD11b antibodies) or integrin beta 7; growth factors such as VEGF; blood group antigens; flk2/flt3 receptor; obesity (OB) receptor; interleukins such as, for example, IL2, IL3, IL4, IL5, IL6 and IL6 receptor, IL13, IL17, IL21, IL22, IL23, IL24, IL26, IL27, IL30, IL32, IL34 and; beta-amyloid; interferons such as interferons I and II, which can include the interferon alphas: IFNA1, IFNA2, IFNA4, IFNA5, IFNA6, IFNA7, IFNA8, IFNA10, IFNA13, IFNA14, IFNA16, IFNA17, IFNA21 and the interferon betas: IFN-beta 1 and IFN-beta 3; anaphylatoxins or complement activators such as C2, C2a, C5, C5a; and protein C.

Although the formulations comprising one or more therapeutic or diagnostic agents are described above with respect to syringe 104 of injection device 100, it should be appreciated that the formulations described above may be injected with any of the variations of injection devices described herein, including injection devices 700 and 1300 described below.

The syringe body 402 and seal 410 and/or plunger may comprise any suitable materials, such as but not limited to glass (e.g., Type 1 glass), a polymer (e.g. a rubber, such as putyl rubber), a metal, or the like. In some variations, the material or materials of the syringe body 402 and/or seal 410 may have properties so as to not substantially interact with the therapeutic or diagnostic agent, resisting adhesion, and/or promoting stability and/or sterility or sterilizability of the formulation. In some variations, the syringe body may comprise a coating. In some variations, the coatings may comprise silicone oils, fluoropolymers (e.g., perfluoropolyether-based chemical coatings, polytetrafluoroethylene (TEFLON®)), or the like. For example, the syringe body may comprise glass that may be siliconized on the inside surface. In some variations, the syringe body 402 and/or seal 410 may comprise materials that limit light transmission to the therapeutic or diagnostic agent (i.e., materials that reflect or absorb light), such as but not limited to materials that block UV light and/or light at given visible wavelengths (e.g., amber-tinted materials), black-out materials blocking all light, and foil linings. The material(s) may be selected for their specific colors, color change resistance (due to aging, due to exposure to the formulation, or due sterilization), leach resistance, in regard to some general or specific formulation characteristics. In some variations, the syringe body 402 may comprise a translucent or transparent material, such that the contents of the syringe body 402 can be viewed through the material. In some variations, the shelf life of the therapeutic or diagnostic agent within the injection device 100 may be up to about 1 year, about 2 years, about 3 years, about 4 years, or about 5 years.

The needle 406 of the syringe 104 may be attached to the distal end of the syringe body 402 of the syringe 104. The proximal end 416 of the needle 406 may be secured to the distal end 418 of the syringe body 402, such that the proximal end 416 of the lumen 408 of the needle 406 is in fluid communication with a distal opening 420 at the distal end 418 of the syringe body 402. The distal end 418 of the needle 406 may have a pointed shape configured to pierce tissue. The needle 406 may thus be configured allow the formulation within the reservoir 414 to flow out through the distal opening 420 in the syringe body 402, through the lumen 408 of the needle 406, and into tissue, when the needle 406 is inserted into tissue. The length and gauge of the needle 406 may be appropriate for the intended use. For example, in some variations the syringe 104 may comprise needle sizes up to, or including but not limited to 7 gauge, 9 gauge, 11 gauge, 13 gauge, 15 gauge, 17 gauge, 19 gauge, 21 gauge, 23 gauge, 25 gauge, 27 gauge, 29 gauge, 31 gauge, and 33 gauge needles, and lengths including those up to about 3 mm, 4 mm, 6 mm, 8 mm, 10 mm, 15 mm, 20 mm, 30 mm, 40 mm or more. The needle may comprise any suitable material, including but not limited to stainless steel. In other variations, the device may be provided without a needle. In some variations, the needleless devices are intended to be attached to a pre-existing needle (e.g., a lumbar puncture needle or a central line catheter).

As shown in FIG. 1, the syringe 104 may further comprise a rigid needle shield 422. In some variations, the injection device 100 may comprise a deshielder configured to allow easy removal of the rigid needle shield 422. In some variations, the deshielder or rigid needle shield 422 may comprise an interlock to resist motion of the syringe 104 within the distal housing 110 before removal of the rigid needle shield 422. In some variations, the deshielder may be integrated with a cap 148 that may fit over the distal housing 110, as described in more detail above. In some variations, the rigid needle shield 422 may be asymmetric to resist rolling of the housing 102 when attached to the injection device 100.

The syringe 104 may be configured to move longitudinally relative to the distal housing 110 from a retracted position (shown in FIGS. 2A-2D and 3A-3B) to an extended position (shown in FIGS. 2G-2N and 3E-3F). In a retracted position, the distal tip 424 of the needle 406 may be shielded from exposure (e.g. the needle 406 may be protected from piercing or otherwise contacting tissue), and thus the distal tip 424 of the needle 406 may be proximal to the distal end of the housing 102 (e.g., the distal end 114 of the distal housing 110). The syringe 104 may be held in a retracted position (i.e., it may resist distal motion relative to the syringe 104) by a restraining element. In some variations, the restraining element may comprise one or more flexures 428, described below. The syringe 104 may be moved toward an extended position by a distal force sufficient to overcome the resistance of the flexures 428, as described below. In an extended position, the distal tip 424 of the needle 406 may be exposed (e.g., the distal tip 424 of the needle 406 may be capable of piercing or other otherwise contacting tissue), and thus the distal tip 424 of the needle 406 may be distal to the distal end of the housing 102 (e.g., the distal end 114 of the distal housing 110). When the syringe 104 is in an extended position, if the needle shroud 202 of the needle safety assembly 200 is in a retracted position, the distal tip 424 of the needle 406 may extend beyond the distal end of the distal housing 110 and the needle shroud 202 to pierce tissue to a desirable depth, as shown in FIGS. 2G-2L. In some variations, the distal tip 424 of the needle 406 may move about 6 mm to 8 mm, about 8 mm to 10 mm, about 10 mm to 12 mm, or about 12 mm to 14 mm between retracted and extended positions. In some variations, the distal tip 424 of the needle 406 may be about 1 mm, about 2 mm, about 3 mm, about 4 mm, about 5 mm, about 6 mm, or about 7 mm proximal to the distal end 114 of the distal housing 110 in a retracted position. In some variations, the distal tip 424 of the needle 406 may be about 4 mm, about 5 mm, about 6 mm, about 7 mm, about 8 mm, about 9 mm, or about 10 mm distal to the distal end 114 of the distal housing 110 in an extended position.

Figure 5:
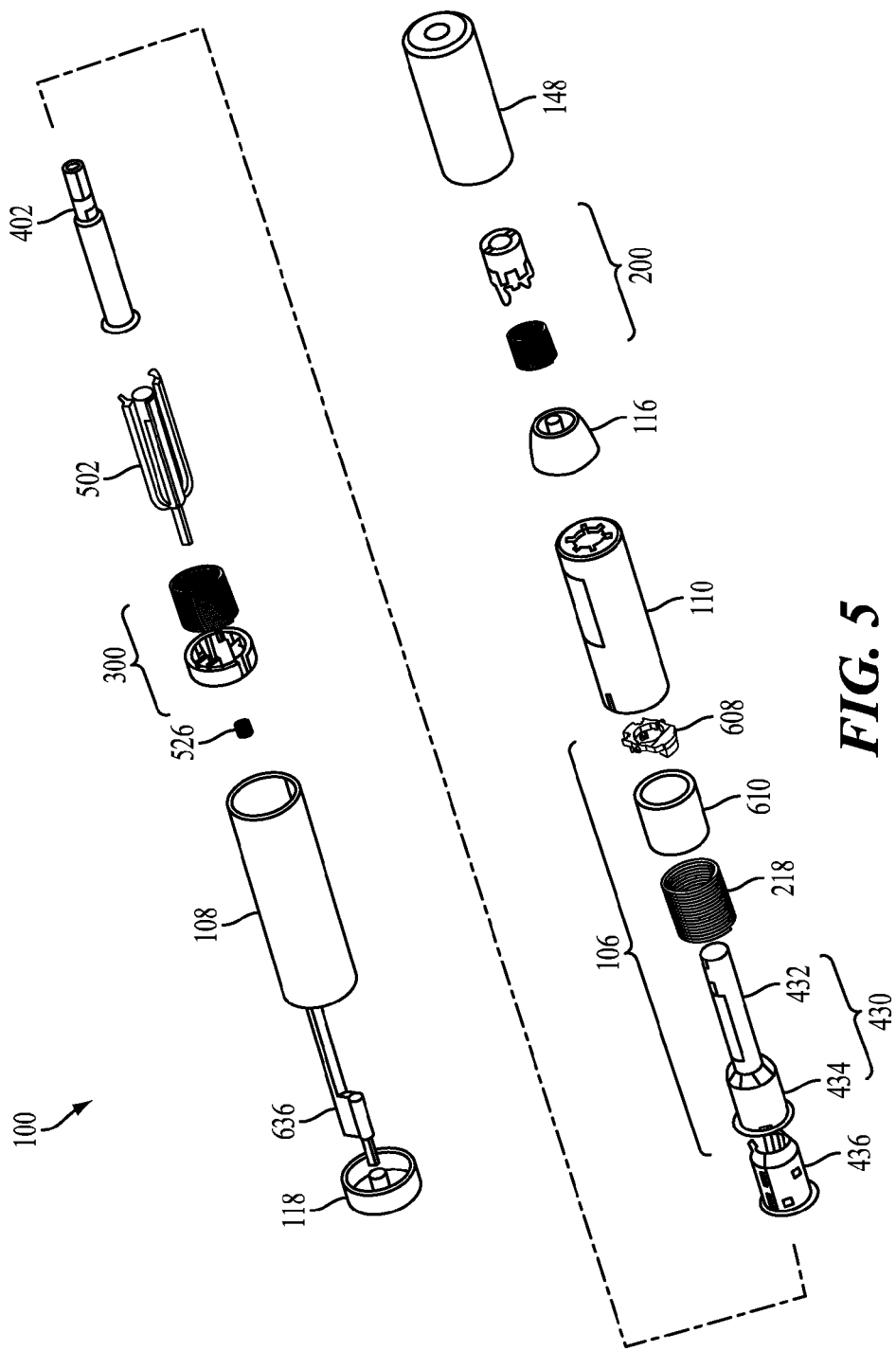
FIG. 5 depicts an exploded perspective view of the injection device 100.

FIG. 5 depicts an exploded perspective view of the injection device 100. In some variations, the injection device 100 may comprise a syringe sleeve 430, as mentioned above, but need not. In these variations, the syringe 104 may be slidably disposed with the syringe sleeve 430. The syringe sleeve 430 may comprise a distal portion 432 and a proximal portion 434. The distal portion 432 may be configured to fit slidably around the syringe body 402. The proximal portion 434 may have a larger diameter (or maximum distance transverse to the longitudinal axis) than the distal portion 432, and may be configured to hold the power assembly 106 in place, as described in more detail below. The syringe sleeve 430 may be fixed relative to the distal housing 110, and may have a longitudinal axis aligned with the longitudinal axis of the housing 102. The syringe sleeve may comprise any suitable material, and in some variations, the syringe sleeve 430 may comprise a deep drawn metal.

Figure 6:
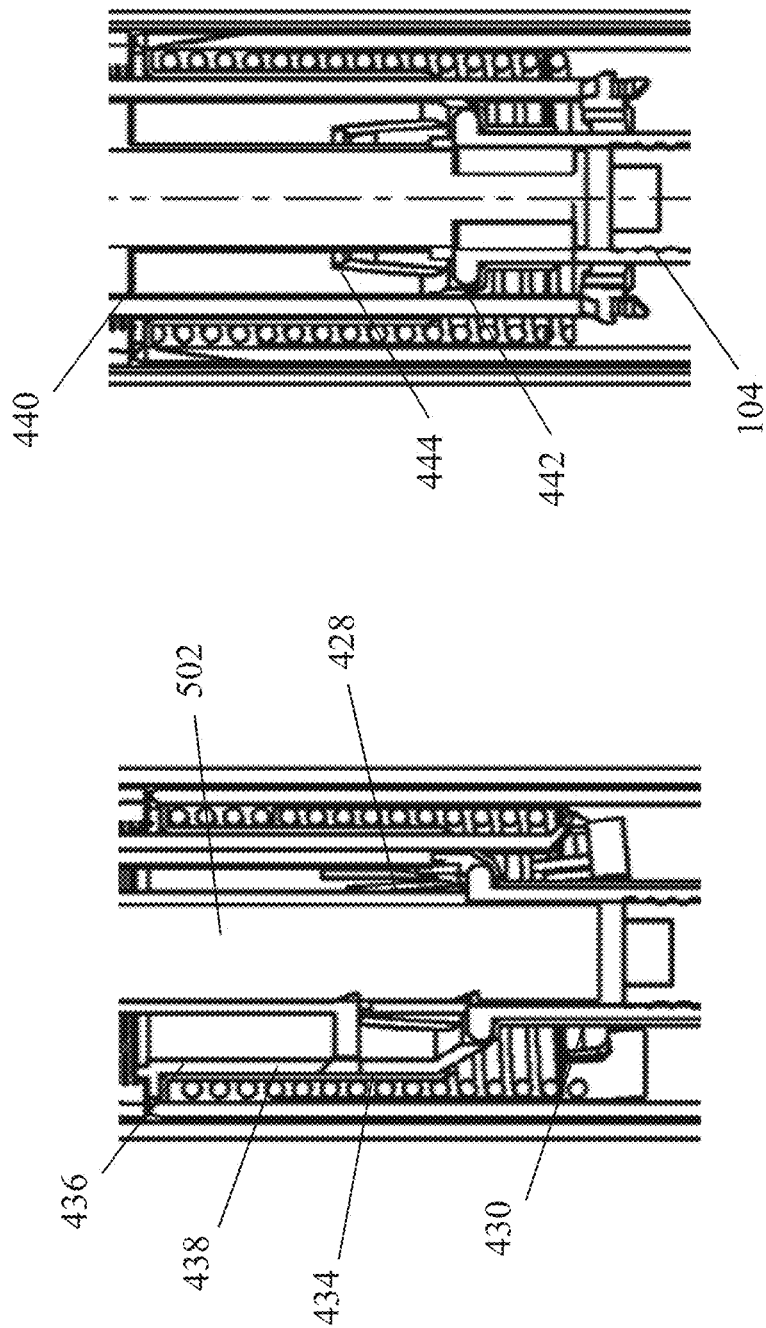
FIGS. 6A-6B are orthogonal longitudinal cross-sectional views of a central portion of the injection device of FIG. 1, showing the interlocker.

The distal portion 432 of the syringe sleeve 430 may also have attached to it an interlocker 436. As shown in FIGS. 6A-6B, the interlocker 436 may comprise a main body 438 that may be fixed within the proximal portion 434 of the syringe sleeve 430. The interlocker 436 may have a proximal opening 440, a distal opening 442, and a lumen 444 therethrough. At least a portion of the ram 502 (described below) may fit through the proximal opening 440 of the interlocker 436, and the syringe body 402 of the syringe 104 may fit through the distal opening 442 of the interlocker 436. The interlocker 436 may further comprise one or more flexures 428 to resist distal movement of the syringe 104, and a biter interlock 448 to hold the biter 608 of the power assembly 106 in place, both of which will be described in more detail below.

Returning to FIGS. 2A-2N, the ram 502 may be directly or indirectly connected to the proximal housing 108, such that movement of the proximal housing 108 can be transmitted to the ram 502. The ram 502 may be configured to transmit distal force on the proximal housing 108 into different motions, depending on the stage of the injection process. In a first stage, distal force on the proximal housing 108 may be transmitted into distal motion of the syringe 104 relative to the distal housing 110. In a second stage, distal force on the proximal housing 108 may be transmitted into displacement of the contents of the reservoir 414 of the syringe 104 (e.g., a fluid or formulation comprising a therapeutic or diagnostic agent) through the lumen 408 of the needle 406.

In some variations, the ram 502 may be configured such that the effects of distal force on the proximal housing 108 may occur in the order described above. That is, the ram 502 may be configured such that distal force on the proximal housing 108 may be transmitted first into distal motion of the syringe 104 relative to the distal housing 108, and then transmitted second into displacement of the contents of the reservoir 414 (e.g., a formulation comprising a therapeutic agent) through the lumen 408 of the needle 406. This may be desirable, for example, because it may allow the syringe 104 to move distally such that the needle 406 may pierce a patient's tissue before the contents of the reservoir 414 are displaced through the lumen 408 of the needle 406.

In some variations, the ordering of effects of distal force on the proximal housing 108 may be due to different amounts of force that are required for each motion. For example, the ram 502 may transmit distal force on the proximal housing 108 into distal motion of the syringe 104 relative to the distal housing 110 when the force on the proximal housing 108 is above a first threshold (e.g., above about 1 N, above about 2 N, above about 3 N, above about 4 N, above about 5 N, above about 6 N, above about 7 N, or higher); and the ram 502 may transmit distal force on the proximal housing 108 into displacement of the contents of the reservoir 414 through the needle 406 when the force on the proximal housing 108 is above a second higher threshold (e.g., above about 1 N, above about 2 N, above about 4 N, above about 6 N, above about 8 N, above about 10 N, above about 12 N, above about 14 N, or higher). These thresholds may in some cases be desirable for other or additional reasons. For example, it may be desirable that the force threshold to initiate distal motion of the syringe be higher than the amount of force required to insert the needle through the skin. It may also be desirable that the force threshold to initiate distal motion of the syringe be high enough to discourage accidental distal motion. Indeed, in some variations, it may be desirable that the force threshold to initiate distal motion of the syringe be high enough so as to force rapid needle insertion. In some variations, the thresholds may be due to the proximal forces from friction on the syringe 104 and ram 502, respectively. In other variations, the thresholds may be due to the proximal forces from other sources on the syringe 104 and ram 502, respectively, such as proximal forces from a flexure or spring. In other variations, one or more of the thresholds may be due to the proximal forces from friction and other sources on the syringe 104, and ram 502, respectively. It should be appreciated that in some other variations, the ram 502 may transmit distal force on the proximal housing 108 into different motions in different orders and by different mechanisms. For example, in some variations the effect of the distal force may be chosen by a mechanism for manual selection by the user. In should also be appreciated that the ram may have fewer or more motions into which it may transmit distal force on the proximal housing 108.

As shown in FIGS. 2A-2N, the ram 502 may comprise a central portion 504 and two arms 506 extending from opposite sides of the central portion 504. The central portion 504 may be divided in a proximal central portion comprising a connector rod 508, and a distal central portion comprising a plunger 510. The two arms 506 may extend from the central portion 504 at the dividing point 512 between the plunger 510 and the connector rod 508. The connector rod 508 may be slidable within a portion of the actuation rod 636 (described in detail below), which may in turn be fixedly attached to the end cap 118 of the proximal housing. However, in other variations (not shown), the connector rod may be configured to directly connect the ram to the proximal housing. In those variations, the connector rod may fit at least partially into a receiving cup on the inner surface of the end cap of the proximal housing. The receiving cup may be located at the center of the end cap and may be configured to hold the ram in a position aligned with the longitudinal axis of the housing.

The plunger 510 may be configured to be slidable within the syringe cavity 404 of the syringe 104. The distal end 516 of the plunger 510 may be configured to engage with the seal 410 of the syringe 104. If the plunger 510 is moved distally relative to and within the syringe cavity 404, the plunger 510 may push the seal 410 distally relative to and within the syringe cavity 404. This movement of the seal 410 may decrease the volume of the reservoir 414 containing the formulation comprising a therapeutic or diagnostic agent. Thus, distal motion of the plunger 510, and in turn of the seal 410, relative to and within the syringe cavity 404 may cause the contents of the reservoir 414 to be displaced through the lumen 408 of the needle 406. The two arms 506 of the ram 502 may extend distally from opposite sides of the ram 502 from its dividing point 512 along the central portion 504. The arms 506 may comprise a proximal curved portion 518 and a distal straight portion 520. The straight portion 520 of the arms 506 may be radially distanced from the plunger 510, such that if the plunger 510 is moved within the syringe cavity 404, the straight portion 520 of the arms 506 may be located outside of the syringe body 402. In some variations, the outer surface of the straight portion of the arms 506 may optionally comprise an indentation ridge for attachment of the indicator, as described above. The arms 506 may additionally be configured to attach to a portion of the power assembly 106 when the syringe 104 is in an extended position, as described below.

As shown in FIGS. 2E-2F, in the first stage of the injection process, distal force on the proximal housing 108 may be transmitted into distal movement of the syringe 104 relative to the syringe sleeve 430 from a retracted position (shown in FIGS. 2C-2D) to an extended position (shown in FIGS. 2G-2H) if the distal housing 110 is held in place (e.g. by pressing the distal end 158 of the nose 116 of the distal housing 110 against a patient's tissue) and if the distal force is above the necessary force threshold. The threshold force required may be due to the first pair of flexures 428, as described above. More specifically, when the threshold distal forced is reached, the flexures 428 may deflect outward and over the proximal lip 452 of the syringe body 402, at which point the flexures 428 may no longer resist distal movement of the syringe 104. Distal force on the proximal housing 108 may then cause distal motion of the ram 502, which may in turn cause distal motion of the syringe 104, via the plunger 510 located within the syringe cavity 404, toward the extended position. The syringe 104 may move distally within the syringe sleeve 430, which may move the needle 406 of the syringe 104 distally toward the distal end of the nose 116 of the distal housing 110. As the distal tip 424 of the needle 406 approaches the distal end 158 of the nose 116 (shown in FIGS. 2E-2F), the needle shroud 202 of the needle safety assembly 200 may be unlocked from a retracted position, as described in detail above. As the distal tip 424 of the needle 406 moves to extend beyond the distal end 158 of the nose 116, the needle 406 may pierce tissue pressed against the distal end 158 of the nose 116. The syringe 104 may continue to move distally relative to the syringe sleeve 430 until the syringe 104 has reached an extended position (shown in FIGS. 2G-2H). At an extended position, the distal tip 424 of the needle 406 may have reached the desired depth, as described above. The forward motion of the syringe 104 beyond the extended position may be limited by the proximal lip 452 contacting the distal end of the proximal portion 434 of the syringe sleeve 430. Because the proximal portion 434 of the syringe sleeve 430 may have a larger diameter (or maximum distance transverse to the longitudinal axis) than the distal portion 432, as described above, the proximal lip 452 of the syringe body 402 may fit within the proximal portion 434 but may not fit within the distal portion 432. In some variations, the injection device 100 may comprise a cushioning element (e.g., a rubber or elastomer overmold on the interlocker 436 or other rubber or elastomer element) with which the proximal lip 452 may come into contact when it reaches its fully proximal position. Additionally or alternatively, the injection device 100 may comprise a damping element, such as but not limited to a rubber or elastomer seal on the outside surface of the syringe body 402. In some variations, the injection device 100 may comprise an insertion detent, which may cause the movement of the distal tip 424 of the needle 406 to occur at a specific rate, in order to achieve a desired insertion speed into tissue.

It should be noted that the syringe 104 may move distally with the ram 502, rather than the ram 502 moving distally relative to the syringe 104 (e.g., due to the plunger 510 moving distally relative to and within the syringe cavity 404) in response to application of distal force on the proximal housing 108, due to the relative amounts of force required to move the syringe 104 relative to the syringe sleeve 430 and to move the ram 502 relative to the syringe 104, as described above, and due to mechanisms that may resist distal motion of the ram 502 relative to the syringe 104. More specifically, the amount of force required to overcome the first set of flexures 428 that may hold the syringe 104 in place relative to the interlocker 436, as described above, may be less than the amount of force to overcome the rate control assembly 604 of the power assembly 106 (described below) and/or the locking portion of the indicator that resists distal motion of the plunger 510 within the syringe cavity 404 of the syringe 104, as described in more detail below. If the distal force on the proximal housing 108 is released while the syringe 104 is moving from a retracted position to an extended position, the syringe 104 may stay in place relative to the syringe sleeve 430.

In the variation shown in FIGS. 2A-2N, distal motion of the plunger 510 within the syringe cavity 404 may be resisted before the syringe 104 is in an extended configuration due to the locking portion of the indicator 300, described above. Until the syringe 104 is in an extended configuration, a protrusion 316 on the inner edge of locking portion 310 may be mated with a recess 330 in the plunger 510, as shown in FIGS. 2A, 2C, and 2E. Inward pressure on the outer tip of the locking portion 310 from the inner surface of the interlocker 436 may resist radially outward movement of the locking portion 310 out of the recess 330, thus keeping the locking portion 310 and the plunger 510 mated. While mated, the indicator 300, the plunger 502, and the syringe 104 may be fixed relative to each other and may move distally together as the syringe 104 is moved toward an extended configuration. Once the syringe 104 is in an extended configuration, as shown in FIG. 2G, the locking portion 310 may align with the indicator recess 328 (described in more detail above). When distal force is applied to the plunger 510 via the proximal housing 108, pressure on the inner edge of the locking portion 310 from the plunger 510 may push the locking portion 310 radially outward and into the indicator recess 328. The locking portion 310 and the plunger 510 may thus no longer be mated, allowing the plunger 510 to move distally.

After the syringe 104 has moved distally relative to the syringe sleeve 430 such that the syringe 104 is in an extended position and the distal tip 424 of the needle 406 is at the desired depth, additional distal force on the proximal housing 108 may be transmitted into distal motion of the ram 502 relative to the syringe cavity 404, if the force is above the necessary force threshold. When the force is above the necessary force threshold, the plunger 510 and seal 410 may be moved distally within the syringe cavity 404, as shown in FIGS. 2I-2J, which may decrease the volume of the reservoir 414 and displace the contents of the reservoir 414 through the lumen 408 of the needle 406, as described above. Distal force on the proximal housing 108 may continue to cause the contents of the reservoir 414 to be displaced through the lumen 408 of needle 408 until the seal 410 has traveled to the distal end 462 of the syringe cavity 404 (shown in FIGS. 2K-2L), at which time the full dosage of the therapeutic or diagnostic agent may have been injected into the patient. In some variations, the total displacement of the plunger 510 during distal motion of the ram 502 relative to the syringe cavity 404 may be about 20 mm to 25 mm, about 25 mm to 30 mm, about 30 mm to 35 mm, about 35 mm to 40 mm, about 40 mm to 45 mm, about 45 mm to 50 mm, about 50 mm to 55 mm, about 55 mm to 60 mm, about 60 mm to 65 mm, about 65 mm to 70 mm, or about 70 mm to 75 mm. In some variations, the threshold force required to move the plunger 510 and seal 410 distally within the syringe cavity 404, once the locking portion 310 and the plunger 510 are no longer mated, may be due to the rate control assembly 604 of the power assembly 106, as described below.

The power assembly may comprise a stored energy source and a rate control assembly. The stored energy source may be configured to provide force to displace the contents of reservoir of the syringe. In some variations, the stored energy source may be configured to do so by contributing to the distal motion of the plunger or seal within the syringe cavity. In some variations, the power assembly may allow a user (a patient or another person) to direct the injection process in an intuitive way by directing the injection by pressing the injection device against a patient's skin, but the power assembly may supply additional supplemental injection force, such that the user does not need to provide the full force needed to carry out the injection. In addition, the power assembly may in some variations assist with providing a desirable user experience. This may include smooth operation, particularly when transitioning between static, slow, and fast injection states. While in the injection device 100 the power assembly supplies an injection force supplemental to the user-supplied injection force, it should be appreciated that in other embodiments, the power assembly may supply the full injection force. It should also be appreciated that in some variations, injection device may not provide a supplemental injection force.

The injection force provided by the power assembly may thus be sufficient (alone or in addition to injection force supplied by the user) to inject a given volume of a given formulation through a given size needle in a given time. In some variations, for example, the power assembly may be capable of 2 mL of 19 cP solution in 10 seconds through a 27 gauge thin-wall needle 17 mm in length. In some variations, the power assembly may provide supplementary injection forces of up to about 5 N, about 10 N, about 15 N, about 20 N, about 25 N, about 30 N, about 35 N, about 40 N, about 45 N, about 50 N, about 55 N, about 60 N, about 65 N, about 70 N, about 75 N, about 80 N, about 85, or about 90 N at the beginning of the injection.

Figure 18:
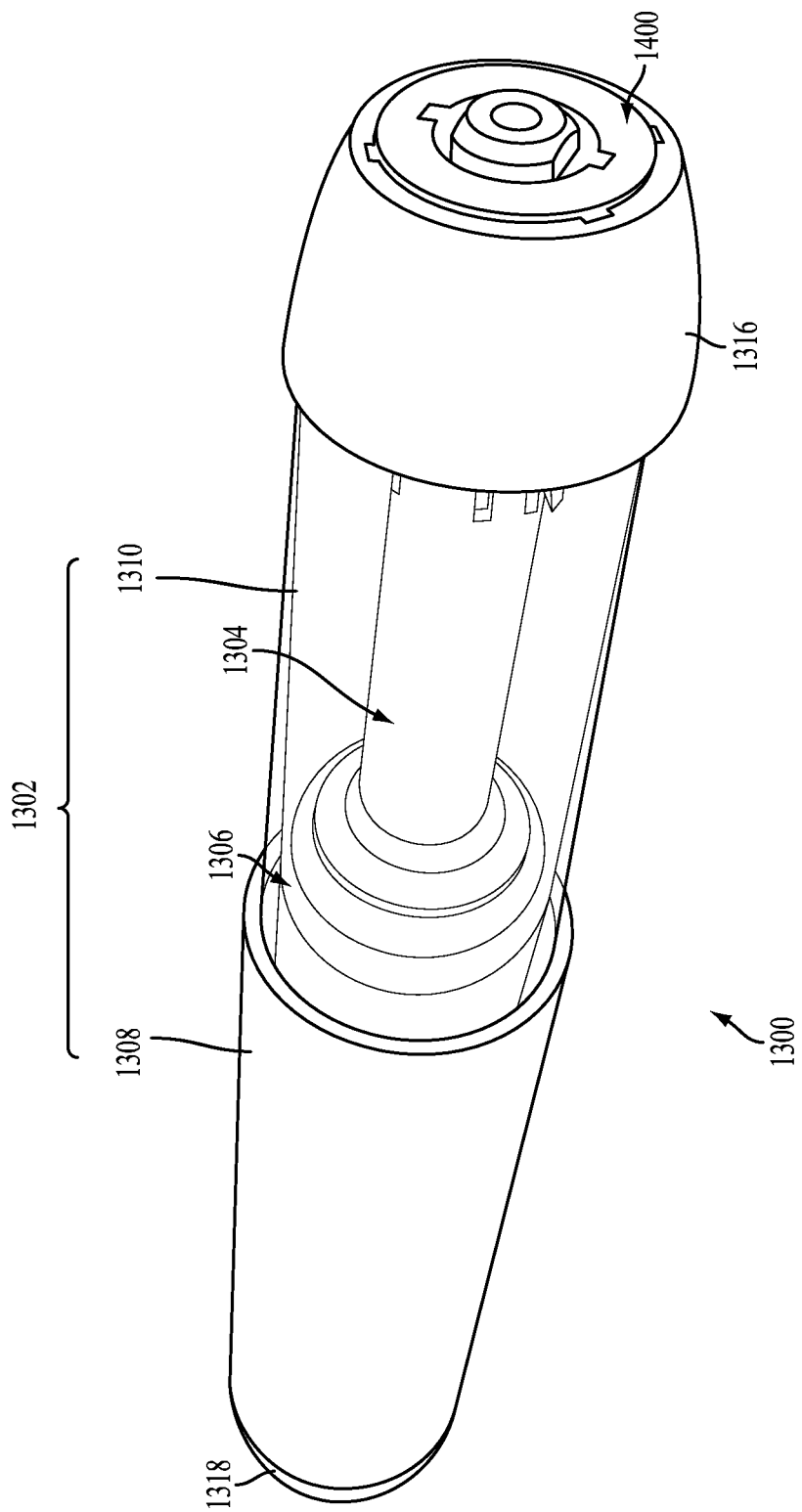
FIG. 18 is a perspective view of another embodiment of an injection device.

In some variations, it may be desirable for the power assembly to deliver a substantially constant force for the duration of the injection. In some variations, a substantially constant force for the duration of the injection may be achieved, for example, using a long spring with a low spring rate. In some of these variations, the spring fade may be about 5-10%, about 10-15%, about 15-20%, about 20-25%, about 25-30%, about 30-35%, or about 35-40% over the course of the injection. In other variations, a substantially constant force for the duration of the injection may be achieved, for example, with a spring having a shorter total length by mounting an extension spring to a compression spring (as described in more detail with respect to the embodiment of the injection device shown in FIG. 10). In other embodiments, a substantially constant force for the duration of the injection may be achieved, for example, with a pressure from a liquid propellant in a supercritical state (as described in more detail with respect to the embodiment of the injection device shown in FIG. 18). In some other variations, the power assembly may provide a varying force for the duration of the injection.

In some variations, the rate control assembly may comprise a braking assembly that may limit or restrict the stored energy source from contributing to the displacement of the contents of the reservoir of the syringe. In some variations, the rate control assembly may be configured to do so by limiting or restricting the distal movement of a plunger or seal within the syringe cavity.

Figure 7:
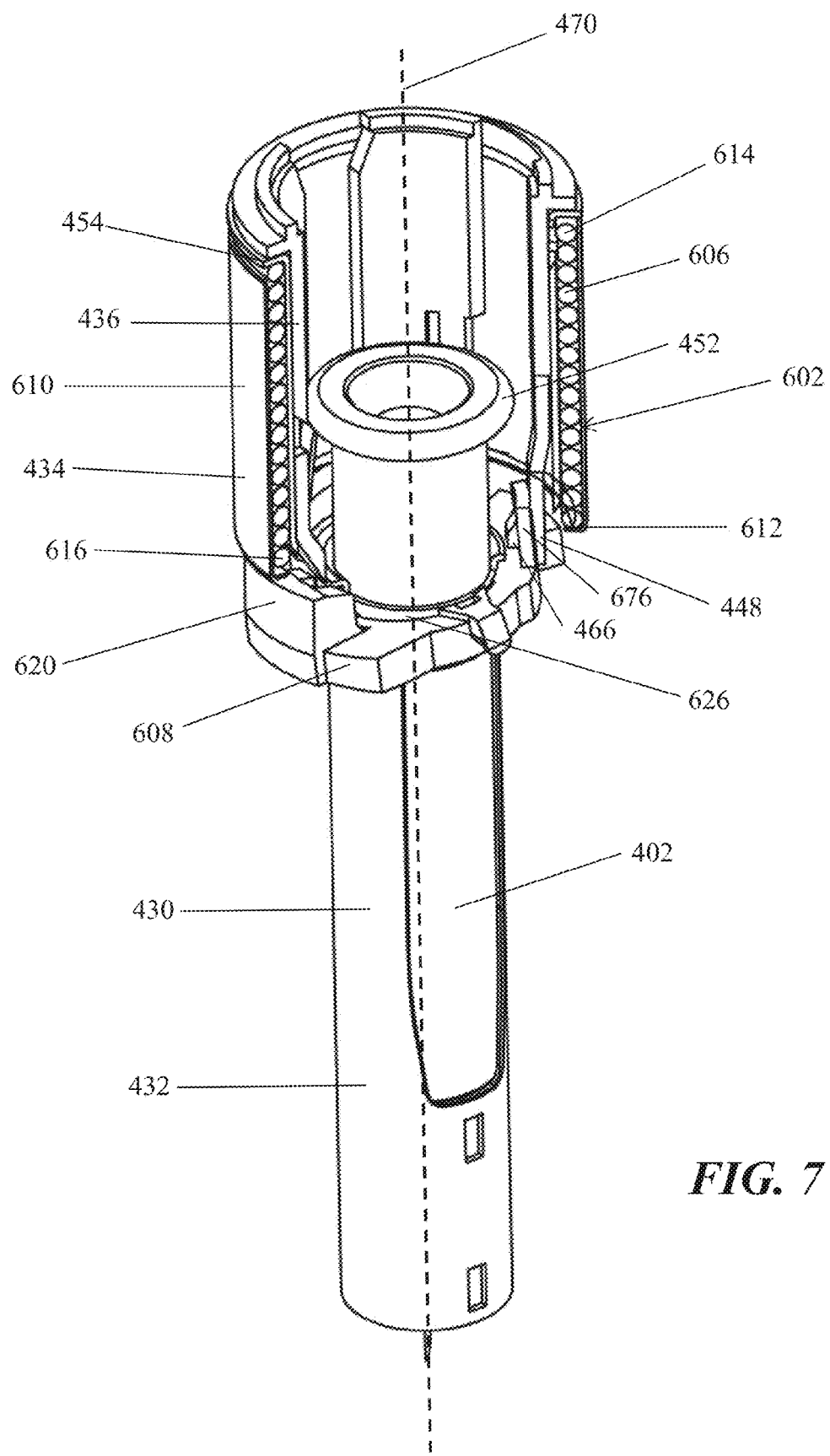
FIG. 7 depicts a perspective view of the stored energy source of the injection device of FIG. 1.

FIG. 7 depicts a perspective view of an example of the stored energy source 602 of the injection device 100. The stored energy source 602 may comprise a compression spring 606. The compression spring 606 may be directly or indirectly attached or in contact with a first surface fixed relative to the distal housing 110 on one end, and may be directly or indirectly attached or in contact with the a second surface fixed relative to the plunger 510 of the ram 502 on the other end. Thus, the force from the compression spring 606 on the first and second surfaces may bias the first and second surfaces away from each other, which may in turn bias the plunger 601 distally relative to the syringe cavity 404. More specifically, the compression spring 606 may be sized to fit within the distal housing 110 and around the proximal portion 434 of the syringe sleeve 430. The compression spring 606 may be housed by a spring sleeve 610, but need not be. In variations having a spring sleeve 610, the spring sleeve 610 may be substantially cylindrical and configured to fit around the compression spring 606. The spring sleeve 610 may be moveable relative to the syringe sleeve 430, and may have an inwardly extending distal lip 612. The distal end 616 of the compression spring 606 may be attached or connected to the distal lip 612. The proximal end 614 of the compression spring 606 may be attached or connected to an inwardly extending proximal lip 454 on the proximal portion 432 of the syringe sleeve 430, which may in turn be fixed relative to the distal housing 110, as described above.

Figure 8A:
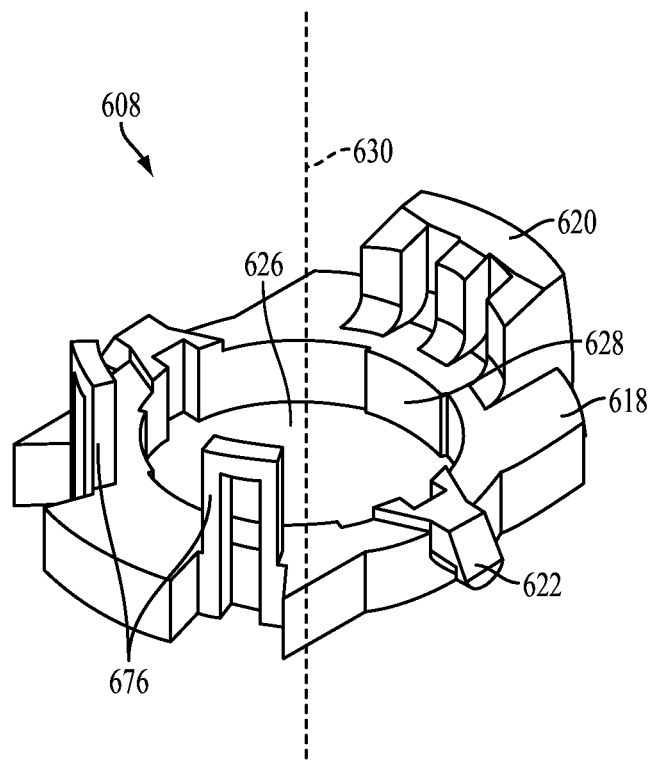
FIGS. 8A-8B are perspective side views of the rate control assembly of the injection device of FIG. 1.
Figure 8B:
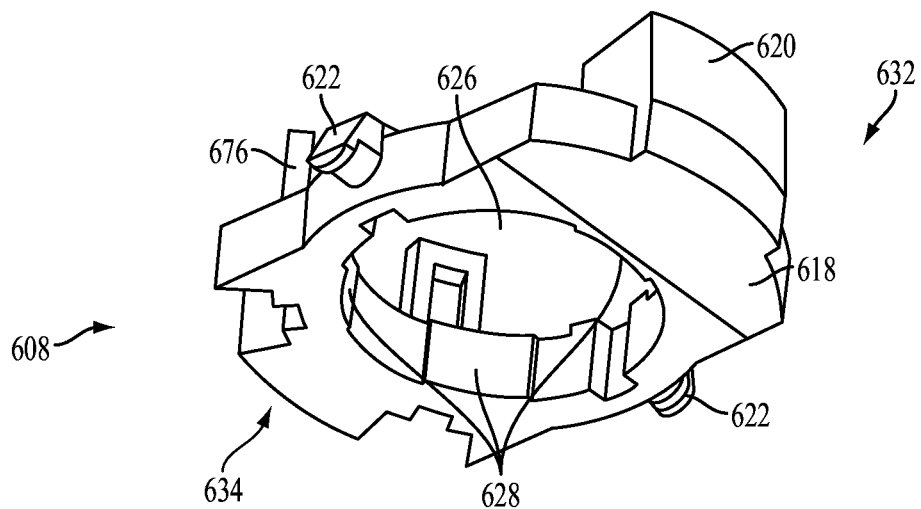

The force from the compression spring 606 against the distal lip 612 of the spring sleeve 610 may be transmitted into distal motion of the ram 502 by a biter 608, as shown in FIGS. 8A-8B. Alternatively, in some variations not having a syringe sleeve, the compression spring may press directly against the biter. As shown in FIGS. 8A-8B, the biter 608 may comprise a main body 618. The main body 618 may be configured to fit within the distal housing 110 and may have a lumen 626 therethrough. The biter 608 may comprise one or more inner projections 628 extending inward into the lumen 626, described in more detail below. In some variations, the biter 608 may comprise two attachment ports 622, which may be configured to engage with the distal ends 538 of the straight portions 520 of the arms 506 of the ram 502 when the syringe 104 reaches an extended position, as shown in FIG. 2H. In some variations, the distal ends 538 of the ram 502 may engage with the attachment ports 622 by deflecting radially outward as the distal ends 538 come into contact with the attachment ports 622 as the ram 502 moves distally, and then snapping into place onto the attachment ports 622. The engagement between the attachment ports 622 and the distal ends 538 is such that the biter 608 may rotate relative to ram 502, as described in more detail below.

As shown in FIG. 7, the lumen 626 of the biter 608 may be configured to fit slidably around the distal portion 432 of the syringe sleeve 430. While the lumen 626 is shown as having a substantially circular cross-section, it should be appreciated that the lumen 626 may have any suitable shape (e.g., having an elliptical cross-section, oblong cross-section, ovoid cross-section, square cross-section, rectangular cross-section, triangular cross-section, etc.), depending in part on the cross-section of the syringe 104 and/or syringe sleeve 430. As shown in FIG. 7, the distal lip 612 of the spring sleeve 610 may press distally against the proximal projection 620 of the biter 608. The compression spring 606 may therefore bias the biter 608 distally away from the proximal end 614 of the spring sleeve 610. This may in turn bias the arms 506 of the ram 502 distally away from the proximal end 614 of the spring sleeve 610, which may bias the plunger 510 of the ram 502 distally relative to the syringe sleeve 430 and within the syringe cavity 404.

Figure 21:
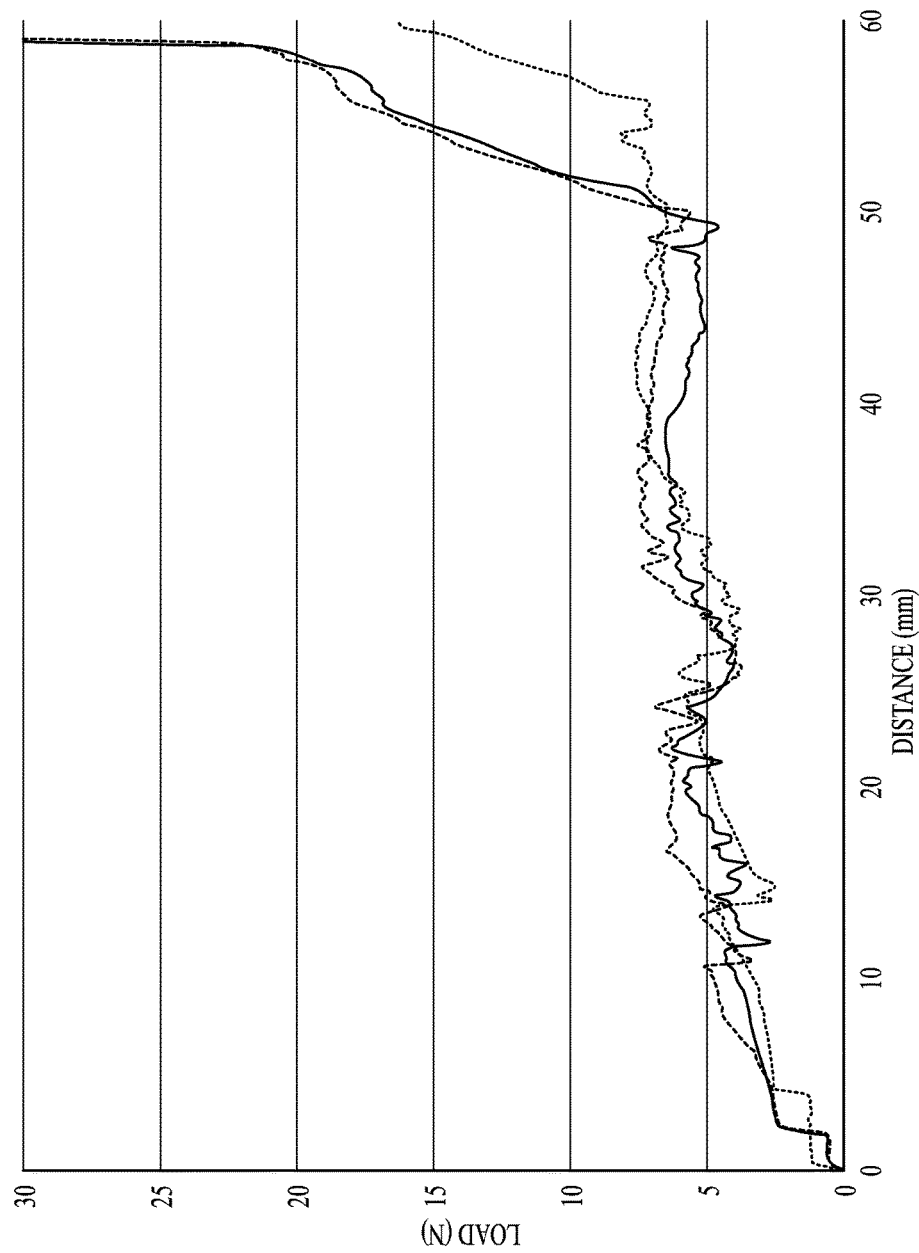
FIG. 21 shows an illustrative graph of the user force required to perform an injection using an injection device similar to the injection device of FIG. 1.

The compression spring 606 may be made of any suitable material, such as but not limited to music wire, stainless steel, and spring steel. The spring rate of the compression spring 606 may be chosen to deliver an appropriate force based on the formulation viscosity, needle choice, volume, and desired injection time, as described above. In some variations, for example, the compression spring 606 may be configured to deliver a force of up to about 5 N, about 10 N, about 15 N, about 20 N, about 25 N, about 30 N, about 35 N, about 40 N, about 45 N, about 50 N, about 55 N, about 60 N, about 65 N, about 70 N, about 75 N, about 80 N, about 85, or about 90 N when the compression spring 606 initially begins to expand. FIG. 21 show an illustrative graph of the user force required to perform an injection using an injection device having a power assembly similar to the power assembly 106 of the injection device 100, illustrating the initial actuation force and relatively stable spring fade. The graph represents a liquid having a viscosity of approximately 9 cP injected through a 27 gauge, thin-wall needle, with the seal displacing the contents of the reservoir at approximately 6 mm/s, which generally requires approximately 15 N of force. However, as seen in the graph, approximately 4 to 6 N of user force was required, thus representing a load multiplication factor around 3. It should be noted that this graph is merely illustrative of the force requirements for a similar device, and is not meant to indicate that the injection device 100 may or must conform to this representation.

As described above, the rate control assembly of the power assembly may at times comprise a braking assembly that may slow, limit, or restrict the stored energy source from providing force to displace the contents of the reservoir of the syringe. In some variations, the rate control assembly may be moveable between a closed configuration and an open configuration. When the rate control assembly is in a closed configuration, the rate control assembly may stop or reduce the displacement of the contents of the reservoir of the syringe. When the rate control assembly is in an open configuration, the rate control assembly may not limit or restrict the displacement of the contents of the reservoir of the syringe. In some variations, the rate control assembly may be configured to limit or restrict the displacement of the contents of the reservoir of the syringe by limiting or restricting the distal motion of a plunger within the syringe cavity when in a closed configuration. When in an open configuration, the rate control assembly may not limit or restrict the distal motion of a plunger within the syringe cavity, thus allowing the stored energy source to act upon the plunger to move it distally relative to and within the syringe cavity, which may move the seal of the syringe distally within the syringe cavity to displace the contents of the reservoir through the lumen of the needle.

The rate control assembly may be a braking assembly. In some variations, force generated by the rate control assembly and/or another component of the injection device 100 may counteract or partially or fully oppose the force from the stored energy source. In some variations, the braking assembly may be friction-based. That is, when the rate control assembly is in a closed configuration, friction between the rate control assembly and another component of the injection device 100 may counteract or partially or fully oppose the force from the stored energy source. In some variations, the force when the rate control element is in a closed configuration (e.g., friction between the rate control assembly in a closed configuration and another component of the injection device 100) may counteract or oppose the force from the stored energy source completely, resisting distal movement of the plunger 510 within the syringe cavity 404 of the syringe 104. In other variations, the force (e.g., friction between the rate control assembly in a closed configuration and another component of the injection device) may partially counteract or oppose the force from the stored energy source, damping the distal movement of the plunger within the syringe cavity due to the stored energy source. In some variations, when the rate control assembly is in an open configuration, there may not be a force (e.g., friction between the rate control assembly and another component of the injection device 100) opposing the stored energy source, which may allow the stored energy source to cause the plunger 510 to be moved distally within the syringe cavity 404 of the syringe 104. In other variations, there may be a force (e.g., friction between the rate control assembly and another component of the injection device 100) opposing the stored energy source, but the force may be less than is required to fully resist the stored energy source from acting on the plunger 510.

Figure 9:
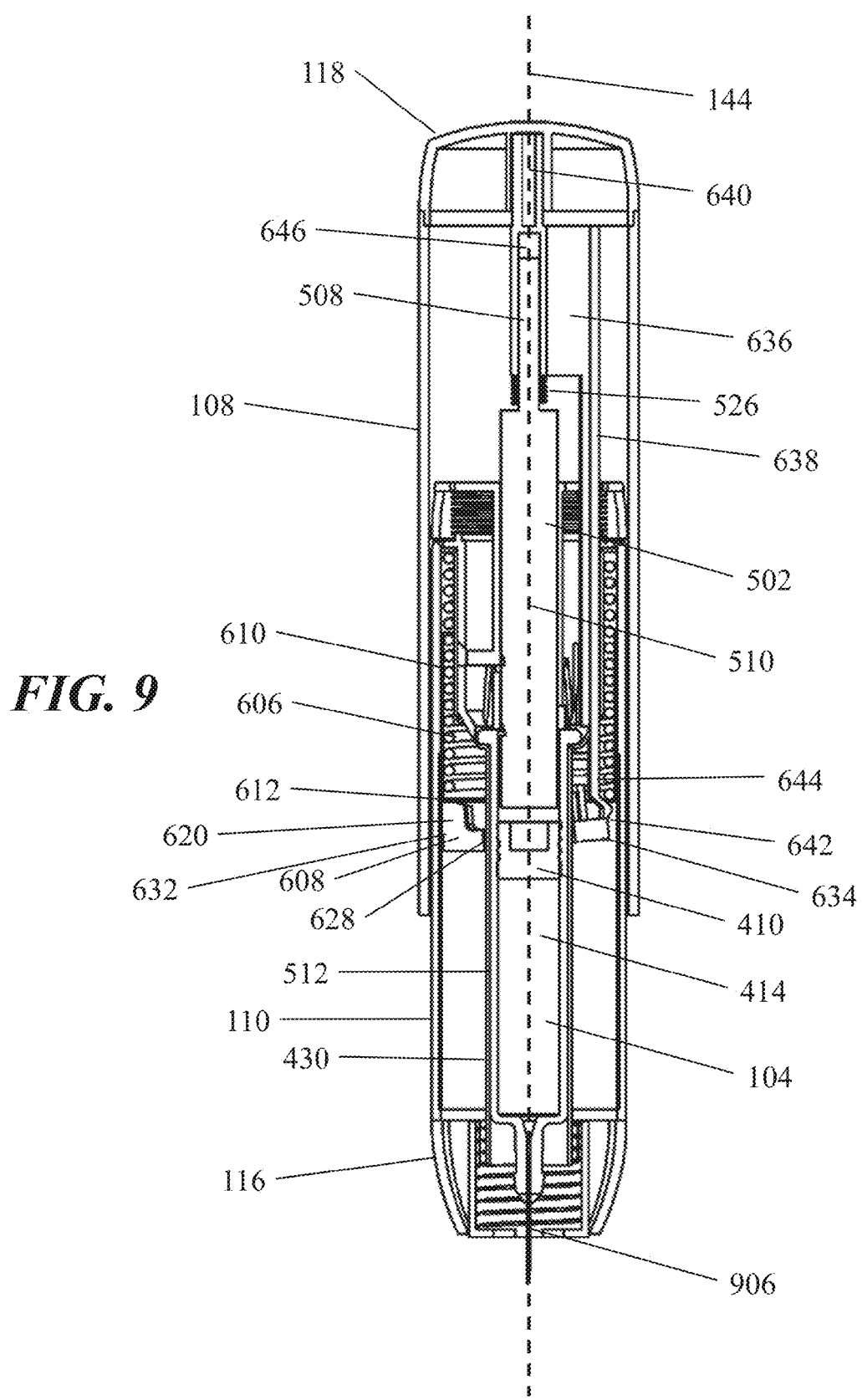
FIG. 9 illustrates a longitudinal cross-sectional view of the rate control assembly.

As shown in FIG. 9, the rate control assembly 604 may comprise the biter 608 discussed above. The biter 608 may be reversibly and selectively moved between open and closed configurations. When the biter 608 is in a closed configuration, friction between the biter 608 and the syringe sleeve 430 may counteract or partially or fully oppose the distal force from the compression spring 606. The friction may be due to contact between the inner projections 628 of the biter 608 and the syringe sleeve 430. The inner projections 628 may be configured such that when the biter 608 is tipped such that the longitudinal axis 630 through the lumen 626 is displaced from the longitudinal axis 144 of the housing 102 (and thus displaced from the longitudinal axis 470 of the syringe sleeve 430), the inner projections 628 come into contact with the syringe sleeve 430 with a force sufficient to create enough friction to counteract or partially or fully oppose the distal force from the compression spring 606. While FIGS. 8A-8B show the biter 608 as comprising three inner projections 628 approximately equally spaced around the circumference of the lumen 626, it should be appreciated that in other variations, the biter may comprise other numbers of inner projections and/or arrangements. For example, in some variations, the biter may comprise two or four inner projections equally spaced around the circumference of the lumen.

When the biter 608 is in an open configuration, the longitudinal axis 630 through the lumen 626 of the main body 618 of the biter 608 may be rotated from the open configuration toward a position parallel to the longitudinal axis 144 of the housing 102 (and thus toward a position parallel to the longitudinal axis 470 of the syringe sleeve 430). While in some cases the biter 608 may rotate such that the longitudinal axis 630 may be parallel to the longitudinal axis 144 of the housing, the longitudinal axis 630 need not rotate so far as to be parallel to the longitudinal axis 144 in order to be in an open configuration. Once rotated into an open configuration, the inner projections 628 may not be in contact with the syringe sleeve 430. Thus, there may not be friction between the biter 608 and the syringe sleeve 430. In some variations, the biter 608 may also, but need not, have an intermediate configuration (not shown), wherein there is friction between the biter 608 and the syringe sleeve 430, but the friction between the biter 608 and the syringe sleeve 430 may be less than the distal force from the compression spring 606. It should be appreciated that some variations of the injection devices described here may not have a syringe sleeve, and in those variations, when the biter is in a closed configuration, there may be friction between the inner projections 628 and the outer surface 512 of the syringe body 402. While the force in the embodiment shown in FIG. 9 is due to friction, it should also be appreciated that in other variations the force may be due to another form of interaction between the braking assembly and another component of the injection device. For example, in some variations, a biter may comprise one or more features (e.g., ridges or teeth) that are configured to mechanically interact or interface with one or more features of a syringe sleeve (e.g., ridges or teeth), which may generate a force that may partially or fully oppose the force from the stored energy source.

In some variations, the rate control assembly 604 may be biased toward a closed configuration, such as by a distal force on the biter 608 that acts radially asymmetrically on the biter 608. In the power assembly 106, the biter 608 may be biased toward a closed configuration by the compression spring 606. The force from the compression spring 606 biasing the distal lip 612 of the spring sleeve 610 away from the proximal lip 454 of the syringe sleeve 430 may cause the distal lip 612 of the spring sleeve 610 to push distally against the proximal projection 620 of the biter 608, as described above. The proximal projection 620 of the biter 608 may extend around less than 180 degrees of the main body 618 of the biter 608 on a first side 632, and therefore the distal force on the proximal projection 620 of the biter 608 from the distal lip 612 of the spring sleeve 610 may cause the biter 608 to tilt such that the first side 632 may move distally relative to the other second side 634 of the biter 608. The longitudinal axis 630 through the lumen 626 of the biter 608 may thus be rotated relative to the longitudinal axis 144 of the housing 102. This may cause the biter 608 to move into a closed configuration and the inner projections 628 of the biter 608 to contact the syringe sleeve 430, as described above. It should be appreciated that while in the embodiment of the biter 608 shown in FIGS. 8A-8B the proximal projection 620 extends approximately 40 degrees around the main body 618 of the biter 608 and is approximately 8 mm in width, in other embodiments, the proximal projection 620 may extend less or more around the biter 608 (e.g., about 10 degrees, about 20 degrees, about 40 degrees, about 60 degrees, about 80 degrees).

The rate control assembly 604 may further have, in addition to open and closed configurations, an inactivated configuration (shown in FIG. 7). In the inactivated configuration, the biter 608 may be held by the interlocker 436, such that it resists movement relative to the interlocker 436. The interlocker 436 may comprise a biter interlock 448, which may comprise a tab 466 that may extend inwardly from the distal end of the biter interlock 448. The tab 466 may be configured to mate with a projection 676 of the biter 608. When the tab 466 is mated with the projection 676, the biter interlock 448 may resist motion of the biter 608 relative to the interlocker 436. As shown in FIG. 8A, the projection 676 may comprise a U-shaped hook, through which the tab 466 may attach, as shown in FIG. 7. The tab 466 may resist distal motion of the projection 676, and in turn of the biter 608 relative to the interlocker 436. The rate control assembly 604 may be released from the inactivated configuration by distal movement of the syringe 104. In the variation shown in FIG. 7, the biter 608 may be released from the interlocker 436 by the proximal lip 452 of the syringe body 402. As the proximal lip 452 moves distally relative to the interlocker 436 as the syringe 104 moves toward an extended configuration, the proximal lip 452 may press against the tab 466 of the biter interlock 448, pushing it radially outward. When the tab 466 is pushed radially outward, it may move outward through the opening in the U-shaped hook of projection 676 and may disengage from the projection 676. The biter 608 may thus no longer be held in place by interlocker 436. While the variation shown in FIG. 7 comprises two biter interlocks 448 configured to mate with two projections 676, it should be appreciated that in other variations, the interlocker 436 may comprise fewer (e.g., zero or one) or more (e.g., three, four, five, or more) biter interlocks and/or projections.

The biter 608 may be moved into an open configuration by rotating the biter 608 such that the longitudinal axis 630 through the lumen 626 of the main body 618 of the biter 608 is moved toward a position parallel to the longitudinal axis 144 of the housing 102 (and thus toward a position parallel to the longitudinal axis 470 of the syringe sleeve 430). As described above, while in some cases the biter 608 may rotate such that the longitudinal axis 630 may be parallel to the longitudinal axis 144 of the housing, the longitudinal axis 630 need not rotate so far as to be parallel to the longitudinal axis 144 in order to be in an open configuration. In some variations, the biter 608 may be moved from a closed configuration to an open configuration by application of a distal force on second side 634 of the biter 608. Such a distal force may counterbalance or partially or fully oppose the distal force on the proximal projection 620 of the biter 608 from the distal lip 612 of the spring sleeve 610. FIG. 9 shows one example of an actuation rod 636 that may apply this distal force. The actuation rod 636 may be selectively and reversibly moved between an advanced position, during which it may engage the biter 608 at a contact point 642 on the second side 634 to urge it toward an open configuration, and a withdrawn position, during which it may not engage the biter 608, thus leaving the biter 608 in a closed configuration. The distal end 644 of the actuation rod 636 may be configured to engage the second side 634 of the biter 608 at the contact point 642. In some variations, the contact point 642 may optionally comprise a concave region to assist in alignment of the actuation rod 636 and biter 608. In some variations, the distal end 644 of the actuation rod 636 may optionally have one or more features to promote engagement with the contact point 642 of the biter 608. When the actuation rod 636 presses on the biter 608 at the contact point 642, the actuation rod 636 may tilt the biter 608 into an open configuration (described above). This may occur when the distal end 644 of the actuation rod 636 presses down on the contact point 642 with sufficient force to counteract or partially or fully oppose the force from the compression spring 606 on the proximal projection of the biter 608.

When the syringe 104 is in an extended position (described above), the actuation rod 636 may be selectively and reversibly moved between advanced and withdrawn positions by applying distal force to the proximal housing 108. When distal force is applied to the proximal housing 108 while the distal housing 110 is held in place (e.g., by pressing the distal end 158 of the nose 116 of the distal housing 110 against a patient's tissue) and the syringe 104 is in an extended position, the proximal housing 108 and the actuation rod 636 may be moved distally relative to the biter 608. The force on the contact point 642 of the biter 608 from the distal end 644 of the actuation rod 636 may move the biter 608 into an open configuration as described above. When the biter 608 is in an open configuration, the distal force applied to the distal end of the housing and the distal force from the compression spring 606 may both act to urge the biter 608 distally. This in turn may urge the plunger 510 distally via the arms 506 of the ram 502, which in turn may urge the seal 410 distally to displace the contents of the reservoir 414 through the lumen 408 of the needle 406, as described above.

In some variations, the actuation rod 636 may be moveable between advanced and withdrawn positions relative to the biter 608 by distal force on the proximal housing 108 because the relative locations of the ram 502 and the actuation rod 636 may be variable. In some variations, the actuation rod 636 may comprise an elongate rod 638 having a proximal end 640 that is fixedly attached to the proximal housing 108. While the actuation rod 636 is shown in FIG. 9 as attaching to the inner surface 186 of end cap 118 of proximal housing 108, it should be appreciated that in other variations the actuation rod 636 may be fixed to the proximal housing 108 at other locations and via other methods, or in other variations may be integral to the proximal housing 108. In contrast, the ram 502 may have extended and retracted positions relative to the actuation rod 636 and/or to the proximal housing 108. In one variation, the connector rod 508 of the ram may fit within a bore 646 in the actuation rod 636, being slidable between an extended position and a retracted position within the bore 646. In another variation (not shown), the proximal end of the ram may be slidable between an extended position and a retracted position within a receiving cup on the inside of the end cap. In some variations, the ram 502 may be biased toward an extended position relative to the proximal end of the proximal housing 108. The biasing may be due to a compression spring 526. More specifically, the compression spring 526 may fit slidably around the connector rod 508 of the ram 502. The ram 502 may be biased toward an extended position relative to the actuation rod 636 by the compression spring 526, which may fit slidably around the connector rod 508 between the plunger 510 and the actuation rod 636. In other variations (not shown) in which the ram is connected to the end cap directly, the proximal end of the compression spring may be in contact with or attached to a portion of the end cap and the distal end of the compression spring may be in contact with a portion of the ram. Thus, the compression spring 526 may bias the ram 502 and the proximal housing 108 away from each other, thus biasing the ram 502 toward an extended position. It should be appreciated that the compression spring 526 may be at other locations in order to bias the ram 502 and the proximal housing 108 away from each other.

Thus, when the syringe 104 is in an extended position (described above), the actuation rod 636 may be selectively and reversibly moved between advanced and withdrawn positions by applying distal force to the proximal housing 108, which may move the ram 502 from an extended to a retracted position relative to the actuation rod 636.

If the distal force on the proximal housing 108 is released, the bias of the ram 502 toward an extended configuration relative to the actuation rod 636 due to the compression spring 526 may cause the proximal housing 108 and actuation rod 636 to move distally away from the ram 502. However, the syringe 104 may stay in place relative to the syringe sleeve 430, and the ram 502 may stay in place relative to the syringe 104. As such, the actuation rod 636 may be moved from an advanced position to a withdrawn position, to move distally away from the biter 608 such that it no longer contacts the biter 608 at the contact point 642. Removing the application of distal force at the contact point 642 may cause the biter 608 to return to a closed configuration, as described above. This may allow the user to selectively and reversibly start and stop, or increase or decrease the speed of, the injection process.

Figure 24A:
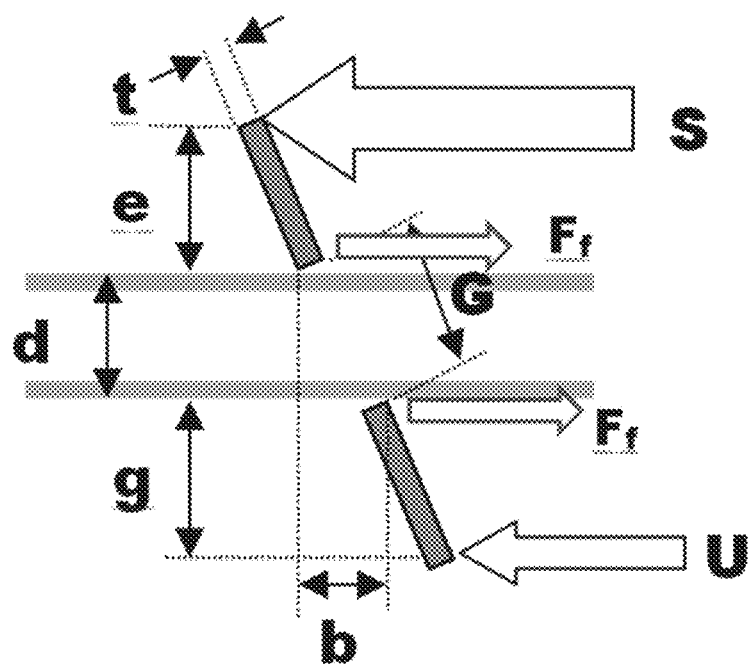
FIG. 24A shows a schematic representation of a model of a two-dimensional friction-based biter having two contact points.
Figure 24B:
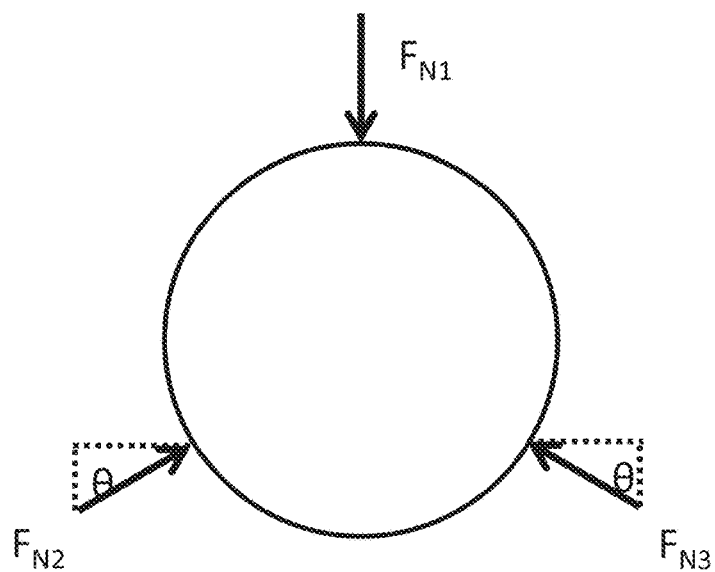
FIG. 24B shows a schematic representation of a model of a friction-based biter having three contact points.

In some variations, but not wishing to be bound by such a theory, the amount of distal force that may be applied to the second side of the a biter having a similar design to the biter 608, in order to move the biter from a closed configuration to an open configuration, may be mathematically described in a two-dimensional model as $$U = \frac{S\left(e + \frac{d}{2} - \frac{b}{2\mu}\right)}{\frac{d}{2} + \frac{b}{2\mu} + g}$$

where U is the distal force applied, S is the force from the compression spring on the biter, μ is the coefficient of friction between the syringe sleeve and the biter, and e, g, d, t, and G represent the distances illustrated schematically in FIG. 24A. In a model having three points of contact between the biter and the syringe sleeve, the amount of distal force that may be applied to the second side of a biter to move it from a closed configuration to an open configuration may similarly be mathematically described as $$U = \frac{S\left(e + \frac{d}{1+\cos\theta} - \frac{b}{(1+\sec\theta)*\mu}\right)}{d - \frac{d}{1+\cos\theta} + \frac{b}{(1+\sec\theta)*\mu} + g}$$

where θ represents the angle of the points of contact, as illustrated schematically in FIG. 24B. It should of course be appreciated that these equations describe highly simplified models and may not represent the actual force required the move the biter 608 described here from a closed to an open configuration.

In some variations, the injection device 100 may comprise an autocomplete mechanism, which may cause the full volume of the reservoir 414 to be automatically displaced through the lumen 408 of the needle 406 within a certain tolerance of the total injection (e.g., within about 85% of the injection, within about 90% of the injection, within about 95% of the injection, or more, or within about 1 mm of full displacement, about 2 mm of full displacement, about 3 mm of full displacement, or about 4 mm of full displacement, etc.), regardless of a user's application of distal force to the proximal housing 108. In some variations, autocompletion may be caused by the biter 608 and syringe sleeve 430 no longer generating a frictional force once the biter 608 moves to a particular distal point along the distal portion 434 of the syringe sleeve. For example, the distal portion 434 of the syringe sleeve 430 may comprise a region near its distal end having a smaller diameter (or maximum distance transverse to the longitudinal axis) smaller than the remainder of the distal portion 434 of the syringe sleeve 430, such that when the biter 608 moves distally to reach this region, the biter 608 may no longer contact the syringe sleeve 430. Thus, there may be no friction between the biter 608 and the syringe sleeve 430, and thus no force opposing the distal force from the compression spring 606. As a result, the dose may autocomplete. As another example, instead of the full diameter of the distal portion 434 being smaller in a region near its distal end, the distal portion 434 of the syringe sleeve 430 may comprise inward notches at the locations at which the biter 608 would contact the syringe sleeve 430 (e.g. at the locations of inner projections 628), which may eliminate or reduce the friction between the biter 680 and syringe sleeve 430 to cause autocompletion.

In some variations, one or more of the elements of injection device 100 may optionally comprise clocking features to correctly orient the elements relative to each other. In some variations, elements of the injection device 100 may comprise longitudinal ribs and grooves (e.g., narrow grooves molded onto the interior of the proximal housing 108 and short mating ribs on the exterior of distal housing 110) that may engage to provide alignment, and may also resist rotation of the elements relative to each other once engaged. In some variations, elements of the injection device 100 may comprise one or more (e.g., two, three, four, five, or more) teeth on a first element and a corresponding one or more (e.g., two, three, four, five, or more) slots in a second element, wherein the teeth and slots are configured to engage when the first and second slots are properly aligned.

Figure 10:
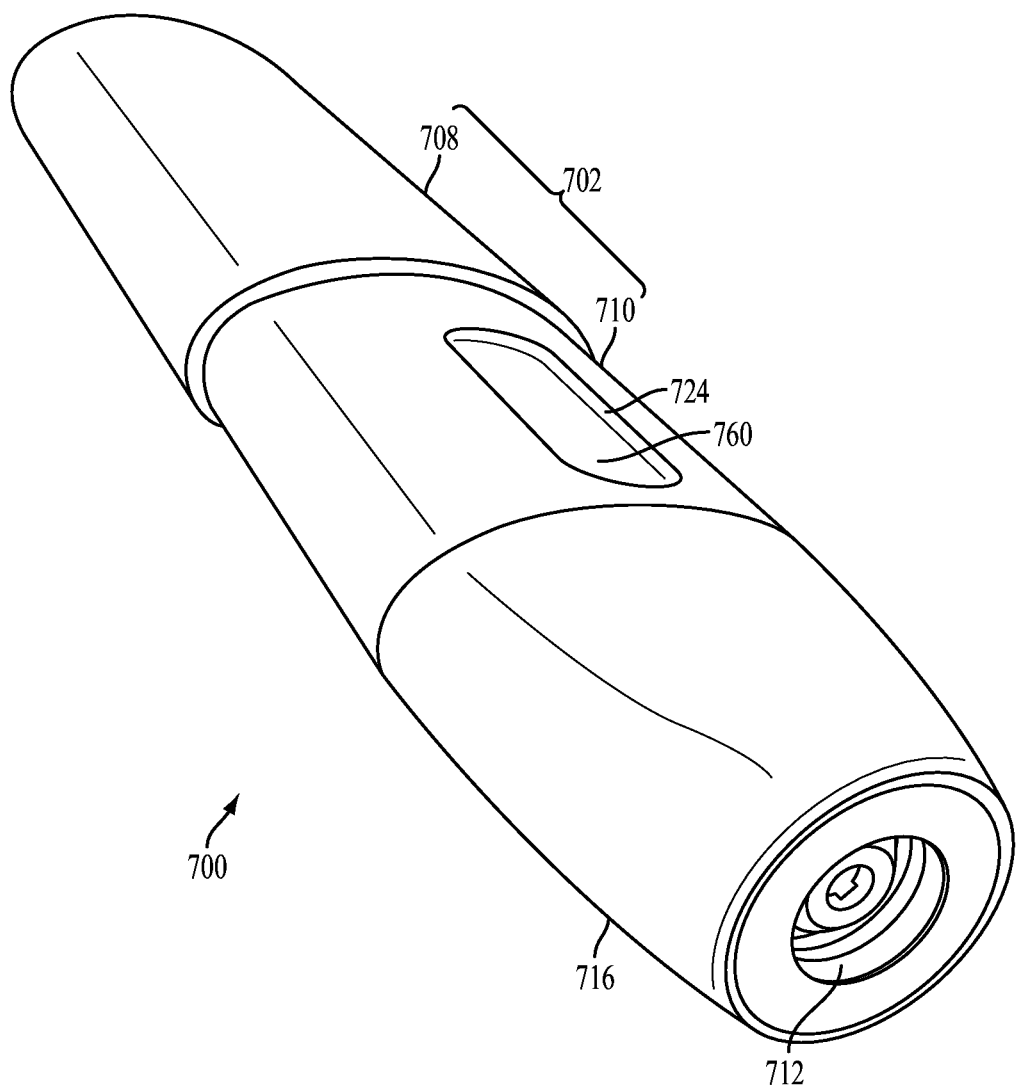
FIG. 10 is a perspective view of another embodiment of an injection device.

Another embodiment of an injection device 700 is depicted in FIGS. 10, 11A-11B, and 12A-12F, comprising a housing 702, a syringe 704, and a power assembly 706. The housing 702 may be similar to the housing 102 described above with respect to injection device 100, and may have the same components, configurations, and functions. As shown in FIG. 10, however, the proximal housing 708 and distal housing 710 may have an elliptical cross-section, which may accommodate the power assembly 706, described below. An elliptical shape may also have certain benefits, including having an ergonomic form, allowing the contents of the syringe to be easily viewed, and resisting rolling of the device when being handled or stored. In some variations, the minor axis of the cross-section of the housing 702 may be less than or equal to about 20 mm, about 25 mm, about 30 mm, about 35 mm, or about 40 mm. Additionally or alternatively, in some variations, the viewing region 724 may comprise an opening 760 in the distal housing 110, which may have a rounded rectangular shape.

Figures 11A, 11B:
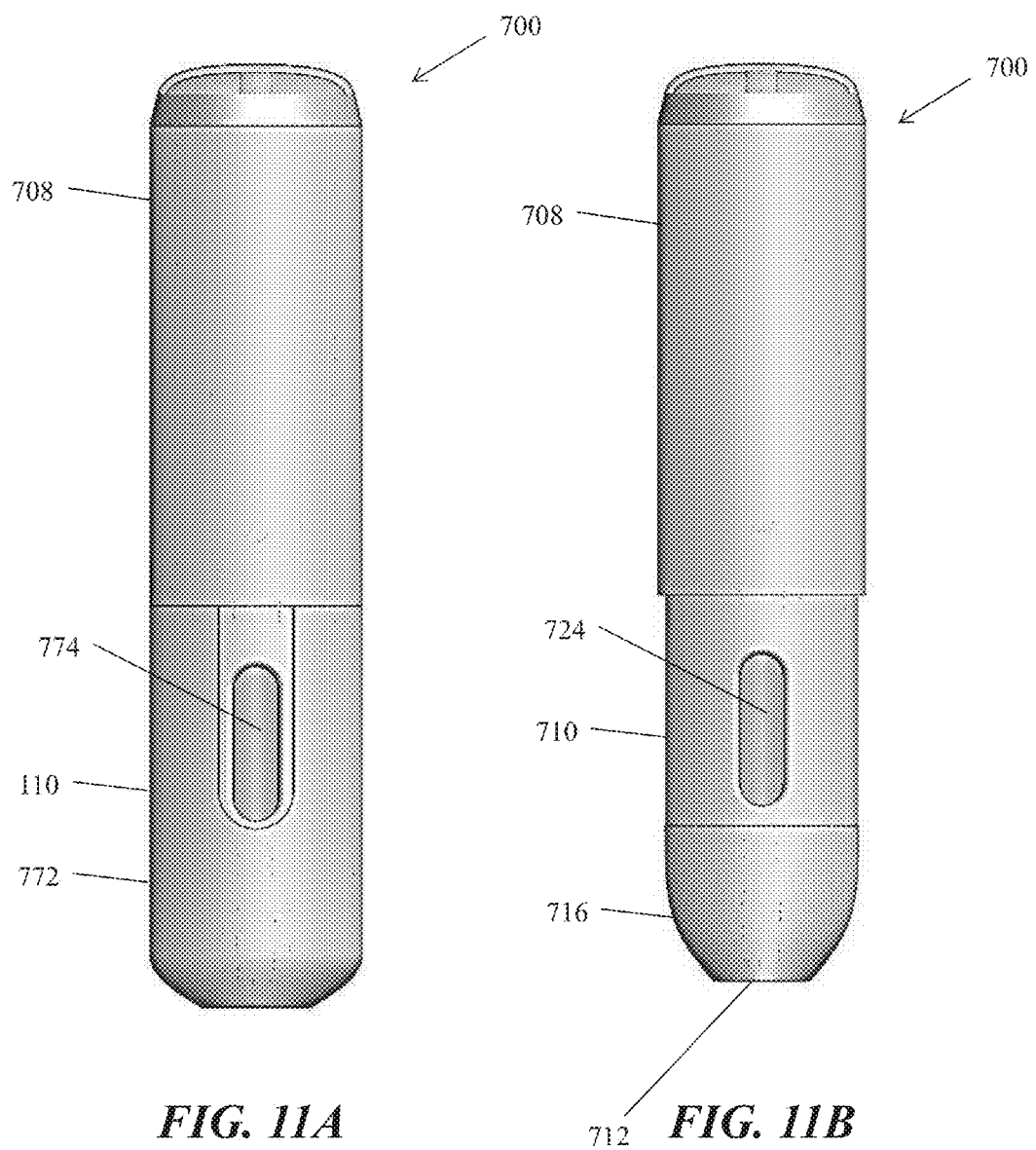
FIGS. 11A-11B are elevational side views of the injection device of FIG. 10 with the cap attached and removed, respectively.

In some variations, the housing 702 may optionally further comprise a cap 772, which may be similar to the cap 148 described above with respect to injection device 100, and may have the same components and functions as described above. FIGS. 11A-11B show side views of the injection device 700 with a cap 772 attached and removed, respectively. The cap 772 may comprise a viewing region 774, which may coincide with the viewing region 724 of the distal housing when the cap 772 is attached to the remainder of the housing 702.

Figure 12A:
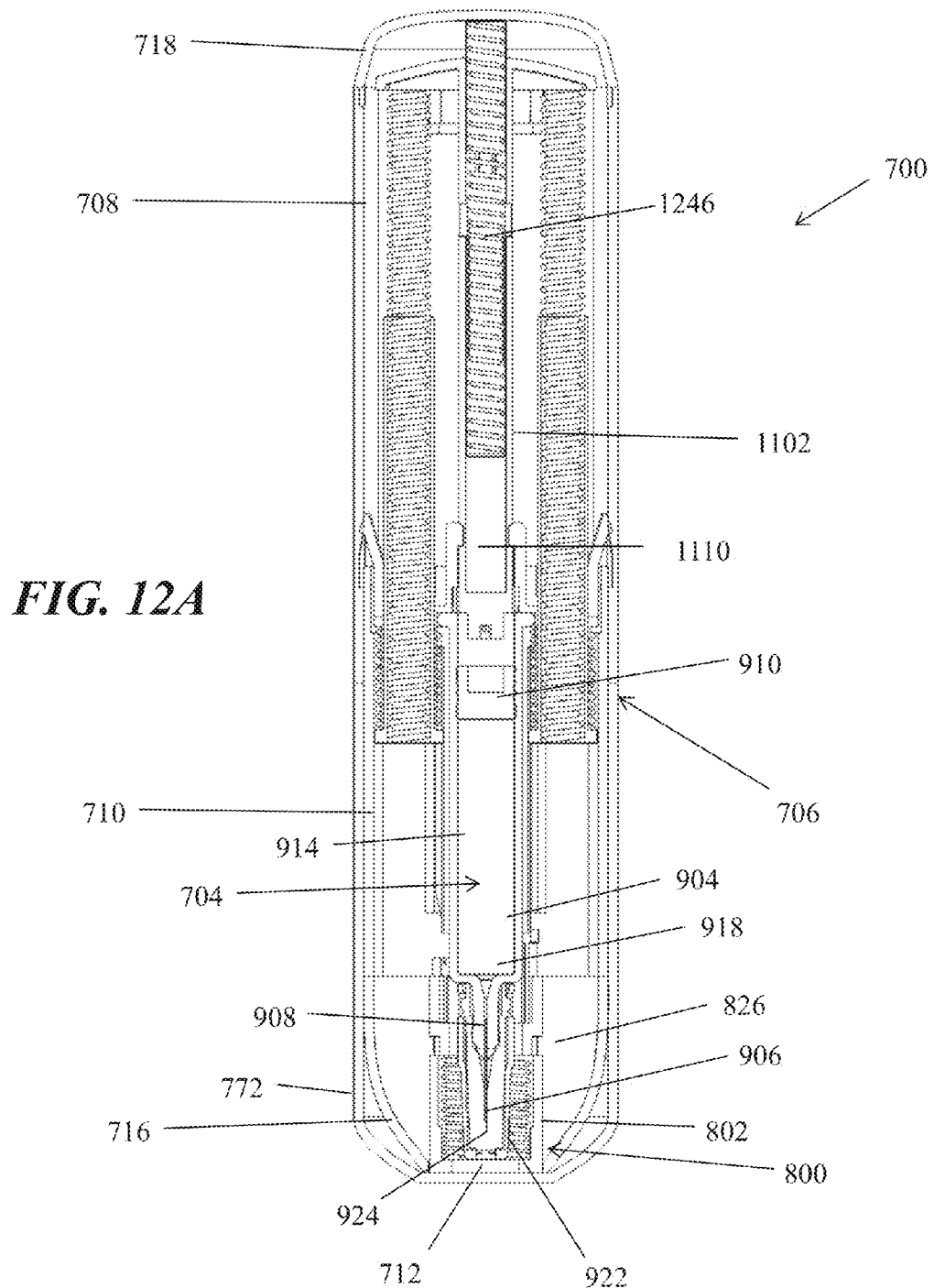
FIGS. 12A-12F are longitudinal cross-sectional views the embodiment of an injection device of FIG. 10 in various stages during use.
Figure 12B:
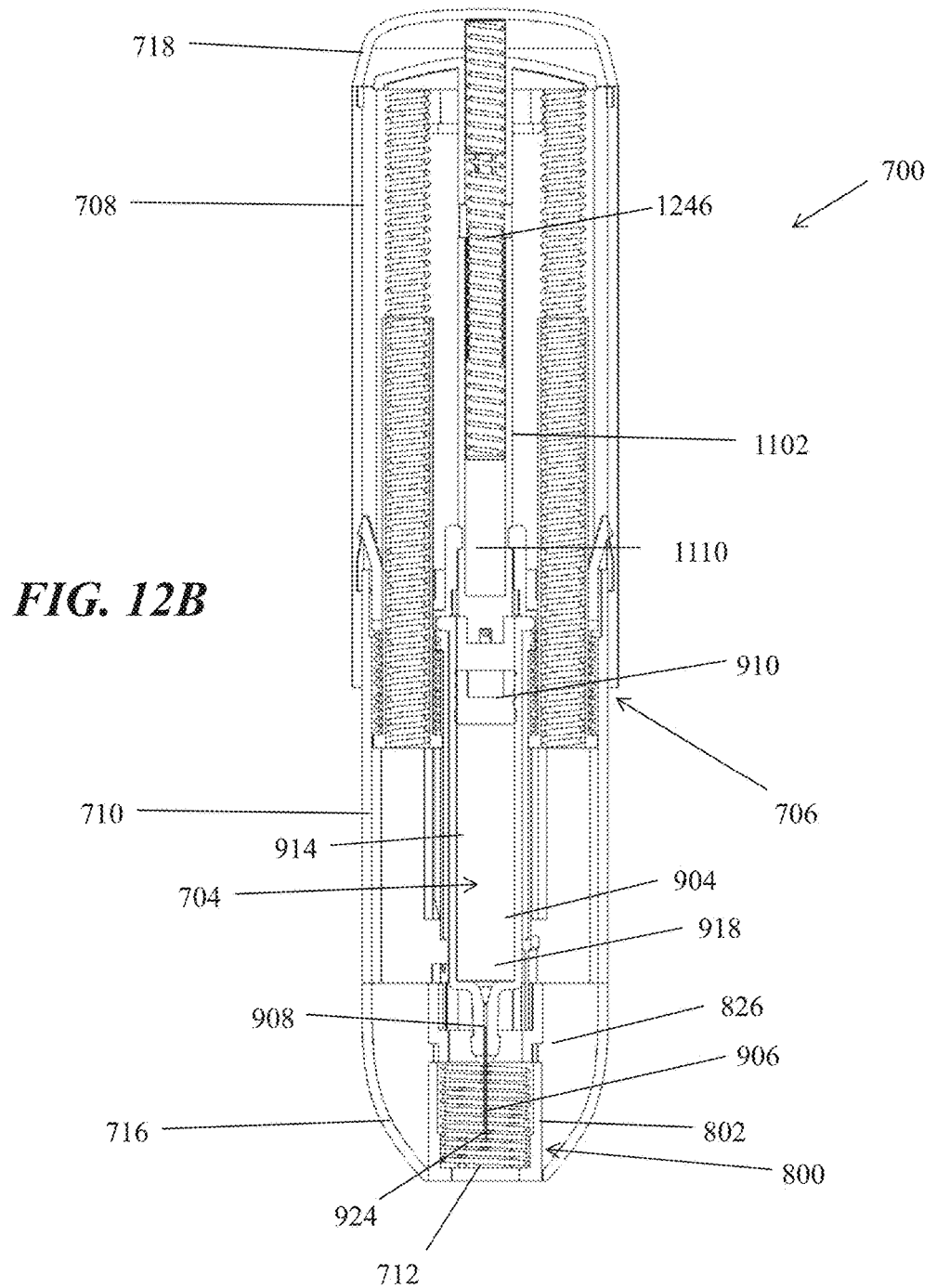
Figure 12C:
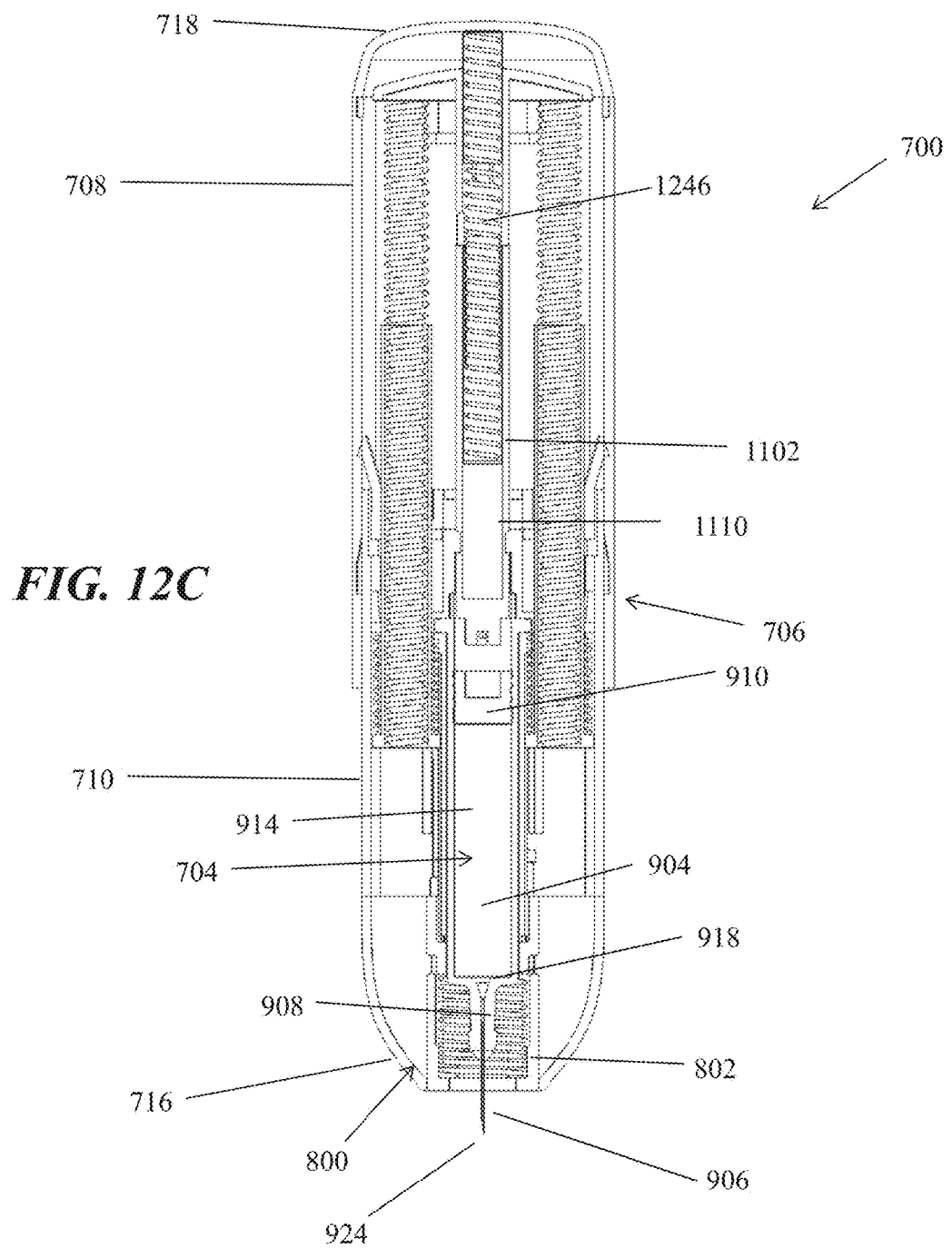
Figure 12D:
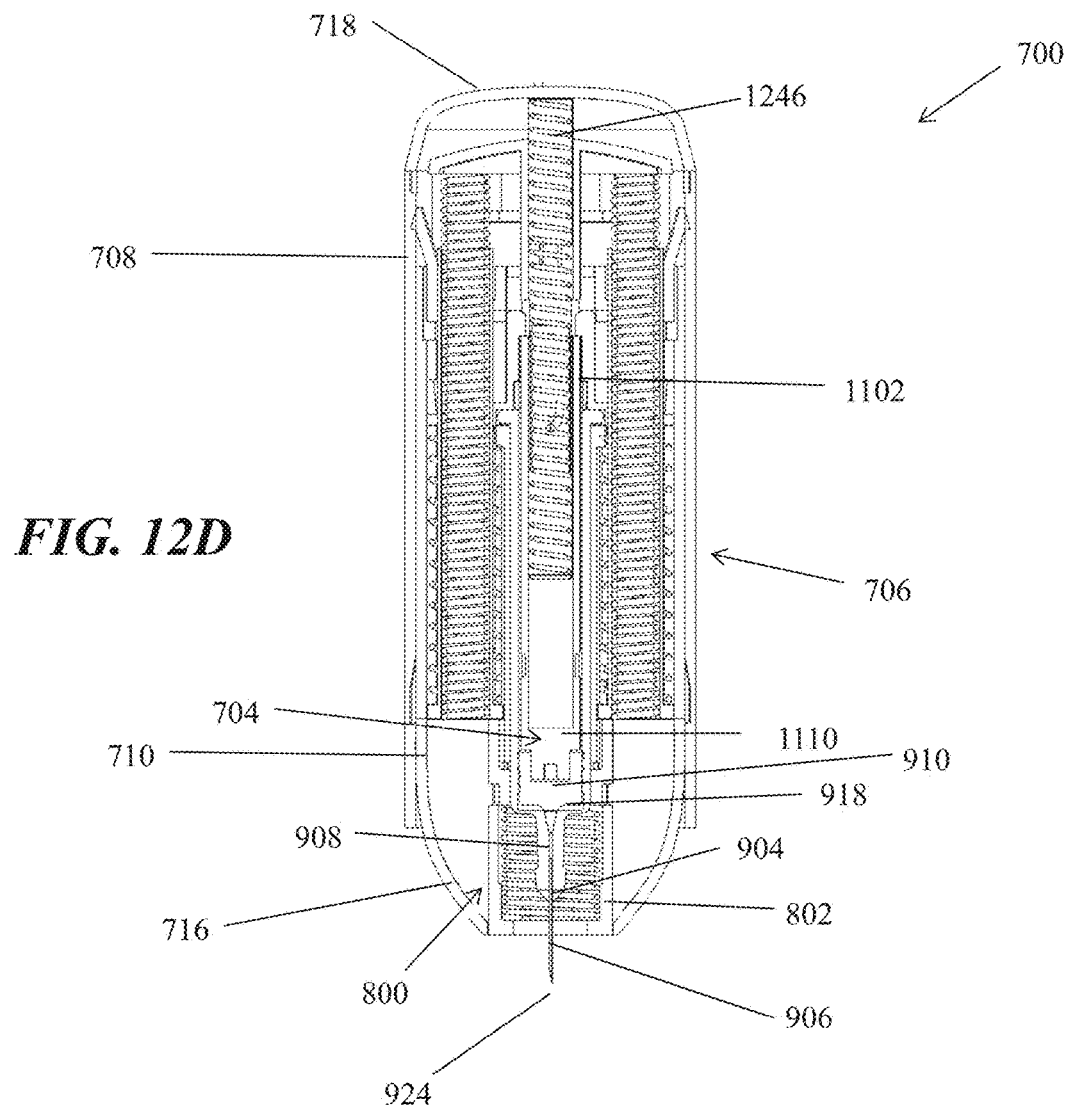
Figure 12E:
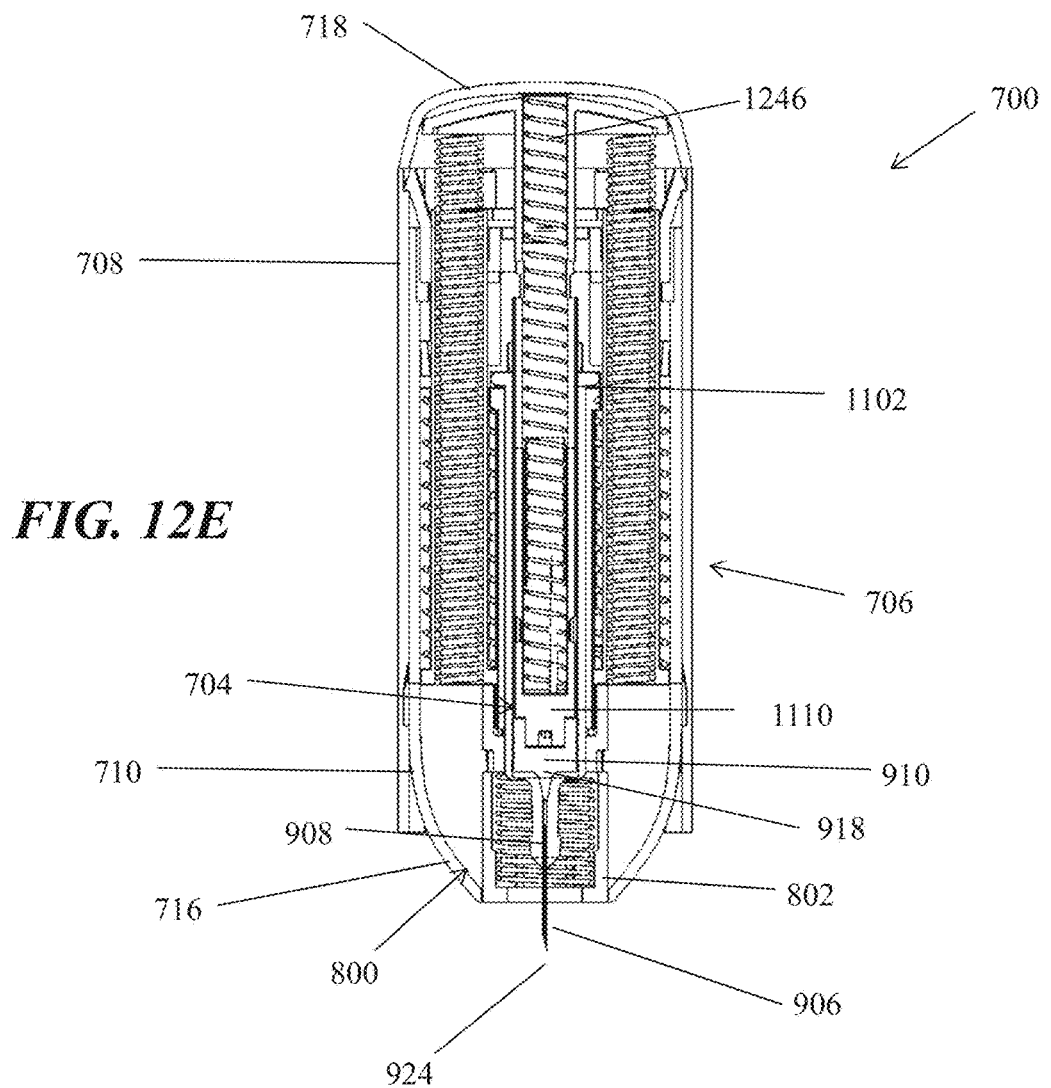
Figure 12F:
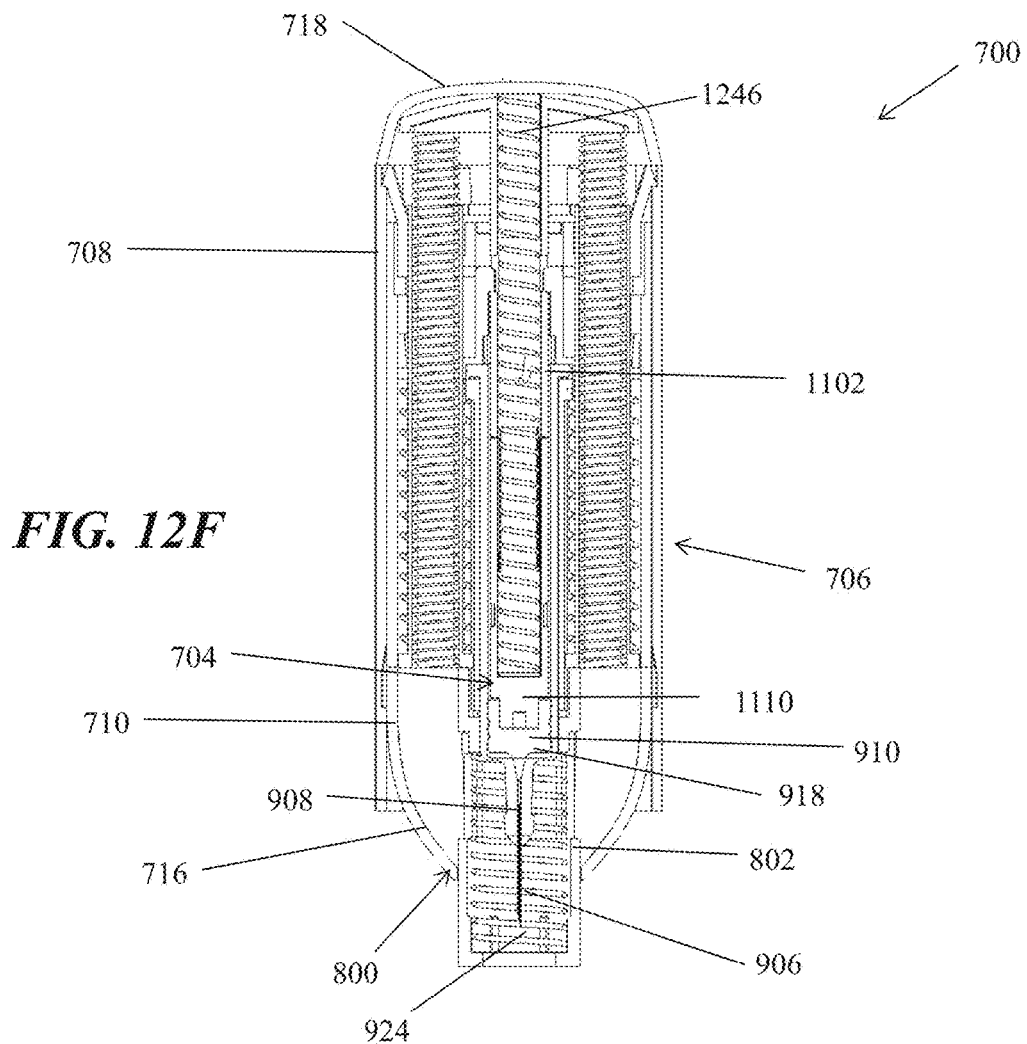
Figure 13D:
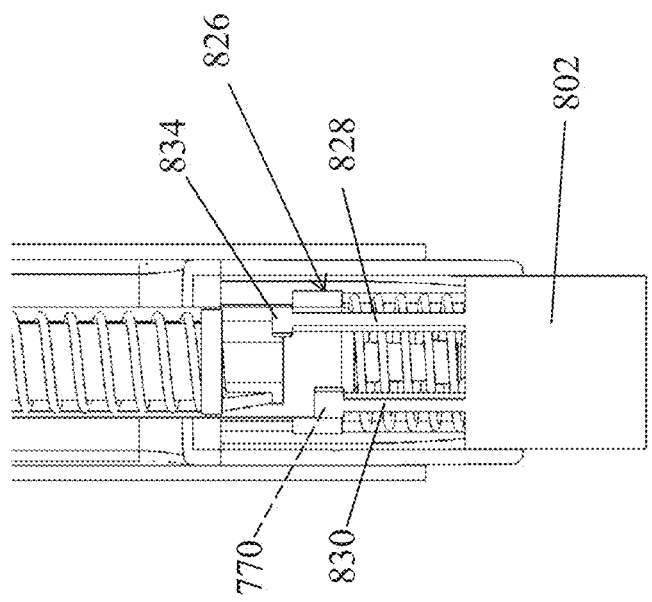
Figure 13C:
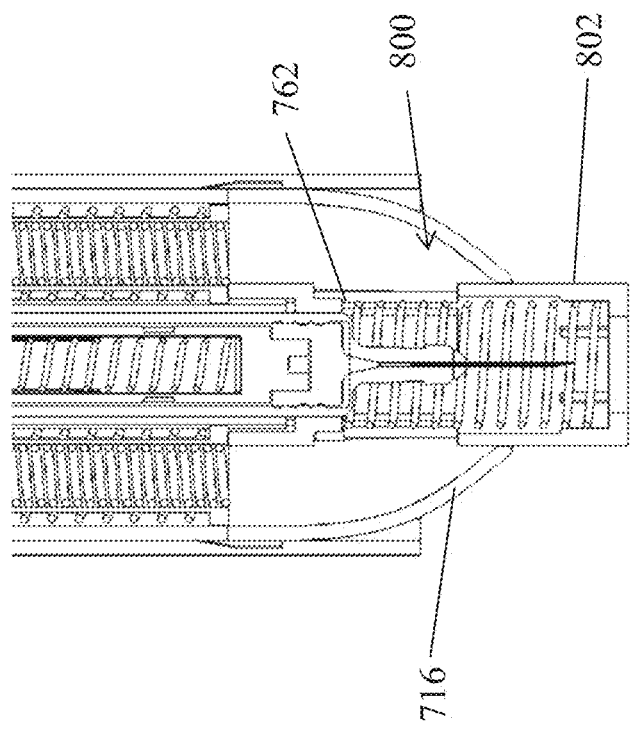

FIGS. 12A-12F depict longitudinal cross-sectional views of the injection device 700 in various stages during use. FIG. 12A depicts the device before use. FIG. 12B depicts the device with the rigid needle shield and cap removed. FIG. 12C depicts the device with the syringe in an extended position. FIG. 12D depicts the device with the plunger moved to the distal position within the syringe cavity. FIG. 12E depicts the device with the end-of-dose indicator in an activated configuration. FIG. 12F depicts the device with the needle shroud extended. FIGS. 13A-13C show longitudinal cross-sectional views of a distal portion of the injection device 700, showing a needle shield assembly. Like the injection device 100, the injection device 700 may comprise a needle safety assembly 800 that may be movable between a retracted position (shown in FIGS. 13A-13B) and an extended position (shown in FIGS. 13C-13D), as described in detail above with regard to needle safety assembly 200. As shown in FIGS. 13A-13D the needle safety assembly 800 may comprise an extendable needle shroud 802, a biasing element 818, and a locking assembly 826, having the same components, positions, and functions as described above with respect to needle safety assembly 800. However, with regard to the biasing element, the biasing element 818 may comprise a compression spring 820, which may have a cylindrical shape and may fit within the lumen 808 of the needle shroud 802. The proximal end 822 of the compression spring 820 may contact a ledge 776 extending radially outward from the inner sheath 762 of the nose 716, and the distal end 824 of the compression spring 820 may contact a lip 816 extending radially inward from the needle shroud 802. While the lip 816 is shown as located at the distal end 812 of needle shroud 802 in FIGS. 13A-13D, it should be appreciated that in other variations a lip may extend from a location proximal to the distal end 812 of the needle shroud 802. In some variations, the proximal end 822 of the compression spring 820 may be fixedly attached to the inner sheath 762 of nose 716, but it need not be (e.g., the compression spring may rest against the nose 716 but may be unattached). It should also be appreciated that in other variations, the proximal end 822 of the compression spring 820 may contact or be fixedly attached a portion of the distal housing 710.

In some variations, locking assembly 826 of the needle safety assembly 800 of injection device 700 may, like the locking assembly 226 of injection device 100, hold the needle shroud 802 in a retracted position and/or in an extended position. In some variations, the locking assembly 826 may comprise one or more latches 828, which may have the same components, positions, and functions as described above with respect to the injection device 100. However, in some variations, the latches 828 may be configured to mate with a portion of the nose 716, such that when mated, the latches 828 resist motion of the needle shroud 802 relative to the distal housing 710. As shown in FIGS. 13A-13D, the nose 716 may comprise an inner sheath 762 comprising four proximal slots 764. The four proximal slots 764 may be located on the inner sheath 762 such that when the tabs 834 of the latches 828 are mated with the proximal slots 764, the needle shroud 802 may be located in a retracted position. When the tabs 834 are mated with the proximal slots 764, the elongate portion 830 of the latches 828 may be flush against the outer surface 958 of the syringe sleeve 930 (described below), while the tabs 834 of the latches 828 may be inserted radially into the proximal slots 764. The locking assembly 826 may resist distal motion due to a biasing force from the biasing element 818 because of the proximally oriented force applied to the distal surface of the tabs 834 by the distal surface of the proximal slots 764.

The locking assembly 826 may be configured such that the needle shroud 802 may be unlocked from a retracted position (e.g., the locking assembly 826 may no longer hold the needle shroud 802 in a retracted position) by distal motion of the syringe 704. In some variations, the tabs 834 may be configured such that they can be released from the proximal slots 764 by distal movement of the syringe body 902 of the syringe 704 relative to the nose 716. For example, in the variation shown in FIGS. 13A-13D, the tabs 834 may have a triangular, proximally tapering shape. Thus, as the syringe body 902 of the syringe 704 is moved distally relative to the nose 716 and within the inner sheath 762, the distal end of the syringe body 902 may engage the inner surface of the tabs 834 protruding through the proximal slots 764. As the syringe body 902 of the syringe 704 continues to slide distally along the inner surface of the inner sheath 762 of the nose 716, the outer surface of the syringe body 902 gradually pushes the tabs 834 further radially out of the proximal slots 764. Once the outer surface of the syringe body 902 has fully pushed the tabs 834 radially out of the proximal slots 764, the tabs 834 may no longer be mated with the proximal slots 764 and may no longer resist distal motion of the needle shroud 802 relative to the distal housing 710. Like the needle shroud 202 of the injection device 100, when the needle shroud 802 of the injection device 700 is unlocked from a retracted position, it may move to an extended position if an appropriate force is applied, or such a force may be partially or fully counterbalanced by an opposing force, as described in detail above with regard to the needle shroud 202. Likewise, the needle shroud 802 of the injection device 700 may be unlocked from a retracted position just before the distal tip 924 of the needle 906 of the syringe 704 extends from the distal end 758 of the nose 716, as described in detail above with regard to the needle shroud 202.

Similarly, the needle shroud 802 of the injection device 700 may additionally or alternatively be configured to be locked in an extended position once moved to an extended position, as described in detail with regard to the needle shroud 202. However, in the variations shown in FIGS. 13A-13D, the inner sheath 762 of the nose 716 may comprise four distal slots 770 configured to mate with the tabs 834 of the latches 828 of the locking assembly 826. As shown in FIGS. 13C-13D, the distal slots 770 may be located on the inner sheath 762 to coincide with the position of the tabs 834 when the needle shroud 802 is in an extended position. When the needle shroud 802 moves into an extended position, the tabs 834 on the latches 828 may mate with the distal slots 770. When the tabs 834 on the latches 828 are mated with the distal slots 770, the locking assembly 826 may resist motion of the needle shroud 802 relative to the nose 716.

Figures 14A, 14B:
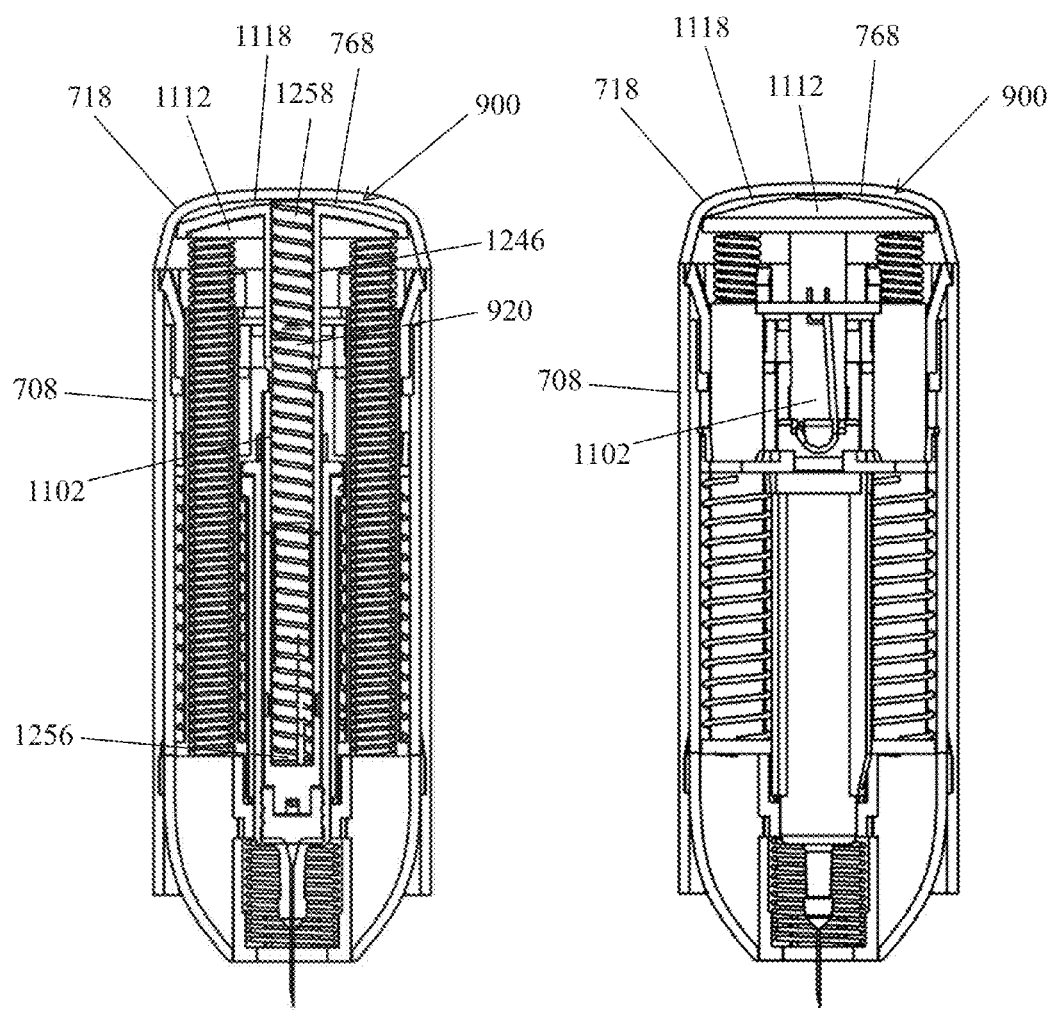
FIGS. 14A-14B are longitudinal cross-sectional views and cut-away elevational side views, respectively, of a proximal portion of the injection device of FIG. 10, showing the end-of-dose indicator in an activated configuration.

The housing 702 may also comprise an indicator that, like the indicators described with respect to the injection device 100, may indicate the progress or completion of the injection, as described in detail above, and may have activated and inactivated configurations. FIGS. 14A-14B are longitudinal cross-sectional views and elevational side views, respectively, of a proximal portion of the injection device 700 showing an end-of-dose indicator 900 having a different visual appearance associated with the activated and inactivated configurations in inactivated and activated configurations. In the variation shown in FIGS. 14A-14B, the indicator 900 may comprise the ram crossbar 1112 of the ram 1102, described in greater detail below. The ram crossbar 1112 may be configured such that when the proximal surface 1118 of the ram crossbar 1112 is adjacent to the inner surface 768 of the end cap 718 of the proximal housing 708, at least a portion of the ram crossbar 1112 may be seen from outside the end cap 718. In some variations, at least a portion of the ram crossbar 1112 may have a color or pigment that may be capable of being more easily noticed, such as but not limited to red, yellow, orange, green, magenta, blue, and the like. In order for the ram crossbar 1112 to be seen through at least a portion of end cap 718, in some variations, at least a portion of the end cap 718 may be translucent or transparent. In variations in which at least a portion of the end cap 718 is translucent, the level of translucency may be such that the coloring of the ram crossbar 1112 may be perceived through the end cap 718 when the ram crossbar 1112 is adjacent to the viewing portion.

The indicator 900 may further comprise a biasing element 920, which may be configured to bias the indicator 900 toward an inactivated configuration. As shown in FIGS. 14A-14B, in some variations, the biasing element 920 may comprise a locking spring 1246, described in greater detail later with respect to the power assembly 706 of injection device 700. The proximal end 1258 of the locking spring 1246 may be attached or in contact with the inner surface 768 of the end cap 718 of the proximal housing 708, while the distal end 1256 of the locking spring 1246 may be attached to or in contact with a portion of the ram 1102, as described in greater detail later. The locking spring 1246 may thus bias the ram crossbar 1112 away from the inner surface 768 of the end cap 718 of the proximal housing 708. The bias of the ram crossbar 1112 away from the inner surface 768 of the end cap 718 may be overcome by distal force on the proximal housing 708 at the completion of the full injection of the contents of the reservoir 914, when the plunger 1110 has traveled the full length of the syringe cavity 904, as described in more detail below.

Figure 15:
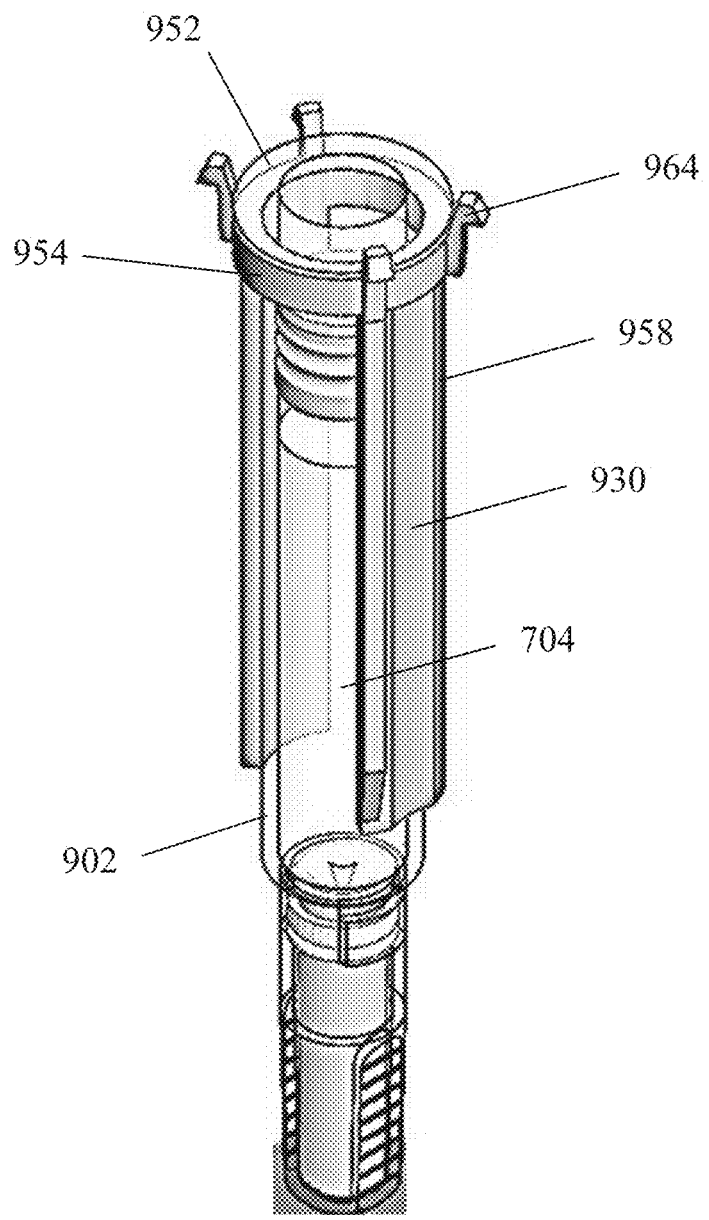
FIG. 15 illustrates a perspective view of the syringe and syringe sleeve of the injection device of FIG. 10.

The syringe 704 of the injection device 700 may be similar to the syringe 104 described above with respect to injection device 100, and may have the same components, positions, and functions as described above. The injection device 700 may further comprise a syringe sleeve 930. FIG. 15 depicts a perspective view of a syringe 704 and syringe sleeve 930 of the injection device 700. The syringe sleeve 930 may attach the syringe body 902 of the syringe 704 to the ram interlock 1226 (described in more detail below). The proximal lip 952 of the syringe body 902 may rest on the proximal lip 954 of the syringe sleeve 930. The proximal lip 954 of the syringe sleeve 930 may comprise four latches 964, which may be configured to attach to four corresponding recesses on the distal side of the ram interlock 1226 (described below). Thus, when the syringe sleeve 930 is attached to the ram interlock 1226, the proximal lip 952 of the syringe body 902 may be fixed between the proximal lip 954 of the syringe sleeve 930 and the ram interlock 1226, causing the syringe body 902 to resist distal motion relative to the syringe sleeve 930. The syringe sleeve may comprise any suitable material or materials, but in some variations, the syringe sleeve 930 may comprise a plastic material.

Figure 16A:
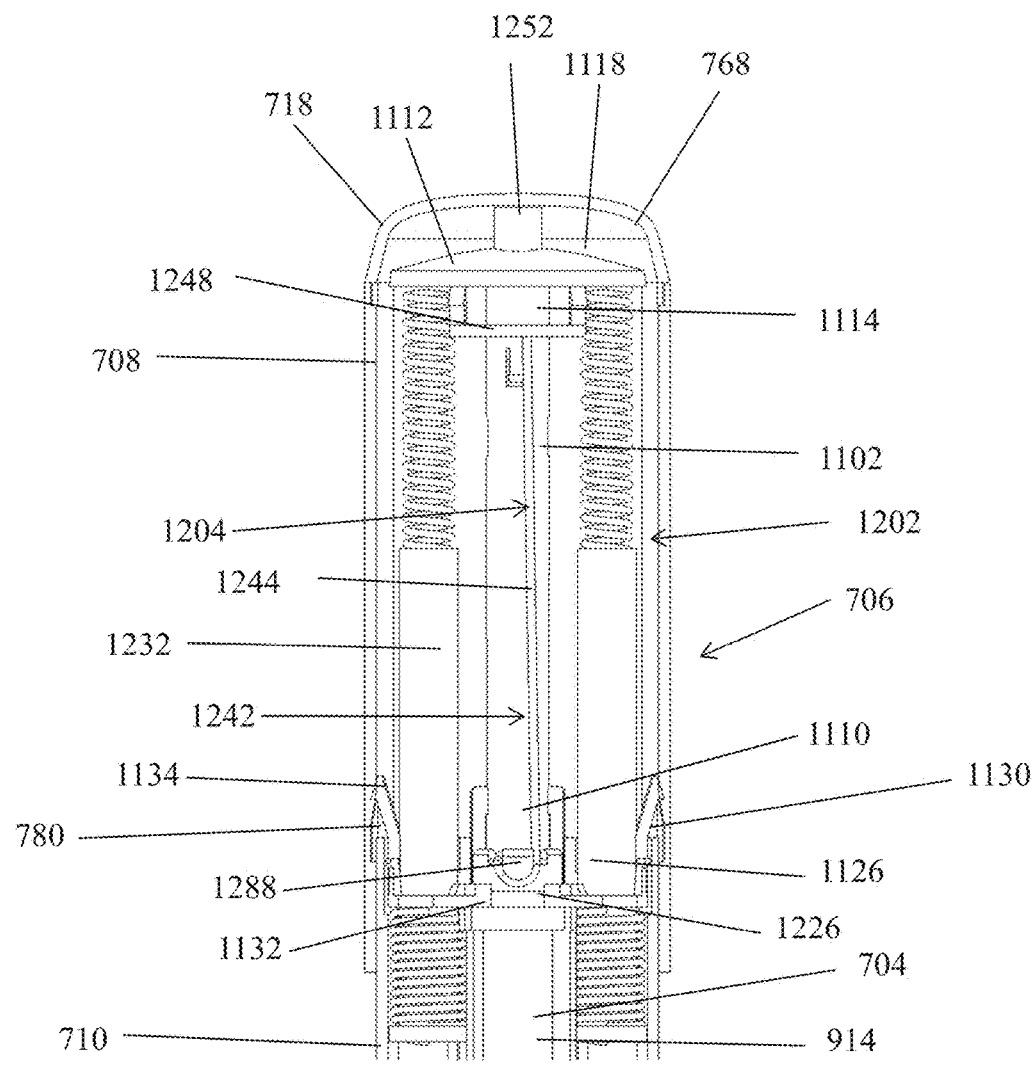
FIGS. 16A-16B depict cut-away side elevational and longitudinal cross-sectional views, respectively, of the ram and power assembly of the injection device of FIG. 10.
Figure 16B:
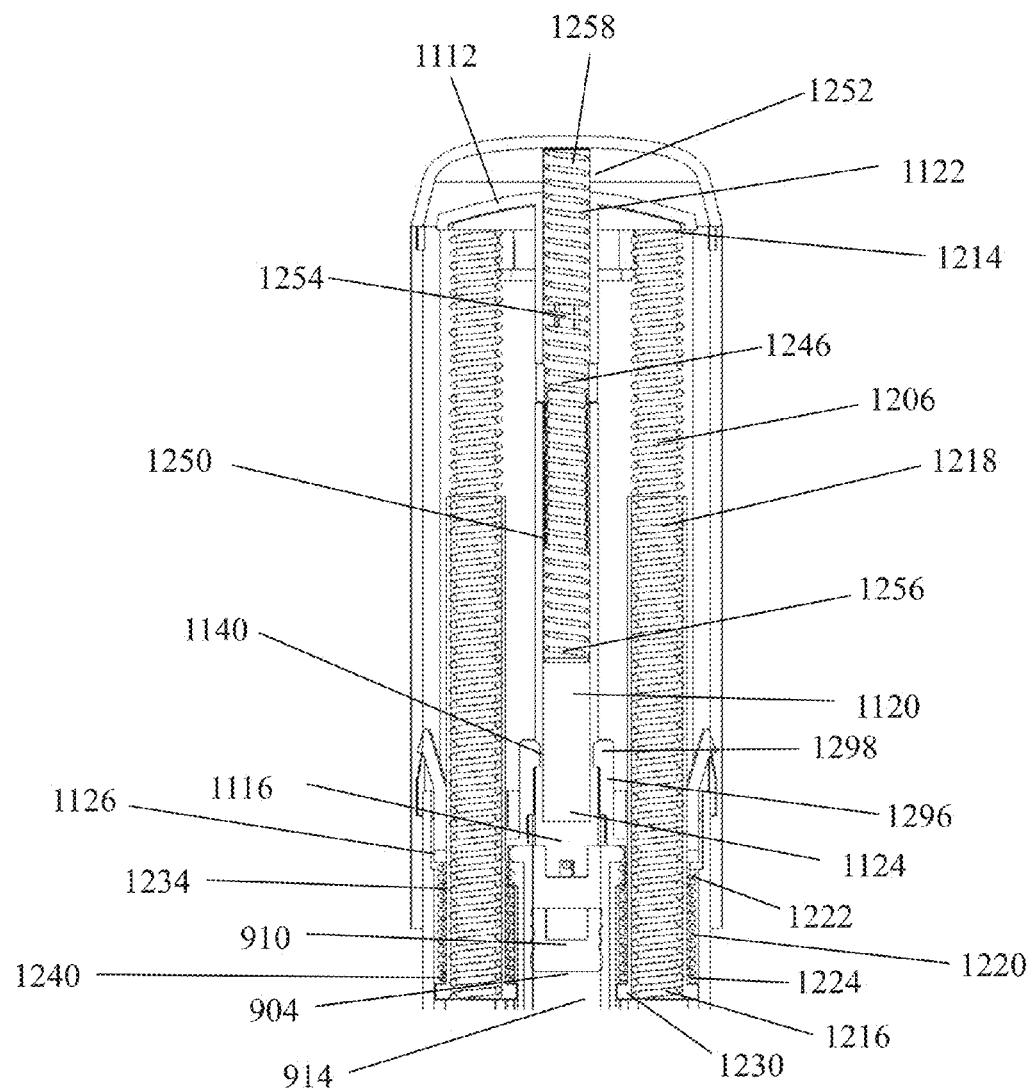

FIGS. 16A-16B depict cut-away side elevational and longitudinal cross-sectional views, respectively, of the ram and power assembly of the injection device of FIG. 10. As in the ram 502 described with respect to the injection device 100, the ram 1102 may be directly or indirectly connected to the proximal housing 708, such that movement of the proximal housing 708 can be transmitted to the ram 1102. The ram 1102 may be configured to transmit distal force on the proximal housing 708 into different motions, depending on the stage of the injection process. In a first stage, distal force on the proximal housing 708 may be transmitted into distal motion of the syringe 704 and power assembly 706 relative to the distal housing 710. In a second stage, distal force on the proximal housing 708 may be transmitted into displacement of the contents of the reservoir 914 of the syringe 704 (e.g., a formulation comprising a therapeutic agent) through the lumen 908 of the needle 906.

In some variations, the ram 1102 may be configured such that these effects of distal force on the proximal housing 708 may occur in the order described above. That is, the ram 1102 may be configured such that distal force on the proximal housing 708 may be transmitted first into distal motion of the syringe 704 and power assembly 706 relative to the distal housing 710, and then transmitted second into displacement of the contents of the reservoir 914 of the syringe 704 (e.g., a formulation comprising a therapeutic agent) through the lumen 908 of the needle 906. This may be desirable, for example, because it may allow the syringe 704 to move distally such that the needle 906 may pierce a patient's tissue before the contents of the syringe cavity 904 are displaced through the lumen 908 of the needle 906.

In some variations, the ordering of effects of distal force on the proximal housing 708 may be due to different amounts of force that are required for each motion. For example, the ram 1102 may transmit distal force on the proximal housing 708 into distal motion of the syringe 704 and power assembly 706 relative to the distal housing 710 when the force on the proximal housing 708 is above a first threshold (e.g., above about 1 N, above about 2 N, above about 3 N, above about 4 N, above about 5 N, above about 6 N, above about 7 N, or higher); and the ram 1102 may transmit distal force on the proximal housing 708 into displacement of the contents of the reservoir 914 of the syringe 704 through the lumen 908 of needle 906 when the force on the proximal housing 708 is above a higher second threshold (e.g., above about 1 N, above about 2 N, above about 4 N, above about 6 N, above about 8 N, above about 10 N, above about 12 N, above about 14 N, or higher). In some variations, the first threshold may be due to the proximal force from flanges on the base retainer cap 1126 (described below) resisting distal movement of ram interlock 1226, to which the syringe 704 is attached, as described in detail below. The second threshold may be due to the force required to overcome a second set of flanges 1296 (described below) and to move the rate control assembly 1204 of the power assembly 706 to an open configuration, as described in detail below. There may also be an intermediate threshold that may need to be overcome in order for the needle 906 to be extended beyond the distal and 758 of the nose cone 716. In some variations, this intermediate threshold may be due to two flexures on the ram interlock 1226, which may interface with two recesses in the distal housing 710. In should be appreciated that in some other variations, the ram 1102 may transmit distal force on the proximal housing 708 into different motion in different orders and by different mechanisms. For example, in some variations the effect of the distal force may be chosen by manual selection by the user. In should also be appreciated that the ram may transmit distal force on the proximal housing into fewer or more different motions.

The ram 1102 may comprise a central portion comprising a plunger 1110 and a ram crossbar 1112 at the proximal end 1114 of the plunger 1110. The plunger 1110 may be configured to be slidable within the syringe cavity 904. The distal end 1116 of the plunger 1110 may be configured to engage with the seal 910 of the syringe 704. If the plunger 1110 is moved distally relative to and within the syringe cavity 904, the plunger 1110 may push the seal 910 distally relative to and within the syringe cavity 904. This movement of the seal 910 may decrease the volume of the reservoir 914 containing the formulation comprising a therapeutic or diagnostic agent. Thus, distal motion of the plunger 1110, and in turn of the seal 910, relative to and within the syringe cavity 904 may cause the contents of the reservoir 914 to be displaced through the lumen 908 of the needle 906. The ram crossbar 1112 may be attached on its distal side to the proximal end 1114 of the plunger 1110. The proximal surface 1118 of the ram crossbar 1112 may be configured to be able to sit adjacent to the inner surface 768 of the end cap 718 of the proximal housing 708, so that the ram crossbar 1112 may serve as an indicator, as described above. The ram 1102 may comprise a bore hole 1120 extending through the ram crossbar 1112 and plunger 1110, and may have a proximal opening 1122 at the proximal surface 1118 of the ram crossbar 1112 and a closed distal end 1124 near the distal end 1116 of the plunger 1110. The bore hole 1120 may be configured to house at least a distal portion of a locking spring 1246 (described in more detail below). The proximal end 1258 of the locking spring 1246 may be attached or in contact with the inner surface 768 of the end cap 718 of the proximal housing 708, while the distal end 1256 of the locking spring 1246 may be attached to or in contact with the distal end 1124 of the bore hole 1120 of the plunger 1110. The locking spring 1246 may thus be configured to transmit motion of the proximal housing 708 to the ram 1102, in addition to acting as part of the rate control assembly 1204 of the power assembly 706, as described below. The plunger 1110 may further comprise two recesses 1140 at its distal end 1116. These recesses 1140 may be configured to engage two flanges 1296 extending from a central lumen 1228 of a ram interlock 1226 (described in more detail below). The flanges 1296 may comprise inwardly facing proximal tabs 1298, which may be configured to the engage the recesses 1140, which may cause the plunger 1110 to resist distal movement relative to the ram interlock 1226.

Figure 16C:
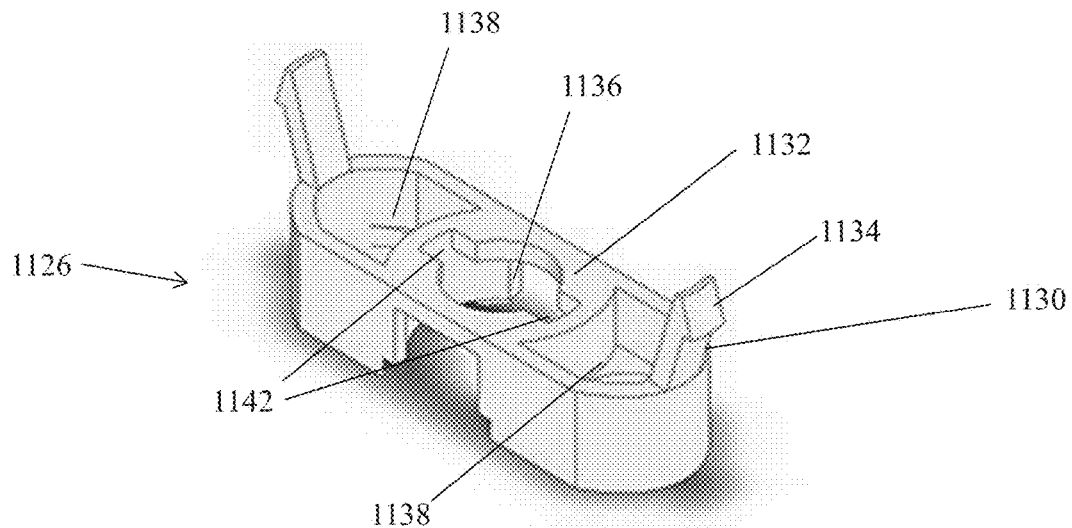
FIGS. 16C-16D shows perspective views of the base retainer cap and ram interlock, respectively.

The injection device 700 may further comprise a base retainer cap 1126. The distal side of the base retainer cap 1126 may be attached to the proximal side of the ram interlock 1226 (described below). As shown in FIGS. 16A-16B and in more detail in FIG. 16C, the base retainer cap 1126 may comprise two flanges 1130, located on opposite sides of the main body 1132 of the base retainer cap 1126. The flanges 1130 may extend proximally and outwardly from the main body 1132, and may have proximal tabs 1134. The proximal tabs 1134 may engage recesses 780 on the inner surface of the proximal housing 708 in order to resist proximal motion of the proximal housing 708 relative to the distal housing 710 after the injection device 700 has been assembled. The main body 1132 of the base retainer cap 1126 may further comprise a central lumen 1136 and two side lumens 1138. The central lumen 1136 may be configured to allow the plunger 1110 of the ram 1102 to move therethrough. The central lumen 1136 may further comprise two recesses 1142 configured to allow the flanges 1296 of ram interlock 1126 to move therethrough (described below). The two side lumens 1138 may be configured to allow a portion of the power assembly 706 to move therethrough, as described below. The base retainer cap 1126 may comprise any suitable material or materials, but in some variations, the base retainer cap 1126 may comprise a plastic material.

Figure 16D:
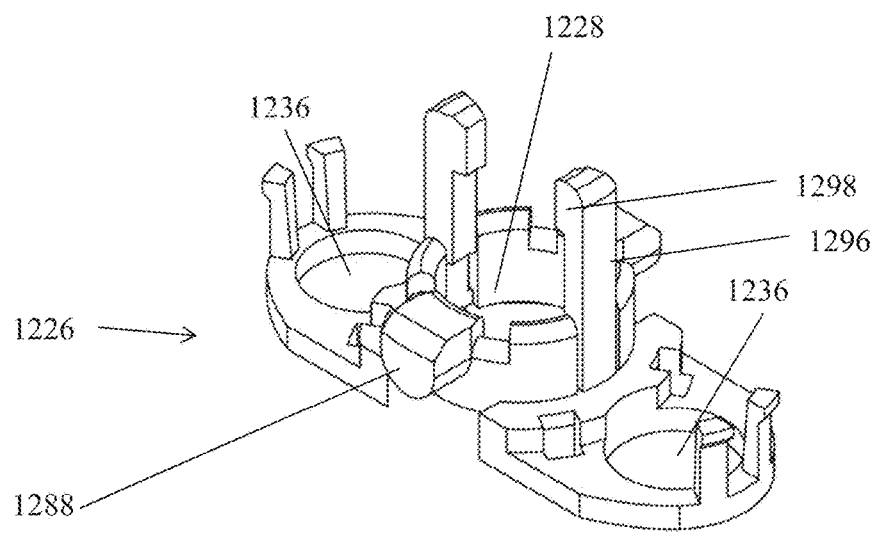

The injection device 700 may further comprise a ram interlock 1226. The ram interlock 1226, shown in more detail in FIG. 16D, may comprise a central lumen 1228, configured to allow the plunger 1110 of the ram 1102 to travel therethrough, and may comprise one side lumen 1236 on each of two opposite sides of the central lumen 1228, each configured to allow one of the two composite springs 1218 to travel therethrough, as described in more detail below. The ram interlock 1126 may further comprise two flanges 1296 extending from the central lumen 1228, which may comprise inwardly facing proximal tabs 1298. In an initial configuration, the inwardly facing proximal tabs 1298 of the flanges 1296 of the ram interlock 1126 may be engaged with recesses 1140 of the plunger 1110, as described above and shown in FIG. 16B, which may cause the plunger 1110 to resist distal movement relative to the ram interlock 1226. The flanges 1296 may be resisted from flexing radially outward (such that the proximal tabs 1298 may disengage with recesses 1140 of the plunger 1110, which would allow the plunger 1110 to move distally relative to the ram interlock 1226) because in the initial configuration the distal face of the base retainer cap 1126 is seated against the proximal face of the ram interlock 1226, such that the flanges 1296 of the ram interlock 1226 are located within recesses 1142 of the base retainer cap 1126. The base retainer cap 1126 may thus exert radially inward pressure on the flanges 1296 to resist them moving radially outward. This may create hoop stress in the central lumen 1228 of the ram interlock 1226.

Application of distal force on the proximal housing 708 may cause the proximal housing 708 to be moved distally. If the distal housing 710 is held in place (e.g. by pressing the distal end 758 of the nose 716 of the distal housing 710 against a patient's tissue), the proximal housing 708 may be moved distally relative to the distal housing 710. The movement of the proximal housing 708 may be transferred via the locking spring 1246 to cause the power assembly 706 and syringe 704 to slide distally relative to the distal housing 710 if the distal force on the proximal housing 708 is above the necessary force threshold. More specifically, distal force on the proximal housing 708 may cause distal motion of the locking spring 1246, and in turn, distal motion of the power assembly 706. Distal motion of the power assembly 706 may in turn cause distal motion of the syringe 704. This may move the syringe 704 from a retracted position (shown in FIGS. 12A-12B) into an extended position (shown in FIG. 12D-12F), as described above with respect to syringe 104 of injection device 100. As the distal tip 924 of the needle 906 approaches the distal opening 712 of the nose 716, the needle shroud 802 of the needle safety assembly 800 may be unlocked from a retracted position, as described in detail above and shown in FIGS. 13A-13D. As the distal tip 924 of the needle 906 moves to extend beyond the distal end 758 of the nose 716, the needle 906 may pierce tissue pressed against the distal end 758 of the nose 716. The syringe 704 may continue to move distally relative to the distal housing 710 until the syringe 704 has reached an extended position, at which point distal motion of the syringe 704 may be stopped by engagement of the syringe sleeve 930 with a portion of the nose 716. At an extended position, the distal tip 924 of the needle 906 may have reached the desired depth, as described above. In some variations, the injection device 700 may comprise an insertion detent, which may cause the movement of the distal tip 924 of the needle 906 to occur at a specific rate during insertion, in order to achieve a desired insertion speed into tissue, as described above.

It should be noted that the power assembly 706 and syringe 704 may move distally together with distal force on the proximal housing 708 in a particular stage of the injection process, rather than the power assembly 706 acting on the syringe 704 (e.g., by moving the plunger 1110 distally within the syringe cavity 904 to act on the seal 910 and displace the contents of the reservoir 914), due to the relative amounts of force required to move the power assembly 706 and the syringe 704 relative to the distal housing 710, and to move the ram 1102 relative to the syringe 704. That is, the amount of force required to move the syringe 704 to an extended position may be less than the amount of force required to cause distal motion of the ram 1102 relative to the syringe 704. In some variations, the ram interlock 1226 and base retainer cap 1126 may prevent distal motion of the ram 1102 relative to the syringe 704 until the syringe 704 is in an extended position. The flanges 1296 of the ram interlock 1226 may be located within recesses 1142 of the base retainer cap 1126, which may exert radially inward pressure on the flanges 1296 to resist them flexing radially outward to disengage with recesses 1140 of the plunger 1110, as described above. As the syringe 704 moves toward an extended configuration, however, the proximal housing 708, power assembly 706, and ram interlock 1226 may move distally with the syringe 704 relative to the distal housing 710, while the base retainer cap 1126 may remain fixed relative to the distal housing 710. The flanges 1296 may be configured to have a length such that they may remain constrained by the base retainer cap 1126 until the syringe 704 has reached an extended position.

After the power assembly 706 and syringe 704 have moved distally relative to the distal housing 710 such that the syringe 704 is in an extended position and the distal tip 924 of the needle 906 is at the desired depth, and, correspondingly, the flanges 1296 of the ram interlock 1226 may be no longer constrained by the base retainer cap 1126, additional distal force on the proximal housing 708 may be transmitted into distal motion of the ram 1102 relative to the syringe cavity 904 if the force is above the necessary force threshold. When the force is above the necessary force threshold, the plunger 1110 and seal 910 may be moved distally within the syringe cavity 904, which may decrease the volume of the reservoir 914 and displace the contents of the reservoir 914 through the lumen 908 of the needle 906, as described above with respect to syringe 104 of injection device 100. Distal force on the proximal housing 708 may continue to cause the contents of the reservoir 914 to be displaced through the lumen 908 of the needle 906 until the seal 910 has traveled to the distal end 918 of the syringe cavity 904 (shown in FIGS. 12D-12E). In some variations, the threshold force required to move the plunger 1110 and seal 910 distally within the syringe cavity 904 may be due to the flanges 1296 of the ram interlock 1226. As described above, the ram interlock 1126 may comprise two flanges 1296 extending from the central lumen 1228, which may comprise inwardly facing proximal tabs 1298. In an initial configuration, the inwardly facing proximal tabs 1298 of the flanges 1296 of the ram interlock 1126 may be engaged with recesses 1140 of the plunger 1110, which may cause the plunger 1110 to resist distal movement relative to the ram interlock 1226. When a threshold force is applied, however, the flanges 1296 may flex radially outward such that the proximal tabs 1298 may disengage with recesses 1140 of the plunger 1110, and thus may allow the plunger 1110 to move distally relative to the ram interlock 1226, subject to the rate control assembly of the power assembly 706, described below. If the distal force on the proximal housing 108 is released while the power assembly 706 and syringe 704 are moving from a retracted position to an extended position, the power assembly 706 and syringe 704 may stay in place relative to the distal housing 710.

As described above with respect to the power assembly 106 of injection device 100, the power assembly may provide an injection force sufficient (alone or in addition to injection force supplied by the user) to inject a given volume of a given formulation through a given size needle in a given time, as described in detail with regard to power assembly 106. Like the power assembly 106, power assembly 706 may comprise a stored energy source and a rate control assembly. As in the power assembly 106 described with respect to injection device 100, the power assembly 706 may comprise a stored energy source 1202, which may be configured to provide force to displace the contents of reservoir 914 of the syringe 704 through the lumen 908 of the needle 906, and a rate control assembly 1204, which may comprise a braking assembly that may limit or restrict the stored energy source 1202 from contributing to the displacement of the contents of the reservoir 914 of the syringe 704 through the lumen 908 of the needle 906. Returning to FIGS. 16A-16B, the stored energy source 1202 may comprise one or more springs to provide injection force. In the injection device 700, the springs of the stored energy source 1202 may pull the ram 1102 distally in order to cause the contents of the reservoir 914 of the syringe 704 to be displaced through the lumen 908 of the needle 906. In some variations, the springs may be composite springs in order to decrease the total length of the spring required to produce a desired force. Such a composite spring may comprise an extension spring located coaxially within a compression spring. It should be appreciated, however, that in other embodiments, the springs may not comprise composite springs, and may instead comprise, for example, a single extension spring or a single compression spring; further, in other embodiments, an injection device may comprise only one composite spring, or may comprise more than two composite springs, such as two, three, four, or more composite springs.

The two composite springs 1218 of the stored energy source 1202 may each have a compression spring 1220 located coaxially about an extension spring 1206. It should be appreciated that in other variations, the extension spring 1206 may be located coaxially within the compression spring 1220. In each of the two composite springs 1218, the proximal end 1222 of the compression spring 1220 may be located distally to the proximal end 1214 of the extension spring 1206, and the proximal end 1222 of the compression spring 1220 may be attached to the ram interlock 1226. The proximal end 1214 of the extension spring 1206 may be attached to the ram crossbar 1112. The distal end 1224 of the compression spring 1220 and the distal end 1216 of the extension spring 1206 may be connected to each other directly or indirectly at a composite spring interface 1230. In some variations, the composite spring interface 1230 may comprise an intermediate component, such as but not limited to a plastic bushing, that may engage the distal end 1224 of the compression spring 1220 and the distal end 1216 of the extension spring 1206. In other variations, the distal end 1216 of the extension spring 1206 may comprise a wire-formed loop having a larger diameter than the compression spring 1220, and the compression spring 1220 may be inserted into the distal end 1216 of the extension spring 1206 to engage the compression spring 1220 and the extension spring 1206. In yet other variations, the extension spring 1206 and compression spring 1220 may be formed as an integrated wireform using a continuous wire.

The spring rates of the extension spring 1206 and compression springs 1220 may be chosen to deliver an appropriate force based on the formulation viscosity, needle choice, volume, and desired injection time, as described above. In some variations, for example, the spring may be configured to deliver a force of up to about 5 N, about 10 N, about 15 N, about 20 N, about 25 N, about 30 N, about 35 N, about 40 N, about 45 N, about 50 N, about 55 N, about 60 N, about 65 N, about 70 N, about 75 N, about 80 N, about 85, or about 90 N when the composite spring 1218 is initially released. In some variations, the composite springs 1218 and/or the extension springs 1220 may comprise music wire, but it should be appreciated that the springs may be made of any suitable material or materials.

In some variations, the composite springs 1218 may additionally comprise a composite spring sleeve 1232, but need not. In variations having composite spring sleeves, the composite spring sleeves 1232 may comprise a cylindrical wall 1234 that may separate the extension spring 1206 and the compression spring 1220. In some variations, the composite spring sleeves 1232 may assist in providing spring guidance. The composite spring sleeves 1232 may pass through the side lumens 1236 on each side of the central lumen 1228 of the ram interlock 1226, and they may pass through the two side lumens 1138 of the base retainer cap 1126. The distal end 1240 of the composite spring sleeve 1232 may serve as the composite spring interface 1230, and as such, may have both the distal end 1224 of the compression spring 1220 and the distal end 1216 of the extension spring 1206 attached to it. In some variations, the ram interlock 1226 and/or spring sleeves 1232 may comprise a plastic material, but it should be appreciated that the ram interlock 1226 and/or spring sleeves 1232 may be made of any suitable material or materials.

The extension springs 1206 may bias the composite spring interfaces 1230 and the ram crossbar 1112 toward each other, while the compression spring 1220 may bias the ram interlock 1226 and the composite spring interfaces 1230 away from each other. The joint effect of the extension springs 1206 and compression springs 1220 of the composite springs 1218 may therefore be to bias the ram interlock 1226 and the ram crossbar 1112 toward each other. By biasing the ram interlock 1226 and the ram crossbar 1112 toward each other, the composite springs 1218 may thus bias the plunger 1110 distally through the central lumen 1228 of the ram interlock 1226. The plunger 1110 may be configured to fit slidably within the syringe cavity 904 and to press against the seal 910, which may in turn cause the contents of the reservoir 914 of the syringe 704 to be displaced through the lumen 908 of the needle 906, as described in detail above with respect to syringe 104 of injection device 100.

The distal movement of the plunger 1110 to press against the seal 910 of the syringe 704, however, may at times be resisted or limited by the rate control assembly 1204. As described above with respect to injection device 100, the rate control assembly may be moveable between a closed configuration and an open configuration. When the rate control assembly is in a closed configuration, the rate control assembly may limit or restrict the displacement of the contents of the reservoir of the syringe. When the rate control assembly is in an open configuration, the rate control assembly may not limit or restrict the displacement of the contents of the reservoir of the syringe. In some variations, the rate control assembly may be configured to limit or restrict the displacement of the contents of the reservoir of the syringe by limiting or restricting the distal motion of a plunger within the syringe cavity when in a closed configuration. When in an open configuration, the rate control assembly may not limit or restrict the distal motion of a plunger within the syringe cavity, thus allowing the stored energy source to act upon the plunger to move it distally relative to and within the syringe cavity, which may move the seal of the syringe distally within the syringe cavity to displace the contents of the reservoir through the lumen of the needle.

As shown in FIG. 16A, the rate control assembly 1204 may comprise a cord tensioning system 1242. The cord tensioning system 1242 may resist the effects of the stored energy source 1202 described above. The cord tensioning system 1242 may be reversibly and selectively moved between tensioned (the "closed" configuration of the rate control assembly) and released (the "open" configuration of the rate control assembly) configurations. Generally, the cord tensioning system 1242 may comprise a tensioning cord 1244 in addition to the locking spring 1246 and ram interlock 1226 mentioned above. When the cord tensioning system 1242 is in a tensioned configuration, the locking spring 1246 may generate a tensioning force on the tensioning cord 1244 of sufficient magnitude to be capable of resisting distal movement of the ram 1102 due to the stored energy source 1202. Sufficient tensioning force in the tensioning cord 1244 may be achieved by wrapping the tensioning cord 1244 around a bollard 1288. In some variations, the bollard 1288 may comprise a portion of the ram interlock 1226, as will be described in more detail below. When the cord tensioning system 1242 is in a released configuration, the cord tensioning system 1242 may allow the distal force on the ram 1102 from the composite springs 1218 to urge the plunger 1110 of the ram 1102 distally, as will be described in more detail below. In some variations, the cord tensioning system 1242 may optionally further comprise a float 1248, a locking spring retainer 1250, and a locking spring cap 1252, which will be explained in more detail below.

As shown in FIGS. 16A-16B, the locking spring 1246 may comprise a compression spring 1254. As described above, at least a distal portion of the locking spring 1246 may be located within the bore hole 1120 of the plunger 1110. The distal end 1256 of the locking spring 1246 may be attached to or in contact with the distal end 1124 of the bore hole 1120 of the plunger 1110. Alternatively, in some variations, at least a distal portion of the locking spring 1246 may be housed in a locking spring retainer 1250. The distal end of the locking spring retainer 1250 may be located proximally to the distal end 1124 of the bore hole 1120, or in other variations, it may be attached to or in contact with the distal end 1124 of the bore hole 1120. In some variations, the locking spring retainer 1250 may comprise a deep drawn metal. In some variations, the locking spring retainer 1250 may comprise a hole in its distal end, which may allow flow of a viscous damping fluid located in the bore hole 1120, and as such, may dampen the motion of the locking spring retainer 1250 under the force of the locking spring 1246. The proximal end 1258 of the locking spring 1246 may be attached or in contact with the inner surface 768 of the end cap 718 the proximal housing 708. The locking spring 1246 may thus bias the plunger 1110 away from the end cap 718 of the proximal housing 708. In some variations, the locking spring 1246 may have a spring rate of about 0.1 N/mm to 0.2 N/mm, 0.2 N/mm to 0.3 N/mm, 0.3 N/mm to 0.4 N/mm, 0.4 N/mm to 0.5 N/mm, 0.5 N/mm to 0.6 N/mm, 0.6 N/mm to 0.7 N/mm, 0.7 N/mm to 0.8 N/mm, 0.9 N/mm to 1 N/mm, or greater. In some variations, the proximal end 1258 of the locking spring 1246 may be housed in a locking spring cap 1252. The locking spring cap 1252 may serve to hide the proximal end 1258 of the locking spring 1246 from view through the end cap 718, for example in variations in which all or a portion of the end cap 718 is made of a clear or translucent material.

Figure 17:
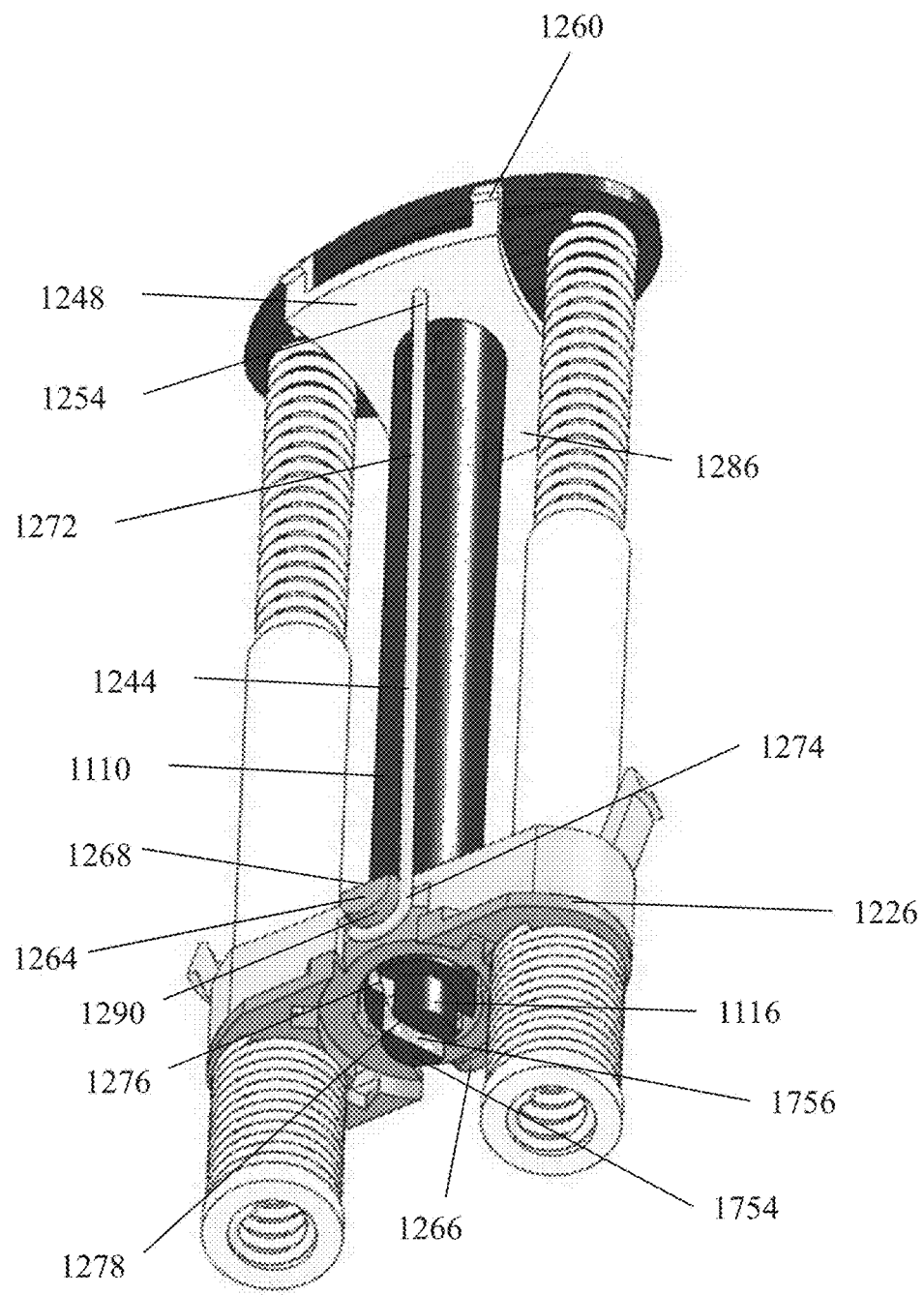
FIG. 17 is a perspective view of the power assembly of the injection device of FIG. 10.

As shown in FIG. 17, the rate control assembly 1204 may further comprise a tensioning cord 1244. The ends of the tensioning cord 1244 may be attached to a float 1248 that may be fixedly attached to the proximal housing 708 (not shown), while the middle of the tensioning cord 1244 may be wound around the ram interlock 1226 at two points and attached in between those two points to the distal end 1116 of the plunger 1110. It should be appreciated that in some variations, the tensioning cord 1244 may be directly attached to the proximal housing 708, instead of to a float. The locking spring 1246, by biasing the plunger 1110 away from the end cap 718 of the proximal housing 708 (not shown), may generate tension in the tensioning cord 1244, thus resisting distal movement of the plunger 1110. More specifically, the float 1248 may be attached to the proximal housing 708 via latches that may snap into matching recesses in the proximal housing 708. In some variations, the float 1248 may comprise a plastic material, though it should be appreciated that the float 1248 may comprise any suitable material or materials.

The first end 1254 of the tensioning cord 1244 may be attached to the float 1248 on a first side of the plunger 1110. The first end 1254 of the tensioning cord 1244 may be attached in any suitable manner to the float 1248. For example, in some variations, the first end 1254 of the tensioning cord 1244 may be attached to the float 1248 by being encapsulated into the plastic material, for example by being insert-molded into the float 1248. In other variations, the first end 1254 of the tensioning cord 1244 may be fitted with a lug or ferrule, which may in turn be attached to a receiving socket in the float 1248. A first portion 1272 of the tensioning cord 1244 may extend distally from the float 1248 toward the ram interlock 1226. The ram interlock 1226 may comprise one or more bollards 1288 that may allow the tensioning cord 1244 to be wrapped around the ram interlock 1226 in a manner generating friction between the tensioning cord 1244 and ram interlock 1226. In some variations, the ram interlock 1226 may comprise a first protrusion 1264 and a second protrusion 1266 located on opposite sides of the ram interlock 1226. The tensioning cord 1244 may have a second portion 1274 that may wrap around a rounded side 1290 of the first protrusion 1264. The tensioning cord 1244 may have a third portion 1276 that may travel from the first protrusions 1264 to the distal end 1116 of the plunger 1110. The distal end 1116 of the plunger 1110 may comprise one or more features that may allow the tensioning cord 1244 to be attached to its distal end 1116. In some variations, the distal end of the plunger 1110 may comprise a slot 1756 across the distal face 1754 of the plunger 1110, through which a fourth portion 1278 of the tensioning cord 1244 may be placed. A fifth portion 1280 of the tensioning cord 1244 may exit the slot 1756 of the plunger 1110 and extend toward the second protrusion 1266 (not shown). A six portion 1282 of the tensioning cord 1244 may wrap around a rounded side 1292 of the second protrusion 1266 (not shown). While in the variation shown the first protrusion 1264 and second protrusion 1266 may comprise first and second horizontal cylindrical segments 1268 and 1270 (not shown), where the first and second horizontal cylindrical segments 1268 and 1270 may be oriented with their rounded sides facing distally, it should be appreciated that first and second protrusions 1264 and 1266 of the ram interlock 1226 may be shaped such that the protrusions are rounded at the points of contact with the tensioning cord 1244, and therefore in some variations may comprise full cylindrical segments. Finally, the tensioning cord 1244 may have a seventh portion 1284 that may extend proximally from the ram interlock 1226 toward the float 1248, where the second end 1256 of the tensioning cord 1244 may be attached to the float 1248 on the second side of the plunger 1110 (not shown). The second end 1256 may be attached to the float 1248 in any suitable manner, including in the manners described above with respect to first end 1254. In other variations, the first end 1254 and second end 1256 may be connected (e.g., the tensioning cord 1244 may be a closed loop, or the first and second ends 1254 and 1256 may be spliced, knotted, or welded together), and the tensioning cord 1244 may extend around the float 1248 to secure it. In some of these variations, the tensioning cord 1244 may sit in a receiving groove in the float 1248.

By wrapping the tensioning cord 1244 as described through the slot 1756 on the distal face 1754 of the plunger 1110, the tension in the tensioning cord 1244 may resist distal movement of the plunger 1110 through the central lumen 1228 of the ram interlock 1226 due to the biasing force from the stored energy source 1202. Due to friction between the tensioning cord 1244 and the first and second protrusions 1264 and 1266 of the ram interlock 1226, the cord tensioning system 1242 may be able to resist higher forces from the stored energy source 1202 than may be provided by the locking spring 1246. Under the principle of the capstan equation (also known as Eytelwein's formula), tension on a cord (e.g., the tensioning cord 1244) may be different on either side of a static cylinder (e.g., first and second protrusions 1264 and 1266 of the ram interlock 1226), such that a holding force on one side of the static cylinder (e.g., the tension supplied by the locking spring 1246) may carry a larger loading force (e.g., the force supplied by the composite springs 1218). The relationship between the holding force and the loading force is dictated by the coefficient of friction between the cord and the static cylinder, as well as the wrap angle—the angle around which the cord contacts the static cylinder. In the cord tensioning system 1242, the tensioning cord 1244 and ram interlock 1226 may comprise any materials having suitable coefficients of friction, such as but not limited to a tensioning cord 1244 comprising aramid fibers and first and second protrusions 1264 and 1266 comprising polycarbonate. In some variations, the coefficient of friction between these two materials may be about 0.1 to 0.2, about 0.2 to 0.3, about 0.3 to 0.4, about 0.4 to 0.5, or greater. Additionally, it may be desirable for the tensioning cord 1244 to comprise a material having suitable ability to hold sustained loads, as well as resist creep and stretch, such as but not limited aramid fibers. The tensioning cord 1244 may be wrapped around the first and second protrusions 1264 and 1266 of the ram interlock 1226 for wrap angles sufficient to generate the desired relationship between the holding force and the loading force. In some variations, the wrap angle may be approximately 180 degrees. In other variations, the wrap angle may be over 360 degrees, for example 720 degrees; that is, the tensioning cord 1244 may be wrapped multiple times around the first and second protrusions 1264 and 1266 of the ram interlock 1226.

The cord tensioning system 1242 may be biased toward the tensioned configuration, such that when no distal force is applied to the proximal housing 708, the cord tensioning system 1242 may resist or limit the stored energy source 1202 from contributing to the displacement of the contents of the reservoir 914 of the syringe 704 through the lumen 908 of the needle 906 by applying a proximal force to the distal end 1116 of the plunger 1110 of the ram 1102, as described above.

Although the cord tensioning system 1242 may be biased toward a tensioned configuration as described above, the cord tensioning system 1242 may be moved toward the released configuration by reducing or releasing the tension on first portion 1272 and seventh portion 1284 of the tensioning cord 1244 (described above). The tension on the first portion 1272 and seventh portion 1280 of the tensioning cord 1244 may be reduced or released by reducing the distance between the first and second ends 1254 and 1256 of the tensioning cord 1244 and the first and second protrusions 1264 and 1266 of the ram interlock 1226. This distance may be reduced by applying distal force to the proximal housing 708. When a distal force is applied to the proximal housing 708 while the distal housing 710 is held in place (e.g. by pressing the distal end 758 of the nose 716 of the distal housing 710 against a patient's tissue), the proximal housing 708 and the float 1248 may be moved distally relative to the first and second protrusions 1264 and 1266 of the ram interlock 1226. When the tension on the first portion 1272 and seventh portion 1284 of the tensioning cord 1244 is reduced, the tension that can be held by the third portion 1276 and the fifth portion 1280 of the tensioning cord 1244 may be correspondingly reduced, based on the capstan equation described above. As a result, the distal force on the plunger 1110 of the ram 1102 due to the stored energy source 1202 may no longer be able to be partially or fully opposed by the tensioning cord 1244 running through the slot 1756 on the distal face 1754 of the plunger 1110, and the tensioning cord 1244 may slip around the first and second protrusions 1264 and 1266 of the ram interlock 1226, which may allow the plunger 1110 to move distally into the syringe cavity 904, as described above and shown in FIG. 12E. This may in turn urge the seal 910 distally to displace the contents of the reservoir 914 through the lumen 908 of the needle 906, as described above.

In some variations, the tensioning cord 1244 may begin to slip around the first and second protrusions 1264 and 1266 of the ram interlock 1226, which may allow the plunger 1110 to move distally into the syringe cavity 904, before the tension on the first portion 1272 and seventh portion 1284 of the tensioning cord 1244 is reduced to zero. In such a case, a portion of the force from the composite springs 1218 may urge the plunger 1110 to move distally within the syringe cavity 904. If a user applies distal force to the proximal housing 708 sufficient to reduce the tension on the first portion 1272 and seventh portion 1284 of the tensioning cord 1244 to zero (e.g., by counterbalancing the full force from the locking spring 1246), the full force from the composite springs 1218 may urge the plunger 1110 to move distally within the syringe cavity 904. If a user applies distal force to the proximal housing 708 beyond the amount needed to reduce the tension on the first portion 1272 and seventh portion 1284 of the tensioning cord 1244 to zero, the additional distal force on the proximal housing 708 may be transferred into additional force urging the plunger 1110 to move distally within the syringe cavity 904.

Figure 22:
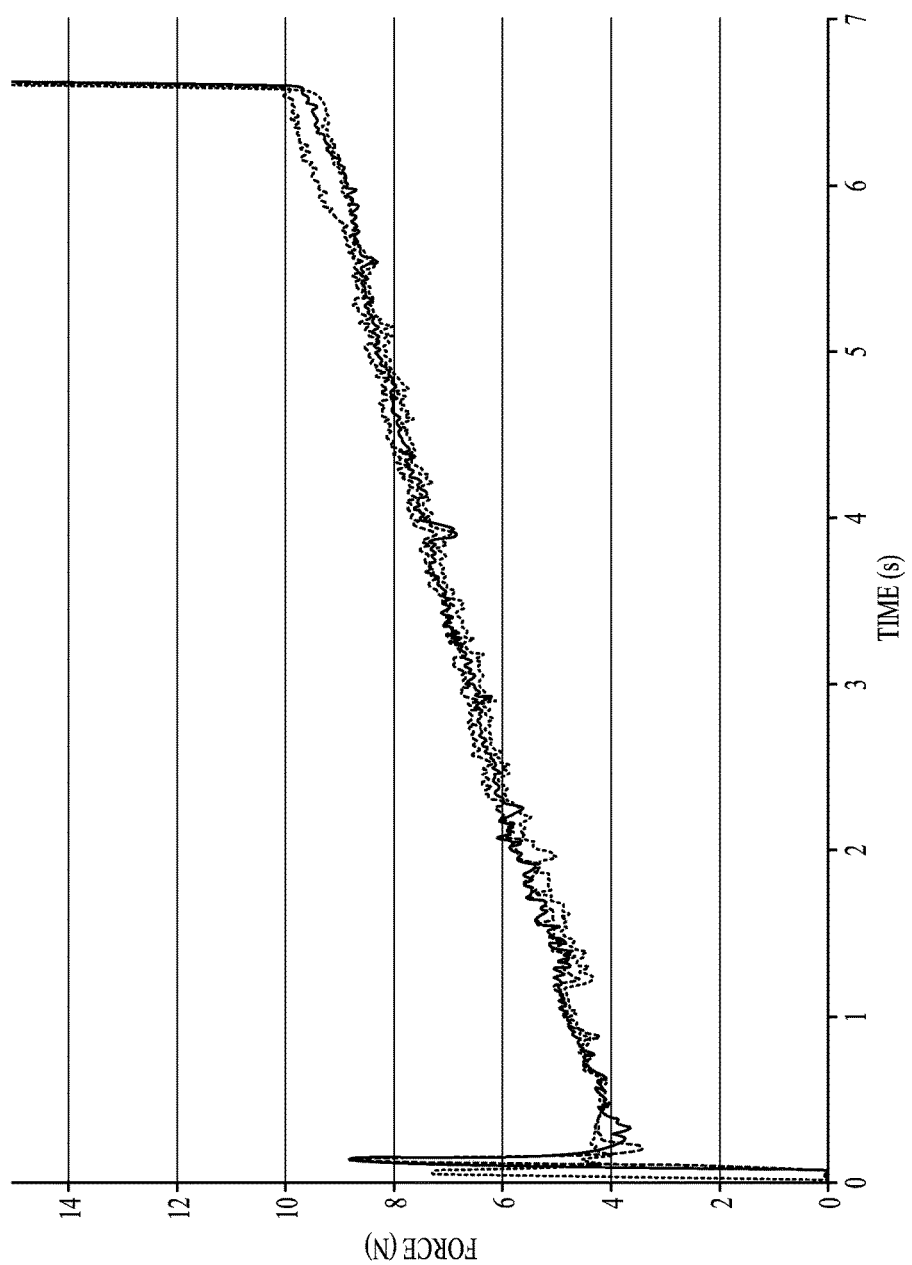
FIG. 22 shows an illustrative graph of the user force required to perform an injection using an injection device similar to the injection device of FIG. 10.

If the distal force on the proximal housing 708 is released, the bias of the proximal housing 708 away from the ram interlock 1226 due to the locking spring 1246 (described above) may cause the proximal housing 708 to move distally away from the ram interlock 1226. The float 1248 may in turn move distally away from the ram interlock 1226, which may restore tension in the first portion 1272 and seventh portion 1284 of the tensioning cord 1244 and return the cord tensioning system 1242 to a tensioned configuration. The rate control assembly 1204 may then resist motion due to the stored energy source 1202. This may allow the user to selectively and reversibly start and stop, or increase or decrease the speed of, the injection process. FIG. 22 shows an illustrative graph of the user force required to perform an injection using an injection device having a power assembly similar to the power assembly 706 of the injection device 700, illustrating the initial actuation force and increasing actuation force throughout the stroke during the injection process. The graph represents the applied force required to maintain substantially constant distal motion of the housing 708 (and thus of the plunger 1110) in order to maintain a substantially constant rate of injection. As shown, the composite spring may relax during the injection stroke, therefore exerting a decreasing force; thus, to maintain a substantially constant rate of injection, the applied force may need to increase with progress of the injection (and thus increase as a function of time, as shown). However, it should be noted that the user need not maintain a substantially constant rate of injection. As shown, an applied force of approximately 4 N is required in the given configuration to sufficiently relax the tensioning cords in order to allow the injection to begin, and subsequently a lesser force may be required to continue the injection, although the resulting injection rate may be slower. It should be noted that this graph is merely illustrative of the user force required for a similar device, and is not meant to indicate that the injection device 700 may or must conform to this representation.

In some variations, the injection device 700 may comprise an autocomplete mechanism, as described with respect to injection device 100. In some variations, the autocomplete mechanism may be based on a relaxation of the locking spring 1246. As described above, the locking spring 1246 may generate a tensioning force on the tensioning cord 1244. When the tension is released, the seal 910 may be able to move distally to displace the contents of the reservoir 914 through the lumen 908 of the needle 906. Thus, the injection may autocomplete by reducing the tensioning force on the tensioning cord 1244 due to the locking spring 1246. In some variations, the tensioning force on the tensioning cord 1244 due to the locking spring 1246 may be reduced by increasing the distance between the proximal and distal ends of the locking spring 1246. In some of these variations, this can be achieved by locating the locking spring retainer 1250 within the bore hole 1120 of the ram 1102 such that the distal end of the locking spring retainer 1250 is located proximally to the distal end 1124 of the bore hole 1120 before autocompletion. Because the distal portion of the locking spring 1246 may be housed in the locking spring retainer 1250, the distal end of the locking spring 1246 may thus be located proximally to the distal end 1124 of the bore hole 1120. When autocompletion is initiated, the locking spring retainer 1250 may move distally within the bore hole 1120, which may in turn allow the distal end of the locking spring 1246 to move distally within the bore hole 1120, relaxing the locking spring 1246. In some variations, autocompletion may be initiated by the ram interlock 1226. The locking spring retainer 1250 may be held at a position proximally to the distal end 1124 of the bore hole 1120 by two hooks (not shown) on the locking spring retainer 1250 that extend outwardly and into corresponding openings (not shown) in the ram 1102. When the injection has proceeded such that the ram 1102 has moved distally such that the openings in the bore hole 1120 are aligned with the inwardly facing proximal tabs 1298 of the flanges 1296 of the ram interlock 1226, the tabs 1298 may enter the openings in the ram 1102 and may apply an inward force that pushes the hooks on the locking spring retainer 1250 such that they disconnect from the openings in the ram 1102. When the hooks disconnect from the openings, the locking spring retainer 1250 may move distally within the bore hole 1120 to the distal end 1124 of the bore hole, due to the biasing force from the locking spring 1246. As described above, when the locking spring retainer 1250 moves distally, the distal end of the locking spring 1246 may also move distally, which may in turn relax the locking spring 1246 and may cause the injection to autocomplete.

In some variations, one or more of the elements of injection device 700 may optionally comprise clocking features to correcting orient the elements relative to each other, as described above with respect to injection device 100. Additionally or alternatively, in variations in which the housing 702 has an elliptical cross-section, the elliptical cross-section may contribute to the correct orientation of the housing elements.

In some variations, it may be desirable to assemble portions of the injection device 700 in a particular order. For example, in some variations, a first portion of the injection device 700 may be assembly by attaching the tensioning cord 1244 may be attached at its first end 1254 and second end 1256 to the float 1248. The tensioning cord 1244 may then be wrapped around the bollards 1288 of the ram interlock 1226—more specifically, the second portion 1274 and sixth portion 1282 may be wrapped around the first protrusion 1264 and the second protrusion 1266 of the ram interlock 1226, respectively. The base retainer cap 1126 may then be placed in line with the ram interlock 1226. Then, the ram 1102 may be put into place such that the fourth portion 1278 of the cord is engaged with the slot 1756 on the distal face 1754 of the plunger 1110, and the ram may be secured by lowering the base retainer cap 1126 onto the ram interlock 1226. The composite springs 1218 may then be installed, which may be done by inserting each composite spring 1218 proximally through the side lumens 1236 of the ram interlock 1226 and side lumens 1138 of the base retainer cap 1126 and attaching the proximal end of the composite spring 1218 to the ram crossbar 1112. A second portion of the injection device 700 may then be assembled by attaching the nose 716 to the remainder of the distal housing 710, such as by sonic welding. The compression spring 820 of the needle safety assembly 800 may then be snapped into the nose 716 of the housing 710, and the locking assembly 826 may be snapped into the nose 716 via the locking assembly 826. A third portion of the injection device 700 may be assembled by placing the syringe sleeve 930 around a pre-filled syringe 704. The third portion may then be attached to the first portion of the injection device 700 by attaching the syringe sleeve 930 to the ram interlock 1226 via the latches 946 on the proximal lip 954 of the syringe sleeve 930. The attached first and third portions may then be inserted into the second portion of the injection device 700 (comprising the distal housing 710). The locking spring retainer 1250, locking spring 1246, and locking spring cap 1252 may then be inserted into the bore hole 1120 of the ram 1102. The proximal housing 702 may then be attached, which may be done by snapping together the float 1248 and the proximal housing 708 via the latches 1260 on the float 1248. The rigid needle shield 922 and cap 772, in variations having a cap 772, may also be installed. It should be appreciated that this order of assembly is only illustrative, and that the elements of the injection device 700 may be assembled in other orders. It should also be appreciated that the assembly process may include additional elements not included in the description above, and that not all of the elements described as being assembled need be incorporated into the device.

Another embodiment of an injection device 1300 is depicted in FIGS. 18 and 19A-19D, comprising a housing 1302, a syringe 1304, and a power assembly 1306. The housing 1302 may be similar to the housing 102, described above with respect to injection device 100, and may have the same components, configurations, and functions. In some variations, this may optionally comprise a cap 1348, which may be similar to the cap 148 described above with respect to injection device 100, and may have the same components and functions as described above.

Figure 19A:
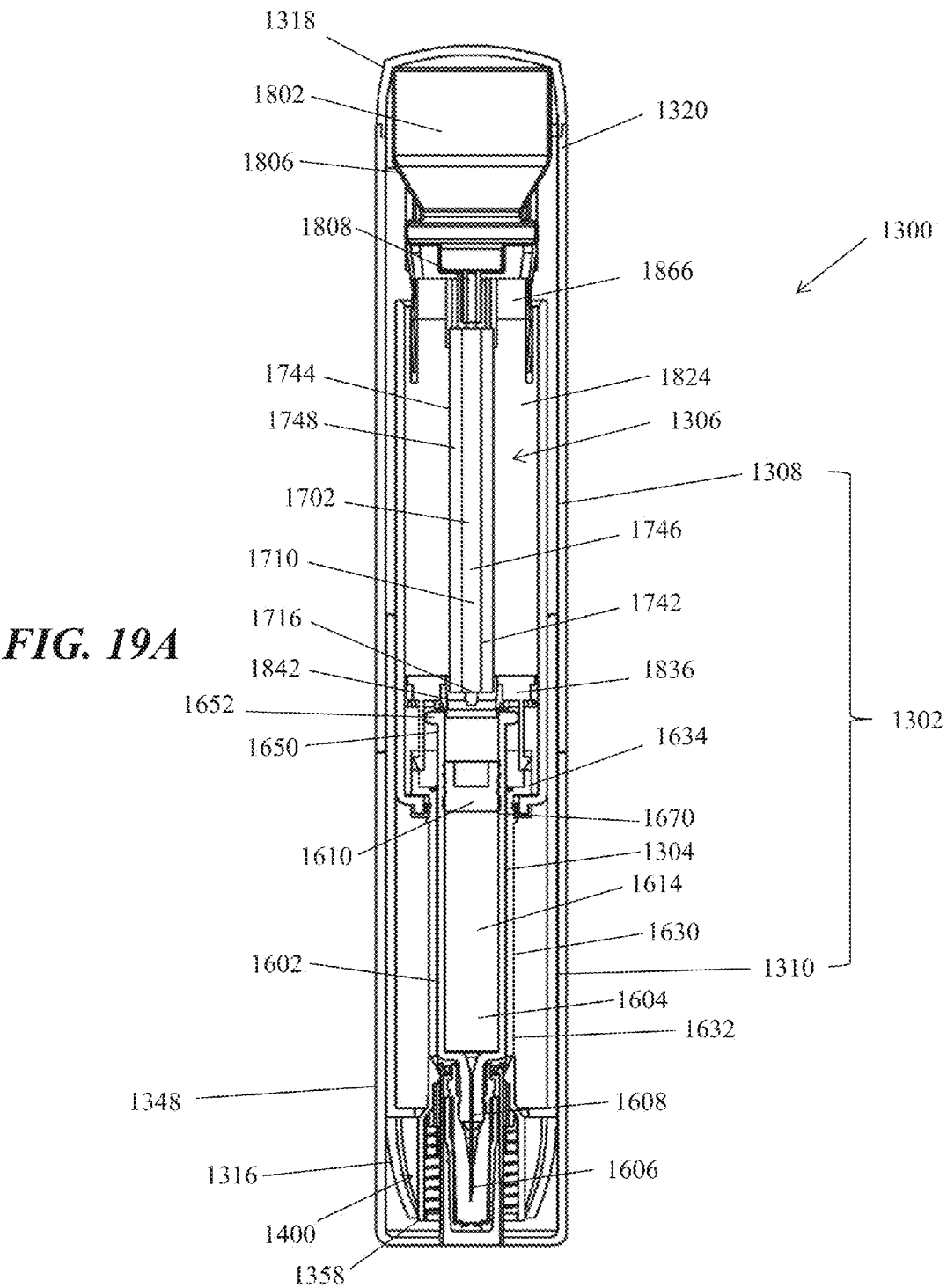
FIGS. 19A-19G illustrate longitudinal cross-sectional views of the embodiment of an injection device of FIG. 17 in various stages during use.
Figure 19B:
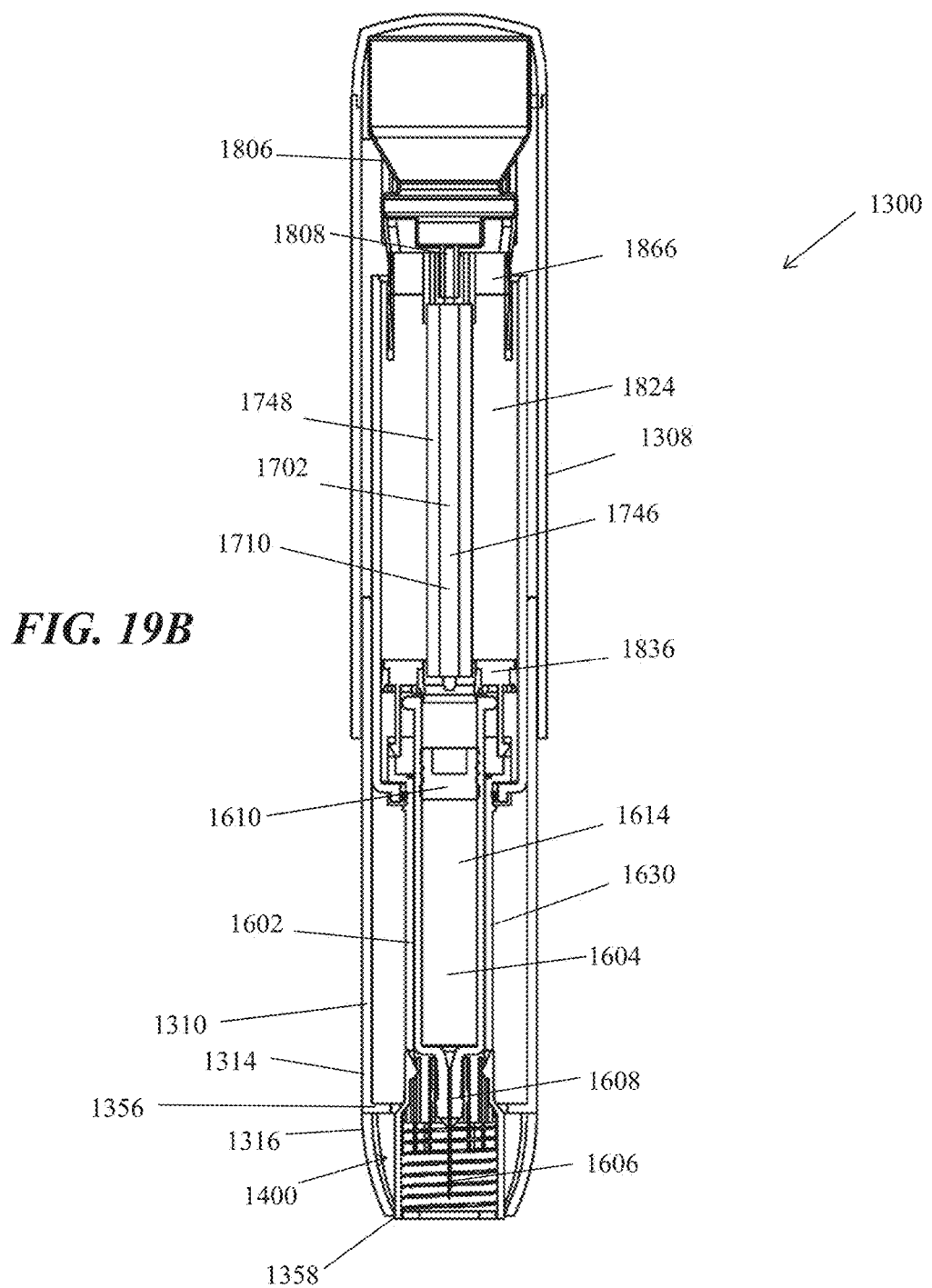
Figure 19C:
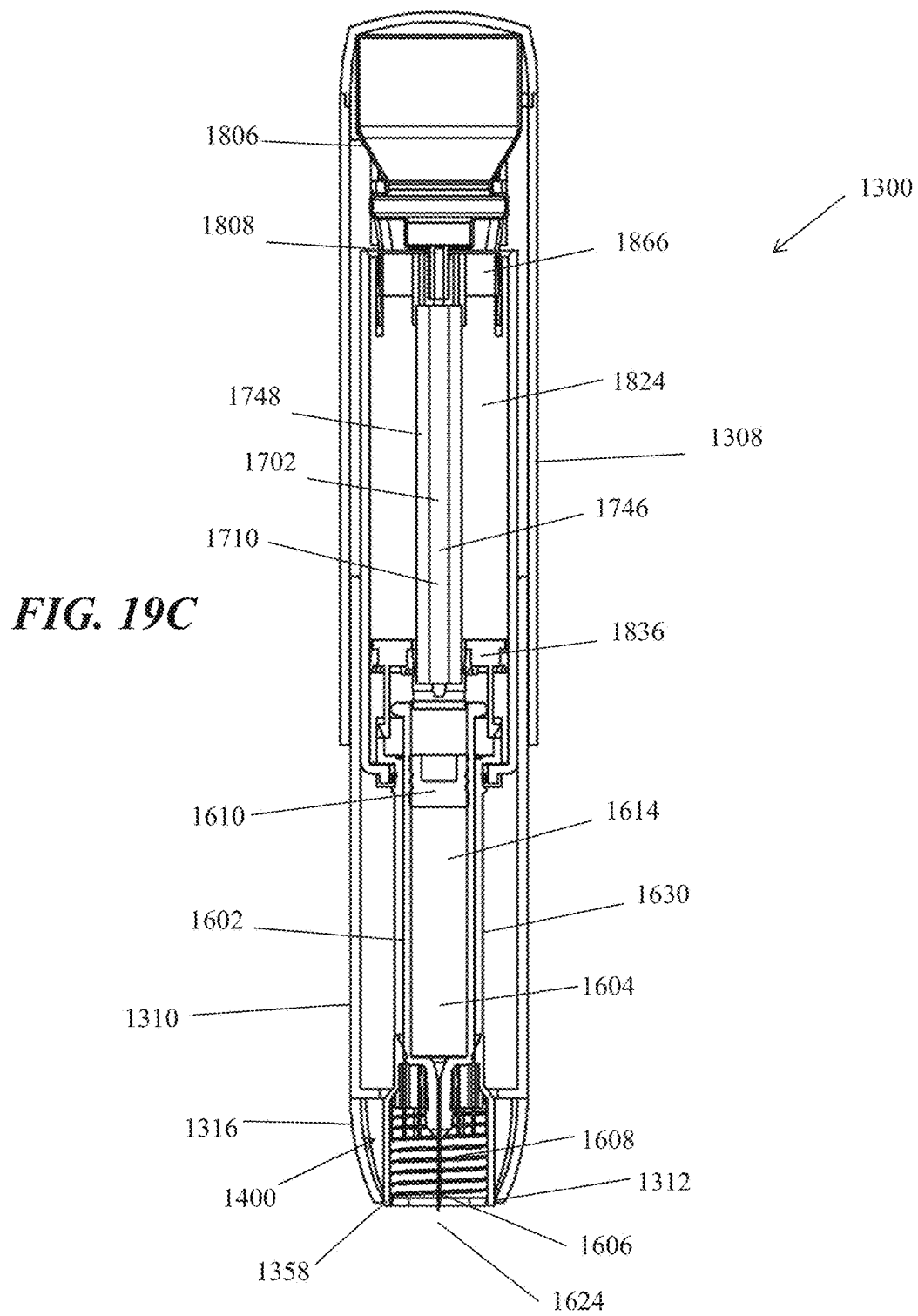
Figure 19D:
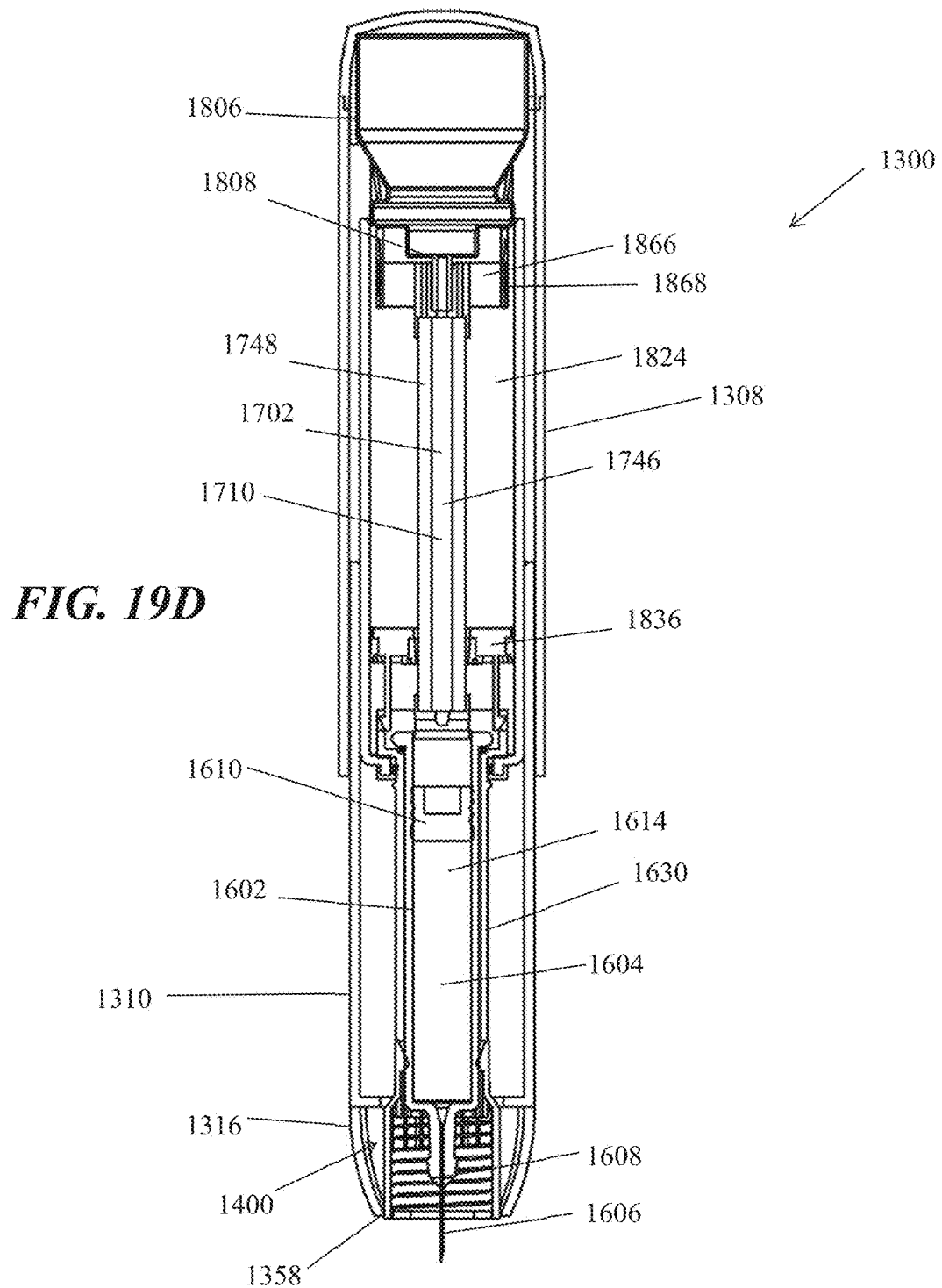
Figure 19E:
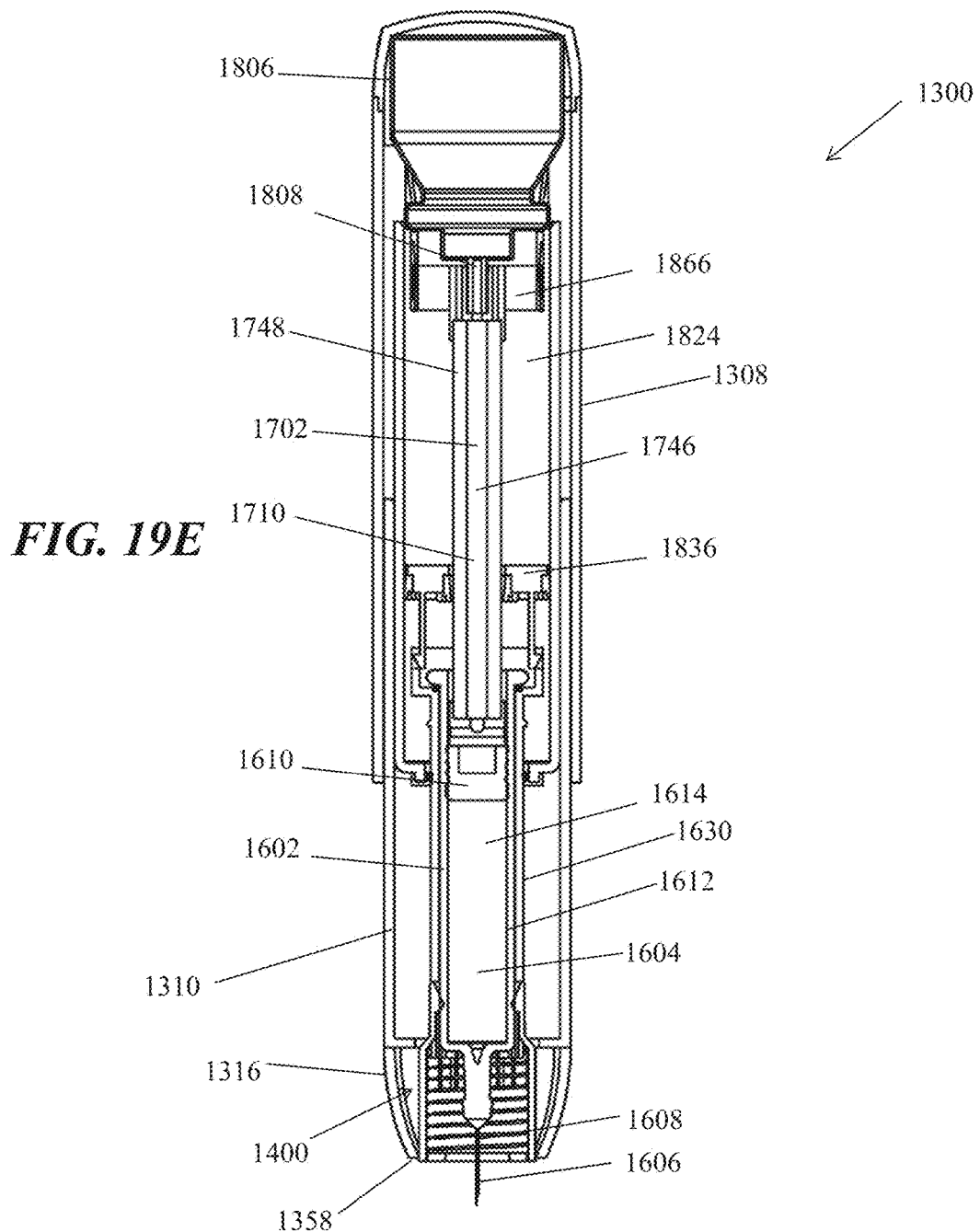
Figure 19F:
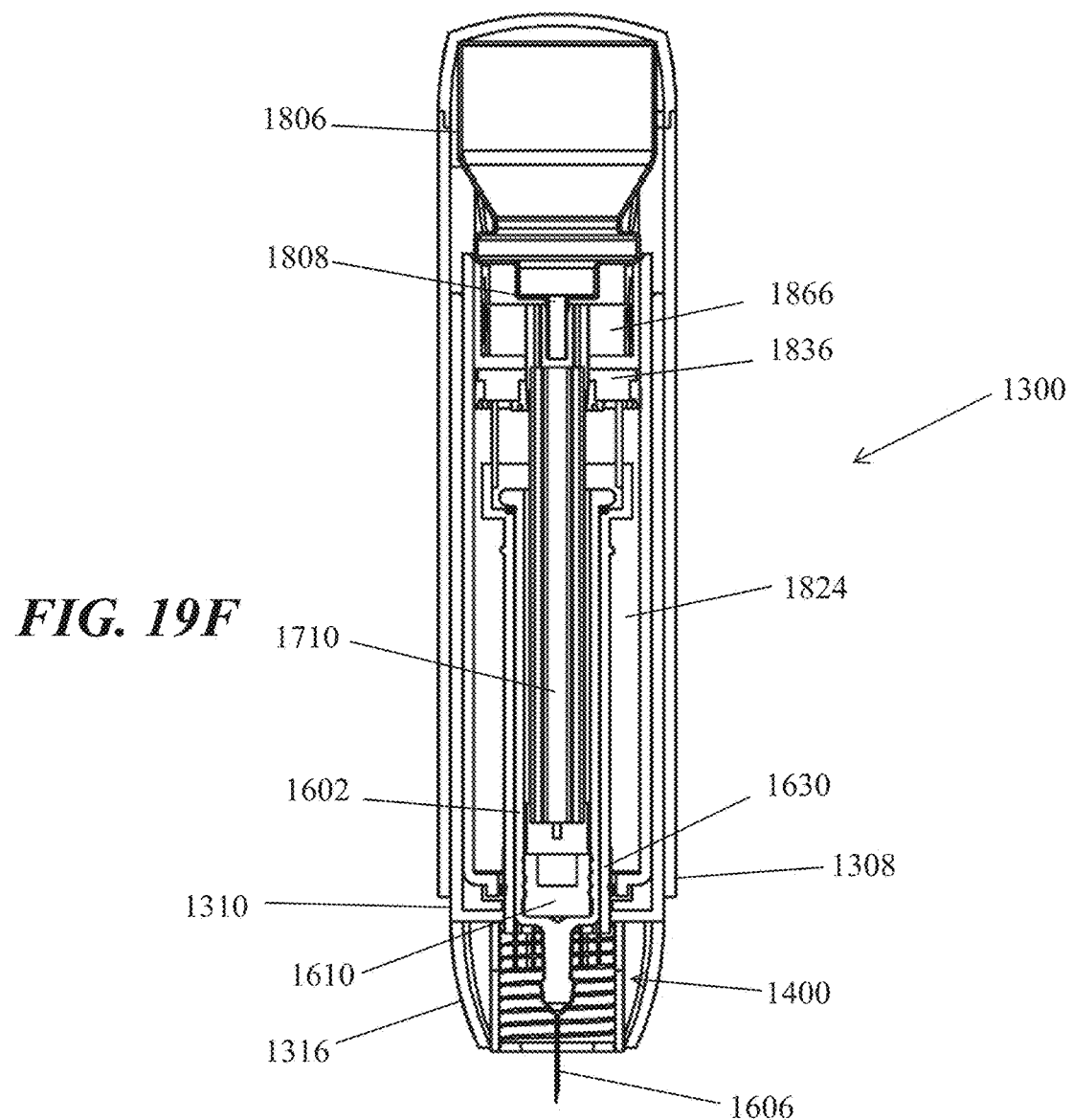
Figure 19G:
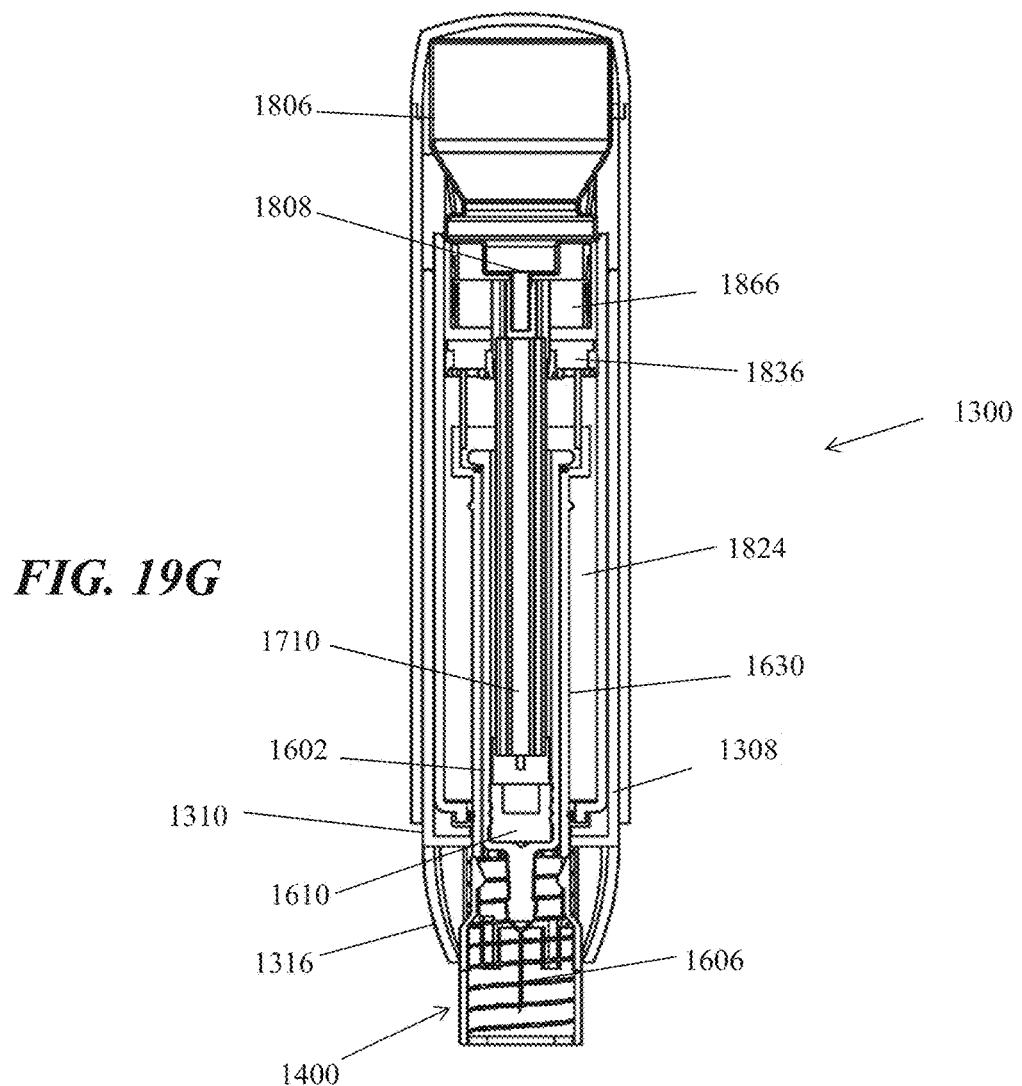

FIGS. 19A-19G illustrate longitudinal cross-sectional views of the embodiment of an injection device of FIG. 17 in various stages during use. FIG. 19A illustrates the device before use. FIG. 19B illustrates the device with the rigid needle shield and cap removed. FIG. 19C illustrates the device with the syringe in a partially extended position. FIG. 19D illustrates the device with the syringe in a fully extended position. FIG. 19E illustrates the device with the plunger moved partially toward the distal position within the syringe cavity. FIG. 19F illustrates the device with the plunger in the distal position within the syringe cavity. FIG. 19G illustrates the device with the needle shroud extended. Like the injection device 100, the injection device 1300 may comprise a needle safety assembly 1400 that may be movable between a retracted position (shown in FIGS. 19A-19B) and an extended position (shown in FIGS. 19D-19G), as described in detail above with regard to needle safety assembly 200. The needle safety assembly 1400 may have the same components, positions, and functions as the needle safety 200 described with respect to injection device 100.

The housing 1302 may also comprise an indicator that, like the indicators described with respect to the injection device 100, may indicate the progress or completion of the injection, as described in detail above, and may have activated and inactivated configurations. In some variations of the injection device 1300, the end-of-dose indicator may comprise a flag. The flag may be spring-biased and may be released by relative motion between the flag and the housing 1302. When the indicator is in an activated configuration, it may be visible through the end cap 1318 of the proximal housing 1308.

The syringe 1304 of the injection device 1300 may be similar to the syringes 104 and 704 described above with respect to injection devices 100 and 700, and may have the same components, positions, and functions as described above.

The injection device 1300 may further comprise a syringe sleeve 1630. The syringe sleeve 1630 may be attached to the distal housing 1310 via a set of flexures and protrusions (not shown) that may hold the syringe sleeve 1630 relative to the ledge 1356 extending radially inward from the distal end 1314 of the distal housing 1310. The syringe 1304 may be slidably disposed with the syringe sleeve 1630. The syringe sleeve 1630 may comprise a distal portion 1632 and a proximal portion 1634. The distal portion 1632 may be configured to fit slidably around the syringe body 1602. The proximal portion 1634 may have a larger diameter (or maximum distance transverse to the longitudinal axis) than the distal portion 1632. In some variations, the syringe sleeve may comprise a transparent or translucent material, such as a plastic. The proximal portion 1634 of the syringe sleeve 1630 may be configured to engage with a syringe cap 1836 (described below). The proximal portion 1634 of the syringe sleeve 1630 may comprise recess, slot, or other indentation configured to mate with tabs on the distal end of latches on the syringe cap 1836, as described below.

As in the embodiments of the injection device 100 and 700, the ram 1702 of the injection device 1300 may be configured to transmit distal force on the proximal housing 1308 into different motions, depending on the stage of the injection process. In a first stage, distal force on the proximal housing 1308 may be transmitted into distal motion of the syringe 1304 and power assembly 1306 relative to the distal housing 1310. In a second stage, distal force on the proximal housing 1308 may be transmitted into displacement of the contents of the reservoir 1614 of the syringe 1304 (e.g., a formulation comprising a therapeutic agent) through the lumen 1608 of the needle 1606.

In some variations, the ram 1702 may be configured such that these effects of distal force on the proximal housing 1308 may occur in the order described above. That is, the ram 1702 may be configured such that distal force on the proximal housing 1308 may be transmitted first into distal motion of the syringe 1304 and power assembly 1306 relative to the distal housing 1310, and then transmitted second into displacement of the contents of the reservoir 1614 of the syringe 1304 (e.g., a formulation comprising a therapeutic agent) through the lumen 1608 of the needle 1606. This may be desirable, for example, because it may allow the syringe 1304 to move distally such that the needle 1606 may pierce a patient's tissue before the contents of the syringe cavity 1604 of the syringe 1304 are displaced through the lumen 1608 of the needle 1606.

In some variations, the ordering of effects of distal force on the proximal housing 1308 may be due to different amounts of force that are required for each motion. For example, the ram 1702 may transmit distal force on the proximal housing 1308 into distal motion of the syringe 1304 and power assembly 1306 relative to the distal housing 1310 when the force on the proximal housing 1308 is above a first threshold (e.g., above about 1 N, above about 2 N, above about 3 N, above about 4 N, above about 5 N, above about 6 N, above about 7 N, or higher); and the ram 1702 may transmit distal force on the proximal housing 1308 into displacement of the contents of the reservoir 1614 of the syringe 1304 through the needle 1606 when the force on the proximal housing 1308 is above a higher second threshold (e.g., above about 5 N, above about 10 N, above about 15 N, above about 20 N, above about 25 N, or higher). In some variations, the thresholds may be due to the proximal forces from friction on the syringe 1304 and ram 1702, respectively. It should be appreciated that in some other variations, the ram 1702 may transmit distal force on the proximal housing 1308 into different motions in different orders and by different mechanisms. For example, in some variations the effect of the distal force may be chosen by a mechanism for manual selection by the user. In should also be appreciated that the ram 1702 may have fewer or more motions into which it may transmit distal force onto the proximal housing 1308.

The ram 1702 may comprise a plunger 1710. The plunger 1710 may be configured to be slidable through the lumen 1842 of the syringe cap 1836 (described below), and may be configured to be slidable within the syringe cavity 1604 of the syringe 1304. The distal end 1716 of the plunger 1710 may be configured to engage with the seal 1610 of the syringe 1304. If the plunger 1710 is moved distally relative to and within the syringe cavity 1604, the plunger 1710 may push the seal 1610 distally relative to and within the syringe cavity 1604. This movement of the seal 1610 may decrease the volume of the reservoir 1614 containing the formulation comprising a therapeutic or diagnostic agent. Thus, distal motion of the plunger 1710, and in turn the seal 1610, relative to and within the syringe cavity 1604 may cause the contents of the reservoir 1614 to be displaced through the lumen 1608 of the needle 1606. The plunger 1710 may comprise an inner tube 1742 located coaxially within an outer tube 1744. The inner tube 1742 and outer tube 1744 may form an inner lumen 1746 within the inner tube 1742, and an outer annular lumen 1748 between the inner tube 1742 and outer tube 1744. In some variations, the outer annular lumen may be divided into two or more (e.g., three, four, etc.) radial segments. The inner lumen 1746 and outer annular lumen 1748 may cooperate with the power assembly 1306 to direct pressure flow from the stored energy source 1802, as described in detail below.

Application of distal force on the proximal housing 1308 may cause the proximal housing 1308 to be moved distally. If the distal housing 1310 is held in place (e.g. by pressing the distal end 1358 of the nose 1316 of the distal housing 1310 against a patient's tissue), the proximal housing 1308 may be moved distally relative to the distal housing 1310. The movement of the proximal housing 1308 may be transferred via the power assembly 1306 (discussed in more detail below) to cause the power assembly 1306 and syringe 1304 to slide distally from a retracted position (shown in FIGS. 19A-19B) relative to the distal housing 1310 if the distal force on the proximal housing 1308 is above the necessary force threshold. The threshold force required may be due to the friction between the outer surface of the syringe body 1602 and the inner surface of the syringe sleeve 1630. In some variations, the friction may additionally or alternatively be generated between the syringe body 1602 and the inner surface of the syringe sleeve 1630 by a seal attached to the inner surface of the syringe sleeve 1630. When the threshold distal force is reached, the power assembly 1306 and syringe 1304 may be moved distally toward the nose 1316 of the distal housing 1310, such that the syringe 1304 may move toward an extended position (described above with respect to syringe 104 of injection device 100), as shown in FIG. 19C.

As the distal tip 1624 of the needle 1606 approaches the distal opening 1312 of the nose 1316, the shield of the needle safety assembly 1400 may be unlocked from a retracted position, as described in detail above with respect to injection device 100. As the distal tip 1624 of the needle 1606 moves to extend beyond the distal end 1358 of the nose 1316, the needle 1606 may pierce tissue pressed against the distal end 1358 of the nose 1316. The syringe 1304 may continue to move distally relative to the syringe sleeve 1630 until the syringe 1304 has reached an extended position, as shown in FIG. 19D. At an extended position, the distal tip 1624 of the needle 1606 may have reached the desired depth (described above). In some variations, when the syringe 1304 reaches an extended position, further distal movement relative to the distal housing 1310 may be resisted by a proximal lip 1652 extending radially outward from the proximal end 1650 of the syringe body 1602, which may be configured such that it may fit within the proximal portion 1634 of the syringe sleeve 1630 but may not be able to enter the distal portion 1632 of the syringe sleeve 1630. Once the syringe 1304 reaches an extended position, the canister manifold 1866 (described below) may also engage with the pressure chamber 1824 via flexures 1868 on the canister manifold 1866.

It should be noted that the power assembly 1306 and syringe 1304 may move distally together with distal force on the proximal housing 1308, rather than the power assembly 1306 acting on the syringe 1304 (e.g., to cause the plunger 1710 to move distally within the syringe cavity 1604 to act on the seal 1610 and displace the contents of the reservoir 1614), due to the relative amounts of force required to move the power assembly 1306 and syringe 1304 relative to the distal housing 1310, and to cause the plunger 1710 to move distally within the syringe cavity 1604. More specifically, the amount of force required to overcome the friction between the outer surface of the syringe body 1602 of the syringe 1304 and the inner surface of the syringe sleeve 1630 may be less than the amount of force to cause the plunger 1710 to move distally within the syringe cavity 1604, described in detail below.

If the distal force on the proximal housing 1308 is released while the power assembly 1306 and syringe 1304 are moving from a retracted position to an extended position, the power assembly 1306 and syringe 1304 may stay in place in an intermediate position relative to the syringe sleeve 1630.

After the power assembly 1306 and syringe 1304 have moved distally relative to the distal housing 1310 such that the syringe 1304 is in an extended position and the distal tip 1624 of the needle 1606 is at the desired depth, additional distal force on the proximal housing 1308 may be transmitted into distal motion of the ram 1702 relative to the syringe cavity 1604, if the force is above the necessary force threshold. When the force is above the necessary force threshold, the plunger 1710 and seal 1610 may begin to be moved distally relative to and within the syringe cavity 1604, as shown in FIG. 19E, which may decrease the volume of the reservoir 1614 and displace the contents of the syringe cavity 1604 through the lumen 1608 of the needle 1606, as described above with respect to injection device 100. The threshold force required to move the plunger 1710 and seal 1610 distally within the syringe cavity 1604 may be due, first, to a ridge 1670 extending radially inward from the inner surface 1612 of the syringe cavity 1604. Before the seal 1610 has been moved within the syringe cavity 1604, the ridge 1670 may be located distally to the seal 1610. When sufficient distal force is applied to the proximal housing 1308 to deflect the seal 1610 distally over the ridge 1670, the seal 1610 is then able to move further distally within the syringe cavity 1604, if the force is sufficient to overcome friction between the seal 1610 and plunger 1710 and the inner surface 1612 of the syringe body 1602, as well as between the plunger 1710 and the syringe cap 1836. Additional force to move the plunger 1710 and seal 1610 distally relative to and within the syringe cavity 1604 may also be due to the power assembly 1306, described below.

As described above with respect to the power assembly 106 of injection device 100, the power assembly may provide an injection force sufficient (alone or in addition to injection force supplied by the user) to inject a given volume of a given formulation through a given size needle in a given time, as described in detail with regard to power assembly 106. Like the power assembly 106, power assembly 1306 may comprise a stored energy source and a rate control assembly. As in the power assembly 106 described with respect to injection device 100, the power assembly 1306 may comprise a stored energy source 1802, which may be configured to provide force to displace of the contents of reservoir 1614 of the syringe 1304 through the lumen 1608 of the needle 1606, and a rate control assembly 1804, which may comprise a braking assembly that may limit or restrict the stored energy source 1802 from contributing to the displacement of the contents of the reservoir 1614 of the syringe 1304 through the lumen 1608 of the needle 1606. In the embodiment of the injection device 1300 shown, the stored energy force 1802 may comprise a compressed gas or liquid propellant in a supercritical state. The compressed gas or liquid propellant may be held within container, such as a canister 1806 (e.g., a double-crimped metal canister), which may be located at the proximal end 1320 of the proximal housing 1308. The canister 1806 may be fixedly attached to the end cap 1318 of the proximal housing 1308, such that distal motion of the proximal housing 1308 may cause distal motion of the canister 1806. In some variations, the canister 1806 may be attached to the end cap 1318 of the proximal housing 1308 by a set of flexures extending distally from the inside of the end cap 1318 that may snap over the canister 1806 to retain it.

The compressed gas or liquid propellant may comprise any gas that is suitable for compression. In some variations, the compressed gas or liquid propellant may comprise a gas that is in a gaseous state at high pressures (e.g., N2, Ar, or compressed air). In these variations, when the compressed gas is released from the canister 1806, the output pressure may decrease as the compressed gas leaves the canister 1806. In other variations, the liquid propellant may comprise a gas that is a saturated liquid at high pressures (e.g., CO2 and R134A (also known as HF134A or HFC-R134a)). In these variations, when the liquid propellant is released from the canister 1806, the output pressure may be constant, as long as some propellant in liquid form remains in the canister 1806. The compressed gas or liquid propellant may have any suitable saturation pressure.

When the compressed gas or liquid propellant in a supercritical state is released from the canister 1806 through a valve 1808 (described below), it may cause the seal 1610 of the syringe 1304 to move distally relative to and within the syringe cavity 1604, which may cause the contents of the reservoir 1614 to be displaced through the needle 1606 of the syringe 1304. In some variations, the force from the compressed gas or liquid propellant may act directly on all or a portion of the proximal side of the seal. In other variations, the force from the compressed gas or liquid propellant may act indirectly on the seal; that is, the force may act on a surface other than the seal, which may in turn cause distal movement of the seal. In yet other variations, the force from the compressed gas or liquid propellant may act both directly and indirectly on the seal. In each of these variations, the force from the compressed gas or liquid propellant may act on surface areas (i.e., the surface area orthogonal to the longitudinal axis) of varying sizes. In some variations, the force may act on a surface having a cross-sectional surface area approximately equal to the cross-sectional surface area of the syringe cavity, for example, by acting directly on the seal. In other variations, the force may act on a surface area smaller than the cross-sectional area of the syringe cavity, for example by acting on a portion of the seal or on an annular surface area radially outside the syringe cavity having a smaller cross-sectional surface area than the syringe cavity. In yet other variations, the force from the compressed gas or liquid propellant may act on a surface area larger than the cross-sectional surface area of the syringe cavity, for example by acting on the seal and on an annular surface area radially outside of the syringe cavity, or by acting on an annular surface area radially outside of the syringe cavity having a larger cross-sectional surface area than the syringe cavity. One portion (e.g., a proximal portion) of the flow path may have the same or different cross-sectional (i.e., orthogonal to the longitudinal axis) profile as a second portion (e.g., a distal portion) of the flow path. In some variations, the flow path of the compressed gas or liquid propellant may be linear, while in other variations, the flow path may be non-linear. For example, there may be no linear flow path between two locations in the flow path of the compressed gas or liquid propellant (e.g., the proximal-most and distal-most locations), or the flow path of the compressed gas or liquid propellant may have two or more segments not parallel to each other.

In variations in which the force may act on a larger surface area, this may allow the compressed gas or liquid propellant to generate more pressure to cause the seal to move distally. The saturation pressure of the compressed gas or liquid propellant, and the cross-sectional surface area of the upon which the pressure may act, may thus be chosen in tandem to delivery an appropriate force based on the formulation viscosity, needle choice, injection volume, and desired injection time. In some variations, for example, the power assembly may be capable of injecting 1.9 mL of 39 cP solution through a 27 gauge needle in 10 seconds by applying about 52-54 N of force. For example, in some variations, the injection device 1300 may use a liquid propellant with a saturation pressure of about 850 PSIa (e.g., CO2) acting on a cross-sectional surface area of about 0.014 square inches, which may supply about 52 N of force. In other variations, the injection device 1300 may use a liquid propellant with a saturation pressure of about 85 PSIa (e.g., R134A) acting on a cross-sectional surface area of about 0.138 square inches. In other variations, the injection device 1300 may use a compressed gas with a typical pressure of about 2700 PSIa (e.g., N2) acting on a cross-sectional surface area of about 0.0043 square inches. In other variations, the injection device 1300 may use a compressed gas with a typical pressure of about 1750 PSIa (e.g., Ar) acting on a cross-sectional surface area of about 0.0067 square inches. It should be appreciated that these pressures, surface areas, and forces are merely illustrative examples; any suitable combination may be chosen to achieve a desired injection force.

Figure 20A:
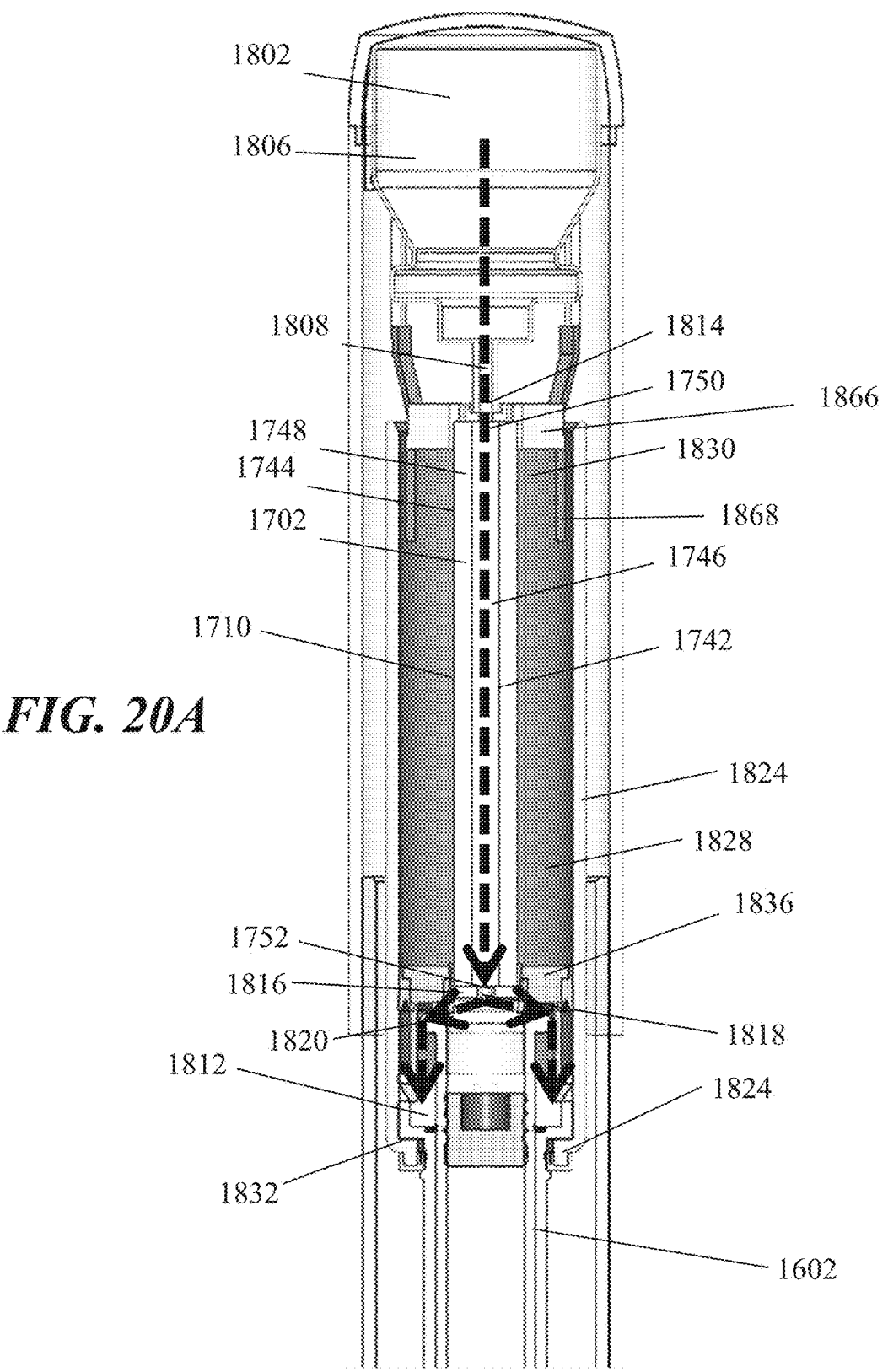
FIG. 20A depicts a longitudinal cross-sectional view of the pressure pathway of the injection device of FIG. 18, with arrow indicating the pathway.

As shown in FIGS. 19A-19G and illustrated with arrows in FIG. 20A, the stored energy source 1802 may comprise a flow-directing assembly for directing the compressed gas or liquid propellant when released. The flow-directing assembly may direct the compressed gas or liquid propellant distally through the inner lumen 1746 of the plunger 1710, radially outward through redirection openings, and into a pressurization region 1812 formed distally to a syringe cap 1836. More specifically, as described above, the plunger of the ram 1702 may comprise an inner tube 1742 located coaxially within an outer tube 1744. The inner tube 1772 and outer tube 1744 may form an inner lumen 1746 within the inner tube 1772, and an outer annular lumen 1748 between the inner tube 1772 and outer tube 1744. The proximal opening 1750 of the inner lumen 1746 may be connected to the proximal opening 1814 of the valve 1808. The distal opening 1752 of the inner lumen 1746 may be in fluid communication with an inflow opening 1818 of a manifold 1816. The inflow opening 1818 of the manifold 1816 may be in fluid communication with one or more outflow openings 1820 of the manifold 1816. In some variations, the manifold 1816 may have four outflow openings 1820 connected to the inflow opening 1818, and the outflow openings 1820 may be located away from the longitudinal axis of the manifold 1816, such that the outflow openings 1820 are directed outside of the syringe body 1602. The outflow openings 1820 of the manifold 1816 may be in fluid communication with the pressurization region 1812.

Figure 20B:
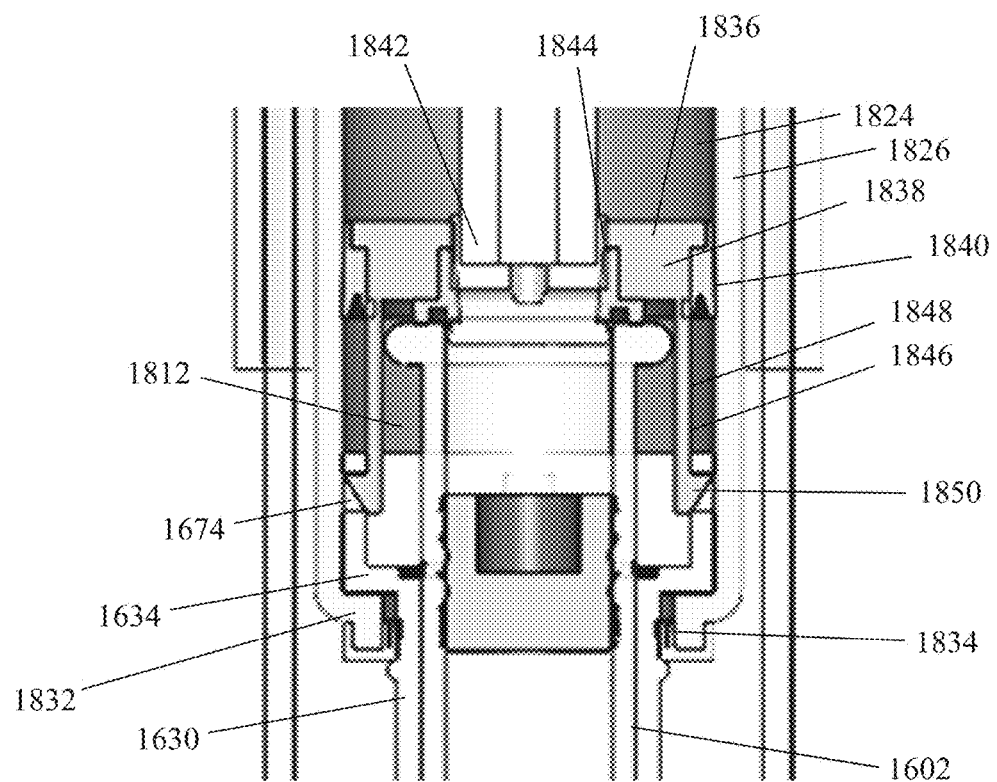
FIG. 20B shows a closer view of a portion of the pressure pathway of FIG. 20A.

As shown in FIG. 20A and in more detail in FIG. 20B, the pressurization region 1812 may be formed within a pressure chamber 1824, distally to a syringe cap 1836 and annularly to the syringe body 1602. The pressure chamber 1824 may comprise a cylinder 1826 having a lumen 1828 between a proximal end 1830 and a distal end 1832. The proximal end 1830 of the pressure chamber 1824 may be engaged with the canister manifold 1866 via flexures 1868 when the syringe 1304 is in an extended position, as described above. The distal end 1832 of the pressure chamber 1824 may form a seal 1834 around the proximal portion 1634 of the syringe sleeve 1630, such that the proximal portion 1634 of the syringe sleeve 1630 may be located within the lumen 1828 of the pressure chamber 1824. The syringe sleeve 1630 may be slidable within the seal 1834. The syringe cap 1836 may comprise a main body 1838, which may be slidably disposed within the pressure chamber 1824. The syringe cap 1836 may create a seal 1840 with the inner surface of the cylinder 1826 of the pressure chamber 1824 sufficient to resist pressurized gas travelling across the seal 1840 between the syringe cap 1836 and the inner surface of the cylinder 1826 of the pressure chamber 1824. The syringe cap 1836 may also have a lumen 1842 therethrough, which may be configured to allow the plunger 1710 of the ram 1702 to move therethrough. There may also be a seal 1844 between the surface of the syringe cap 1836 forming the lumen 1842 and the plunger 1710 sufficient to resist pressurized gas travelling across the seal 1844 between the syringe cap 1836 and the plunger 1710. Extending distally from the main body 1838 of the syringe cap 1836 may be one or more latches 1846. Each latch 1846 may comprise an elongate portion 1848 having a proximal portion attached to the main body 1838 of the syringe cap 1836, and a tab 1850 located at the distal end of the elongate portion 1848. The tab 1850 may be configured to fit into a recess, slot, or other indentation (e.g. recess 1674) in the proximal portion 1634 of the syringe sleeve 1630, described above. When the latches 1846 are engaged with the syringe sleeve 1630, the position of the syringe cap 1838 may be fixed relative to the position of the syringe sleeve 1630.

The seal 1834 between the pressure chamber 1824 and the proximal portion 1634 of the syringe sleeve 1630, the seal 1840 between the syringe cap 1836 and the pressure chamber 1824, and the seal 1844 between the syringe cap 1836 and the plunger 1710 may thus create a variable-volume pressurization region 1812. The volume of the pressurization region 1812 may be at a minimum when the proximal portion 1634 of the syringe sleeve 1630 is adjacent to the distal end 1832 of the pressure chamber 1824, as shown in FIG. 20A. As the compressed gas or liquid propellant flows into the pressurization region 1812, the pressure from the compressed gas or liquid propellant may urge the distal end 1832 of the pressure chamber 1824 distally relative to the syringe sleeve 1630, in order to increase the volume of the pressurization region 1812. The volume of the pressurization region 1812 may be at a maximum when the pressure chamber 1824 has moved fully distally such that the distal end 1832 of the pressure chamber 1824 may be adjacent to the distal end 1314 of the distal housing 1310, as shown in FIG. 19F.

As the pressure chamber 1824 is urged distally relative to the syringe sleeve 1630, this may in turn urge the plunger 1710 distally relative to the syringe cavity 1604. As the plunger 1710 slides distally relative to and within the syringe cavity 1604, this may in turn push the seal 1610 distally relative to the syringe cavity 1604, which may in turn decrease the volume of the reservoir 1614 of the syringe 1304. This may cause the contents of the reservoir 1614 to be displaced through the lumen 1608 of the needle 1606 of the syringe 1304, as described above.

Figure 20C:
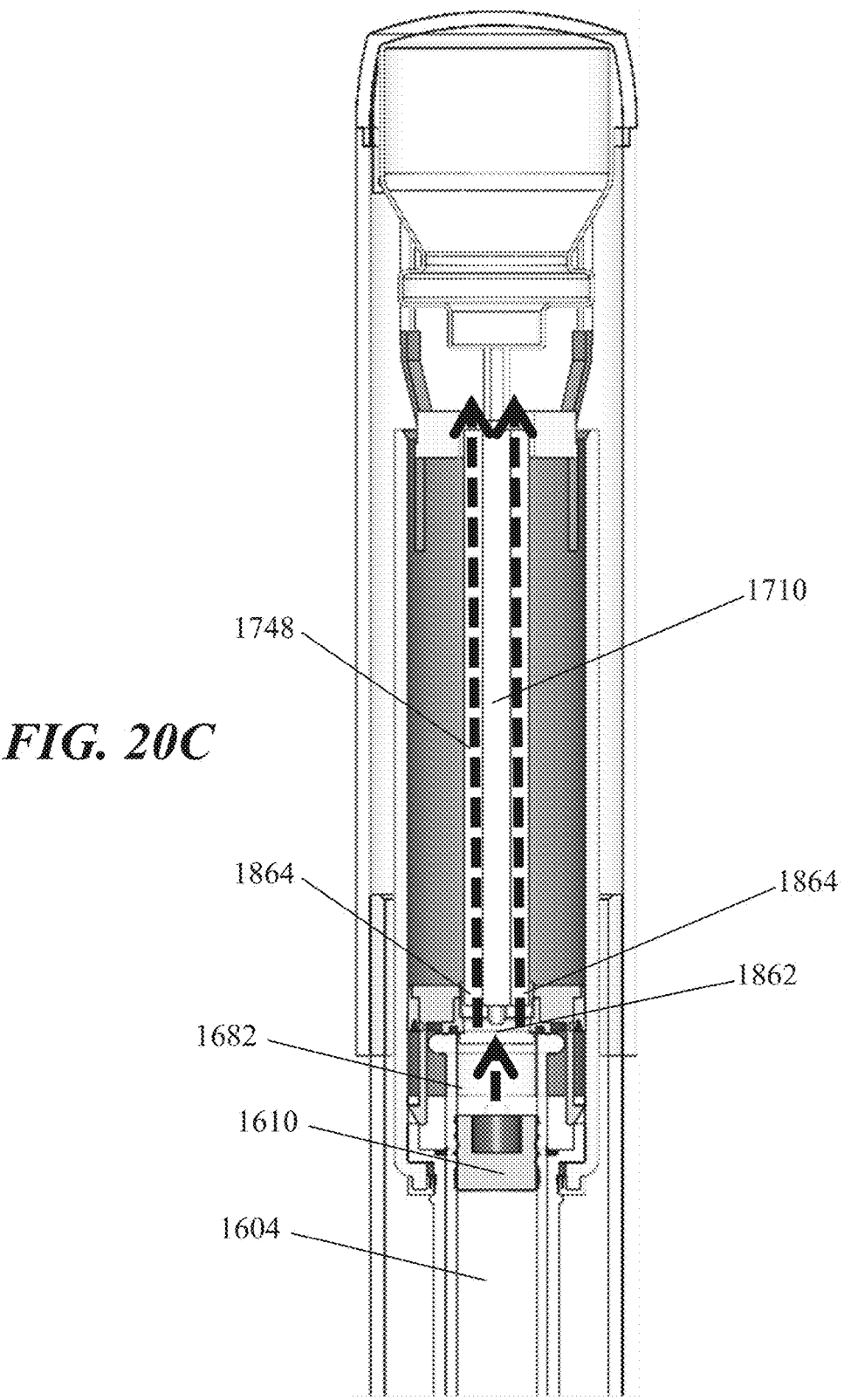
FIG. 20C depicts a longitudinal cross-sectional view of the venting pathway of the injection device of FIG. 18.

As shown with arrows in FIG. 20C, the injection device 1300 may further comprise a venting pathway for gas at atmospheric pressure into the region 1682 of the syringe cavity 1604 proximal to the seal 1610. This may limit the development of negative pressure in the region 1682 as the seal 1610 moves distally relative to and within the syringe cavity 1604. Limiting the development of negative pressure in the region 1682 may be desirable to avoid an unpleasant force profile experience for the user as the injection proceeds, and/or may be desirable to limit the risk that any leakage from the pressurization region 1812 could cause direct pressurization of the seal 1610, which in turn might increase the risk of leakage into the reservoir 1614, in those variations of the device in which direct pressurization of the seal 1610 is not intended. In some variations, this venting pathway may be created by further venting openings in the manifold 1816. The manifold 1816 may comprise one or more inflow venting openings 1862 in fluid communication with the region 1682 of the syringe cavity 1604 proximal to the seal 1610, and one or more outflow venting openings 1864 in fluid communication with ambient pressure within the housing 1302 via the outer annular lumen 1748 of the plunger 1710.

The distal movement of the plunger 1710 to press against the seal 1610 of the syringe 1304, however, may at times be resisted or limited by the rate control assembly 1804. In some variations, the rate control assembly 1804 may comprise a valve 1808 and canister manifold 1866, as shown in FIGS. 19A-19G. When the valve 1808 is in a closed configuration, the valve 1808 may limit the ability of the compressed gas or liquid propellant to leave the canister 1806, and thus the compressed gas or liquid propellant may not act upon the pressure chamber 1824 to move the pressure chamber 1824 distally, and therefore may not provide force causing distal movement of the plunger 1710 and seal 1610 within the syringe cavity 1604 of the syringe 1304, as described above. When the valve 1808 is in an open configuration, the compressed gas or liquid propellant may be able to leave the canister 1806 and act upon the pressure chamber 1824 distally, and may therefore provide force to distally move the plunger 1710 and the seal 1610 within the syringe cavity 1604 to displace the contents of the reservoir 1614 through the lumen 1608 of the needle 1606. In some variations, the valve 1808 may also have an intermediate configuration, wherein the valve 1808 partially restricts the flow of the compressed gas or liquid propellant, but need not have such an intermediate configuration. The canister manifold 1866 may create a seal between the valve 1808 and pressure chamber 1824. The canister manifold 1866 may comprise any suitable material, such as but not limited to a compliant material such as plastic with an overmold of thermoplastic elastomer.

Figure 23:
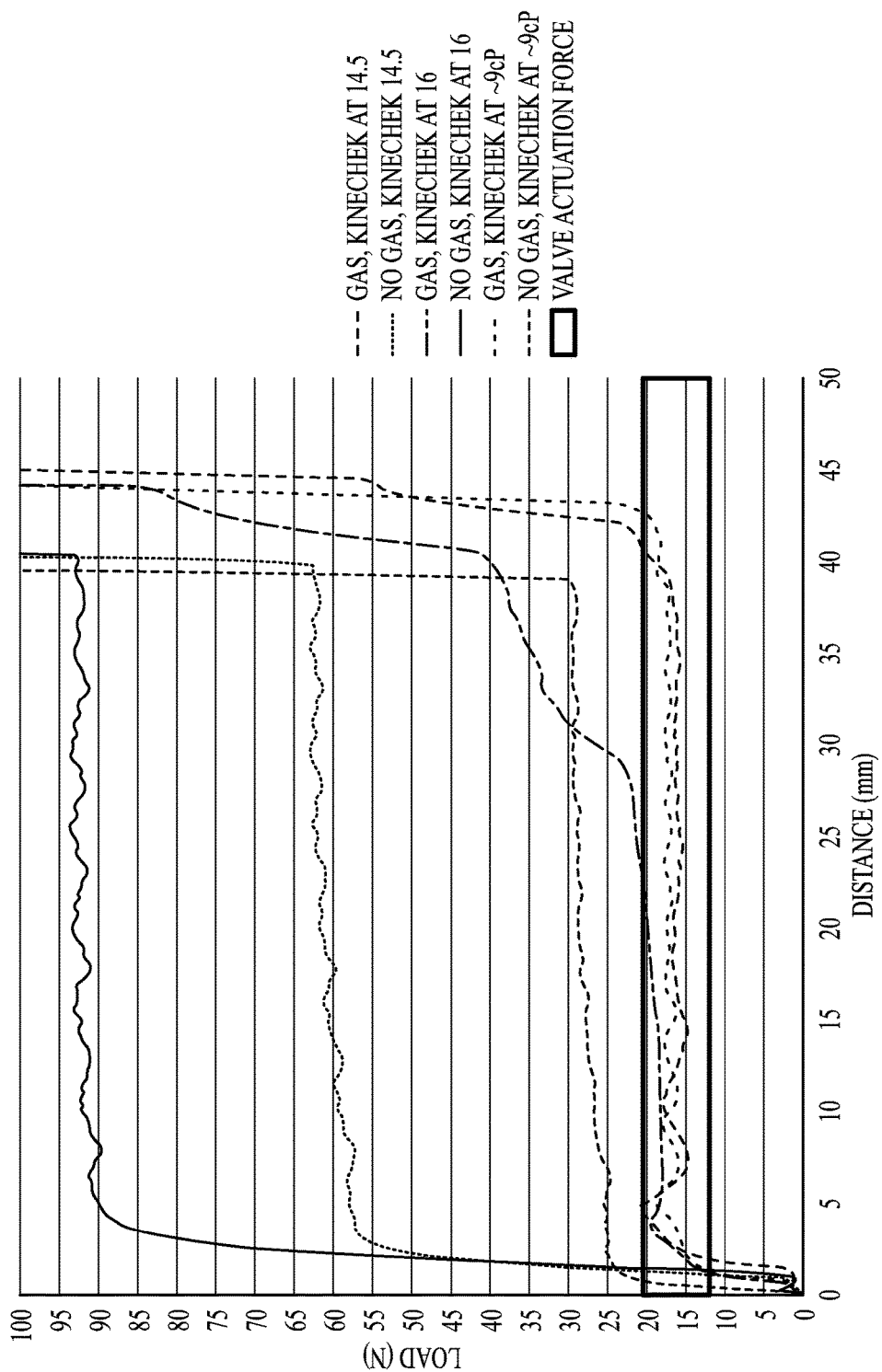
FIG. 23 shows a graph of an illustrative load multiplication factor for an injection device similar to the injection device of FIG. 18.

In some variations, the valve 1808 may be biased toward the closed configuration. The valve 1808 may be moved into an open configuration by applying distal force on the valve 1808 by the canister 1806. This distal force may be applied by applying distal force to the proximal housing 1308. When a distal force is applied to the proximal housing 1308 while the distal housing 1310 is held in place (e.g. by pressing the distal end 1358 of the nose 1316 of the distal housing 1310 against a patient's tissue), the proximal housing 1308 and the canister 1806 may be moved distally relative to the distal housing 1310, as well as relative to the pressure chamber 1824 and canister manifold 1866. This may cause the valve 1808 to press against the canister manifold 1866, which may cause the valve 1808 to open. As a result, the valve 1808 may open, releasing the pressurized gas from the canister 1806 and through the valve 1808, the canister manifold 1866, the inner lumen 1746 of the plunger 1710, and the manifold 1816, and into the pressurization region 1812, as described above. This may cause the volume of the pressurization region 1812 to increase, which may urge the plunger 1710 and seal 1610 distally into the syringe cavity 1604 of the syringe 1304 to displace the contents of the reservoir 1614 through the lumen 1608 of the needle 1606, as described above. FIG. 23 shows a graph of illustrative forces for an injection device having a power assembly similar to the power assembly 1306 of the injection device 1300. The graph illustrates the amount of user force required to displace simulated liquids having a range of viscosities with and without a canister installed in the injection device, with the seal displacing the contents of the reservoir at a rate of approximately 6 mm/s. As can be seen, the force required with the canister installed is approximately the same for all three stimulated viscosities—about 15 to 18 N of force from the user, approximately the valve actuation force—whereas significantly higher forces are required when the canister is not installed. Thus, the graph indicates the forces that can be generated by the power assembly in order to achieve the required injection force. It should be noted that this graph is merely illustrative of the forces for a similar device, and is not meant to indicate that the injection device 700 may or must conform to this representation.

If the distal force on the proximal housing 1308 is released, the bias of the valve 1808 toward the closed configuration may cause the valve 1808 to close, stopping or reducing the inflow of pressurized gas into the pressurization region 1812. When the inflow of pressurized gas into the pressurization region 1812 is stopped, the existing pressure in the pressurization region 1812 may cause the pressure chamber 1824 to continue to move distally relative to the syringe sleeve 1630 until the pressure in the pressurization region 1812 drops to the same level as ambient pressure. After this initial coasting period, the displacement of the contents of the reservoir 1614 through the needle 1606 may stop. This may allow the user to selectively and reversibly start and stop the injection process. In some variations, the power assembly 1306 may comprise a mechanism to stop the injection process without allow for a coasting period. In some such variations, such a mechanism may depressurize the pressurization region 1812 when distal force on the proximal housing 1308 is released. For example, the seal between the valve 1808 and the canister manifold 1866 may be configured to leak when the distal force on the proximal housing 1308 is released.

It should be appreciated that in some variations, the rate control assembly 1804 may comprise different type of valve or additional elements. For example, in variations of the injection device using a compressed gas or liquid propellant with high pressures, the valve may comprise a puncture mechanism and/or a pressure regulator, but need not. A puncture mechanism, such as but not limited to a spring-loaded pin with a grenade-pin type release mechanism, or a spring-loaded gas canister with a stationary pin, may release the higher pressure gas. A pressure regulator, such as but not limited to a diaphragm regulator using a spring to regulate force on a popper valve, may bring the gas down to a safe and usable pressure.

In some variations, the injection device 1300 may comprise an autocomplete mechanism. In some variations, the autocomplete mechanism may allow the valve 1808 to be locked in an open configuration. When the valve is locked in an open configuration, force from the compressed gas or liquid propellant may cause the seal to be moved distally until the injection is complete and the full contents of the reservoir have been displaced. In these variations, the injection device may further comprise a pressure relief port that may allow pressure to be released once the full contents of the reservoir have been displaced, to prevent pressure build-up after the completion of the injection.

In some variations, one or more of the elements of injection device 1300 may optionally comprise clocking features to correctly orient the elements relative to each other, as described above with respect to injection device 100.

Figure 26:
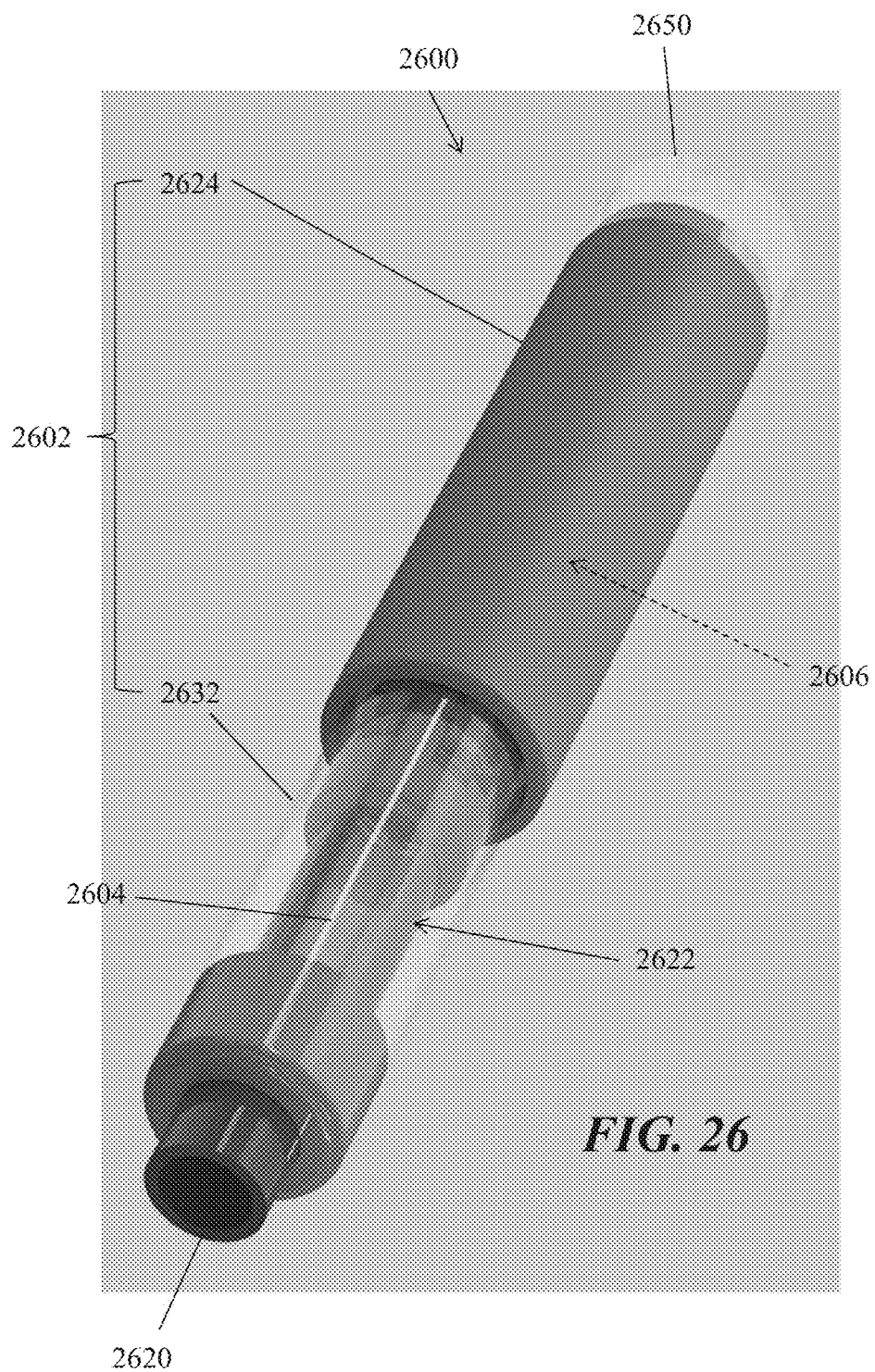
FIG. 26 is a perspective view of another embodiment of an injection device.

Another embodiment of an injection device 2600 is shown in FIGS. 26 and 27A-27H. FIG. 26 is a perspective view of injection device 2600, while FIGS. 27A-27H illustrate longitudinal cross-sectional views of the embodiment of an injection device 2600 of FIG. 26 in various stages during use. As shown there, the injection device 2600 may comprise a housing 2602, a syringe 2604, and a power assembly 2606. The housing 2602 may be similar to the housing 102, described above with respect to injection device 100, and may have the same components, configurations, and functions. In some variations, this may optionally comprise a cap, which may be similar to the cap 148 described above with respect to injection device 100, and may have the same components and functions as described above.

The syringe 2604 of the injection device 2600 may be similar to the syringe 104 described above with respect to injection devices 100, and may have the same components, positions, and functions as described above.

Figure 27A:
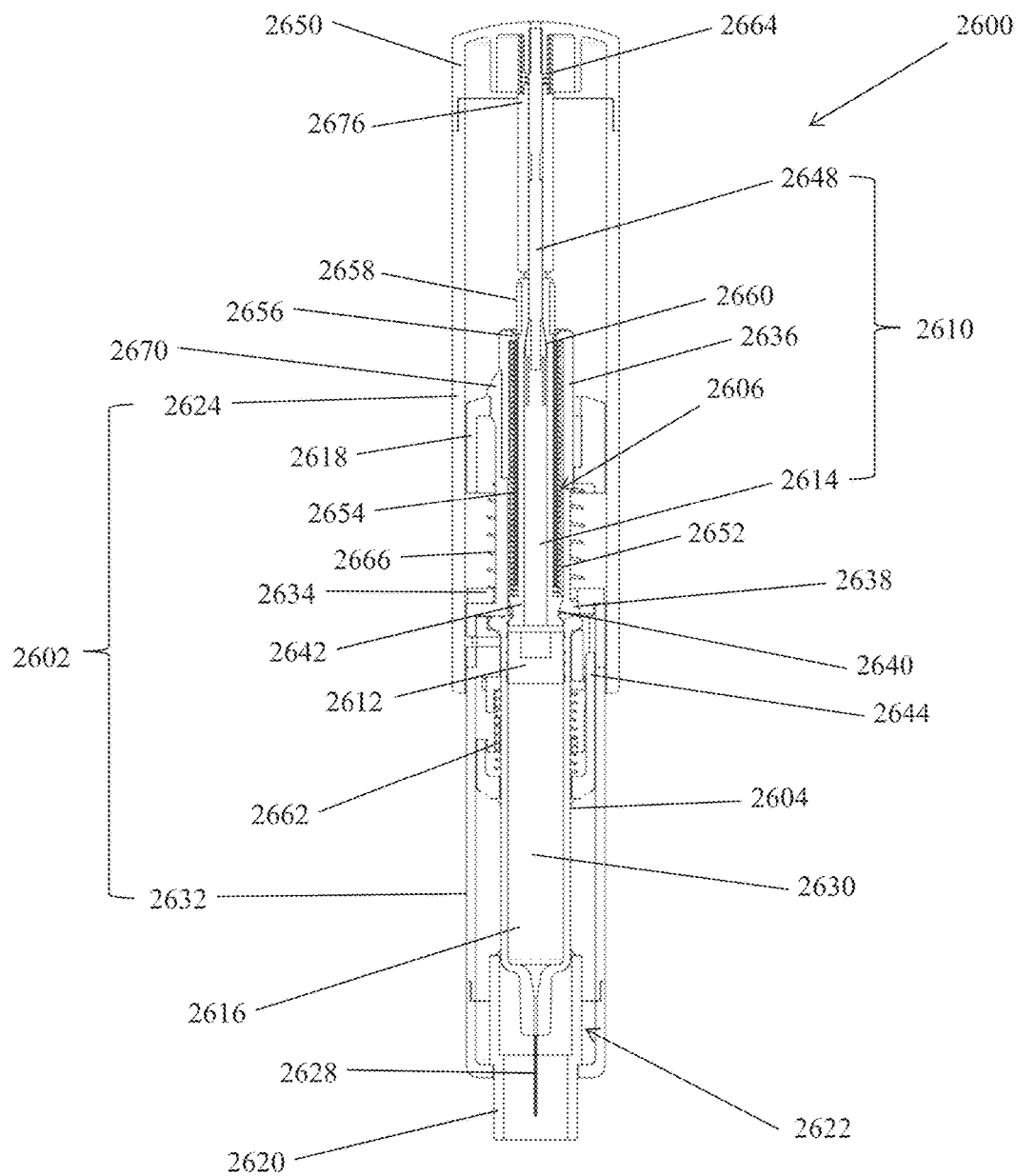
FIGS. 27A-27H illustrate longitudinal cross-sectional views of the embodiment of an injection device of FIG. 26 in various stages during use.
Figure 27B:
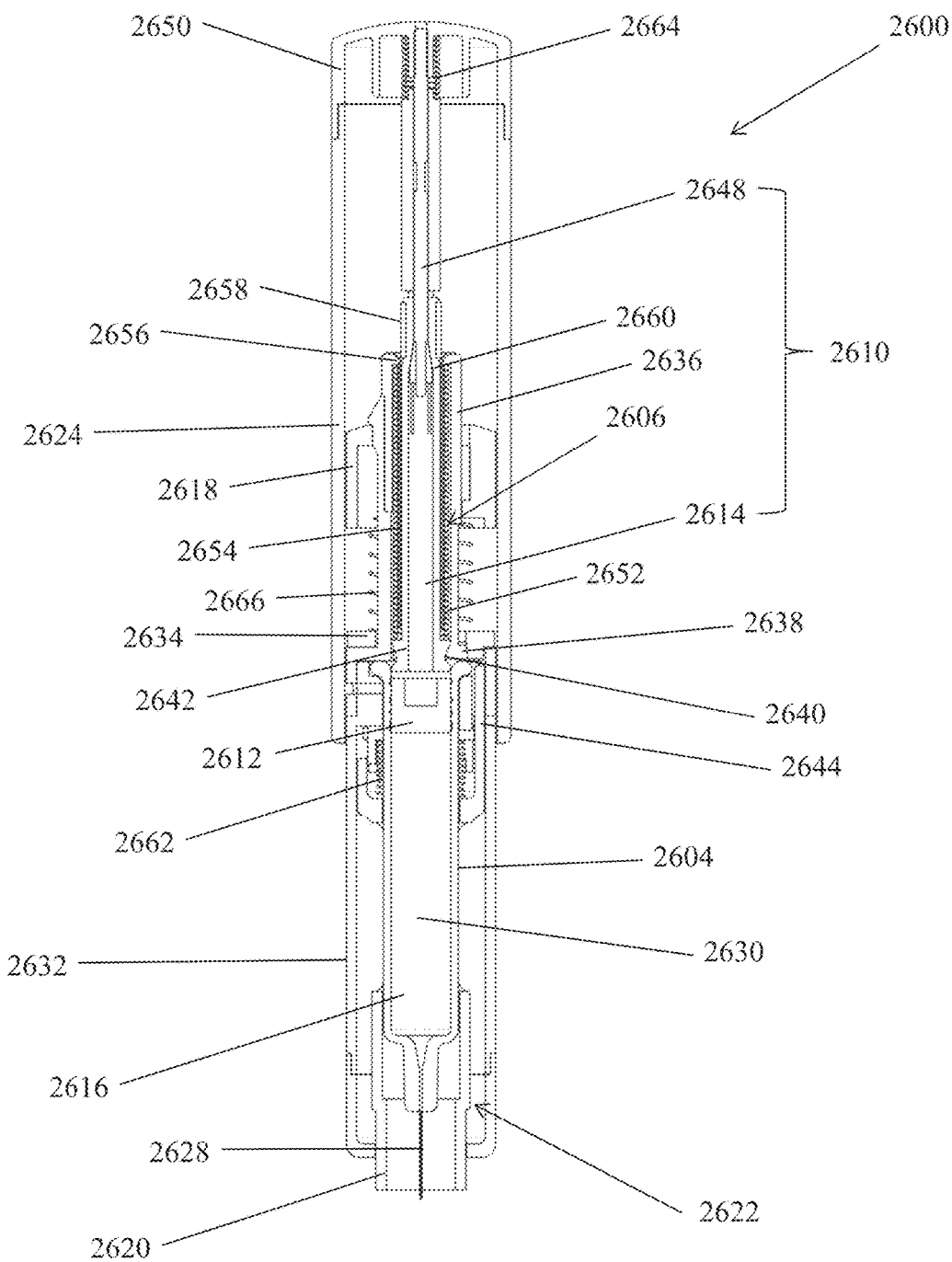
Figure 27C:
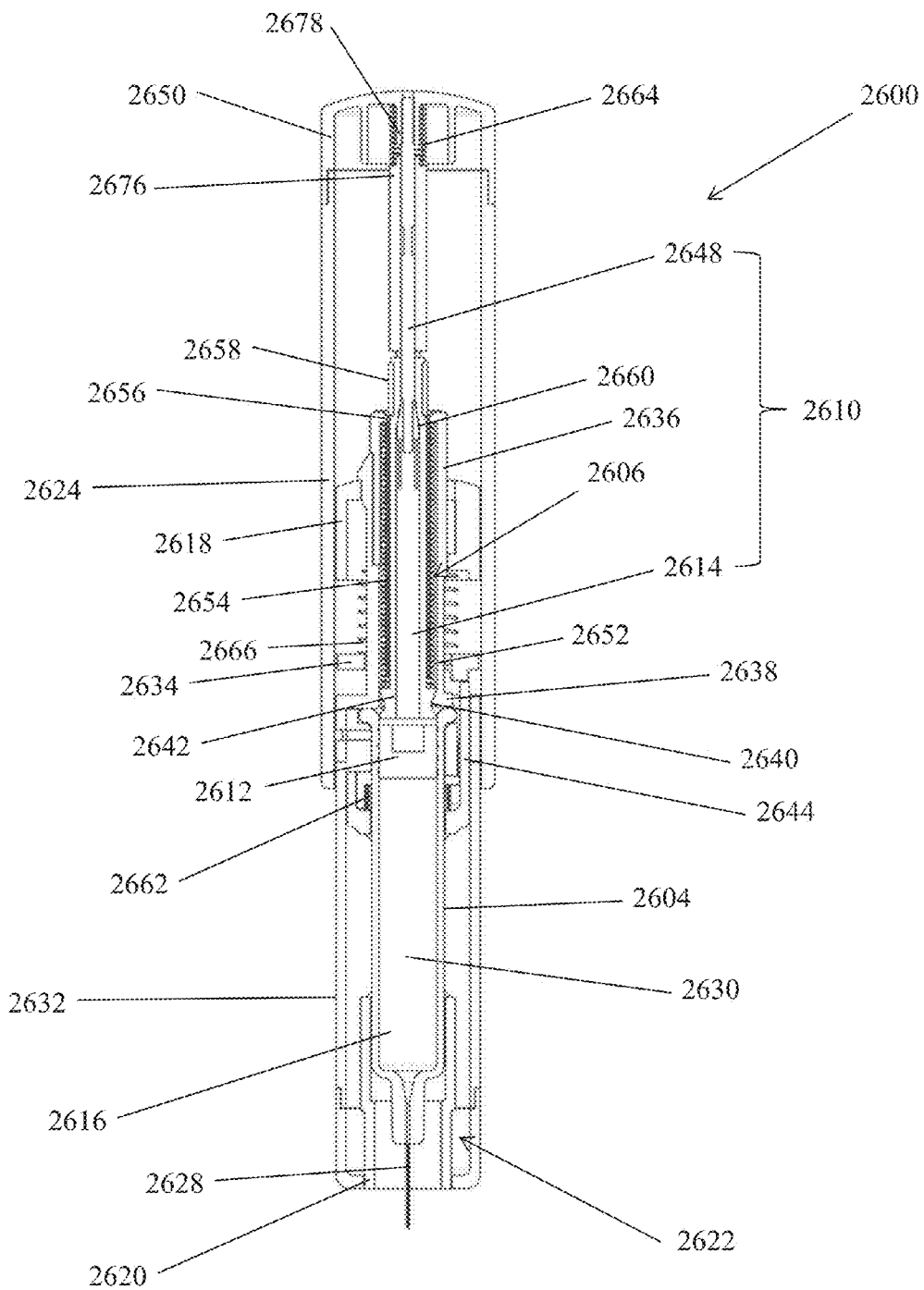
Figure 27D:
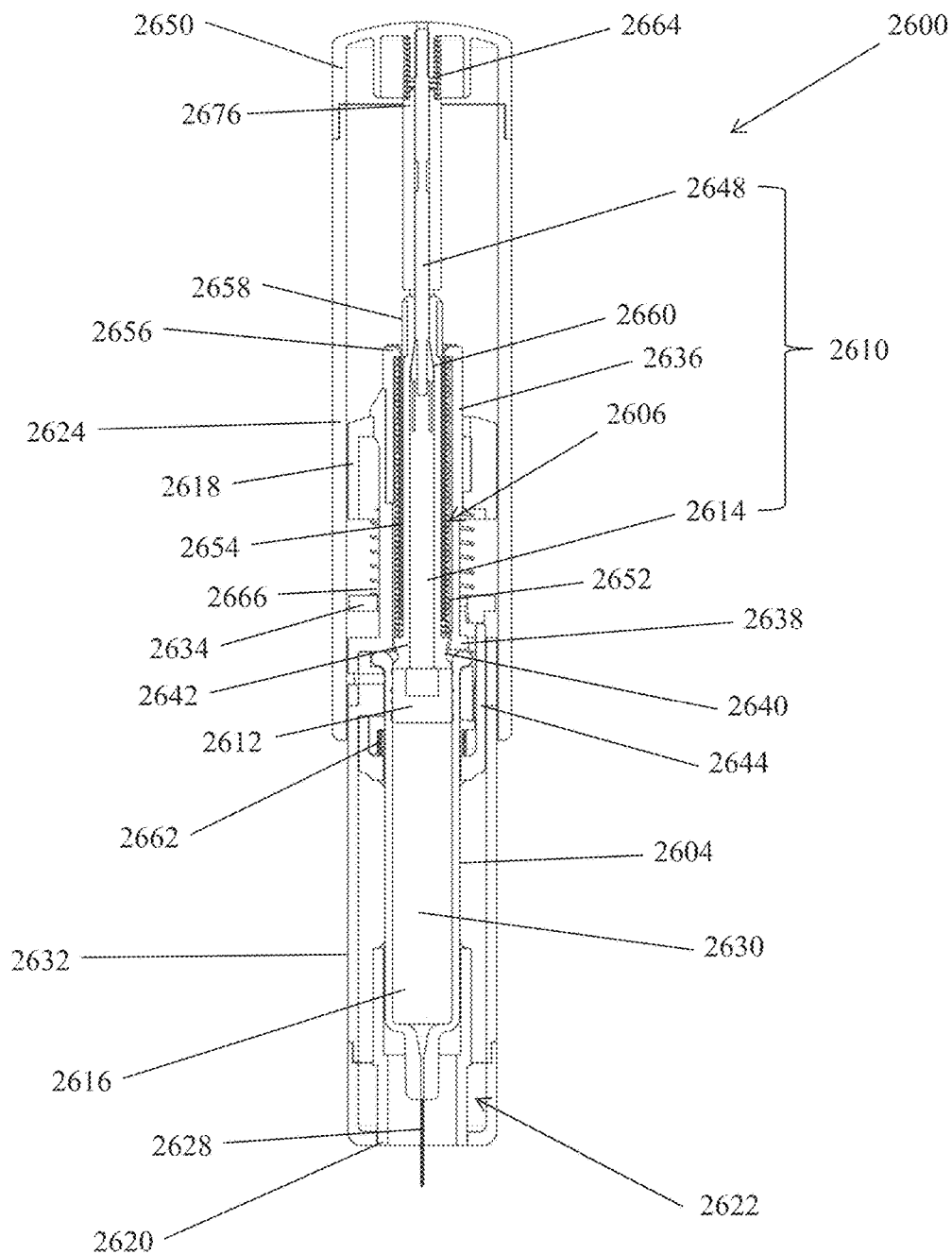
Figure 27E:
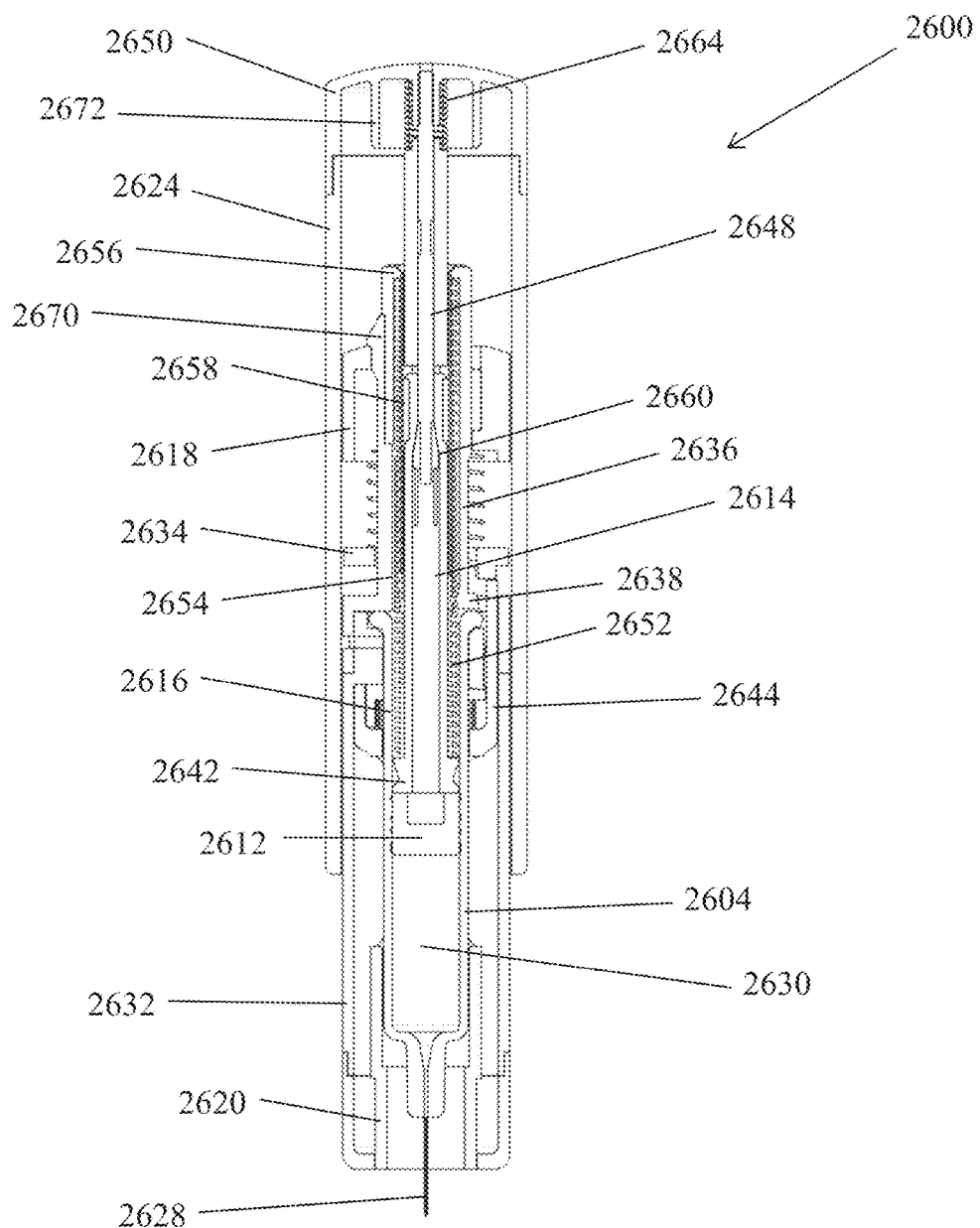
Figure 27F:
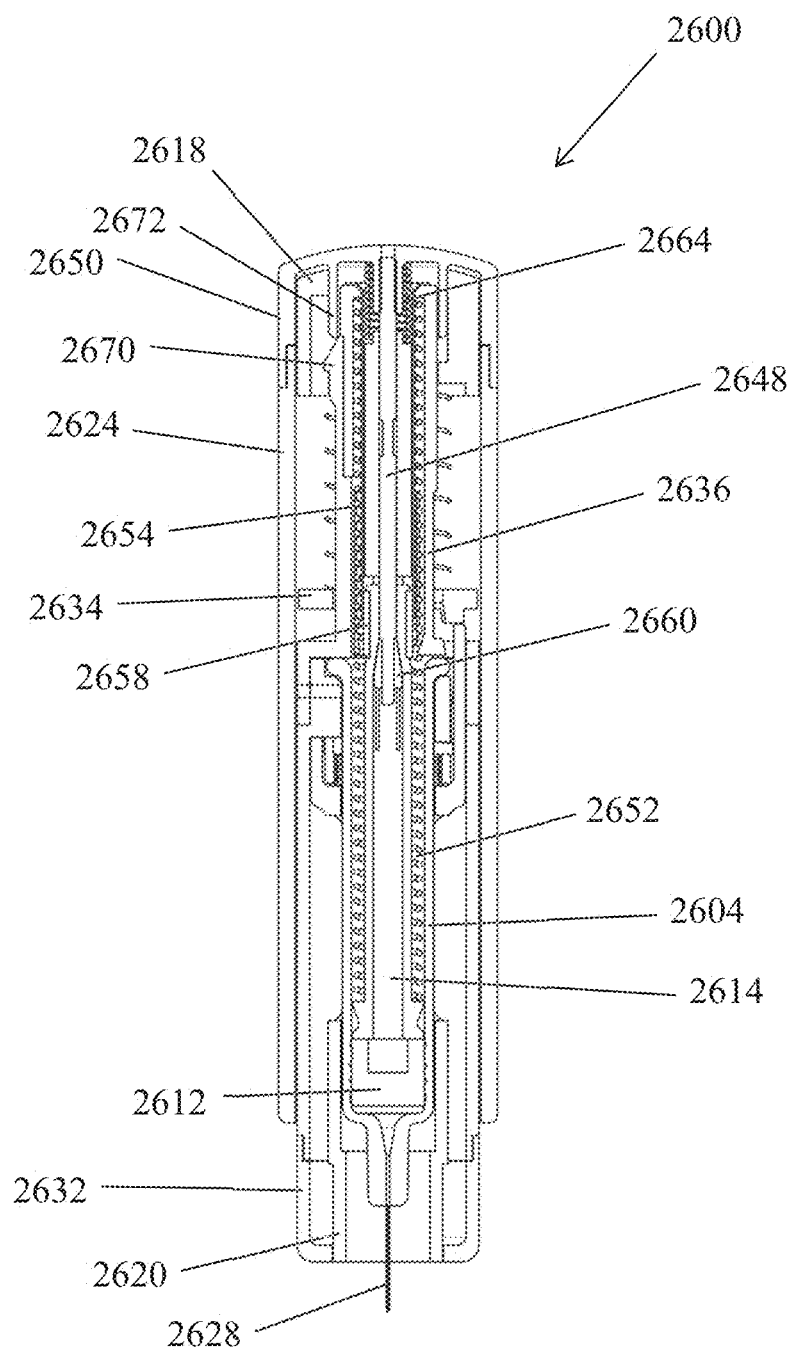
Figure 27G:
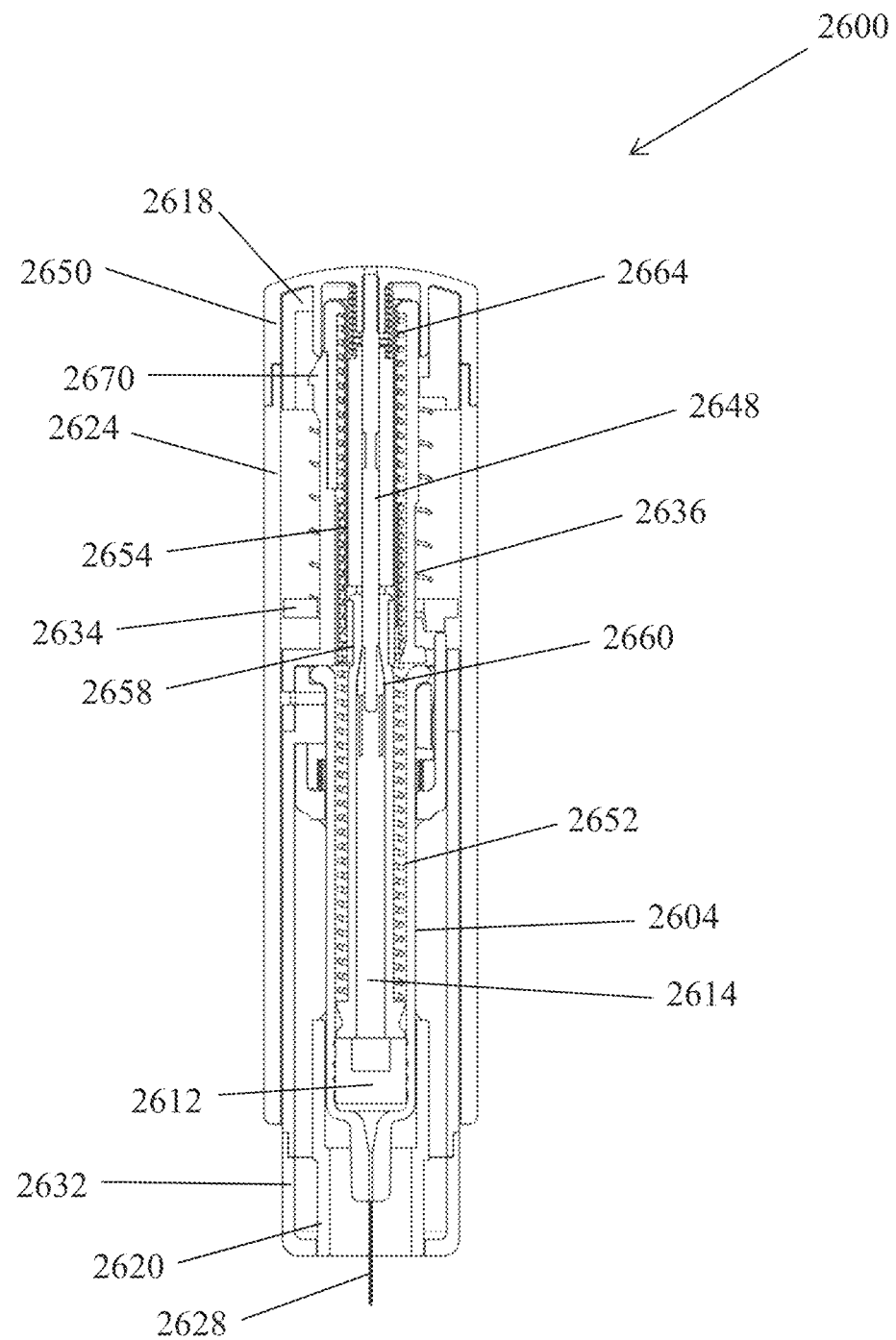
Figure 27H:
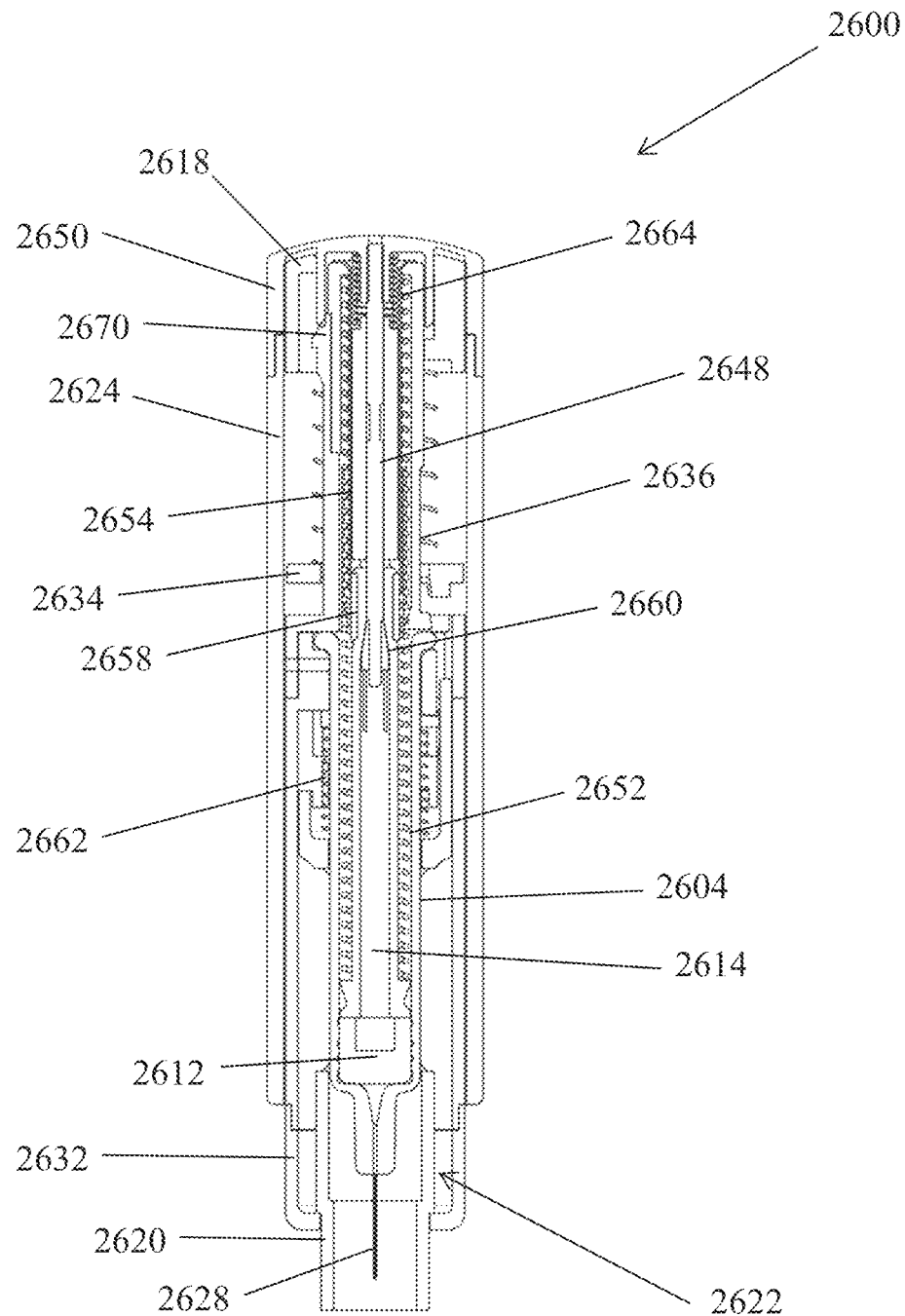

In general, the injection device 2600 may initially be in a state having a needle safety assembly 2622 extending from the distal end of the housing 2602, such that the syringe is fully contained within the housing 2602 and needle safety assembly 2622, without any exposure of the needle 2628 of the syringe 2604, as shown in FIG. 27A. In variations comprising a cap, the cap may be removed from the injection device 2600 before use. The distal end of the injection device 2622 may then be pressed against a patient's tissue. Proximal force from the patient's tissue (e.g., by the user (the patient or another person) holding the housing 2602 and pressing the injection device 2600 against the tissue) may overcome the needle safety assembly's bias toward an extended position, moving the needle safety assembly 2622 from an extended to a retracted position, as shown in FIG. 27B (partially retracted) and FIG. 27C (fully retracted). Retraction of the needle safety assembly 2622 may expose the needle 2628 of the syringe 2604, allowing the needle 2628 to pierce the patient's tissue. Retraction of the needle safety assembly 2622 may release a locking mechanism comprising an interlock ring 2634, which prevents distal motion of a plunger 2614 within the syringe 2604 before the needle safety assembly 2622 is retracted. Once the locking mechanism is released, as shown in FIG. 27C, a user's application of distal force on the proximal housing may cause the plunger 2614 to move distally to contact the seal 2612 of the syringe 2604, as shown in FIG. 27D, and then may cause both the plunger 2614 and seal 2612 to move distally within the syringe cavity 2616. This may in turn cause the contents of the reservoir 2630 of the syringe 2604 to be delivered to the patient via the needle 2628. During the injection process, the injection force applied by the user may be amplified by a stored energy source, while still allowing the user to selectively start and stop the injection process at will. A power spring 2652 may be configured to press the plunger 2614 distally within the syringe cavity 2616, but when no force is applied by the user, the power spring 2652 may be prevented from acting on the plunger 2614 by friction generated by braking pad(s) 2658. When a user applies force to the injection device, the force may reduce or eliminate the friction generated by the braking pad(s) 2658, thus allowing the power spring 2652 to act on the plunger. Once the plunger 2614 and seal 2612 have been depressed such that the full or nearly full dose has been delivered to the patient, the dose may autocomplete and/or an end-of-dose indicator may be activated. FIG. 27F illustrates the device with the plunger 2614 and seal 2612 nearly in the final distal position within the syringe cavity, with the end-of-dose indicator 2618 in an activated configuration. FIG. 27G illustrates the device with plunger 2614 and seal 2612 in the final distal position within the syringe cavity. After the dose is complete, if the injection device 2600 is removed from the patient, the needle safety assembly 2622 may return to the extended position as shown in FIG. 27H, where a locking ring 2668 may prevent the needle safety assembly 2622 from re-retracting.

Thus, as illustrated in the explanation above, depending on the stage of the injection process, distal force on the proximal housing 2624 may be transmitted into different motions. In a first stage, distal force on the proximal housing 2624 may be transmitted into distal motion of injection device 2600 relative to the needle safety assembly 2622, if the needle shroud 2620 of the needle safety assembly 2622 is held in place (e.g., by pressing the distal end of the shroud 2620 against a patient's tissue). In a second stage, distal force on the proximal housing 2624 may be transmitted into displacement of the contents of the reservoir 2630 of the syringe 2604 (e.g., a formulation comprising a therapeutic agent) through the lumen of the needle 2628.

In some variations, the ram 2610 may be configured such that these effects of distal force on the proximal housing 2624 may occur in the order described above. That is, the ram 2610 may be configured such that distal force on the proximal housing 2624 may be transmitted first into distal motion of injection device 2600 relative to the needle safety assembly 2622, and then transmitted second into displacement of the contents of the reservoir 2630 of the syringe 2604 (e.g., a formulation comprising a therapeutic agent) through the lumen of the needle 2628. This may be desirable, for example, because it may allow the syringe 2604 to move distally such that the needle 2628 may pierce a patient's tissue before the contents of the syringe cavity 2616 of the syringe 2604 are displaced through the lumen of the needle 2628.

In some variations, the ordering of effects of distal force on the proximal housing 2624 may be due to different amounts of force that are required for each motion. For example, the ram 2610 may transmit distal force on the proximal housing 2624 into distal motion of the rest of the injection device 2600 relative to the needle safety assembly 2622 when the force on the proximal housing 2624 is above a first threshold (e.g., above about 1 N, above about 2 N, above about 3 N, above about 4 N, above about 5 N, above about 6 N, above about 7 N, or higher); and the ram 2610 may transmit distal force on the proximal housing 2624 into displacement of the contents of the reservoir 2630 of the syringe 2604 through the needle 2628 when the force on the proximal housing 2624 is above a higher second threshold (e.g., above about 5 N, above about 10 N, above about 15 N, above about 20 N, above about 25 N, or higher). It should be appreciated that in some other variations, the ram 2610 may transmit distal force on the proximal housing 2624 into different motions in different orders and by different mechanisms. For example, in some variations the effect of the distal force may be chosen by a mechanism for manual selection by the user. In should also be appreciated that the ram 2610 may have fewer or more motions into which it may transmit distal force onto the proximal housing 2624.

As described briefly above, in some configurations application of distal force on the proximal housing 2624 may cause distal motion of injection device 2600 relative to the needle safety assembly 2622. In an initial configuration before use, as shown in FIG. 27A, if the shroud 2620 of the needle safety assembly 2622 is held in place (e.g., by pressing the distal end of the shroud 2620 against a patient's tissue), the proximal housing 2624, distal housing 2632, power assembly 2606 (discussed in more detail below), and syringe 2604 may slide distally relative to the needle safety assembly 2622. In effect, this may move the needle safety assembly 2622 from an extended position (as shown in FIG. 27A), through a partially retracted position (as shown in FIG. 27B), and finally to a fully retracted position (as shown in FIG. 27C), in which the distal end of the shroud 2620 is flush with the distal end of the distal housing 2632. As the needle safety assembly 2622 retracts, the distal tip of the needle 2628 may move beyond the distal end of the shroud 2620, and the needle 2628 may pierce tissue pressed against the distal end of the shroud 2620. When the needle safety assembly 2622 is fully retracted, the distal tip of the needle 2628 may have reached the desired depth (described above), and further distal movement of the needle 2628 may be resisted by the distal end of the distal housing 2632 pressing against tissue.

The force required to cause retraction of the needle safety assembly 2622 may be determined by a biasing element that may bias the needle safety assembly 2622 toward the extended position. For example, as shown in FIGS. 27A-27H, the biasing element may comprise a compression spring 2662. The compression spring 2662 may have a proximal end fixed relative to the housing 2602 and a distal end fixed relative to the needle safety assembly 2622, therefore biasing the shroud 2620 distally relative to the housing 2602. When the needle safety assembly 2622 is in an extended position, the compression spring 2662 may be in an extended position, as shown in FIG. 27A. As the needle safety assembly 2622 moves toward the fully retracted position, it may compress, as shown in FIGS. 27B-27C. The needle safety assembly 2622 may remain in the fully retracted position throughout the injection, as shown in FIGS. 27D-27G, until the proximal force on the shroud 2620 is removed (e.g., the distal end of the injection device 2600 is removed from a patient's tissue), as described in more detail below.

Figure 30:
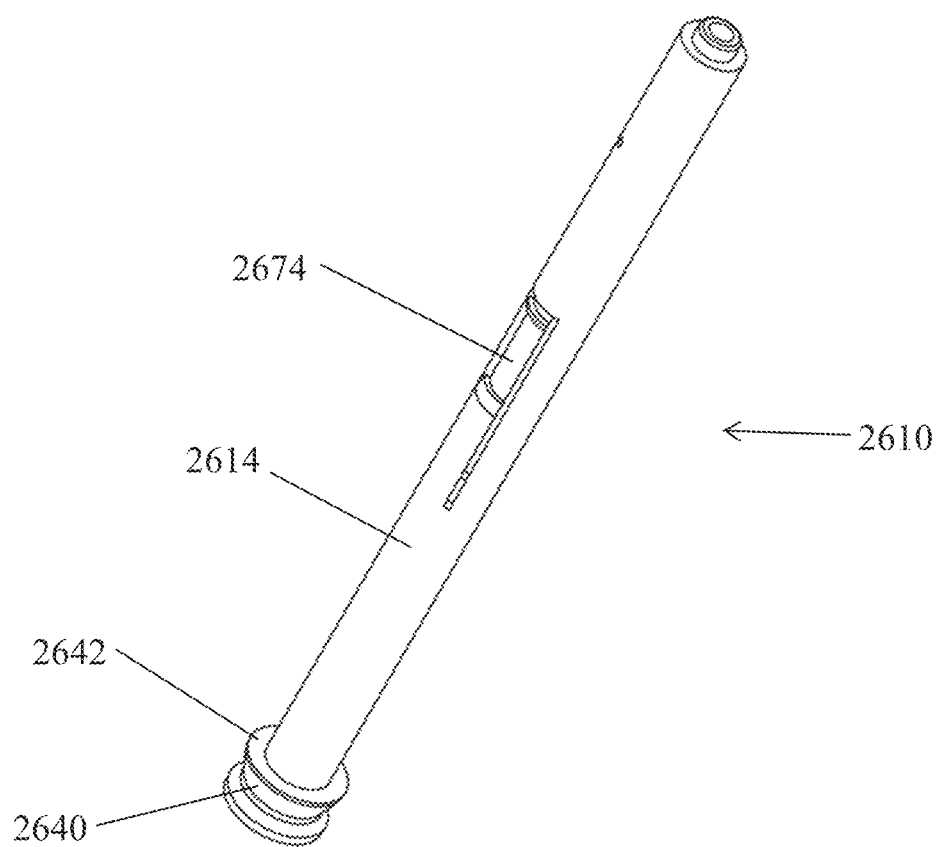
FIG. 30 depicts a perspective view of the ram of the injection device of FIG. 26.

The beginning of the injection (e.g., via distal motion of a plunger 2614 within the syringe cavity 2616) may be restricted by a locking mechanism before the needle safety assembly 2622 is fully retracted. In some variations, the locking mechanism may comprise an interlock ring 2634. The ram housing 2636 may comprise one or more flexures 2638 configured to restrict movement of the ram 2610 distally relative to the syringe 2604. As shown in FIG. 30, the plunger 2614 (described in more detail below) may comprise a notch 2640 at its distal end, which may extend circumferentially around the middle of a widened region 2642 at the distal end of the plunger 2614. A wedge-shaped portion of the flexure(s) 2638 of the ram housing 2636 may fit into the notch 2640 in an initial locked state, as shown in FIG. 27A. When the wedge-shaped portions of the flexure(s) 2638 are engaged with the notch 2640, they may restrict distal movement of the ram 2610. In order for the ram 2610 to move distally, the flexure(s) 2638 may be flexed outward. Interlock ring 2634 may comprise a ring-like structure (shown isolated in FIG. 29B) shaped and sized to fit around the ram housing 2636 and within the proximal housing 2624 and/or distal housing 2632. When the interlock ring 2634 is in its locked position (as shown in FIG. 27A), it may be located around the flexure(s) 2638 of the ram housing 2636, which may in turn act as a hoop to restrict outward flexion of the flexure(s) 2638. The flexure(s) 2638 may be allowed to flex outward by displacement of the interlock ring 2634 such that it is no longer located around the flexure 2628, and thus no longer restraining it. FIG. 27C shows such an unlocked configuration. As shown there, the flexure(s) 2638 may have room to flex outward when the interlock ring 2634 is in a proximal, unlocked position. While the embodiment of the injection device 2600 comprises three flexures 2638, it should be appreciated that in other variations the injection device 2600 may comprise fewer (e.g., one or two) or more (e.g., four, five, six, or more) flexures.

The release of the locking mechanism may be tied to the retraction of the needle safety assembly 2622. That is, the locking mechanism may restrict distal motion of the plunger 2614 (described in more detail below) until the needle safety assembly 2622 is fully retracted, and thus until the needle 2628 is at its desired depth. In some variations, retraction of the needle safety assembly 2622 may cause proximal displacement of the interlock ring 2634. For example, the needle safety assembly 2622 may comprise a proximal portion configured to engage the interlock ring 2634. In injection device 2600, the proximal portion of the needle safety assembly 2622 may comprise one or more arms 2644. When the arm(s) 2644 are in the proximal position (i.e., when the needle safety assembly 2622 is retracted), the arm 2644 may engage the interlock ring 2634. In FIG. 27B, the proximal tip of arm 2644 can be seen about to engage the interlock ring 2634. In FIG. 27C, the proximal tip of the arm 2644 has pressed against the distal side of the interlock ring 2634, moving it proximally relative to the ram housing 2636 and into the unlocked configuration.

Figure 28A:
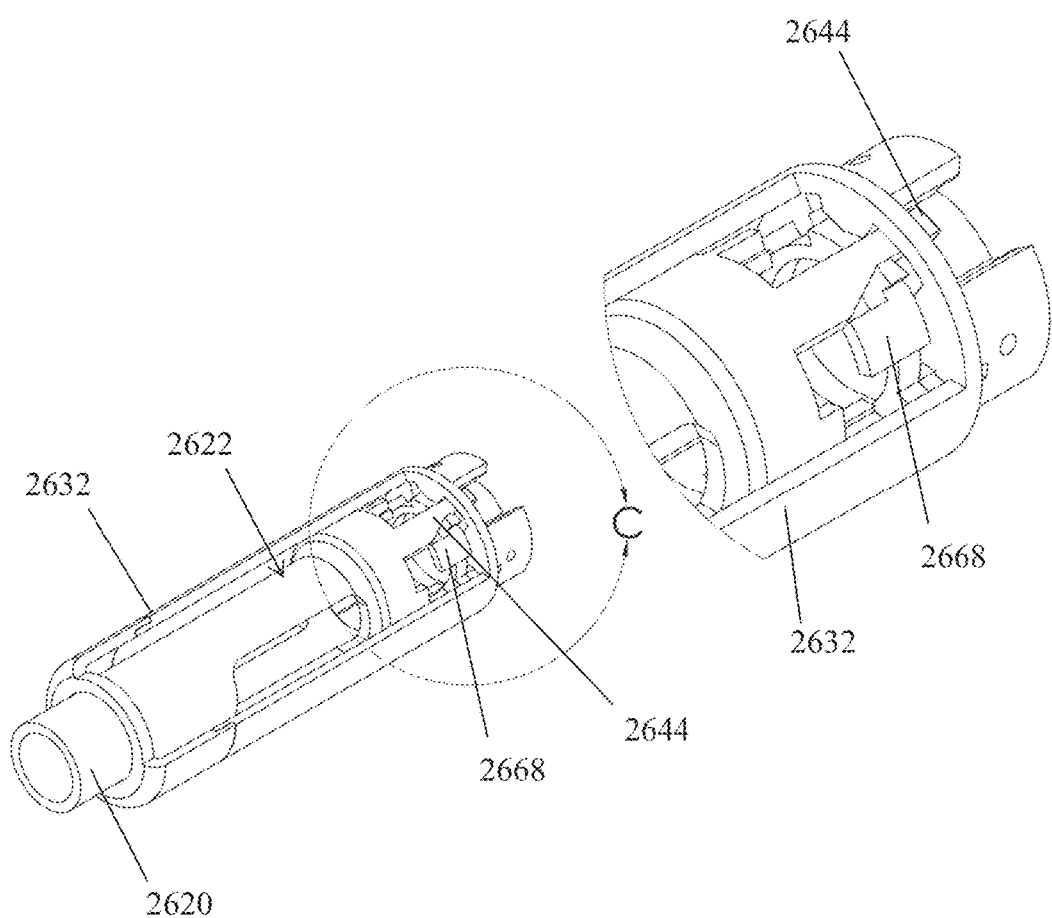
FIGS. 28A, 28B, and 28C show a distal portion of the injection device of FIG. 26 with the needle safety assembly in initial extended, retracted, and locked extended configurations, respectively.
Figure 28B:
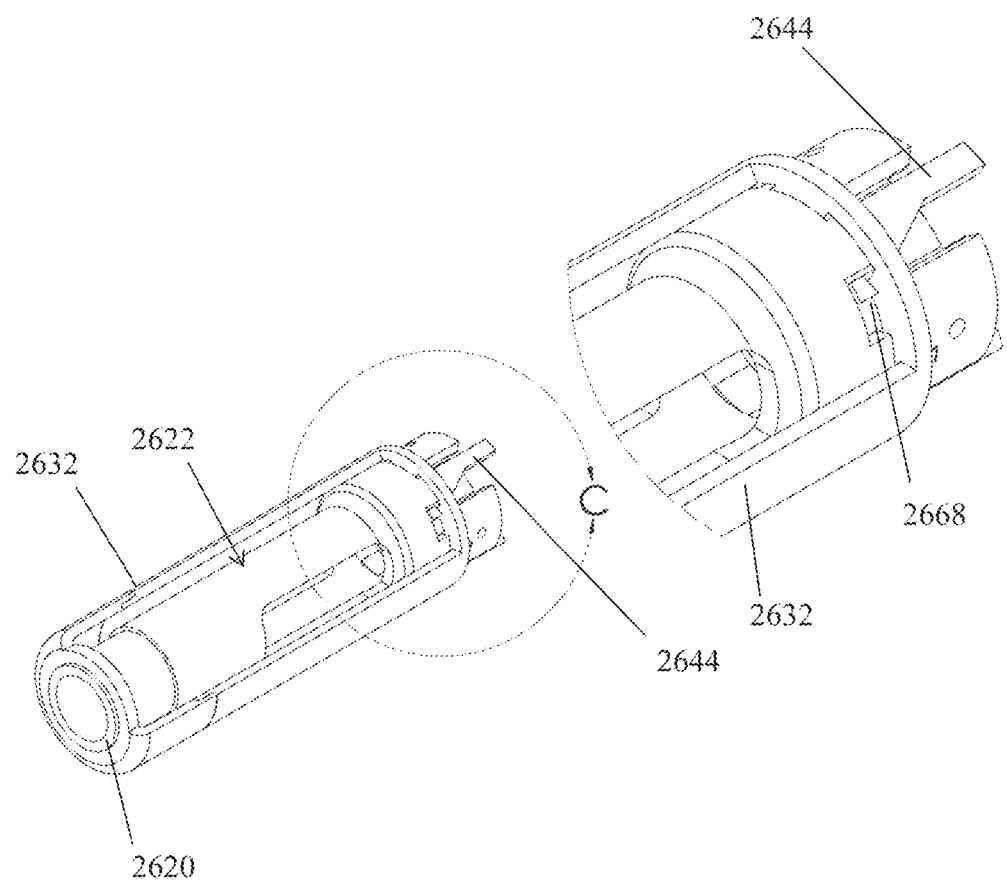

A perspective view of the needle safety assembly 2622 is shown in FIG. 29A. While shown as having three arms 2644, it should be appreciated that the needle safety assembly 2622 may have fewer (e.g., zero, one, or two) arms, or more (e.g., four, fix, or six) arms. FIG. 28A shows a cutaway perspective view of a distal end of the injection device 2600, showing the needle safety assembly 2622 in a first configuration with the shroud 2620 in an initial extended position. FIG. 28B shows the same view in a second configuration, with the shroud 2620 in a retracted position. As can be seen in these figures, as the shroud 2620 moves from the extended position to the retracted position, the needle safety assembly 2622 (including the arms 2644) moves proximally relative to the distal housing 2632, such that it may contact the interlock ring 2634. A perspective view of an interlock ring 2634 is shown in FIG. 29B. As shown there, in some variations the interlock ring 2634 may comprise one or more protrusions 2646 on the distal surface (e.g., as shown there, three protrusions), which may correspond to the arms 2644 on the needle safety assembly 2622 and may be configured to be engaged by the arms 2644.

After the needle safety assembly 2622 is retracted, and thus the interlock ring 2634 is displaced into an unlocked configuration, as shown in FIG. 27C, additional distal force on the proximal housing 2624 may be transmitted into the distal movement of the ram 2610. The ram 2610 may comprise a rod 2648 and a plunger 2614. The rod 2648 may be fixedly attached on its proximal end to the end cap 2650 of the proximal housing 2624, and thus may transmit distal force on the proximal housing 2624 into distal force on the ram 2610. The ram 2610 may further comprise a plunger 2614. All or a proximal portion of the plunger 2614 may be hollow, and the distal end of the rod 2648 may extend through an open proximal end of the hollow plunger 2614. The rod 2648 may be slidable within the proximal portion of the plunger 2614 within a limited range of motion. This range of motion may be defined by a variable gap between the end cap 2650 and the proximal end 2676 of the plunger 2614, which may allow the rod 2648 (which is fixedly attached to the end cap 2650) to slide distally within the plunger 2614 until the interior of the end cap 2650 (e.g., contacts a protruding tubular boss of the end cap) contacts the proximal end 2676 of the plunger 2614. This range of motion may facilitate variable application of a braking force, as described in more detail below.

The plunger 2614 may be configured to be slidable within the syringe cavity 2616 of the syringe 2604. The distal end of the plunger 2614 may be configured to engage with the seal 2612 of the syringe 2604. Initially, distal force on the proximal housing 2624 may cause the ram 2610 to move distally, causing the flexure 2638 of the ram housing 2636 to be deflected radially outward, until the distal end of the plunger 2614 of the ram 2610 contacts the seal 2612, as shown in FIG. 27D. In some variations, the initial distance between the distal end of the plunger 2614 and the seal may be between about 1 mm and about 10 mm. Once the distal end of the plunger 2614 has contacted the seal 2612, additional distal force on the proximal housing 2624 may be transmitted distal movement of the plunger 2614 within the syringe cavity 2616. If the plunger 2614 is moved distally relative to and within the syringe cavity 2616, the plunger 2614 may push the seal 2612 distally relative to and within the syringe cavity 2616. This movement of the seal 2612 may decrease the volume of the reservoir 2630 containing the formulation comprising a therapeutic or diagnostic agent. Thus, distal motion of the plunger 2614, and in turn of the seal 2612, relative to and within the syringe cavity 2616 may cause the contents of the reservoir 2630 to be displaced through the lumen of the needle 2628. When the force is above a necessary force threshold, distal force on the proximal housing 2624 may continue to cause the contents of the reservoir 2630 to be displaced through the lumen of the needle 2628 until the seal 2612 has traveled to the distal end of the syringe cavity 2616, at which time the full dosage of the therapeutic or diagnostic agent may have been injected into the patient, as described in more detail above with respect to injection device 100.

In some variations, once the locking mechanism is unlocked (e.g., the interlock ring 2634 is displaced), the threshold force required to move the plunger 2614 and seal 2612 distally within the syringe cavity 2616 may be governed by the power assembly 2606. As described above with respect to the injection device 100, the power assembly 2606 may comprise a stored energy source and a rate control assembly. The stored energy source may be configured to provide force to displace the contents of the reservoir 2630 of the syringe 2604 by contributing to the distal motion of the plunger 2614 and seal 2612 within the syringe cavity 2616. The rate control assembly may comprise a braking assembly that may limit or restrict the stored energy source from contributing to the displacement of the contents of the reservoir 2630 of the syringe 2604.

In injection device 2600, the stored energy source may comprise a power spring 2652 (e.g., a compression spring). The power spring 2652 may be directly or indirectly attached or in contact with a first surface fixed relative to the syringe 2604 on one end, and may be directly or indirectly attached or in contact with a second surface fixed relative to the plunger 2614 of the ram 2610 on the other end. Thus, the force from the power spring 2652 on the first and second surfaces may bias the first and second surfaces away from each other, which may in turn bias the plunger 2614 distally relative to the syringe cavity 2616. In the variation shown in FIGS. 26 and 27A-27H, the power spring 2652 may be located within a ram housing 2636 and around the plunger 2614 of the ram 2610. The ram housing 2636 may be located proximally to the syringe 2604 and fixed relative thereto. The power spring 2652 may be configured to fit within the syringe cavity 2616 when the power spring 2652 is in an extended configuration. A spring sleeve 2654 may be located between the power spring 2652 and the plunger 2614 of the ram 2610. In the variation shown in FIGS. 27A-27H, the proximal end of the power spring 2652 may be attached or connected to a proximal lip 2656 of the ram housing 2636, while the distal end of the power spring 2652 may be attached or connected to the proximal side of the widened distal portion 2642 of the plunger 2614.

The power spring 2652 may be made of any suitable material, such as but not limited to music wire, stainless steel, and spring steel. The spring rate of the power spring 2652 may be chosen to deliver an appropriate force based on the formulation viscosity, needle choice, volume, and desired injection time, as described above. In some variations, for example, the power spring 2652 may be configured to deliver a force of up to about 5 N, about 10 N, about 15 N, about 20 N, about 25 N, about 30 N, about 35 N, about 40 N, about 45 N, about 50 N, about 55 N, about 60 N, about 65 N, about 70 N, about 75 N, about 80 N, about 85, or about 90 N when the power spring 2652 initially begins to expand.

As described above, the rate control assembly of the power assembly 2606 may slow, limit, or restrict the stored energy source from providing force to displace the contents of the reservoir 2630 of the syringe 2604. In injection device 2600, the rate control assembly may comprise a friction-based braking assembly. The rate control assembly may have a closed configuration where friction from the rate control assembly may counteract or partially or fully oppose the force from the stored energy source. The rate control assembly may also have an open configuration, where there is not a friction force opposing the stored energy source, or where the friction force opposes the stored energy force but is less than is required to fully resist the stored energy source from acting on the plunger 2614.

In the variation of FIG. 26, the braking assembly may comprise one or more braking pad(s) 2658, which may be attached to the outer surface of the plunger 2614. The portion of the plunger 2614 comprising the braking pad(s) 2658 may be hollow and flexible, such that the outward force from within the plunger 2614 may flex the braking pad(s) 2658 radially outward. For example, the braking pad(s) 2658 may be located on flexures 2674 of the plunger 2614 that are configured to be flexed radially outward. Flexures 2674 can be seen more clearly in FIG. 30, which shows a perspective view of the ram 2610. The braking pad(s) 2658 may comprise any suitable material configured to form a high-friction interface with the spring sleeve 2654. For example, the braking pad(s) 2658 may comprise an elastomer (e.g., rubber, thermoplastic elastomer), which may form a high friction interface with a metal spring sleeve. If outward force from within the plunger 2614 presses the braking pad(s) 2658 radially outward (e.g., by flexing the flexures 2674 outward) into the spring sleeve 2654, friction between the braking pad(s) 2658 and spring sleeve 2654 may be created or increased. In some variations, the braking assembly may comprise two braking pads 2658 (e.g., located on two radially opposite flexures 2674 of the plunger 2614). However, in other variations the braking assembly may comprise fewer (e.g., one) or more (e.g., three, four, five, six, or more) braking pads 2658, although it should be appreciated that in some instances it may be desirable for the radial loads generated by the braking pads to be radially symmetric, such that unopposed radially loads are avoided.

As shown in FIGS. 27A-27H, in one variation the outward force on the braking pad(s) 2658 may be achieved by a wedge-shaped stopper 2660. The stopper 2660 may be located at the distal end of the rod 2648, which as described above may be located slidably within the hollow proximal portion of the plunger 2614. The hollow proximal portion of the plunger 2614 may have a corresponding conical or wedge-shaped interior shape, located near or adjacent to the baking pad(s) 2658. When the rate control assembly is in a closed configuration, the stopper 2660 may exert a proximal force relative to the plunger 2614. This proximal force may press the stopper 2660 proximally against the corresponding wedge-shaped interior of the plunger 2614, flexing the braking pad(s) 2658 outward. When the braking pad(s) 2658 are located adjacent to the spring sleeve 2654, this may generate sufficient friction to oppose the stored energy source (i.e., the rate control assembly may be in a closed configuration). In contrast, when the stopper 2660 is not pressed proximally against the corresponding wedge-shaped interior of the plunger 2614, and thus the braking pad(s) 2658 are not flexed outward, the friction between the braking pad(s) 2658 and the spring sleeve 2654 may be reduced or eliminated, such that the stored energy source (e.g., the power spring 2652) may act on the plunger 2614 (i.e., the rate control assembly may be in an open configuration).

In some variations, the stopper 2660 may be proximally biased relative to the plunger 2614, such that the stopper 2660 is biased toward a configuration in which it presses proximally against the interior surface of the plunger 2614, such that the rate control assembly is in a closed configuration. This proximal bias may be generated by a biasing element configured to bias the end cap 2650 of the proximal housing 2624 and the plunger 2614 away from each other. As described above, the rod 2648 may be fixedly attached on its proximal end to the end cap 2650 of the proximal housing 2624, while the distal end of the rod 2648 may extend through an open proximal end of the hollow plunger 2614 such that the rod 2648 is slidable within the plunger 2614 within a limited range of motion. As shown in FIGS. 27A-27H, in one variation the biasing element may comprise a compression spring 2664 having a proximal end fixed relative to the rod 2648 (e.g., attached to the interior surface of the end cap 2650 at a distal end) and a distal end fixed relative to the ram 2610. When distal force is not being applied to the proximal housing 2624, the stopper 2660 may thus be naturally biased proximally against the interior of the plunger 2614, pressing the braking pad(s) 2658 outwards. In contrast, when sufficient distal force is applied to the proximal housing 2624 to overcome the biasing element, the stopper 2660 may not press against the interior of the plunger 2614, and thus the braking pad(s) 2658 may not be pressed outwards, such that the rate control assembly is in an open configuration.

When the braking pad(s) 2658 are located adjacent to a surface with which they are configured to form a high-friction interface (e.g., the spring sleeve 2654), outward flexion of the braking pad(s) 2658 toward the adjacent surface may generate friction. This friction may be sufficient to oppose the stored energy source (e.g., the power spring 2652), such that the plunger 2614 and seal 2612 are not moved distally within the syringe cavity 2616, and the injection does not proceed. In contrast, when the braking pad(s) 2658 are located adjacent to a surface with which they are configured to form a high-friction interface (e.g., the spring sleeve 2654) but the braking pad(s) 2658 are not flexed outwards, there may be no friction force, or the friction force may be low enough, that the stored energy source (e.g., the power spring 2652) can act on the plunger 2614 to move the plunger 2614 and seal 2612 distally within the syringe cavity 2616, causing the injection to proceed.

In some variations, the friction force generated at the high-friction interface (e.g., between the braking pad(s) 2658 and the spring sleeve 2654) may be at least 2 times the force generated by the biasing element (e.g., by compression spring 2664). In some variations, the friction force generated at the high-friction interface may be at least 3 times the force generated by the biasing element. In some variations, the friction force generated at the high-friction interface may be at least 5 times the force generated by the biasing element. In some variations, the friction force generated at the high-friction interface may be at least 10 times the force generated by the biasing element. Accordingly, in these variations, the braking pad(s) may be able to resist motion of the plunger when the power spring is 2, 3, 5, or 10 times more powerful than the biasing element. For example, in one variation, the power spring 2652 may apply an initial force in a compressed configuration of approximately 15 N, while the biasing element may comprise a compression spring 2664 configured to apply a force of about 7 N-8 N.

As shown in FIGS. 27A-27C, before the plunger 2614 and seal 2612 have advanced within the syringe cavity 2616, the braking pad(s) 2658 may be located proximal to the proximal end of the spring sleeve 2654. In this position, the braking pad(s) 2658 may not be adjacent to another surface, and thus, may not generate any friction. As such, after the interlock ring 2634 is displaced to allow distal motion of the plunger 2614, the power spring 2652 may initially act unopposed on the plunger 2614, moving the plunger 2614 distally until the braking pad(s) 2658 enter the spring sleeve 2654. In some variations, this may allow the initial space between the plunger 2614 and the seal 2612 to be quickly closed by distal motion of the plunger 2614. It may also in some variations be desirable that the braking pad(s) 2658 not be located adjacent to the spring sleeve 2654 or another surface in an initial state, so as to avoid the braking pad(s) experiencing a compression-set. The braking pad(s) 2658 may thus enter the spring sleeve 2654 immediately after initiation of the injection.

Additional distal force applied to the proximal housing 2624 may cause the plunger 2614 and seal 2612 to advance distally within the syringe cavity 2616, beginning to force the contents of the reservoir 2630 out through the lumen of the needle 2628. As the plunger 2614 and seal 2612 move distally, as shown in FIG. 27E, the braking pad(s) 2658 may accordingly move distally relative to the spring sleeve 2654. When no distal force is applied to the proximal housing 2624 (or when the distal force is below the threshold), the proximal bias on the stopper 2660 may be sufficient to oppose the power spring 2652, causing the injection to stop. When instead sufficient distal force is applied to the proximal housing 2624 to overcome the proximal bias on the stopper 2660, the rate control assembly may be in an open configuration (e.g., the braking pad(s) 2658 may not be pressed radially outward by the stopper 2660), and the power spring 2652 may apply force to push the plunger 2614 and seal 2612 distally within the reservoir 2630 of the syringe 2604. As shown in FIG. 27E, the power spring 2652 may press against the proximal side of the widened region 2642 at the distal end of the plunger 2614. As the power spring 2652 expands during injection, the power spring 2652 may extend into the syringe cavity 2616.

After the plunger 2614 and seal 2612 have begun to advance within the syringe cavity 2616, the braking pad(s) 2658 may move distally to a position adjacent the interior surface of the spring sleeve 2654, as shown in FIG. 27E. As such, the rate control assembly may be reversibly and selectively moved between open and closed configurations by application of distal force to the proximal housing 2624. When distal force is applied to the proximal housing 2624 while the distal end of the injection device 2600 is held in place (e.g., by pressing the distal end of the injection device 2600 against a patient's tissue) the rate control assembly may be moved to an open configuration. More specifically, the distal force may overcome the bias of the compression spring 2664. As a result, the rod 2648 and stopper 2660 may be moved distally relative to the plunger 2614, which may in turn remove outward pressure on the braking pad(s) 2658 and reduced the friction between the braking pad(s) 2658 and the spring sleeve 2654. This may in turn allow the power spring 2652 to act on the plunger 2614 to urge the seal 2612 distally to displace the contents of the reservoir 2630 through the lumen of the needle 2628. If the distal force on the proximal housing 2624 is released, the bias of the rate control assembly toward a closed configuration may cause the injection to stop. When distal force is released, the biasing force on the ram 2610 and stopper 2660 may cause them to move proximally relative to the plunger 2614, applying an outward force on the braking pad(s) 2658. As a result, friction between the braking pad(s) 2658 and the spring sleeve 2654 may resist the force of the stored energy source.

Figure 31:
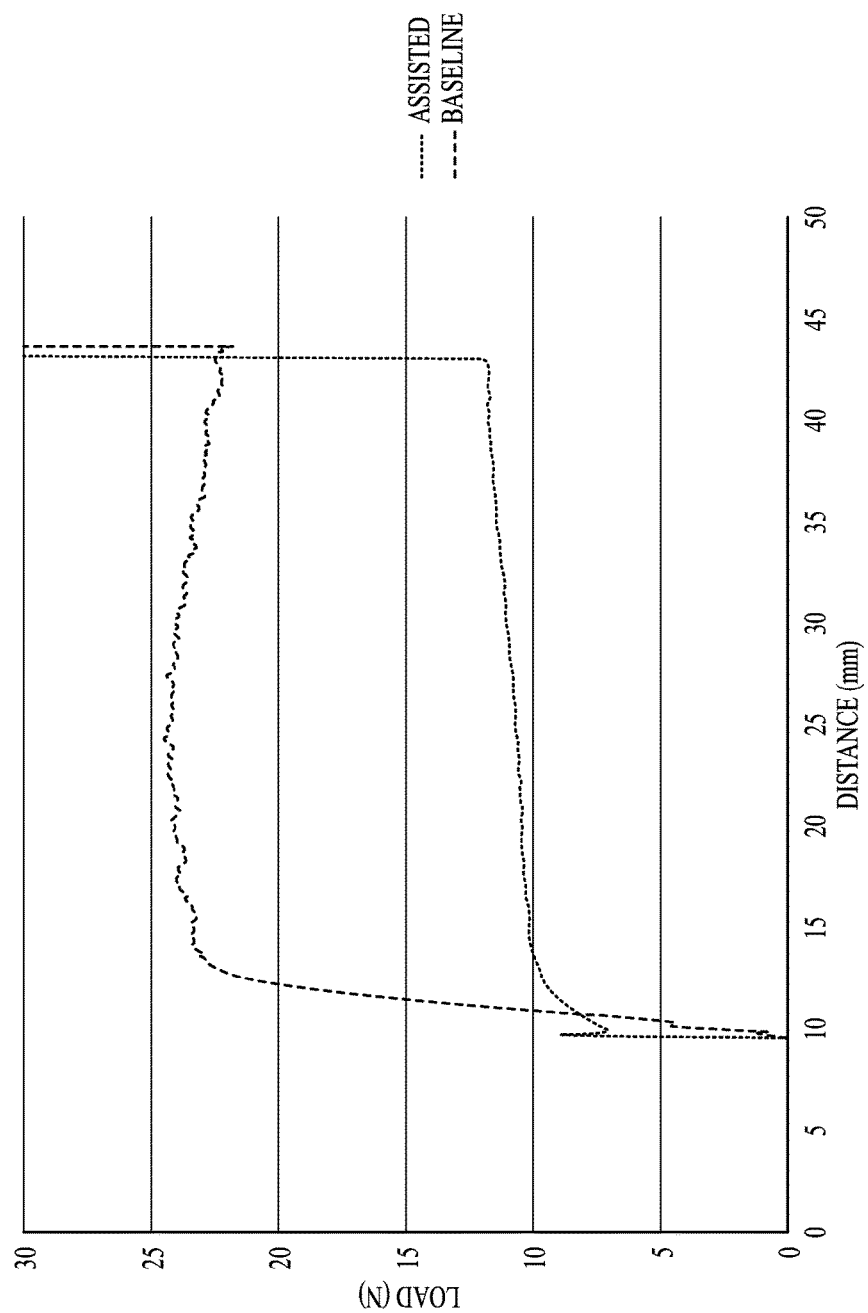
FIG. 31 shows an illustrative graph of the user force required to perform an injection using an injection device similar to the injection device of FIG. 26.

It should be appreciated that in this configuration, the force applied to the proximal housing 2624 is also applied to the plunger 2614. That is, the total force moving the seal 2612 distally within the syringe cavity 2616 includes both a user's force and the force generated by the stored energy source (e.g., the power spring 2652). This may allow the user to increase the speed of the injection process beyond the maximum speed generated by the stored energy source alone. Similarly, the user may be able to slow the speed of the injection process by applying sufficient distal force to partially but not fully open the rate control assembly (e.g., to decrease but not eliminate the friction between the braking pad(s) 2658 and the spring sleeve 2654). As such, the user may be able to selectively and reversibly start and stop, or increase or decrease the speed of, the injection process. FIG. 31 shows an illustrative graph of the user force required to perform an injection using an injection device having a power assembly similar to the power assembly 2606 of the injection device 2600. As shown, in one variation, the user force required is approximately 10 N with the power assembly (indicated as "Assisted"), while without the power assembly (indicated as "Baseline"), the user force required is approximately 23 N. Thus, the device may have a force multiplication factor of about 2.3. It should be noted that this graph is merely illustrative of the user force required for a similar device, and is not meant to indicate that the injection device 2600 may or must conform to this representation.

In some variations the injection device 2600 may comprise an autocomplete mechanism, which may cause the full volume of the reservoir 2630 to be automatically displaced through the lumen of the needle 2628 within a certain tolerance of the total injection (e.g., within about 85% of the injection, within about 90% of the injection, within about 95% of the injection, or more, or within about 1 mm of full displacement, about 2 mm of full displacement, about 3 mm of full displacement, or about 4 mm of full displacement, etc.), regardless of a user's application of distal force to the proximal housing 2624. In some variations, autocompletion may be caused by the braking pad(s) 2658 no longer contacting the spring sleeve 2654. For example, when the seal 2612 is near the distal end of the syringe cavity 2616, the plunger 2614 may have travelled distally within the syringe cavity 2616 such that the braking pad(s) 2658 may reach the distal end of the spring sleeve 2654. When the braking pad(s) 2658 move distally beyond the spring sleeve 2654, they may no longer be in contact with the spring sleeve 2654. Accordingly, there may be no friction between the braking pad(s) 2658 and the spring sleeve 2654, and thus no force opposing the distal force from the power spring 2652. As a result, the dose may autocomplete due to distal force on the plunger 2614 from the power spring 2652.

Injection device 2600 may also comprise an indicator that, like the indicators described with respect to the injection device 100, may indicate the progress or completion of the injection, and may have activated and inactivated configurations. In some variations of the injection device 2600, the indicator may comprise an end-of-dose indicator 2618 to alert the user that the full dose has been displaced from the reservoir 2630 of the syringe 2604, and/or that the seal 2612 has traveled the full length of the reservoir 2630 to the distal end of the syringe cavity 2616. Additionally or alternatively, the end-of-dose indicator 2618 may alert the user that nearly (e.g., greater or equal to about 85%, greater or equal to about 90%, greater or equal to about 95%, or more) the full dose has been displaced and/or that the seal 2612 has traveled nearly (e.g., greater or equal to about 85%, greater or equal to about 90%, greater or equal to about 95%, or more, or within about 1 mm of full displacement, about 2 mm of full displacement, about 3 mm of full displacement, or about 4 mm of full displacement, etc.) the full length of the reservoir 2630 to the distal end of the syringe cavity 2616. In variations in which the injection device has both an autocomplete mechanism and an end-of-dose indicator, these may be triggered at the same time. If the end-of-dose indicator is deployed before the dose has been fully delivered, this may reduce the likelihood that a user fails to deliver the full dose.

The end-of-dose indicator 2618 may have different visual appearances associated with the inactivated and activated configurations. FIGS. 27A-27E show the end-of-dose indicator 2618 in the inactivated configuration, while FIGS. 27F-27H show the end-of-dose indicator 2618 in an activated configuration. The end-of-dose indicator 2618 may be seen through the housing in the activated configuration, while not seen through the housing in the inactivated configuration.

In the variation shown in FIGS. 27A-27H, the end cap 2650 of the proximal housing 2624 may be configured such that when the end-of-dose indicator 2618 is adjacent to the inner surface of the end cap 2650, at least a portion of the end-of-dose indicator 2618 may be seen from outside the end cap 2650 through a viewing portion. In some variations, at least a portion of the end-of-dose indicator 2618 may have a color or pigment that may be capable of being more easily noticed, such as but not limited to red, yellow, orange, green, magenta, blue, and the like. In order for the end-of-dose indicator 2618 to be seen through at least a portion of end cap 2650, in some variations, at least a portion of the end cap 2650 may be translucent. In variations in which a portion of the end cap 2650 is translucent, the level of translucency may be such that the coloring of the end-of-dose indicator 2618 may be perceived through the end cap 2650 only when the end-of-dose indicator 2618 is adjacent or nearly adjacent to the viewing portion. In other variations, the end cap 2650 may comprise a transparent or open region configured such that no portion of the end-of-dose indicator is visible in the inactivate configuration, and the end-of-dose indicator 2618 is only visible through the viewing portion when the end-of-dose indicator 2618 is adjacent to the transparent or open region, for example, because of the viewing angle. For instance, in some such variations, the viewing portion may comprise a transparent region around the circumference of the end cap 2650, and the end-of-dose indicator 2618 may only be visible through the viewing portion when aligned adjacent to the viewing portion. The end-of-dose indicator 2618 may comprise a lumen therethrough, such that the end-of-dose indicator 2618 fits within the proximal housing 2624 and around the ram housing 2636.

A biasing element may be configured to bias the end-of-dose indicator 2618 toward an activated configuration. The biasing element may have a compressed configuration and an expanded configuration. The biasing element may be in a compressed configuration when the end-of-dose indicator 2618 is in an inactivated configuration, and the biasing element may be in an expanded configuration when the end-of-dose indicator 2618 is in an activated configuration. In some variations, the biasing element may comprise a compression spring 2666. The proximal end of the compression spring 2666 may be connected to or in contact with the end-of-dose indicator 2618, and the distal end of the compression spring 2666 may be connected to or in contact with an object distal to the end-of-dose indicator 2618, such as the interlock ring 2634 (described above). The biasing element may thus bias the end-of-dose indicator 2618 toward the proximal end of the proximal housing 2624.

As shown in FIGS. 27A-27E, the ram housing 2636 may comprise one or more latch(es) 2670, which may hold the end-of-dose indicator 2618 in an inactivated configuration until released. The latch(es) 2670 may each comprise a radially outward-extending lip that may press distally against the proximal surface of the end-of-dose indicator 2618. This lip may resist the biasing force from the biasing element (e.g., compression spring 2666) tending to push the end-of-dose indicator 2618 toward an activated configuration. When the end-of-dose indicator 2618 is released from the latch(es) 2670, the indicator may no longer be held in an inactivated configuration. The end-of-dose indicator 2618 may be released by radially inward force on the latch(es) 2670. In the variation shown in FIGS. 27A-27H, the radially inward force may be applied by a portion of the end cap 2650. As shown in FIG. 27E, the end cap 2650 may comprise a rim 2672 extending distally from the interior of the end cap 2650, which may in some variations have a cup shape as shown. As end cap 2650 moves distally relative to the latch(es) 2670 and ram housing 2636 during the injection, the rim 2672 may come into contact with an angled portion of the latch(es) 2670, as shown in FIG. 27F. This may generate a radially inward force on the latch(es) 2670. The latch(es) 2670 may thus be flexed inwardly, releasing the radially outward-extending lip from the proximal surface of the end-of-dose indicator 2618. The ram housing 2636 may comprise any suitable number of latches 2670, such as but not limited to one, two, three, four, five, six, or more. The rim 2672 may have any suitable corresponding configuration, such as but not limited to a continuous cup shape, or individual arms each configured to contact a latch 2670. Once released, the biasing force from the compression spring 2666 may cause the end-of-dose indicator 2618 to move proximally toward an activated configuration, as shown in FIGS. 27F-27H. In some variations, the end-of-dose indicator 2618 may be configured to produce a sudden, audible, and/or tactile indication of having delivered the full or nearly full dose.

After completion of the injection, the injection device 2600 may be removed from the patient. When proximal force from the tissue on the shroud 2620 of the needle safety assembly 2622 is removed, a biasing element (e.g., the compression spring 2662) may cause the needle shroud 2620 to return to an extended configuration. In some variations, the shroud 2620 of the needle safety assembly 2622 may additionally or alternatively be configured to be locked in an extended configuration after moving from a retracted configuration to an extended configuration. This feature may limit the ability of a needle 2628 to extend from the distal end of the nose to pierce or otherwise contact tissue or other surfaces after the injection device 2600 has been removed from a patient's tissue. This may make the injection device 2600 safer for the user and/or patient by limiting accidental needlesticks. It should be appreciated that in some variations, the needle safety assembly 2622 may enter the locked extended configuration if the injection 2600 is removed from the patient before the injection has fully completed.

Figure 28C:
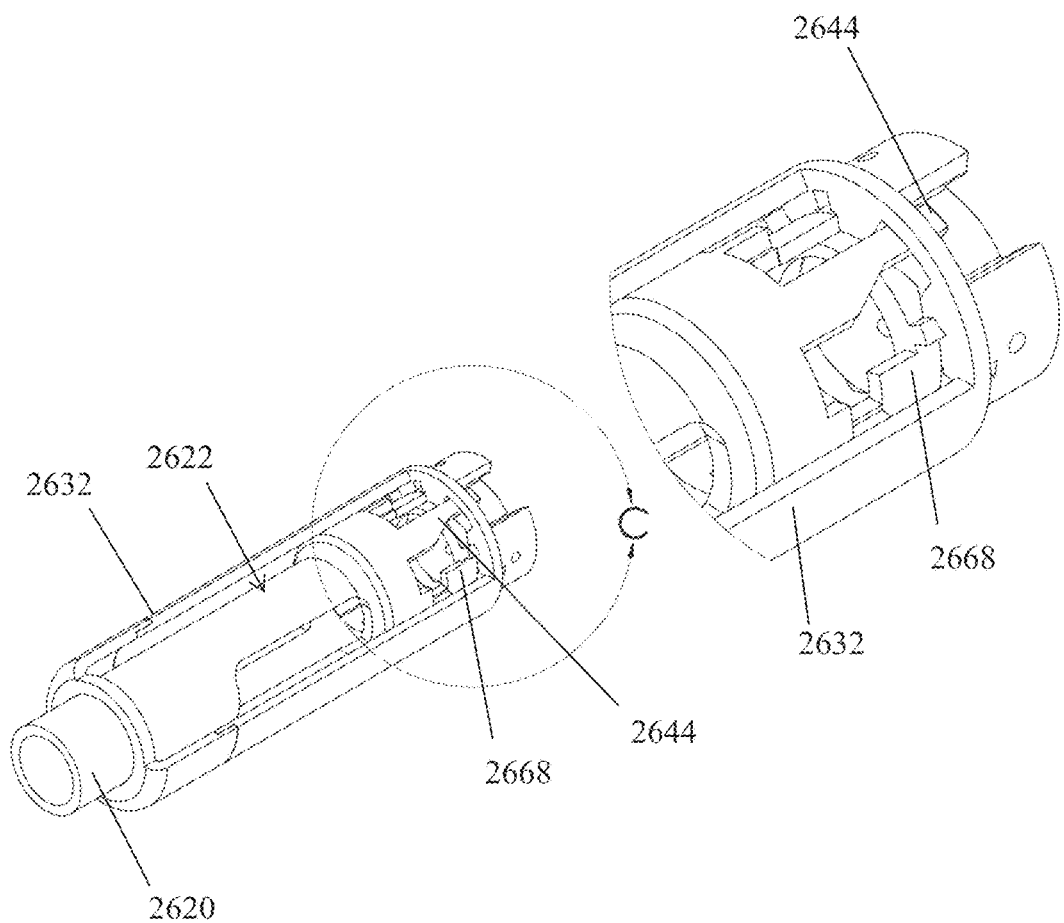

FIGS. 28A-28C show one variation of a mechanism by which the needle safety assembly 2622 may be able to be initially retracted by proximal force on the shroud 2620, but after having been retracted, re-extension of the needle safety assembly 2622 may cause it to lock into the extended position. The needle safety assembly 2622 may comprise a shroud locking ring 2668, shown isolated in FIG. 29C. The shroud locking ring 2668 may sit between the proximal portion of the needle safety assembly 2622 and distal housing 2632. The shroud locking ring 2668 may be movable between three configurations: a first, stable configuration when the needle safety assembly 2622 is initially extended; a second, unstable configuration when the needle safety assembly 2622 is retracted; and a third, stable configuration when the needle safety assembly 2622 is extended after having been retracted. The initial stable configuration is shown in FIG. 28A. As the needle safety assembly 2622 moves toward a retracted configuration as shown in FIG. 28B, proximal movement of the proximal end of the needle safety assembly 2622 may cause the shroud locking ring 2668 to rotate into the second, unstable configuration. As the needle safety assembly 2622 moves back toward a retracted configuration as shown in FIG. 28C, the distal movement of the proximal end of the needle safety assembly 2622 may cause the shroud locking ring 2668 to rotate into the third, stable configuration. Once the shroud locking ring 2668 has entered the third, stable configuration, it may block distal movement of the needle safety assembly 2622.

More specifically, when the needle safety assembly 2622 is initially in the extended position, the shroud locking ring 2668 may sit in a first, stable configuration against an internal shoulder of the distal housing 2632, and may be biased proximally toward the internal shoulder by compression spring 2662. The shroud locking ring 2668 and internal shoulder of the distal housing 2632 may comprise ramped surfaces, such that the shroud locking ring 2668 can sit against the internal shoulder in two different stable positions. When the needle safety assembly 2622 retracts, a ramped surface 2680 on each arm 2644 of the needle safety assembly 2622 may move into contact with a tab 2684 of the shroud locking ring 2668. As the needle safety assembly 2622 and arm 2644 move proximally, this may exert force on the tab 2684 that may cause the shroud locking ring 2668 to rotate (e.g., by between about 10 degrees and about 30 degrees, by about 15 degrees, or any suitable range). During this motion, the shroud locking ring 2668 may move distally relative to the internal shoulder of the distal housing 2632, allowing the shroud locking ring 2668 to rotate over a peak formed by the ramped surfaces of the internal shoulder. After the shroud locking ring 2668 rotates over the peak, the compression spring 2662 may bias the shroud locking ring 2682 back against the internal shoulder of the distal housing 2632. Once the needle safety assembly 2622 is in a fully retracted position, steps 2686 on the needle safety assembly 2622 may interface with tabs 2684 to prevent further rotation of the shroud locking ring 2668. When the needle safety assembly 2622 moves back toward a retracted configuration after having been in the retracted position, the needle safety assembly 2622 may disengage from the shroud locking ring 2682, and the shroud locking ring 2682 may further rotate under the bias from compression spring 2662 until it reaches the second, stable configuration against the internal shoulder of the distal housing 2632. In this configuration, further rotation of the shroud locking ring 2668 may be resisted by tabs 2688 on the needle safety assembly 2622, but preventing further retraction of the needle safety assembly 2622.

While the variation of the injection device described immediately above is configured to lock in the extended configuration after having been in a retracted configuration, it should be appreciated that in other variations, the needle shroud may not be configured to lock when re-entering an extended position (e.g., in some variations, the needle shroud may continue to be able to be retracted from an extended position in response to distal force).

In some variations, one or more of the elements of injection device 2600 may optionally comprise clocking features to correctly orient the elements relative to each other, as described above with respect to injection device 100.

While embodiments have been described and presented herein, those embodiments are provided by way of example only. Variations, changes, and substitutions may be made without departing from the embodiments provided by way of example. It should be noted that various alternatives to the exemplary embodiments described herein may be employed.

What is claimed is:

1. A device for injecting an agent, comprising:
a syringe comprising a syringe cavity, a plunger element slidably received in the syringe cavity, and a hollow needle in fluid communication with the syringe cavity, wherein the plunger element is configured to move from a proximal position to a distal position;
a power assembly configured to transmit force to the plunger element; and
a brake assembly configured to be actuated by a user, and reversibly resist movement of the plunger element in at least one intermediate position between the proximal position and the distal position, wherein the brake assembly comprises a braking pad attached to the plunger element, and wherein the braking pad is configured to resist movement of the plunger element by moving radially outward.

2. The device of claim 1, wherein the brake assembly is biased to resist movement of the plunger element when in an inactivated state, and permits movement of the plunger element when in an activated state.

3. The device of claim 2, wherein the brake assembly is biased by a brake spring to resist movement of the plunger element.

4. The device of claim 1, wherein the power assembly comprises a mechanical spring.

5. The device of claim 1, wherein the plunger element is further configured to simultaneously receive user-applied force that moves the plunger element toward the distal position.

6. The device of claim 1, further comprising a housing wherein the syringe is located in the housing.

7. The device of claim 6, wherein the housing is coupled to the plunger element.

8. The device of claim 7, wherein the housing is configured to transmit user-applied force to the plunger element.

9. The device of claim 1, wherein the brake assembly acts on a surface fixed relative to the syringe to reversibly resist movement of the plunger element.

10. The device of claim 1, wherein the power assembly is configured to pull the plunger element toward the distal position.

11. The device of claim 1, wherein the power assembly is configured to push the plunger element toward the distal position.

12. The device of claim 10, wherein the power assembly is further configured to push and pull the plunger element toward the distal position.

13. The device of claim 6, wherein the syringe is slidably located in the housing and the syringe is configured to move from a retracted position where a distal tip of the needle lies within the housing, toward an extended position where the distal tip of the needle extends distal to the housing.

14. The device of claim 1, further comprising an extendable needle shroud, wherein the needle shroud is configured with a releasably locked, retracted state relative to the syringe, and an unlocked state that permits movement toward an extended position relative to the syringe.

15. The device of claim 13, further comprising an extendable needle shroud, wherein the needle shroud is configured with a releasably locked, retracted state relative to the syringe, and an unlocked state that permits movement toward an extended position relative to the syringe, and wherein the needle shroud is further configured to change to the unlocked state before the distal tip of the needle extends distal to the housing.

16. The device of claim 15, wherein the needle shroud is further configured to relock when the needle shroud reaches the extended state.

17. A device for injecting an agent, comprising:
a housing having a longitudinal axis;
a syringe containing the agent within a syringe cavity, wherein the syringe is located within the housing;
a plunger slidable within the syringe, configured to be moveable between a proximal position and a distal position, wherein moving the plunger toward the distal position displaces the agent from the syringe;
a power assembly comprising a spring in contact with the plunger configured to bias the plunger toward the distal position; and
a brake assembly configured to be actuated by a user, comprising a braking pad configured to be reversibly moveable between a first configuration and a second configuration, wherein the braking pad generates friction to resist movement of the plunger in the second configuration, and wherein the braking pad is attached to the plunger, and wherein the braking pad is configured to be moveable from the first configuration to the second configuration by radially outward movement.

18. The device of claim 17, further comprising a stopper located within the plunger and movable between a proximal position and a distal position within the plunger, wherein the stopper is configured such that moving the stopper from the distal position to the proximal position moves the braking pad from the first configuration to the second configuration.

19. The device of claim 18, wherein the stopper is biased toward the proximal position.

20. The device of claim 18, wherein the stopper is configured to be moveable between the proximal position and distal position by application of distal force on the housing.

21. The device of claim 17, further comprising a retractable needle shroud configured to be moveable between a retracted position and an extended position.

22. The device of claim 17, further comprising an end-of-dose indicator moveable between an inactivated and an activated configuration.

23. The device of claim 1, further comprising an extendable needle shroud, wherein the needle shroud is configured with an unlocked extended state that permits movement toward a retracted position relative to the syringe and a locked extended state.

24. The device of claim 23, wherein the needle shroud is configured to enter the locked extended state when the needle shroud extends from a retracted state.

* * * * *

UNITED STATES PATENT AND TRADEMARK OFFICE
CERTIFICATE OF CORRECTION

PATENT NO. : 10,252,005 B2
APPLICATION NO. : 14/541095
DATED : April 9, 2019
INVENTOR(S) : Gordon D. Row It is certified that error appears in the above-identified patent and that said Letters Patent is hereby corrected as shown below:

On the Title Page

Item (72) Inventors, the following information for one additional inventor should be added after Inventor: Adrian Bischoff, Cambridge, MA (US)
--Genevieve R. K. Laing, San Francisco, CA (US)--

Signed and Sealed this
Eleventh Day of April, 2023

Katherine Kelly Vidal
*Director of the United States Patent and Trademark Office*